(12) United States Patent
Meanwell et al.

(10) Patent No.: US 7,485,633 B2
(45) Date of Patent: *Feb. 3, 2009

(54) CYCLOPROPYL FUSED INDOLOBENZAZEPINE HCV NS5B INHIBITORS

(75) Inventors: Nicholas A. Meanwell, East Hampton, CT (US); Robert G. Gentles, Wallingford, CT (US); Min Ding, Glastonbury, CT (US); John A. Bender, Middletown, CT (US); John F. Kadow, Wallingford, CT (US); Piyasena Hewawasam, Middletown, CT (US); Thomas W. Hudyma, Durham, CT (US); Xiaofan Zheng, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/684,710

(22) Filed: Mar. 12, 2007

(65) Prior Publication Data

US 2007/0184024 A1    Aug. 9, 2007

Related U.S. Application Data

(63) Continuation-in-part of application No. 11/507,731, filed on Aug. 22, 2006.

(60) Provisional application No. 60/716,187, filed on Sep. 12, 2005, provisional application No. 60/809,979, filed on Jun. 1, 2006.

(51) Int. Cl.
*A61K 31/55*  (2006.01)
*A61P 31/00*  (2006.01)
*C07D 223/14* (2006.01)

(52) U.S. Cl. .................................. 514/214.01; 540/576

(58) Field of Classification Search ............ 514/214.01; 540/576
See application file for complete search history.

(56) References Cited

U.S. PATENT DOCUMENTS

| 7,153,848 | B2 | 12/2006 | Hudyma et al. | 514/214.01 |
|---|---|---|---|---|
| 2006/0046983 | A1 | 3/2006 | Hudyma et al. | 514/211.09 |
| 2006/0166964 | A1 | 7/2006 | Hudyma et al. | 514/211.09 |
| 2007/0060565 | A1 | 3/2007 | Meanwell et al. | 514/214.01 |
| 2007/0078122 | A1 | 4/2007 | Bergstrom et al. | 514/214.01 |
| 2007/0185083 | A1 | 8/2007 | Bergstrom et al. | 514/214.01 |

FOREIGN PATENT DOCUMENTS

| WO | WO2005/080399 | 9/2005 |
|---|---|---|
| WO | WO2006/040039 | 4/2006 |
| WO | WO2006/046030 | 5/2006 |
| WO | WO 2006/046039 | 5/2006 |
| WO | WO2007/029029 | 3/2007 |

OTHER PUBLICATIONS

U.S. Appl. No. 11/752,354, filed May 23, 2007, Robert G. Gentles, et al.
U.S. Appl. No. 11/753,137, filed May 24, 2007, Carl P. Bergstrom.
U.S. Appl. No. 11/756,203, filed May 31, 2007, Kap-Sun Yeung, et al.

*Primary Examiner*—Brenda L Coleman
(74) *Attorney, Agent, or Firm*—James Epperson

(57) ABSTRACT

The invention encompasses compounds of Formula I, pharmaceutically acceptable salts thereof, compositions, and methods of using the compounds. The compounds have activity against hepatitis C virus (HCV) and are useful in treating those infected with HCV.

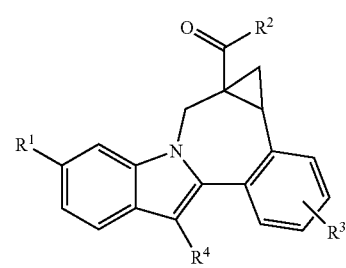

3 Claims, No Drawings

CYCLOPROPYL FUSED INDOLOBENZAZEPINE HCV NS5B INHIBITORS

CROSS REFERENCE TO RELATED APPLICATIONS

This application is a continuation-in-part of U.S. Non-Provisional patent application Ser. No. 11/507,731 filed Aug. 22, 2006, and claims the benefit of U.S. Provisional Patent Application Ser. Nos. 60/716,187 filed Sep. 12, 2005 and 60/809,979 filed Jun. 1, 2006.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV NS5B inhibitors have been disclosed. See WO 2006/046039; WO 2006/046030; WO 2006/029912; WO 2005/080399; WO 2005080399; WO 2005014543; WO 200307945; WO 2003010140; WO 2003010141; WO 200204425; WO 200147883; Harper, S. A. et al. *J. Med. Chem.* 2005, 48, 4547; and Harper, S. A. et al. *J. Med. Chem.* 2005, 48, 1314, and references cited therein.

DESCRIPTION OF THE INVENTION

The invention encompasses compounds of formula I, pharmaceutically acceptable salts thereof, compositions, and methods of treatment using these compounds.

One aspect of the invention is a compound of formula I

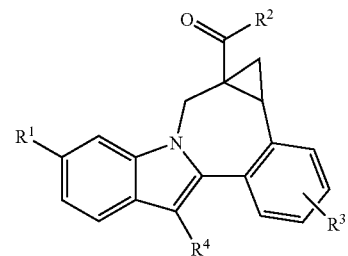

wherein:
$R^1$ is $CO_2R^5$ or $CONR^6R^7$;
$R^2$ is hydroxy, alkoxy, benzyloxy, $NR^8R^9$, or

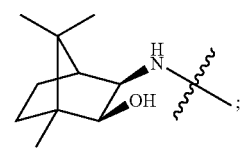

$R^3$ is hydrogen, halo, alkyl, alkenyl, hydroxy, benzyloxy, or alkoxy;
$R^4$ is $C_{5-7}$cycloalkyl;
$R^5$ is hydrogen or alkyl;
$R^6$ is hydrogen, alkyl, cycloalkyl, alkoxy, or $SO_2R^{10}$;
$R^7$ is hydrogen, alkyl, or cycloalkyl;
or $NR^6R^7$ taken together is pyrrolidinyl, piperidinyl, piperazinyl, N-(alkyl)piperazinyl, homomorpholinyl, homopiperidinyl, morpholinyl, or thiomorpholinyl;
$R^8$ is hydrogen, alkyl, cycloalkyl, hydroxyalkyl, alkoxyalkyl, aminoalkyl, alkylaminoalkyl, dialkylaminoalkyl, $(CO_2R^5)$alkyl, or $(CON(R^5)(R^5))$alkyl;
$R^9$ is hydrogen, alkyl, cycloalkyl, hydroxyalkyl, dihydroxyalkyl, alkoxyalkyl, aminoalkyl, alkylaminoalkyl, dialkylaminoalkyl, $(CO_2R^5)$alkyl, or $(CON(R^5)(R^5))$alkyl;

or $NR^8R^9$ taken together is pyrrolidinyl, piperidinyl, piperazinyl, homomorpholinyl, homopiperidinyl, morpholinyl, or thiomorpholinyl, and is substituted with 0-2 substitutents selected from halo, hydroxy, alkyl, hydroxyalkyl, alkoxyalkyl, amino, alkylamino, dialkylamino, aminoalkyl, alkylaminoalkyl, dialkylaminoalkyl, pyrrolidinyl, piperidinyl, piperazinyl, N-(alkyl)piperazinyl, morpholinyl, thiomorpholinyl, and pyridinyl; and $R^{10}$ is alkyl, haloalkyl, cycloalkyl, phenyl, amino, alkylamino, dialkylamino, benzylamino, or (benzyl)(alkyl)amino;

or $R^{10}$ is pyrrolidinyl, piperidinyl, piperazinyl, homomorpholinyl, homopiperidinyl, morpholinyl, or thiomorpholinyl, and is substituted with 0-2 substitutents selected from halo and alkyl;

or a pharmaceutically acceptable salt thereof.

Another aspect of the invention is a compound of formula I

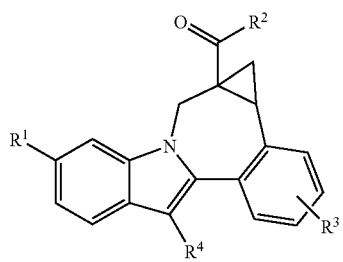

wherein:
$R^1$ is $CO_2R^5$ or $CONR^6R^7$;
$R^2$ is hydroxy, alkoxy, or $NR^8R^9$;
$R^3$ is hydrogen, halo, alkyl, alkenyl, hydroxy, benzyloxy, or alkoxy;
$R^4$ is $C_{5-7}$cycloalkyl;
$R^5$ is hydrogen or alkyl;
$R^6$ is hydrogen, alkyl, cycloalkyl, alkoxy, or $SO_2R^{10}$;
$R^7$ is hydrogen, alkyl, or cycloalkyl;
$R^8$ is hydrogen, alkyl, cycloalkyl, hydroxyalkyl, alkoxyalkyl, aminoalkyl, alkylaminoalkyl, dialkylaminoalkyl, $(CO_2R^5)$alkyl, or $(CON(R^5)(R^5))$alkyl;
$R^9$ is hydrogen, alkyl, cycloalkyl, hydroxyalkyl, alkoxyalkyl, aminoalkyl, alkylaminoalkyl, dialkylaminoalkyl, $(CO_2R^5)$alkyl, or $(CON(R^5)(R^5))$alkyl;
or $NR^8R^9$ taken together is pyrrolidinyl, piperidinyl, piperazinyl, homomorpholinyl, homopiperidinyl, morpholinyl, or thiomorpholinyl, and is substituted with 0-2 substitutents selected from halo, hydroxy, alkyl, amino, alkylamino, dialkylamino, aminoalkyl, alkylaminoalkyl, dialkylaminoalkyl, pyrrolidinyl, piperidinyl, piperazinyl, N-(alkyl)piperazinyl, morpholinyl, and thiomorpholinyl; and $R^{10}$ is alkyl, haloalkyl, cycloalkyl, amino, alkylamino, or dialkylamino;

or $R^{10}$ is pyrrolidinyl, piperidinyl, piperazinyl, homomorpholinyl, homopiperidinyl, morpholinyl, or thiomorpholinyl, and is substituted with 0-2 substitutents selected from halo and alkyl;

or a pharmaceutically acceptable salt thereof.

Another aspect of the invention is a compound of formula I

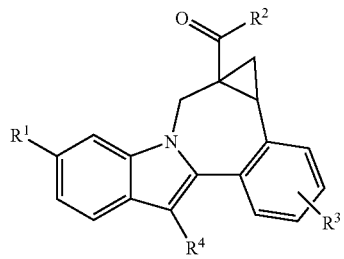

wherein:
$R^1$ is $CO_2R^5$ or $CONR^6R^7$;
$R^2$ is hydroxy, alkoxy, or $NR^8R^9$;
$R^3$ is hydrogen, halo, alkyl, or alkoxy;
$R^4$ is $C_{5-7}$cycloalkyl;
$R^5$ is hydrogen or alkyl;
$R^6$ is hydrogen, alkyl, cycloalkyl, alkoxy, or $SO_2R^{10}$;
$R^7$ is hydrogen, alkyl, or cycloalkyl;
$R^8$ is hydrogen, alkyl, cycloalkyl, hydroxyalkyl, alkoxyalkyl, aminoalkyl, alkylaminoalkyl, or dialkylaminoalkyl;
$R^9$ is hydrogen, alkyl, cycloalkyl, hydroxyalkyl, alkoxyalkyl, aminoalkyl, alkylaminoalkyl, or dialkylaminoalkyl;
or $NR^8R^9$ taken together is pyrrolidinyl, piperidinyl, piperazinyl, homomorpholinyl, homopiperidinyl, morpholinyl, or thiomorpholinyl, and is substituted with 0-2 substitutents selected from halo, hydroxy, alkyl, amino, alkylamino, dialkylamino, pyrrolidinyl, piperidinyl, piperazinyl, N-(alkyl)piperazinyl, morpholinyl, and thiomorpholinyl;

$R^{10}$ is alkyl, haloalkyl, cycloalkyl, amino, alkylamino, dialkylamino;

or $R^{10}$ is pyrrolidinyl, piperidinyl, piperazinyl, homomorpholinyl, homopiperidinyl, morpholinyl, or thiomorpholinyl, and is substituted with 0-2 substitutents selected from halo and alkyl;

or a pharmaceutically acceptable salt thereof.

Another aspect of the invention is a compound of formula I where $R^1$ is carboxy.

Another aspect of the invention is a compound of formula I where $R^1$ is $CONR^6R^7$, $R^6$ is $SO_2R^{10}$, and $R^7$ is hydrogen.

Another aspect of the invention is a compound of formula I where $R^2$ is $NR^8R^9$.

Another aspect of the invention is a compound of formula I where $R^3$ is hydrogen.

Another aspect of the invention is a compound of formula I where $R^3$ is halo, alkyl, or alkoxy.

Another aspect of the invention is a compound of formula I where $R^4$ is cyclohexyl.

Another aspect of the invention is a compound of formula I where $R^{10}$ is dialkylamino.

Another aspect of the invention is a compound of formula I where $R^{10}$ is pyrrolidinyl, piperidinyl, piperazinyl, homomorpholinyl, homopiperidinyl, morpholinyl, or thiomorpholinyl, and is substituted with 0-2 substitutents selected from halo and alkyl.

Any scope of any variable, including $R^1$, $R^2$, $R^3$, $R^4$, $R^5$, $R^6$, $R^7$, $R^8$, $R^9$, $R^{10}$, can be used independently with the scope of any other variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substitutents. Parenthetic and multiparenthetic terms are intended to clarify bonding relationships to those skilled in the art. For example, a term such as ((R)alkyl) means an alkyl substitutent further substituted with the substituent R.

As an artifact of the software used to generate structures for some of the compounds, some compounds are missing hydrogens, especially hydrogens attached to a heteroatom. The specification should be read so as to include omitted hydrogens where one skilled in the art would reasonably understand a hydrogen would be part of the compound.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the compound below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

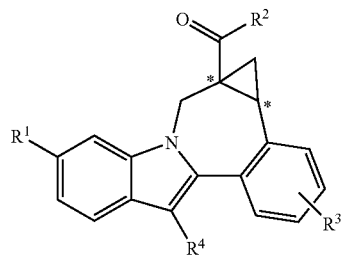

Synthetic Methods

Formula I compounds may be made by methods known in the art including those described below. Some reagents and intermediates are known in the art. Other reagents and intermediates can be made by methods known in the art using readily available materials. The variables used to describe the synthesis of formula I compounds are intended only to illustrate how to make and are not to be confused with variables used in the claims or in other sections of the specification.

Abbreviations used within the schemes generally follow conventions used in the art. Some examples are as follows: THF means tetrahydrofuran; DMF means N,N-dimethylformamide; RCM means ring-closing methasis; Boc means tert-butoxycarbonyl; TFA means trifluoracetic acid; DMA means N,N-dimethylacetamide; PPh$_3$ means triphenylphosphine; OAc means acetate; Me means methyl; COD (or cod) means 1,5-cyclooctadiene; dtbpy means 4,4'-di-tert-butyl-2,2'-bipyridine; dba means dibenzylideneacetone; Xantphos means 4,5-bis(diphenylphosphino)-9,9-dimethylxanthine; aq means aqueous; EtOH means ethanol; MeOH means methanol; TBTU means 2-(1H-benzotriazole-1-yl)-1,1,3,3-tetramethyluronium tetrafluoroborate; DMSO means dimethylsulfoxide; HATU means O-(7-azabenzotriazol-1-yl)-N,N,N',N'-tetramethyluronium hexafluorophosphate; EEDQ means 2-ethoxy-1-ethoxycarbonyl-1,2-dihydroquinoline; WSC means 1-[3-(dimethylamino)propyl]-3-ethylcarbodiimide hydrochloride; DMAP means 4-dimethylaminopyridine; n-Bu means n-butyl; BEMP means 2-tert-butylimino-2-diethylamino-1,3-dimethylperhydro-1,3,2-diazaphosphorine, polymer-bound; DIPEA means diisopropylethylamine; and TEA means triethylamine.

Some diester intermediates useful for the synthesis of formula I compounds may be prepared by using the general methodology depicted in Scheme 1.

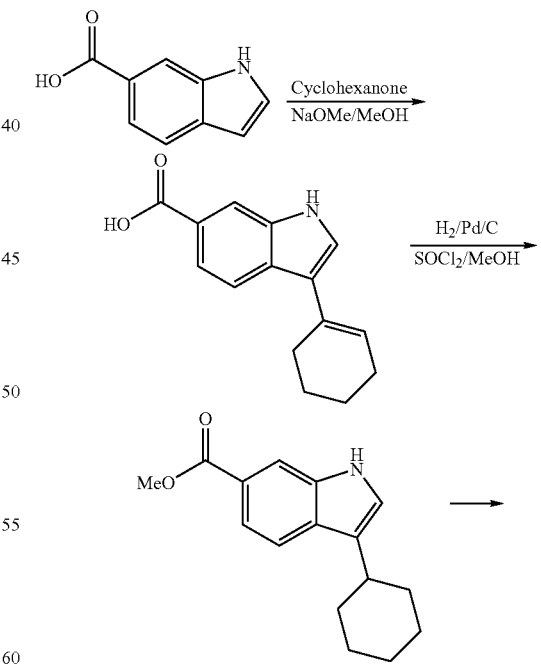

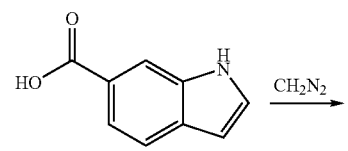

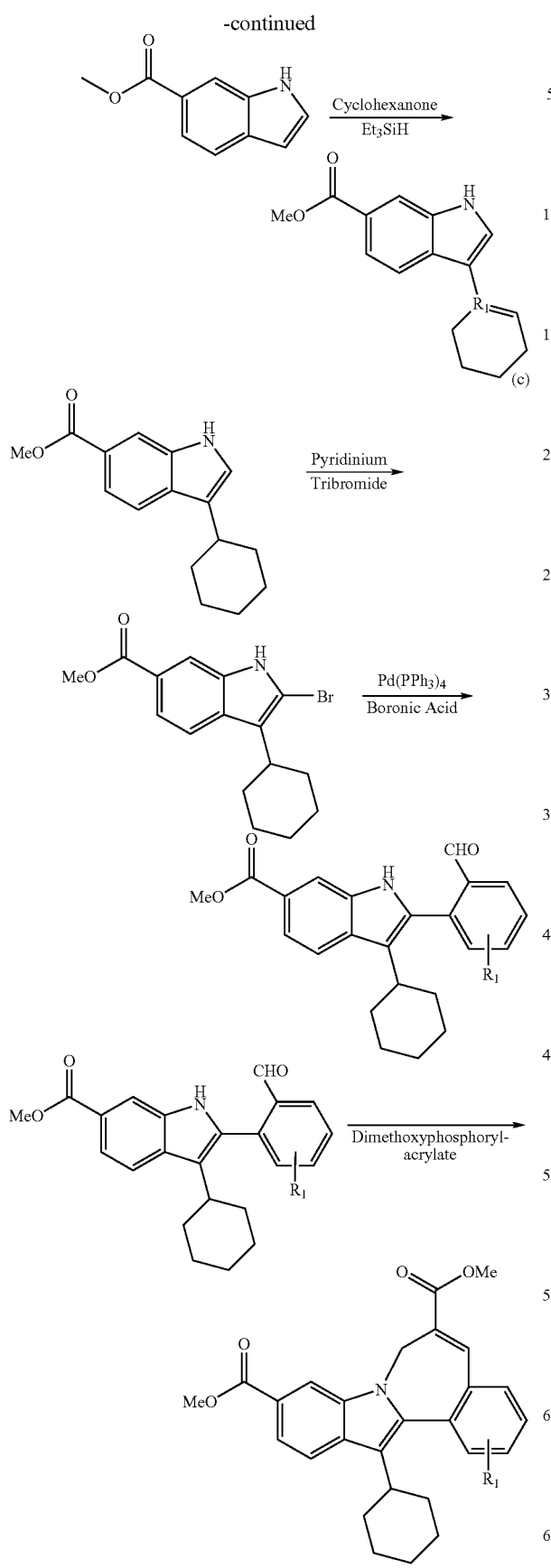

Condensation of 1H-indole-6-carboxylic acid with cyclohexanone can generate 3-cyclohexenyl-1H-indole-6-carboxylic acid. This indole ester can be subjected to sequential reduction and esterification to provide methyl 3-cyclohexanyl-1H-indole-6-carboxylate.

Alternatively, methyl 3-cyclohexanyl-1H-indole-6-carboxylate can be prepared in a two step procedure that involves an initial esterification of 1H-indole-6-carboxylic acid, for example using diazomethane in ether, followed by sequential condensation with cyclohexanone, followed by reduction.

Treatment of the resultant indole ester with pryridinium tribromide in a mixture of THF and chloroform can generate methyl 2-bromo-3-cyclohexanyl-1H-indole-6-carboxylate. This intermediate can be used in a variety of couplings, for example with 2-formyl-phenyl boronic acids using appropriate palladium catalysts, to generate the aromatic aldehyde intermediates shown. NMR analysis of this class of compound indicated that the aryl aldehydes are sometimes observed to exist in equilibrium with the related ring-closed hemiaminals, as shown below.

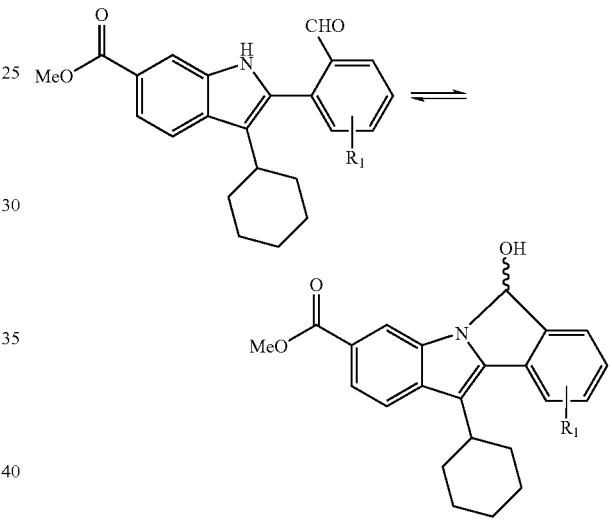

These intermediates can then be transformed into indolobenzazepine diester intermediates, for example by treating with methyl 2-(dimethoxyphosphoryl)acrylate under the influence of cesium carbonate in DMF via consecutive Michael and Horner Emmons reactions.

The resultant diester intermediates may be converted to cyclopropyl derivatives, for example as shown in Scheme 2.

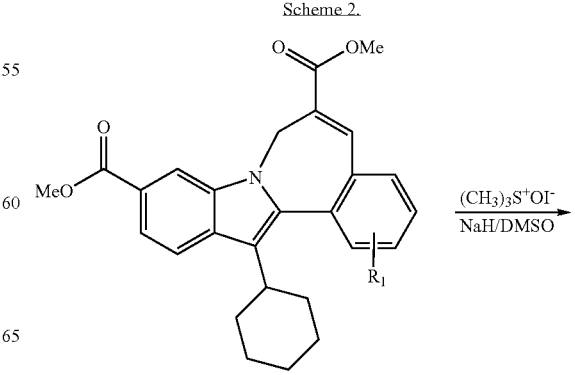

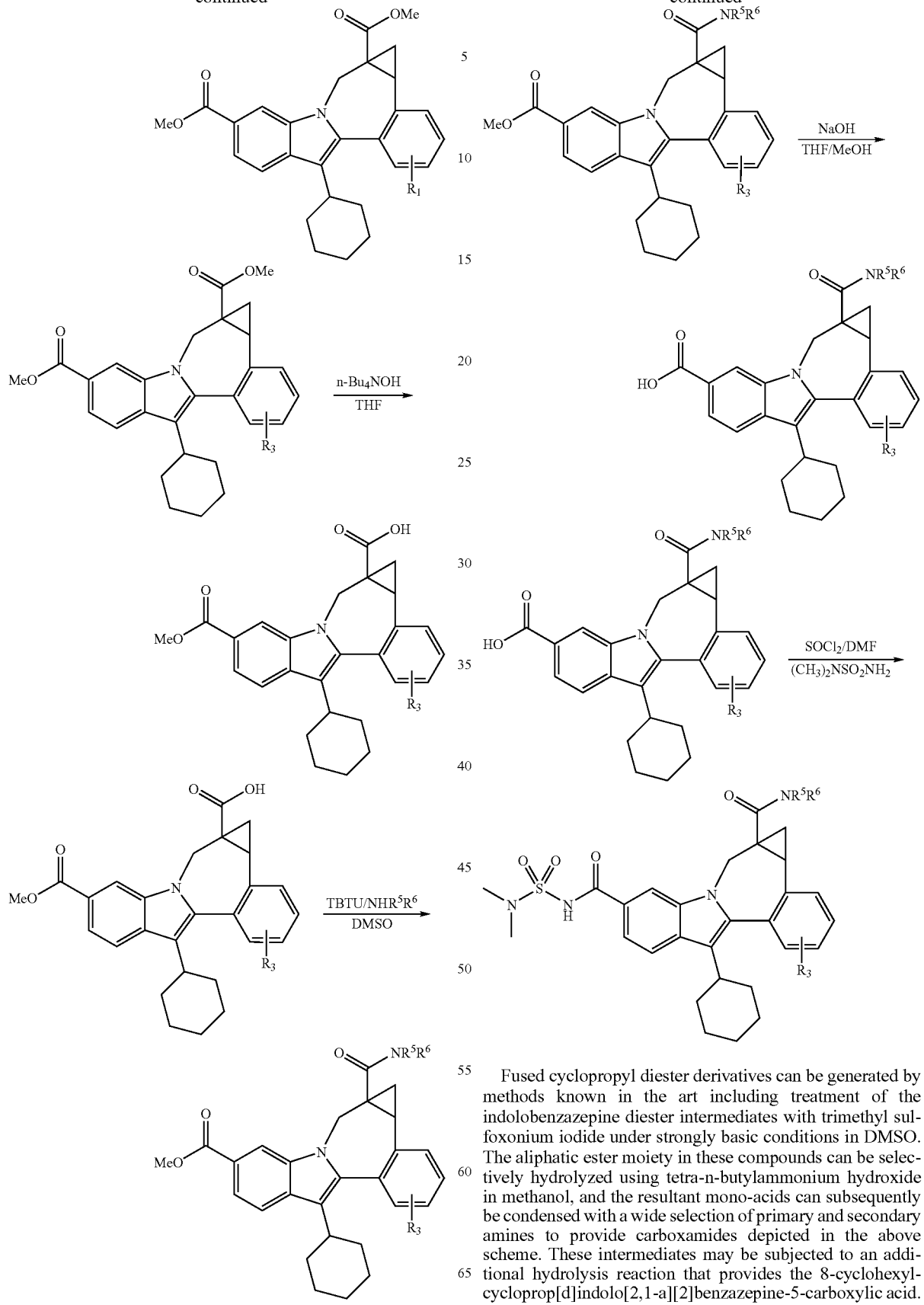

Fused cyclopropyl diester derivatives can be generated by methods known in the art including treatment of the indolobenzazepine diester intermediates with trimethyl sulfoxonium iodide under strongly basic conditions in DMSO. The aliphatic ester moiety in these compounds can be selectively hydrolyzed using tetra-n-butylammonium hydroxide in methanol, and the resultant mono-acids can subsequently be condensed with a wide selection of primary and secondary amines to provide carboxamides depicted in the above scheme. These intermediates may be subjected to an additional hydrolysis reaction that provides the 8-cyclohexyl-cycloprop[d]indolo[2,1-a][2]benzazepine-5-carboxylic acid. Additionally, these compounds can serve as intermediates in additional coupling reactions with appropriate sulfonyl ureas that can generate acyl sulfonyl urea compounds.

In an alternative procedure, indolo[2,1-a][2]benzazepine-10-carboxylate intermediates may first be subjected to a base catalysed selective hydrolysis reaction that results in the generation of the mixed acid-ester class of compound (see Scheme 3). Subsequent coupling with amines can generate carboxamides. These intermediates can be cyclopropanated, for example by treatment with trimethylsulfoxonium iodide under basic conditions, to generate the cyclopropyl ring-fused derivatives. Subsequent hydrolysis of the remaining ester moiety can generate carboxylic acid compounds of formula I. These compounds may be converted to their corresponding acyl sulfonyl ureas derivatives.

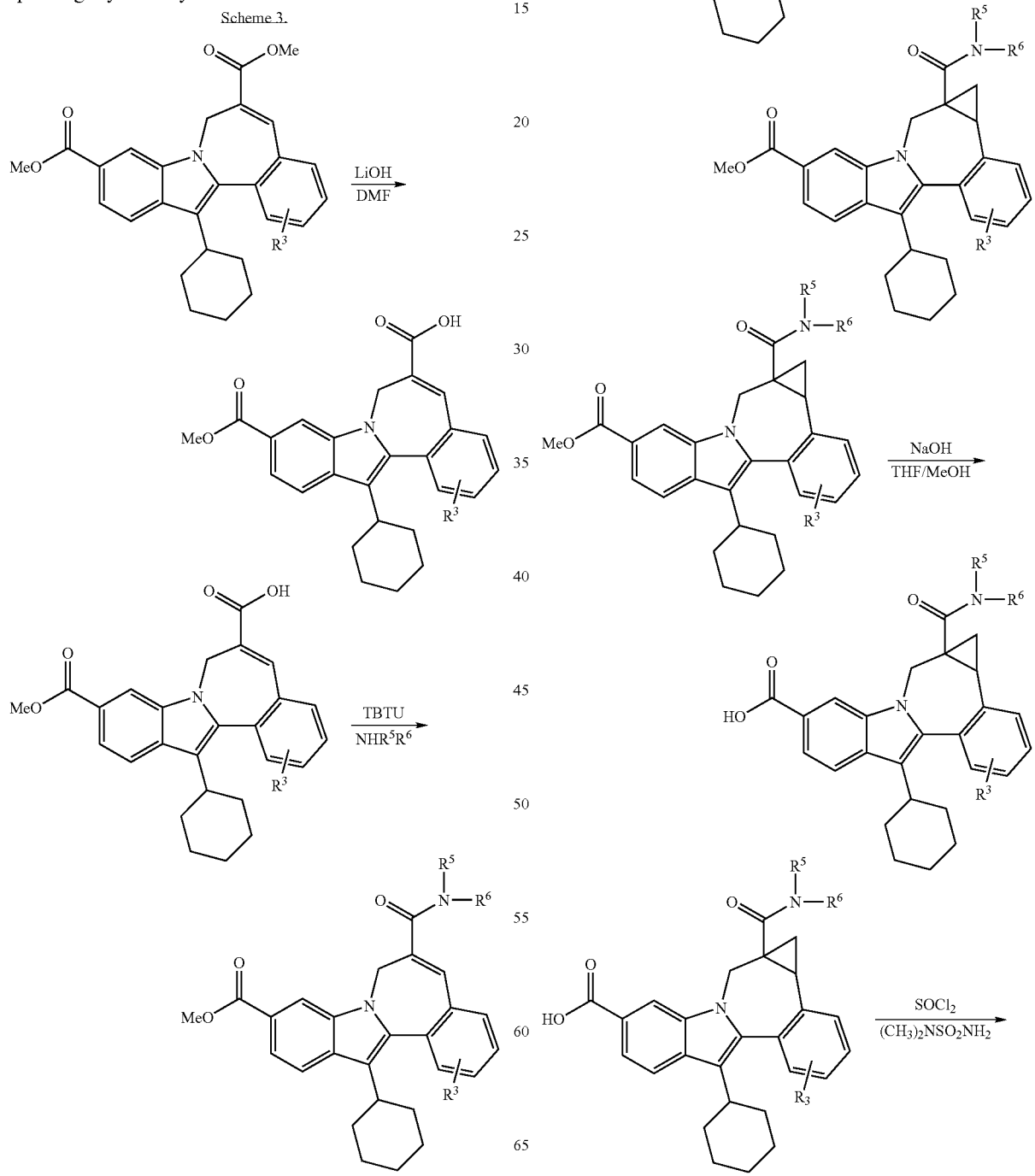

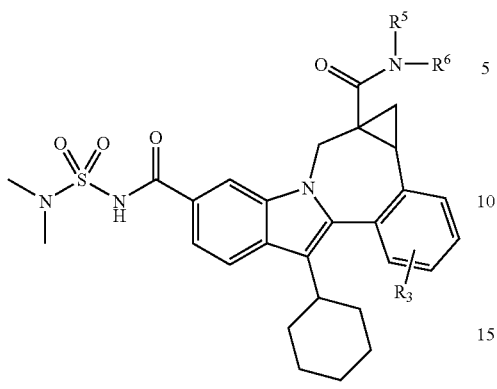
Additional methodology that can be used to make further examples is shown in scheme 4.
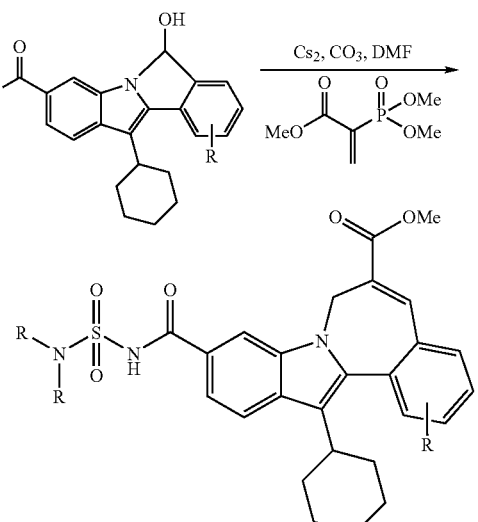
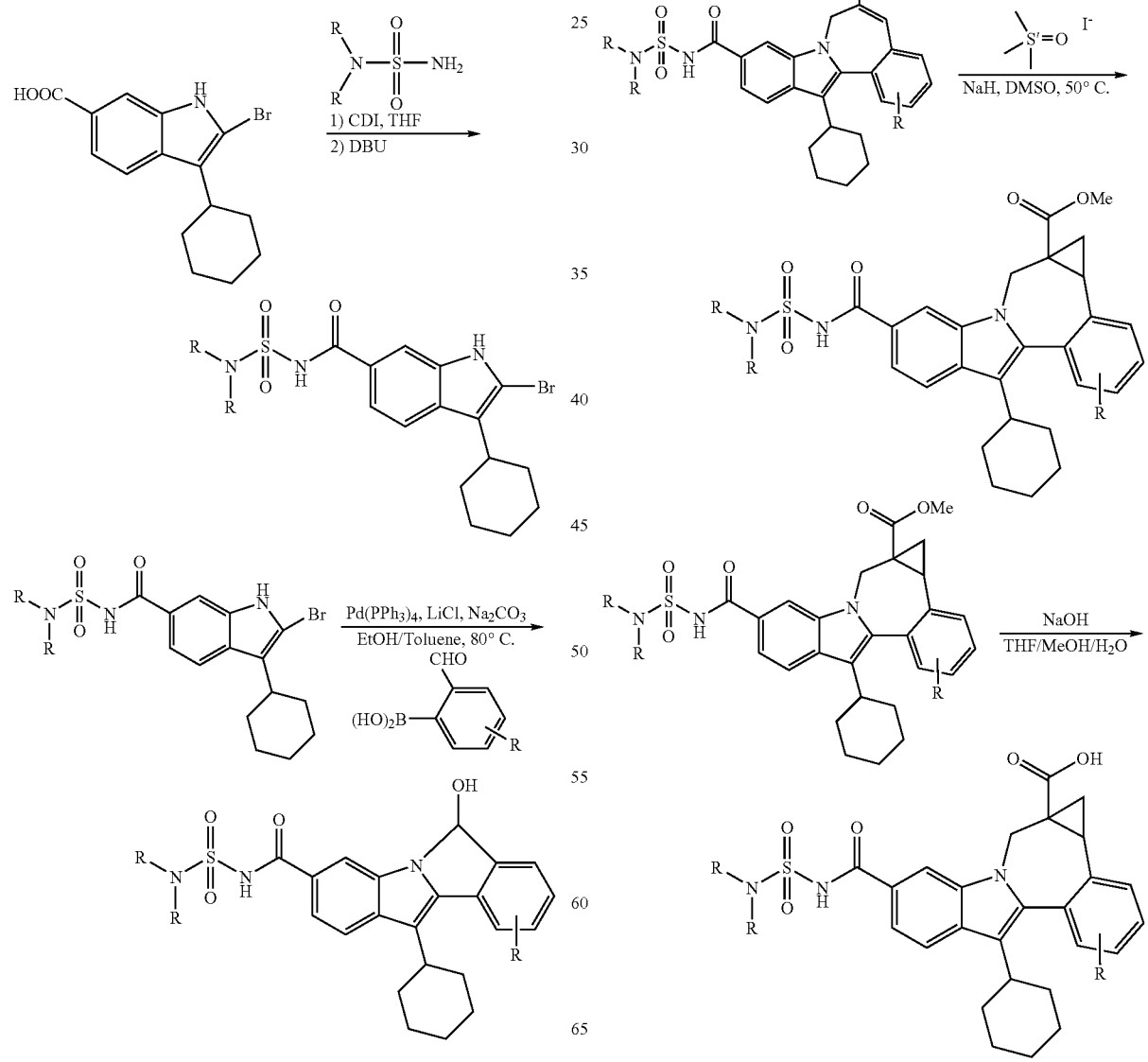

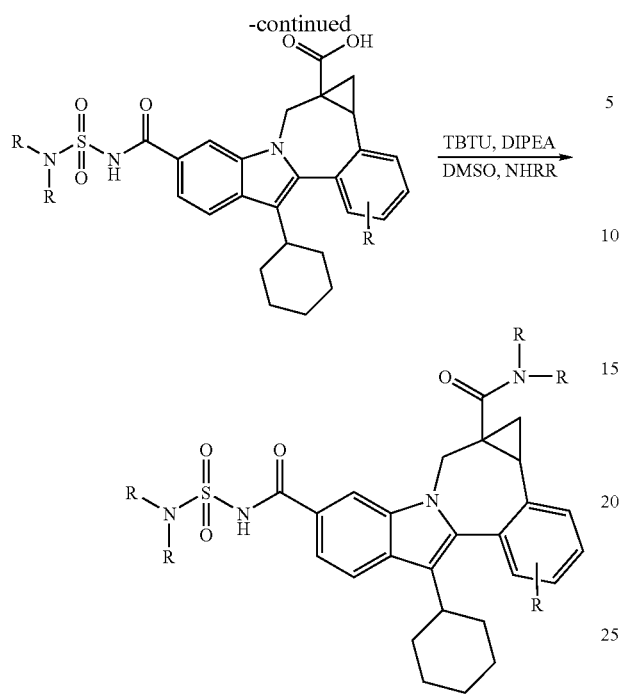

2-Bromo-3-cyclohexyl-1H-indole-6-carboxylic acid, (scheme 1) can be condensed with a variety of sulfonyl ureas, using for example, 1,1'-carbonyldiimidazole in combination with 1,8-diazabicyclo[5.4.0]undec-7-ene in anhydrous THF. The resultant acyl sulfamides can be subjected to known coupling reactions, for example with a diversity of 2-formyl boronic acids or esters using Suzuki coupling conditions, to provide cyclic hemiaminal intermediates of the type depicted. These compounds can be subsequently converted to indolobenzazepine derivatives using the sequence of reactions previously described. Related fused cyclopropyl ester derivatives can be generated by methods known in the art, including treatment of the indolobenzazepine esters with trimethyl sulfoxonium iodide under strongly basic conditions in DMSO. The residual aliphatic ester moiety in the resultant fused cyclopropanes can be hydrolyzed and the product acids can be condensed with a diversity of amines, using for example, O-(1H-benzotriazol-1-yl)-N,N,N',N'-tetramethyluronium tetrafluoroborate and diisopropyl ethyl amine in DMSO, to give examples of cyclopropyl carboxamides.

An intermediate useful for the synthesis of some further compounds involves the preparation of (+/−) 8-cyclohexyl-1,1a,2,12b-tetrahydro-11-methoxy-1a-(methoxycarbonyl)-cycloprop[d]indolo[2,1-a][2]benzazepine-5-carboxylic acid, tert-butyl ester, as shown in Scheme 5.

Scheme 5.

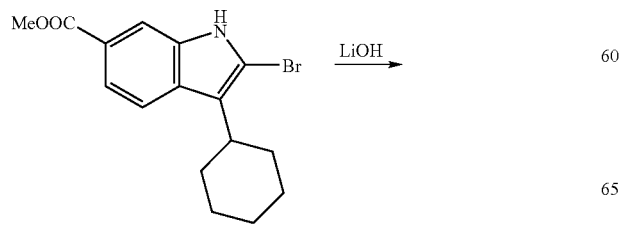

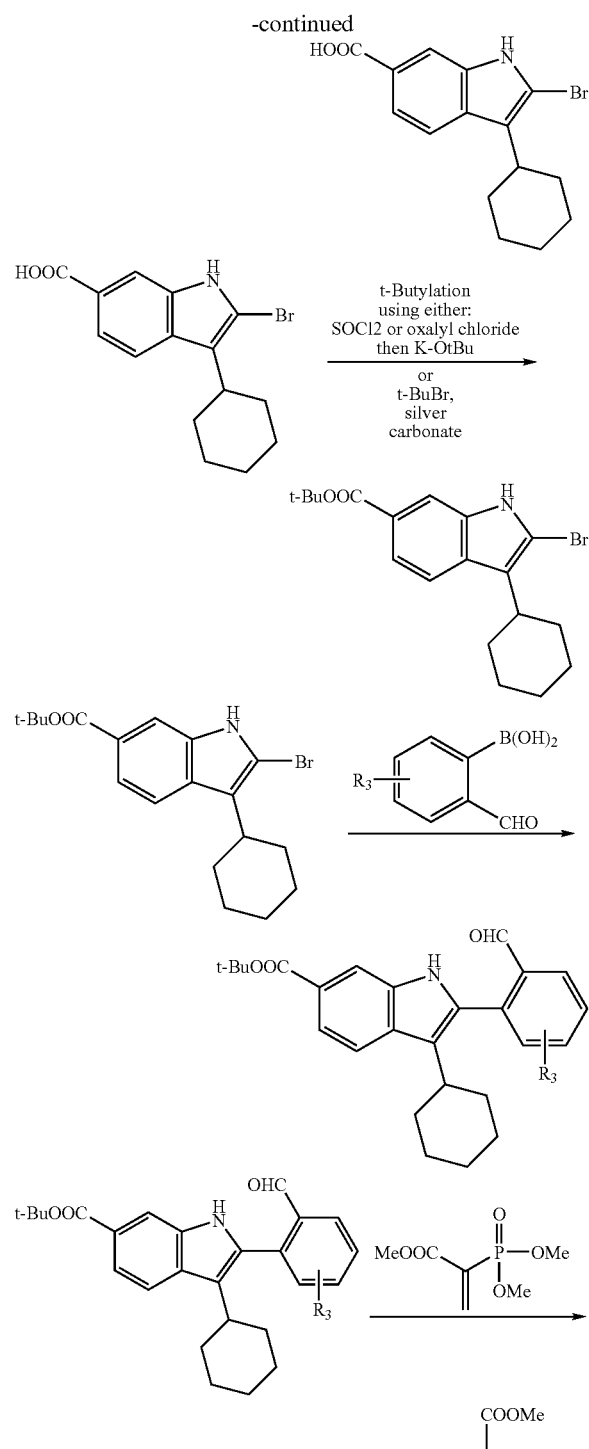

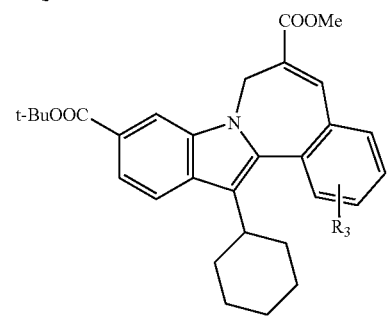

This methodology involves base catalyzed hydrolysis of the indole methyl ester shown, followed by its reaction with either thionyl chloride and potassium tertiary butoxide, or by alkylation with silver carbonate and tertiary butyl bromide. The resultant compound can be transformed using chemistry analogous to that outlined previously to provide the mixed ester indolobenzazepines shown in scheme 5.

The resultant (+/−) 8-cyclohexyl-1,1a,2,12b-tetrahydro-11-methoxy-1a-(methoxycarbonyl)-cycloprop[d]indolo[2,1-a][2]benzazepine-5-carboxylic acid, tert-butyl ester can be useful in an alternative procedure that can be employed for the preparation of acylsulfamide and acylsulfonamide compounds as shown in scheme 6.

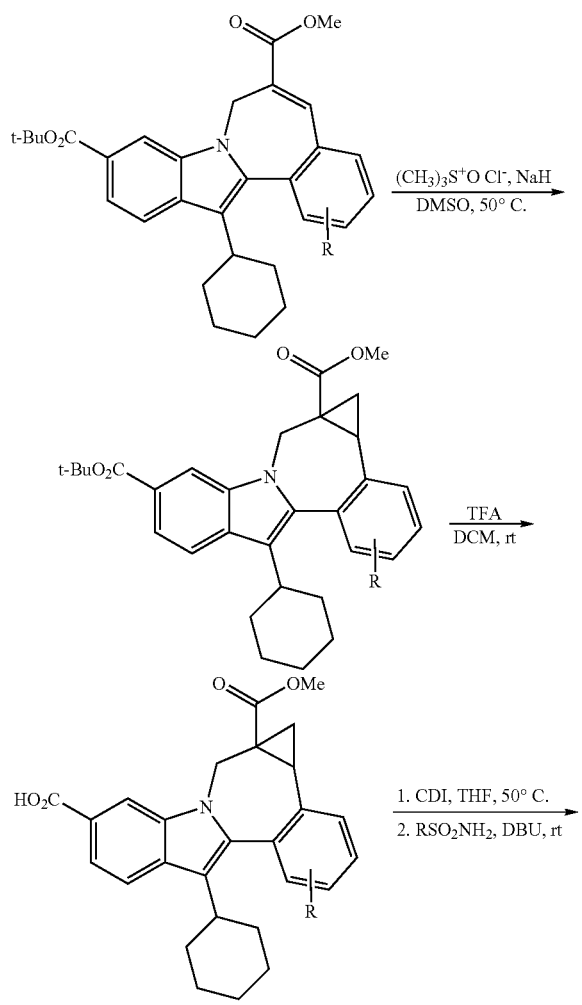

-continued

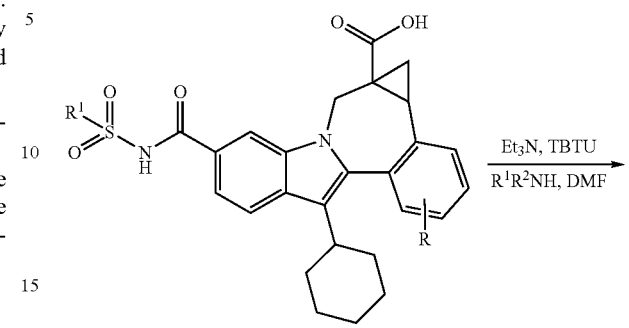

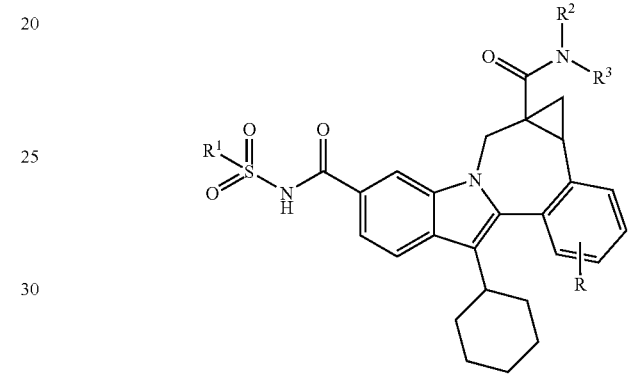

Cyclopropanation of an intermediate t-butyl ester indolobenzazepine and subsequent cleavage of the t-butyl ester group can generate the related indole acid which can be coupled to a diversity of sulfonamides and sulfonylureas. Subsequent hydrolysis of the residual ester moiety affords the related bridged acids, which can be coupled with a diversity of amines, using for example, O-(1H-benzotriazol-1-yl)-N,N,N',N'-tetramethyluronium tetrafluoroborate and diisopropyl ethyl amine in DMSO, to provide further carboxamides examples.

Some of the compounds discussed exist as mixtures of stereoisomers. The invention encompasses all stereoisomers of the compounds. Methods of isolating and separating stereoisomeric mixtures are well known in the art. One method is shown below and involves the syntheses of diastereomeric amides as shown in Scheme 7. Diastereomeric esters can also be prepared.

Scheme 7.

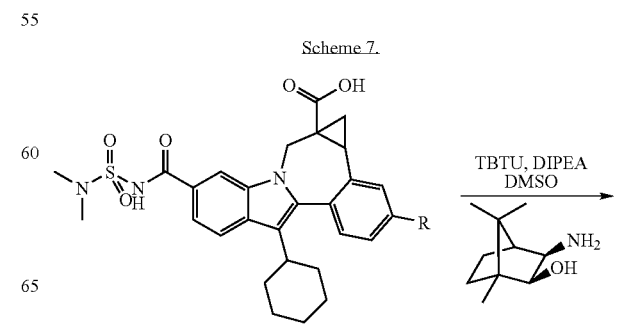

-continued

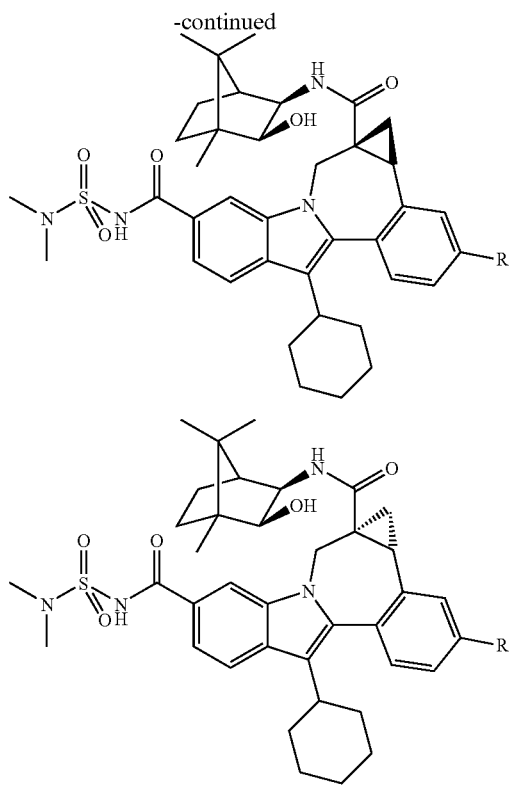

Diastereomers separated by reverse phase HPLC

Some diastereomeric amides can be separated using reverse phase HPLC to provide optically active carboxamides. Subsequently, these compounds can be hydrolyzed and the resultant optically active acids can be coupled to a diversity of amines, using for example, O-(1H-benzotriazol-1-yl)-N,N,N',N'-tetramethyluronium tetrafluoroborate and diisopropyl ethyl amine in DMSO, to provide further examples of optically active examples, as shown in scheme 8.

Scheme 8.

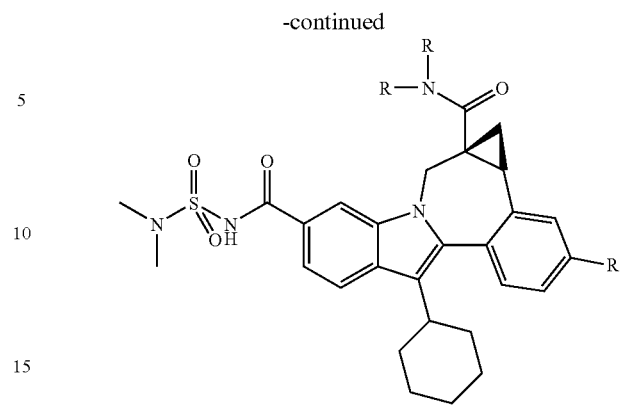

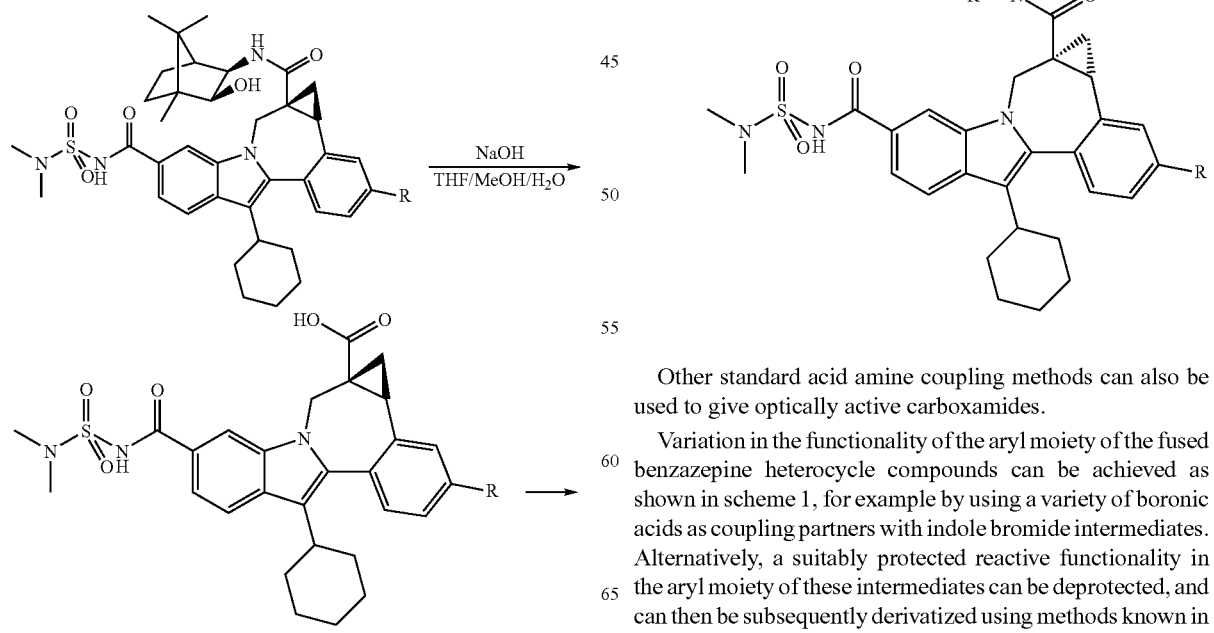

Other standard acid amine coupling methods can also be used to give optically active carboxamides.

Variation in the functionality of the aryl moiety of the fused benzazepine heterocycle compounds can be achieved as shown in scheme 1, for example by using a variety of boronic acids as coupling partners with indole bromide intermediates. Alternatively, a suitably protected reactive functionality in the aryl moiety of these intermediates can be deprotected, and can then be subsequently derivatized using methods known in the art, some examples of which are depicted in scheme 9.

Scheme 9.
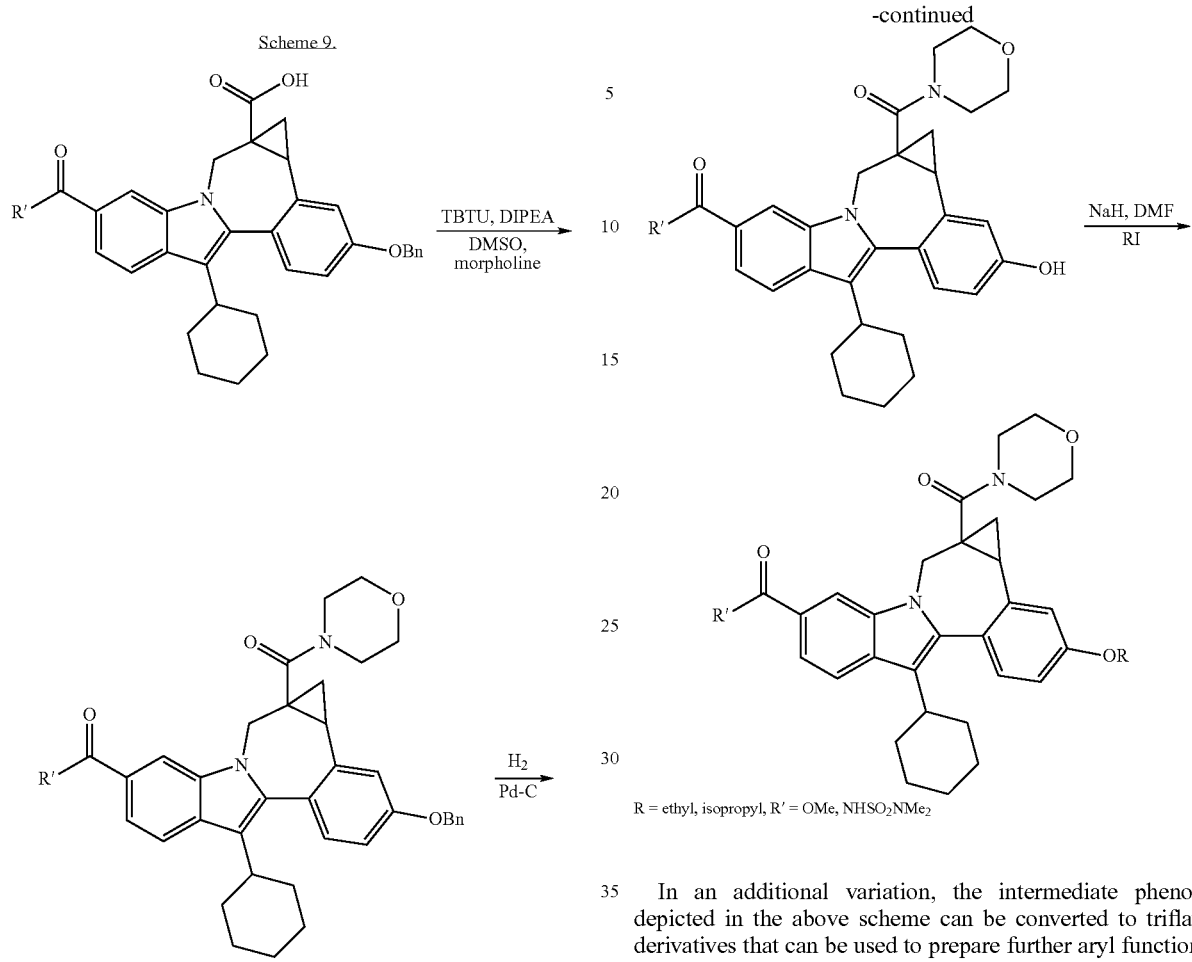
In an additional variation, the intermediate phenols depicted in the above scheme can be converted to triflate derivatives that can be used to prepare further aryl functionalized examples using a diversity of coupling reactions, some of which are outlined in scheme 10.
Scheme 10.
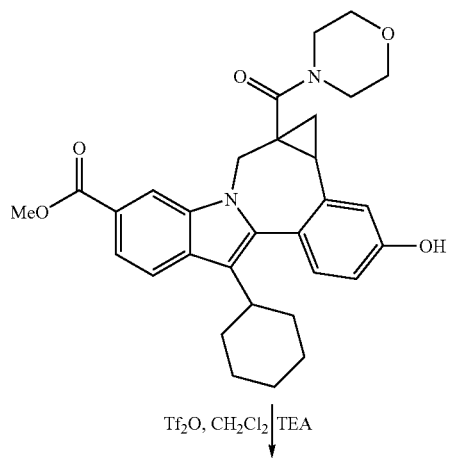

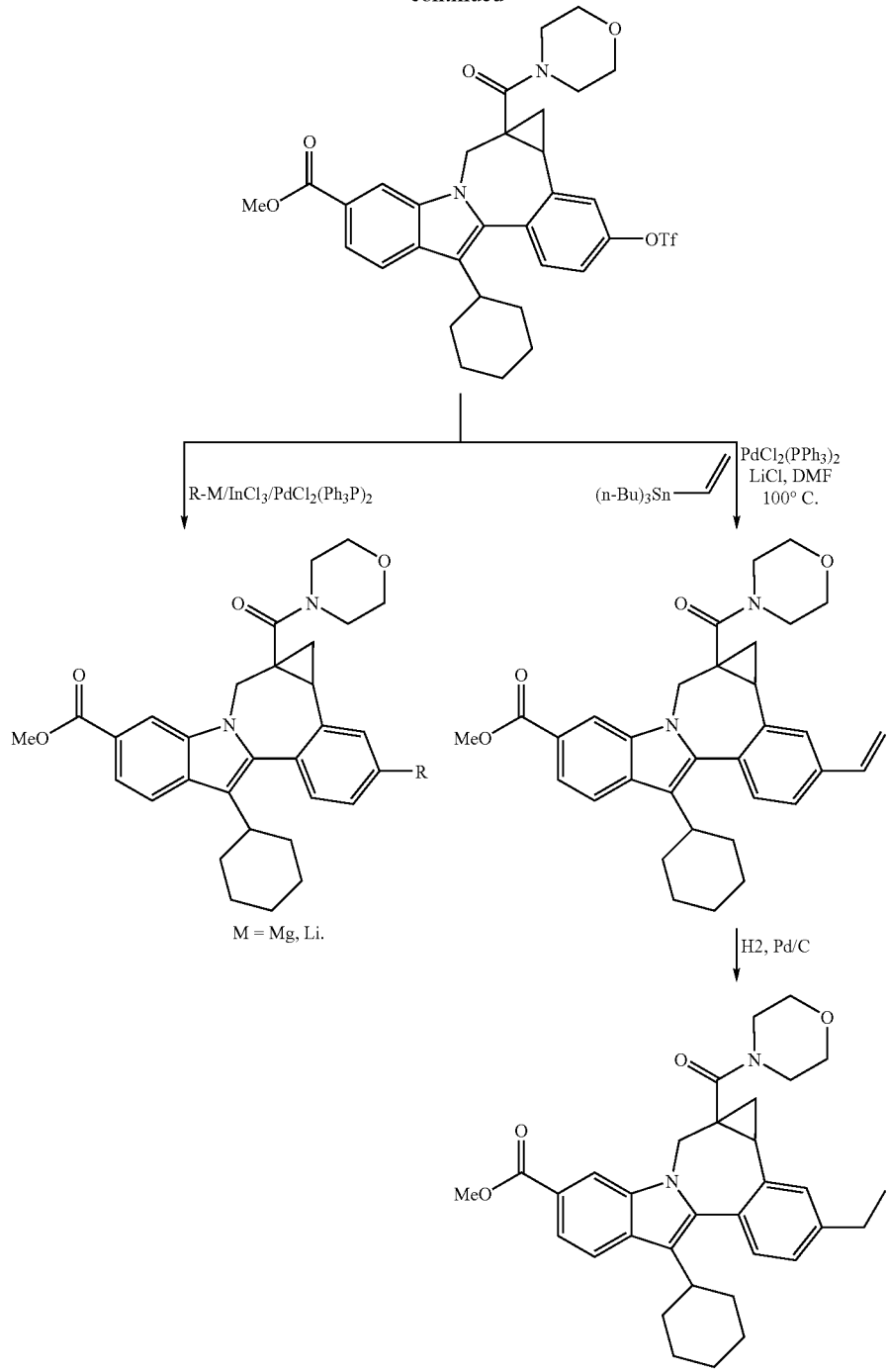

In the case of the examples shown in Scheme 10, the product esters can be hydrolyzed and subsequently coupled with a diversity of sulfonyl ureas to furnish further acyl sulfamide examples, as described previously.

Biological Methods

Formula I compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 μl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 μCi (0.29 μM total UTP). Reactions were initiated by the addition of enzyme, incubated at 30° C. for 60 min, and stopped by adding 25 μl of 50 mM EDTA containing SPA beads (4 μg/μl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 μg/μl beads. Order of addition in the assay: enzyme (14 nM) was added to diluted compound followed by the addition of a mixture of template (0.2 nM), 3H-UTP (0.6 μCi, 0.29 μM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 uM final from a 2 mM stock.

To prepare plates, HCV replicon cells, with or without a *Renilla* luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for Formula I compounds are reported in Table 1.

TABLE 1

| Structure | IC$_{50}$ | EC$_{50}$ |
|---|---|---|
| 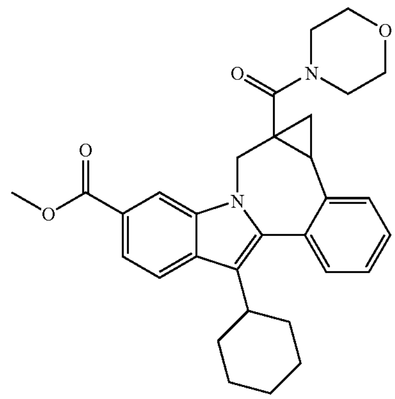 | A | E |
| | B | E |
| | B | E |
| | B | E |

TABLE 1-continued
| Structure | IC$_{50}$ | EC$_{50}$ |
|---|---|---|
| 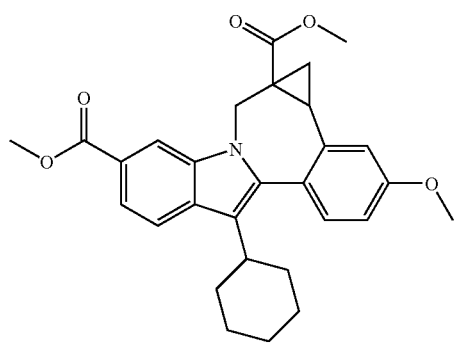 | A | E |
| 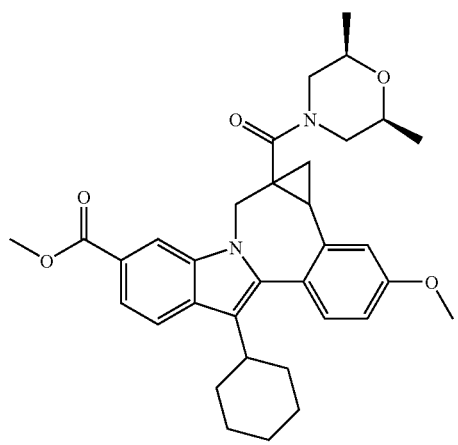 | | |
| 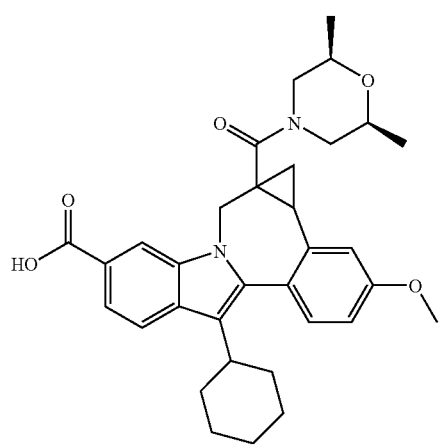 | B | E |

TABLE 1-continued
| Structure | IC$_{50}$ | EC$_{50}$ |
|---|---|---|
| 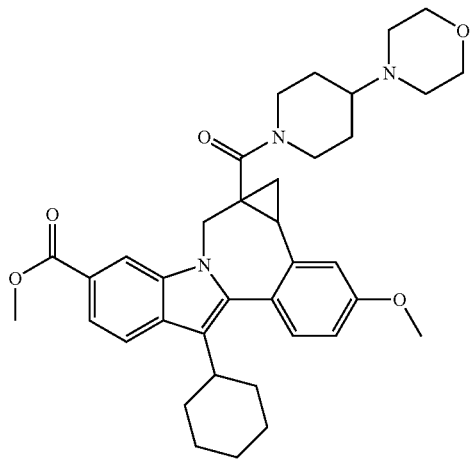 | | |
| 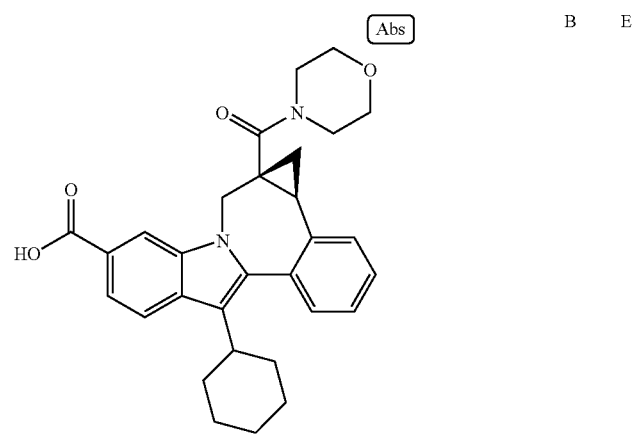 | B | E |
| 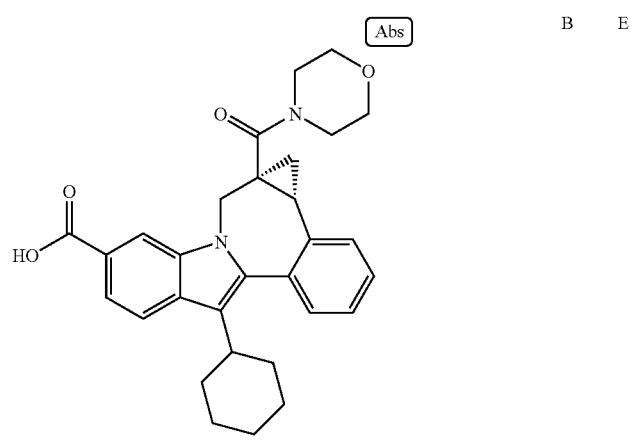 | B | E |

TABLE 1-continued
| Structure | IC$_{50}$ | EC$_{50}$ |
|---|---|---|
| 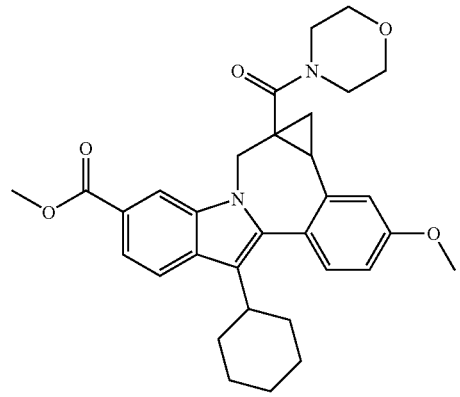 | | |
| 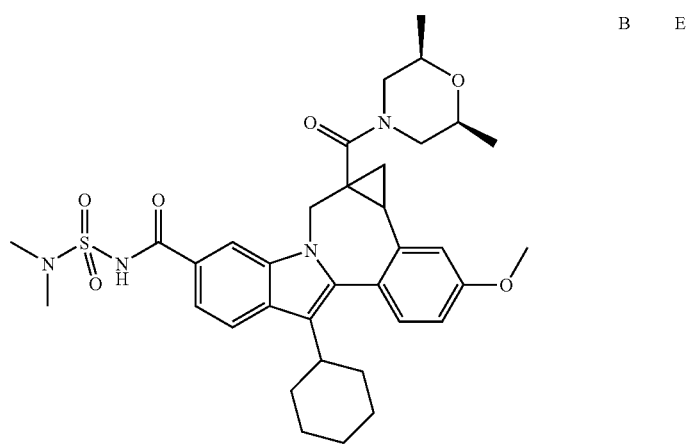 | B | E |
| 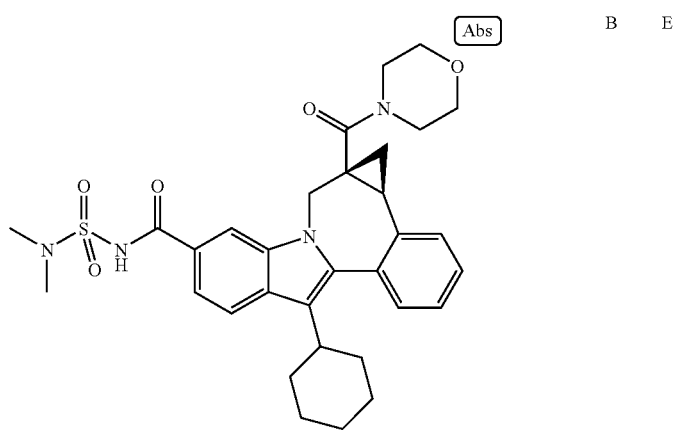 | B | E |

TABLE 1-continued
| Structure | IC$_{50}$ | EC$_{50}$ |
|---|---|---|
| 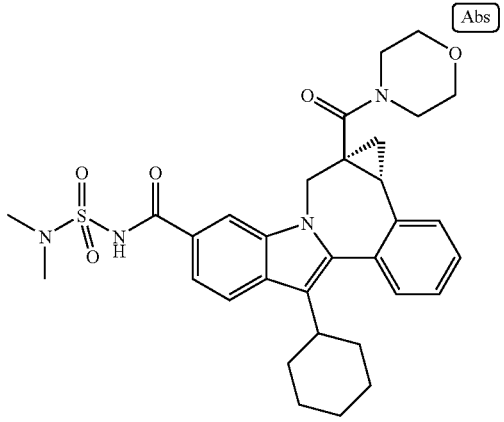 | B | E |
| 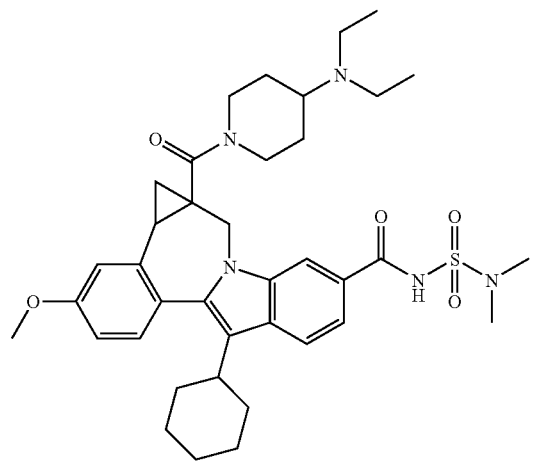 | B | E |
| 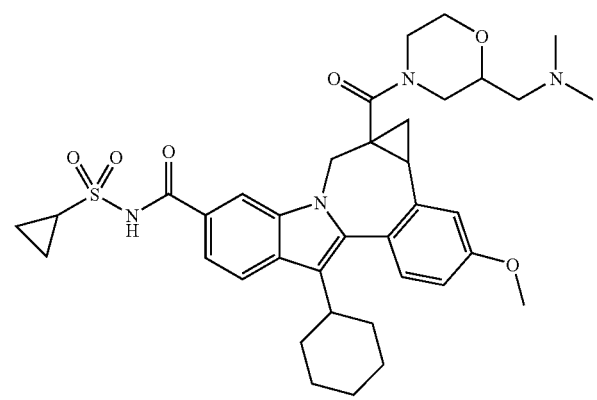 | B | E |

TABLE 1-continued
| Structure | IC$_{50}$ | EC$_{50}$ |
|---|---|---|
| 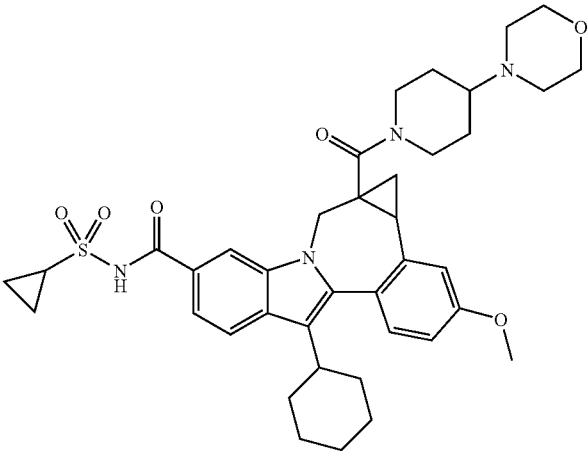 | B | E |
| 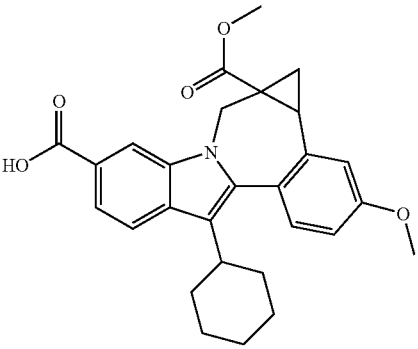 | B | D |
| 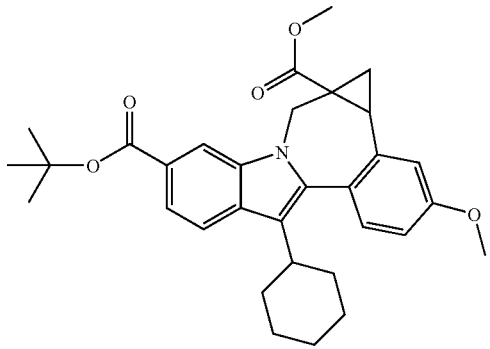 | A | C |
| 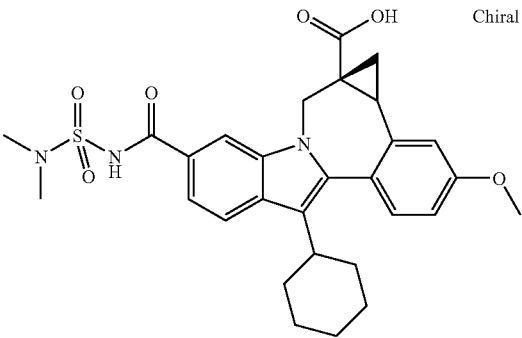 Chiral | B | D |

TABLE 1-continued

| Structure | IC$_{50}$ | EC$_{50}$ |
|---|---|---|
| | B | D |
| | B | E |
| | B | E |
| | B | E |

TABLE 1-continued

| Structure | IC$_{50}$ | EC$_{50}$ |
|---|---|---|
| | B | E |
| | B | E |
| | B | E |
| | B | E |

TABLE 1-continued

| Structure | IC$_{50}$ | EC$_{50}$ |
|---|---|---|
| | A | |
| | B | E |
| | A | |
| | B | E |

TABLE 1-continued
| Structure | IC$_{50}$ | EC$_{50}$ |
|---|---|---|
| 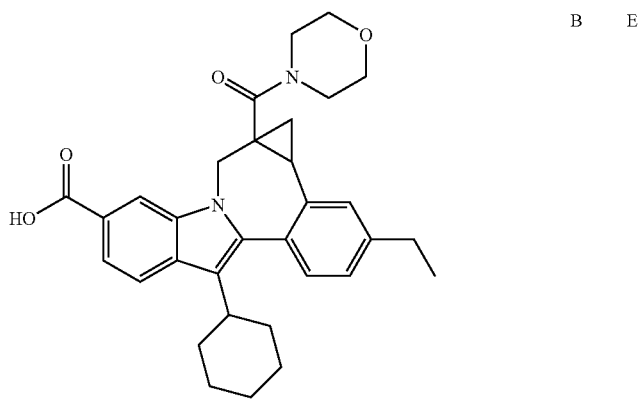 | B | E |
| 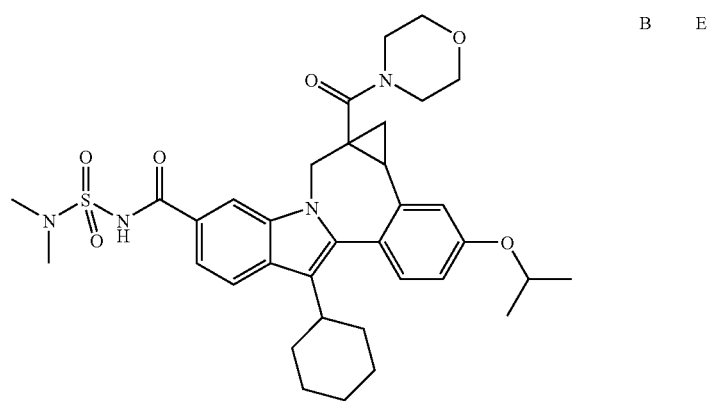 | B | E |
| 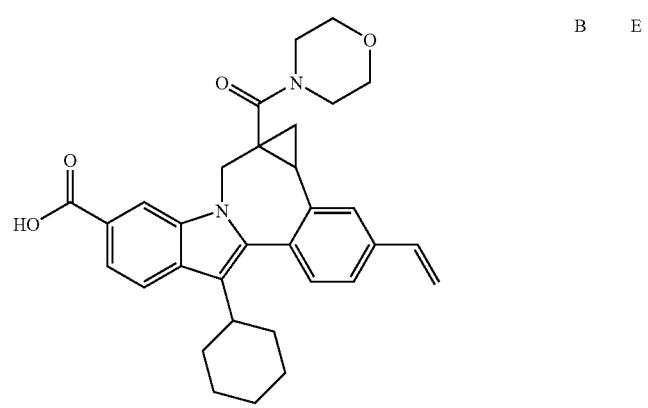 | B | E |

TABLE 1-continued

| Structure | IC$_{50}$ | EC$_{50}$ |
|---|---|---|
| | B | E |
| | B | E |
| 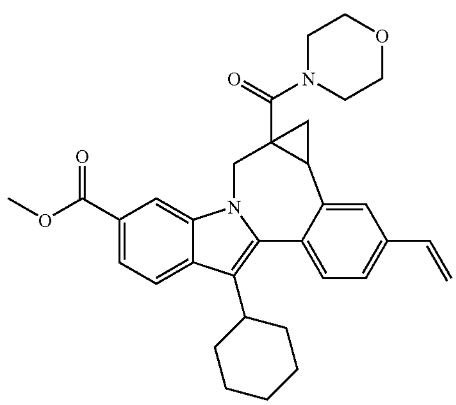 | A | |
| | B | E |

TABLE 1-continued
| Structure | IC$_{50}$ | EC$_{50}$ |
|---|---|---|
| 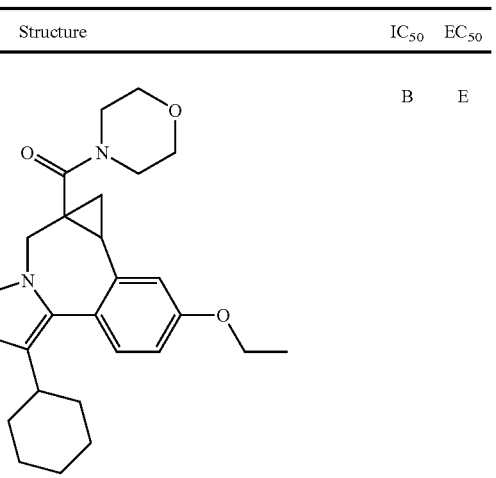 | B | E |
| 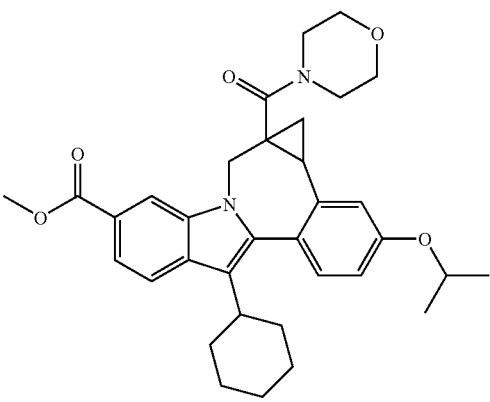 | B | E |
| 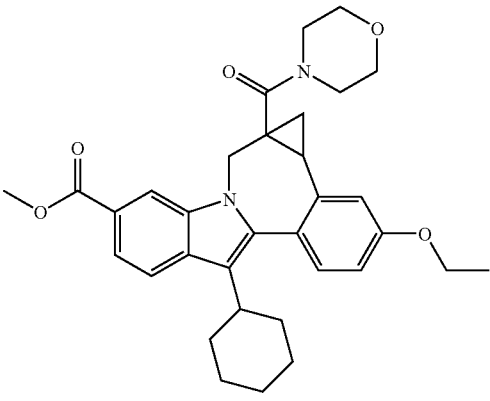 | A | |
| 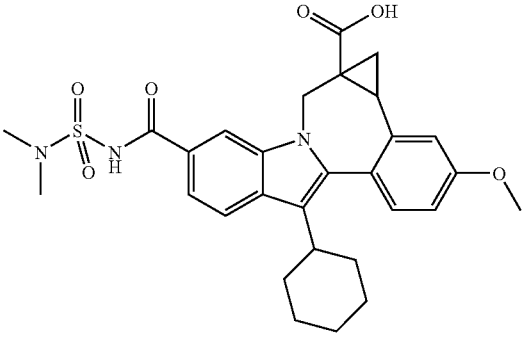 | | |

TABLE 1-continued
| Structure | IC$_{50}$ | EC$_{50}$ |
|---|---|---|
| 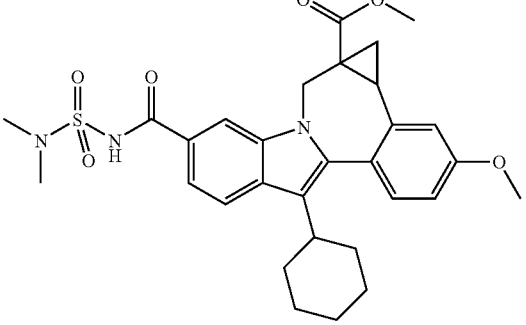 | | |
| 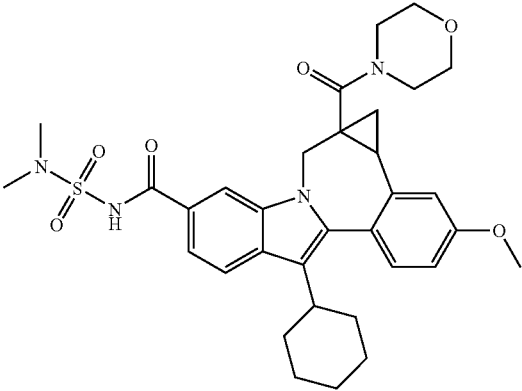 | B | E |
| 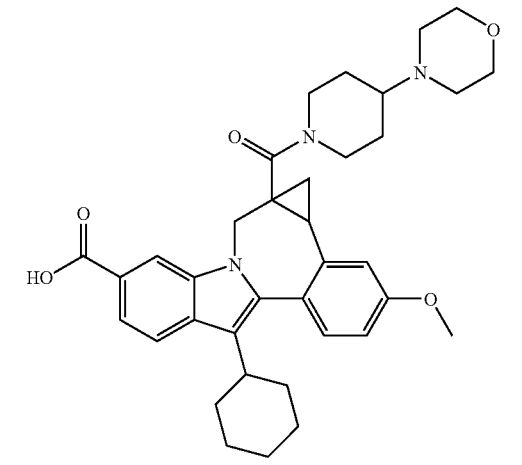 | B | E |
| 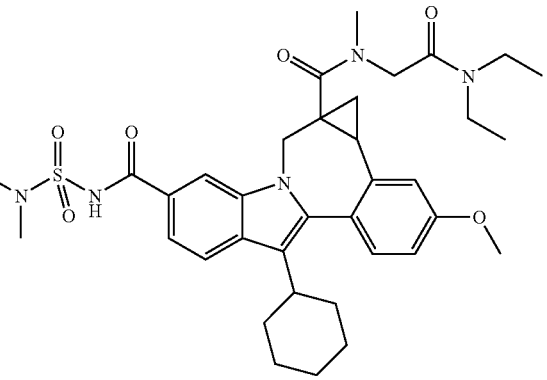 | B | E |

TABLE 1-continued
| Structure | IC$_{50}$ | EC$_{50}$ |
|---|---|---|
| 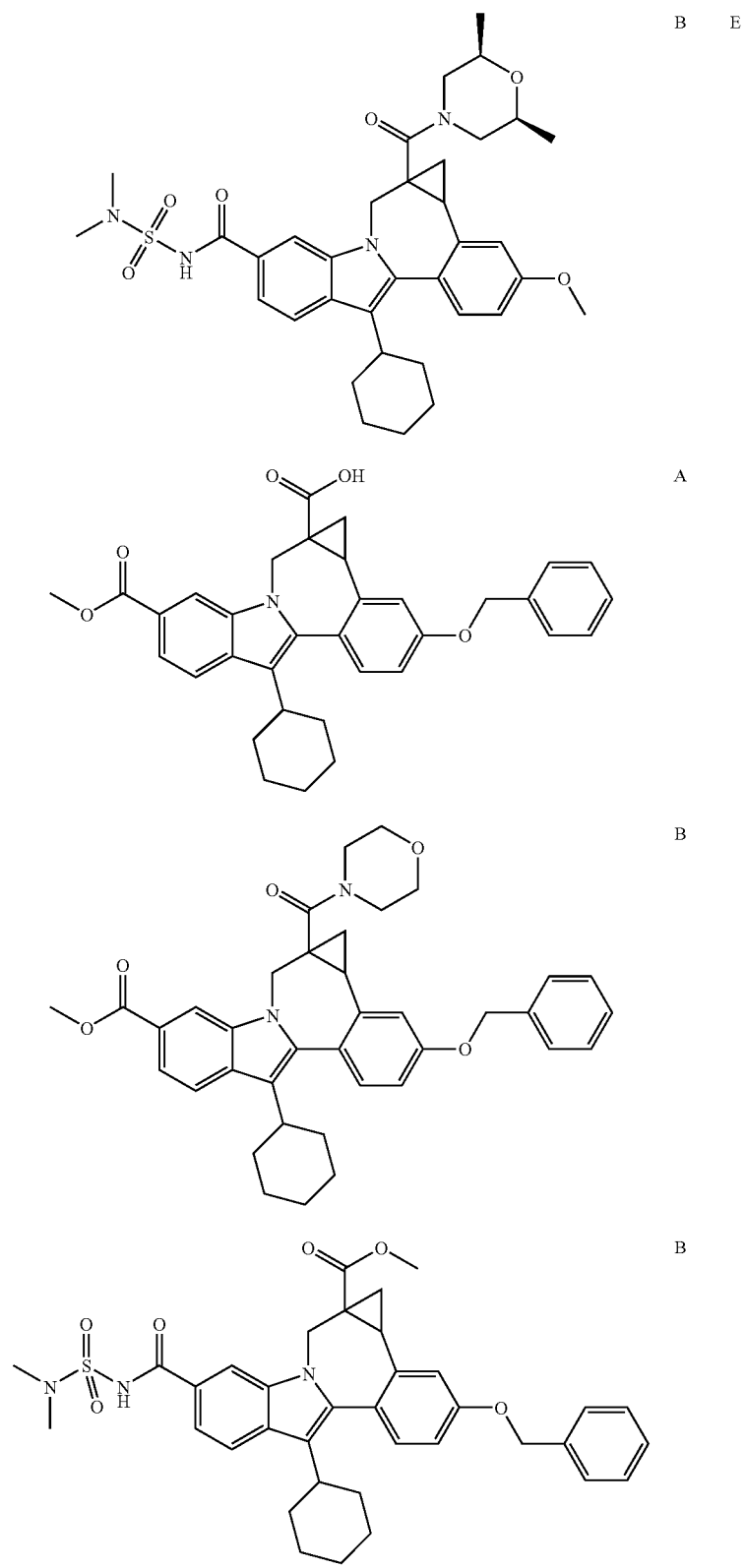 | B | E |
| 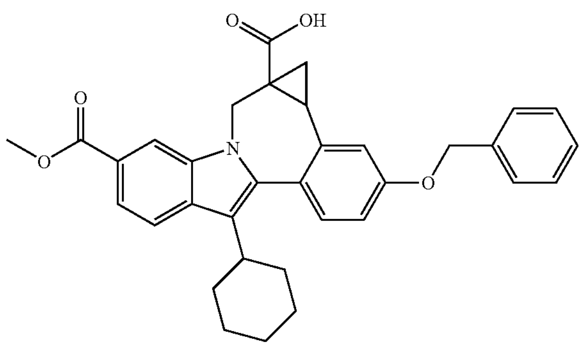 | A | |
| | B | |
| | B | |

TABLE 1-continued
| Structure | IC$_{50}$ | EC$_{50}$ |
|---|---|---|
| 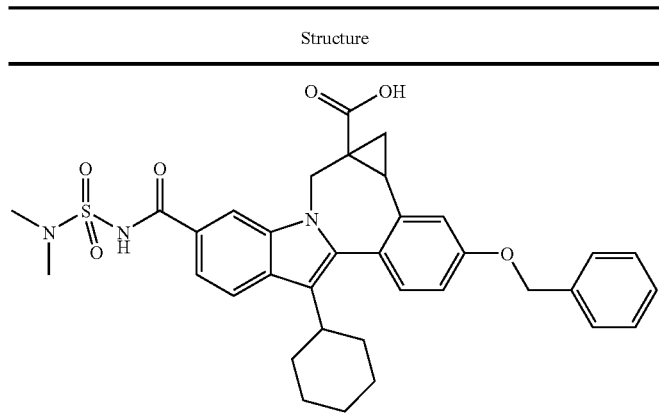 | B | |
| 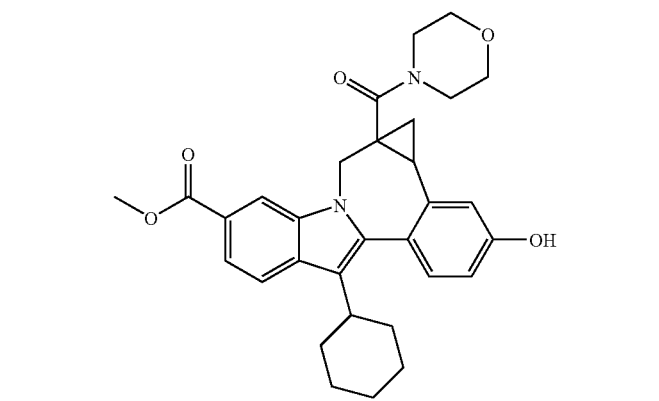 | B | |
| 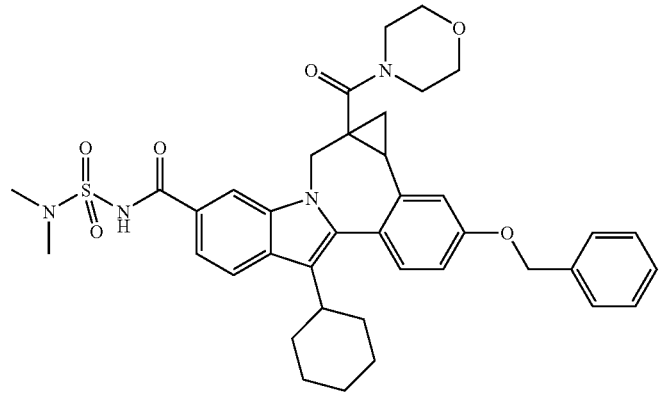 | B | |
| 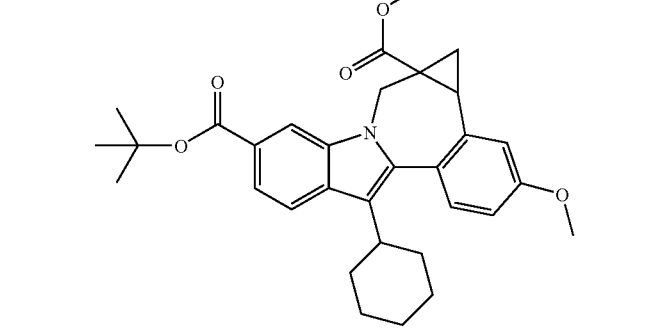 | A | |

TABLE 1-continued
| Structure | IC$_{50}$ | EC$_{50}$ |
|---|---|---|
| 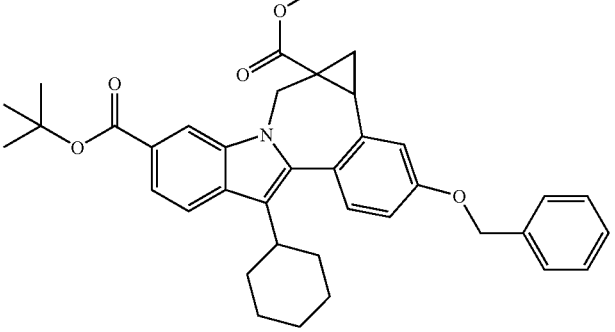 | A | |
| 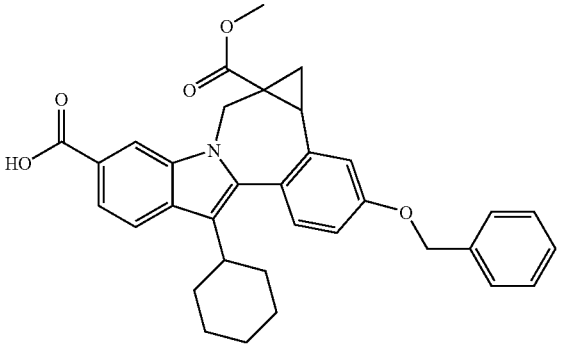 | B | |
| 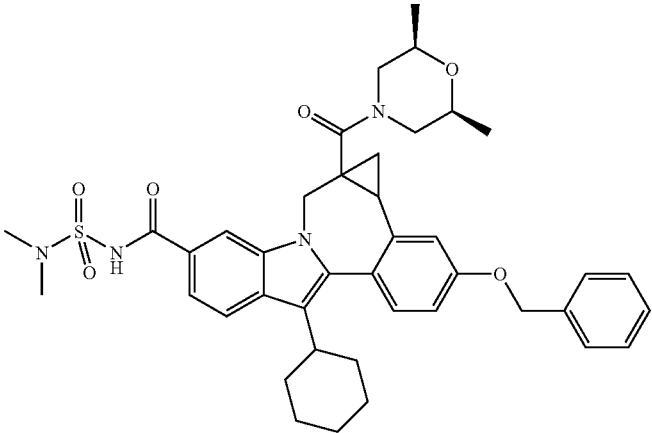 | B | E |
| 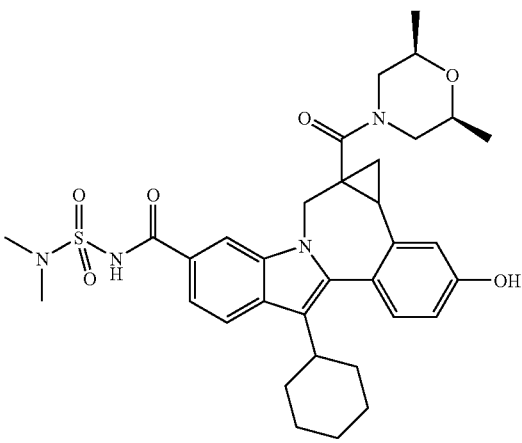 | B | E |

TABLE 1-continued
| Structure | IC$_{50}$ | EC$_{50}$ |
|---|---|---|
| 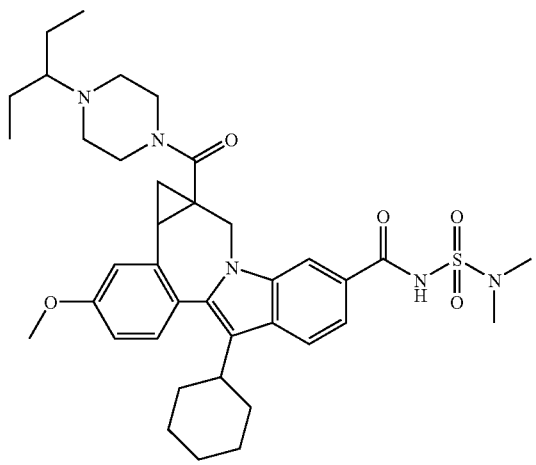 | B | E |
| 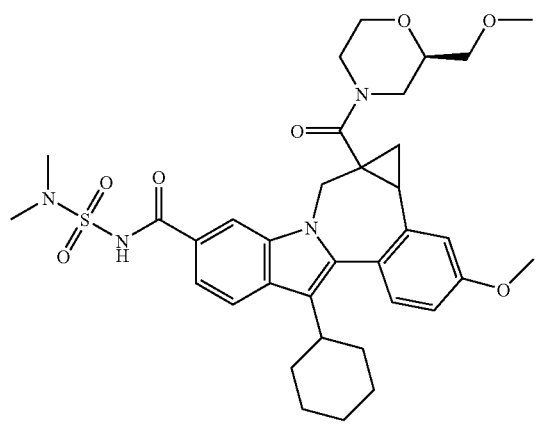 | B | E |
| 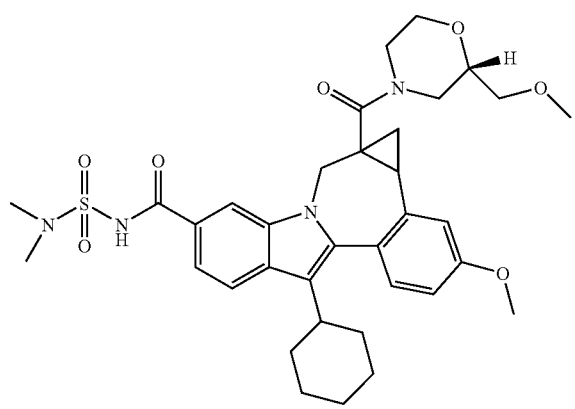 | B | E |

TABLE 1-continued
| Structure | IC$_{50}$ | EC$_{50}$ |
|---|---|---|
| 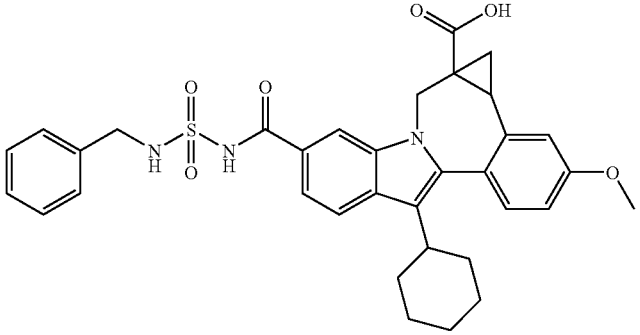 | B | |
| 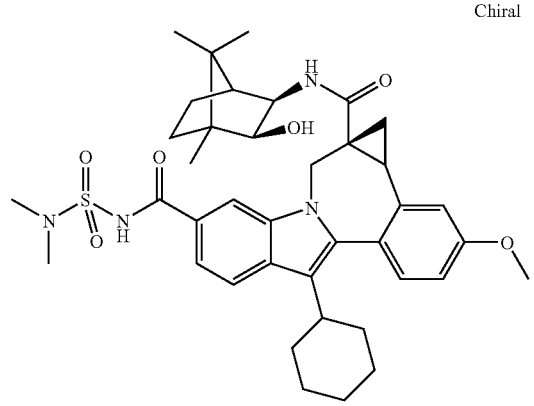 Chiral | B | E |
| 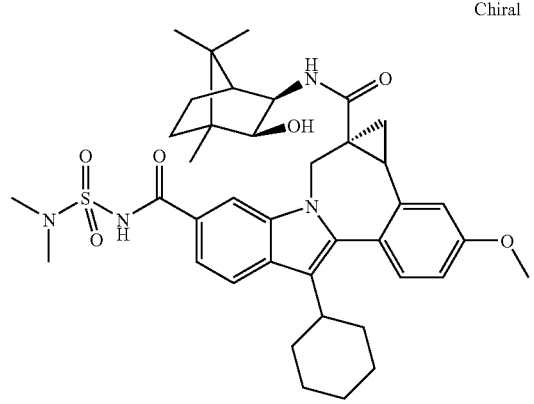 Chiral | B | |
| 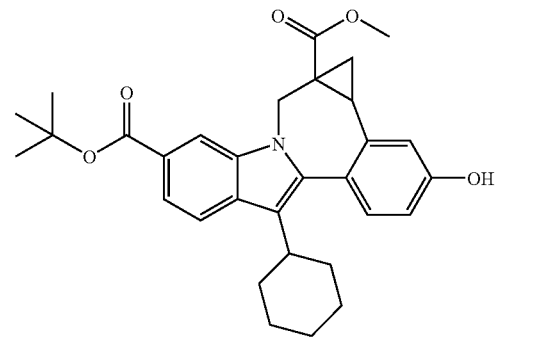 | D | A |

TABLE 1-continued
| Structure | IC$_{50}$ | EC$_{50}$ |
|---|---|---|
| 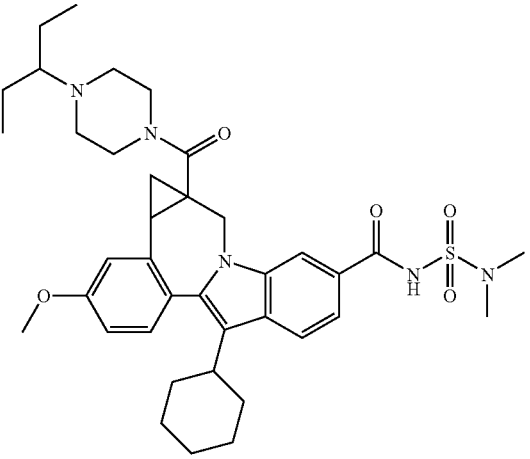 | B | B |
| 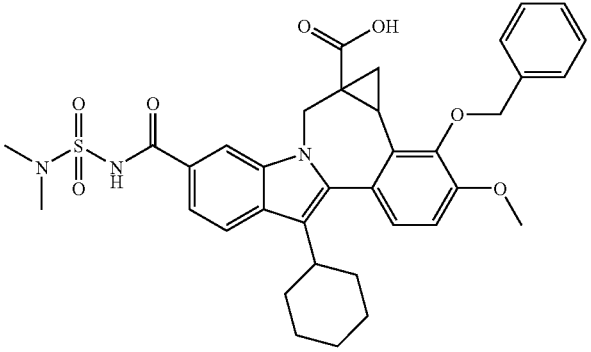 | B | A |
| 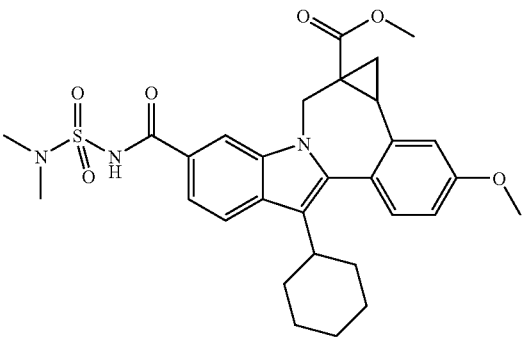 | | |
| 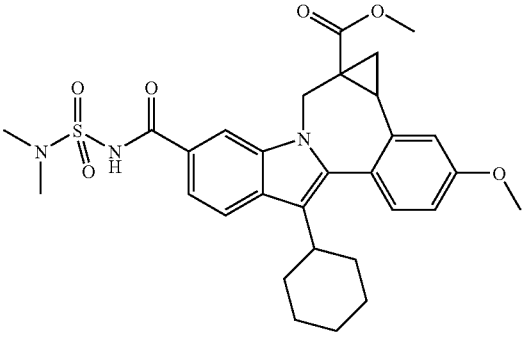 | | |

TABLE 1-continued
| Structure | IC$_{50}$ | EC$_{50}$ |
|---|---|---|
| 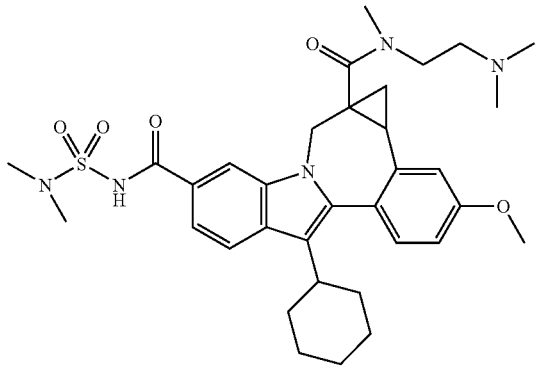 | B | B |
| 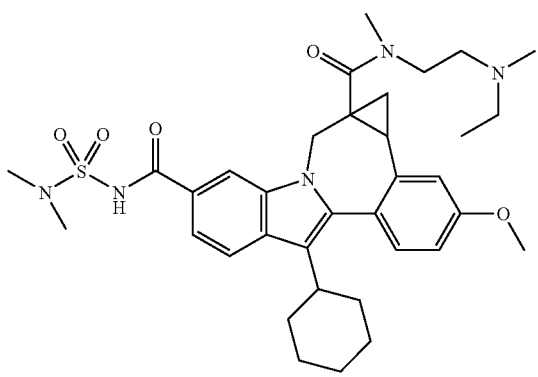 | B | B |
| 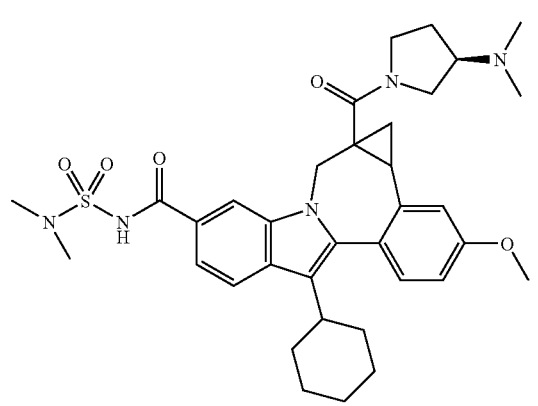 | B | B |
| 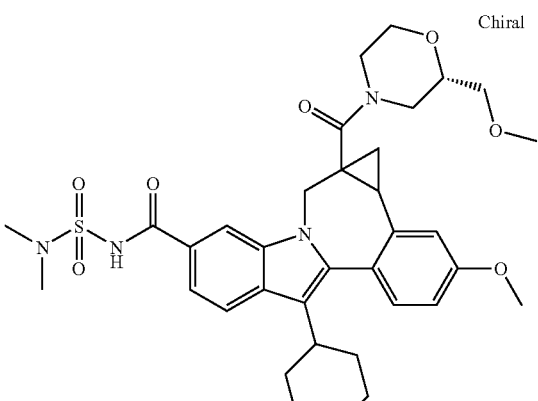 Chiral | B | B |

TABLE 1-continued
| Structure | IC$_{50}$ | EC$_{50}$ |
|---|---|---|
| 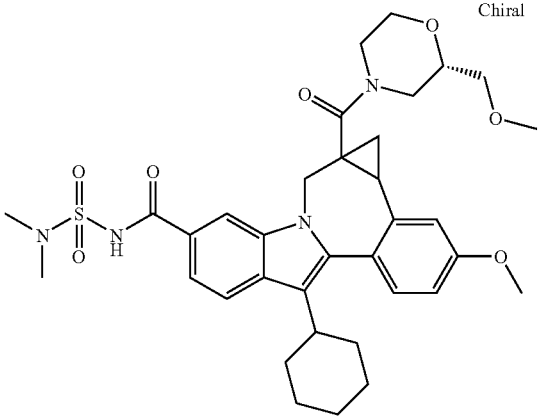 Chiral | B | B |
| 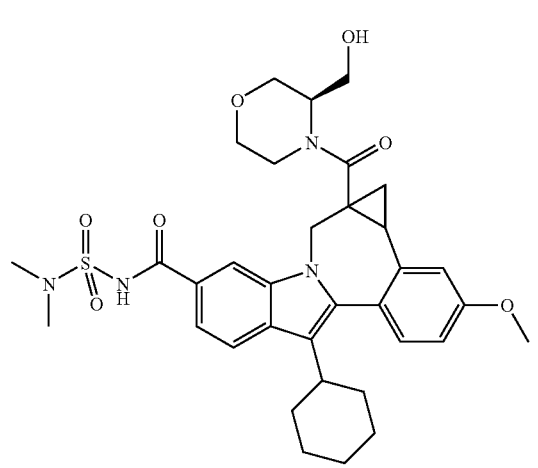 | B | B |
| 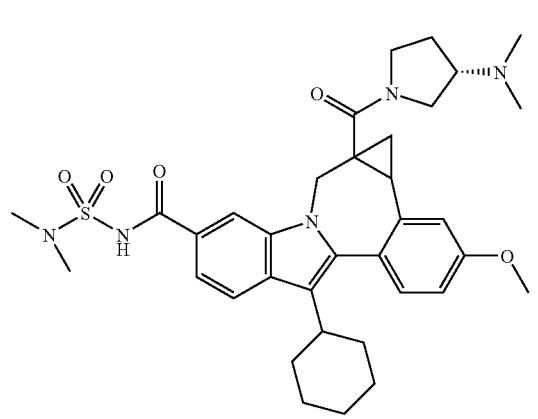 | B | B |

TABLE 1-continued

| Structure | IC$_{50}$ | EC$_{50}$ |
|---|---|---|
| | B | B |
| | B | B |
| | B | B |

TABLE 1-continued

| Structure | IC$_{50}$ | EC$_{50}$ |
|---|---|---|
| | B | B |
| | B | B |
| 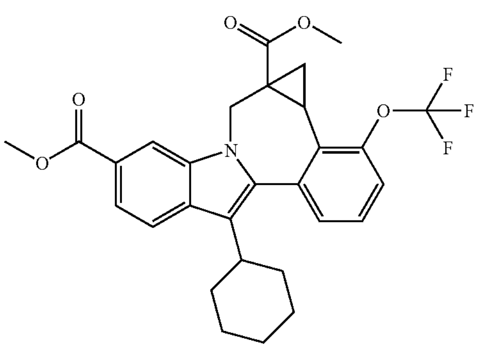 | C | F |
| | | |

TABLE 1-continued

| Structure | IC$_{50}$ | EC$_{50}$ |
|---|---|---|
| | | |
| | B | B |
| 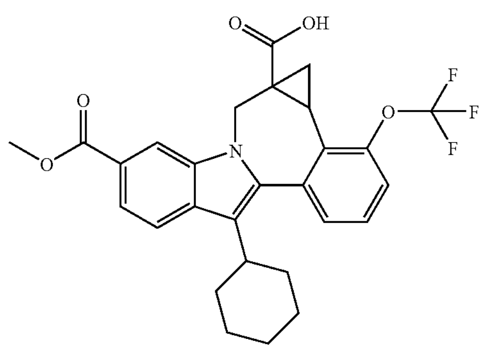 | D | |
| | B | B |

TABLE 1-continued
| Structure | IC$_{50}$ | EC$_{50}$ |
|---|---|---|
| 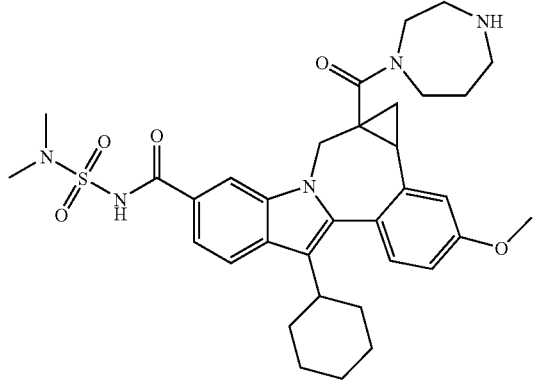 | B | B |
| 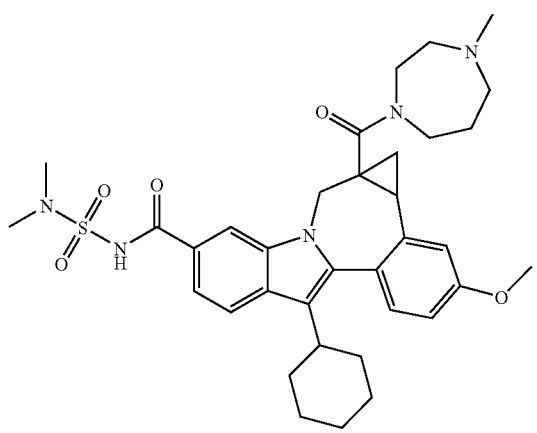 | B | B |
| 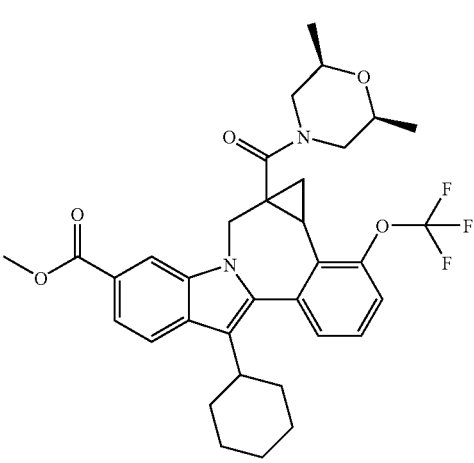 | D | |

TABLE 1-continued

| Structure | IC$_{50}$ | EC$_{50}$ |
|---|---|---|
| | B | B |
| | B | B |
| (Chiral) | | |

TABLE 1-continued
| Structure | IC$_{50}$ | EC$_{50}$ |
|---|---|---|
| 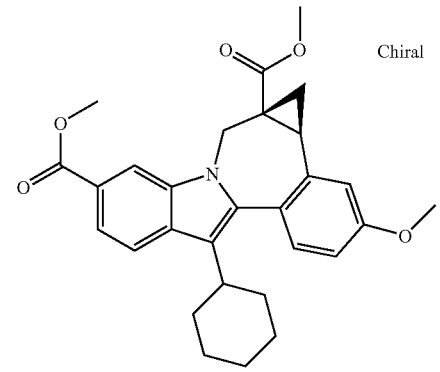 | | |
| 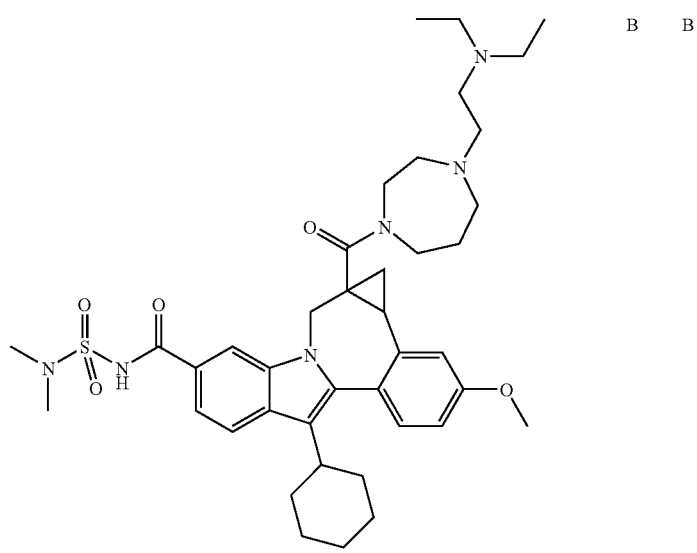 | B | B |
| 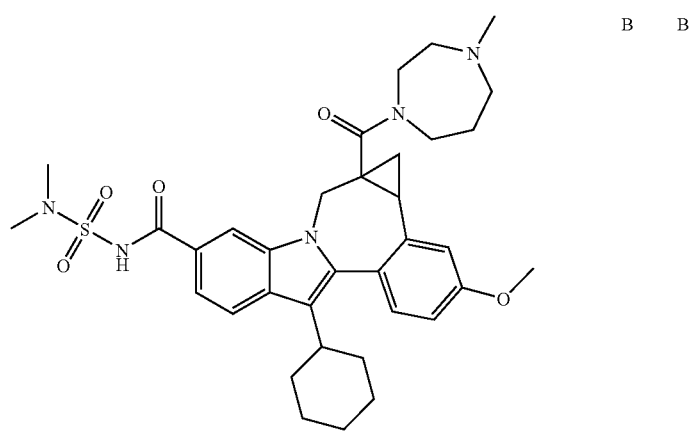 | B | B |

TABLE 1-continued
| Structure | IC$_{50}$ | EC$_{50}$ |
|---|---|---|
| 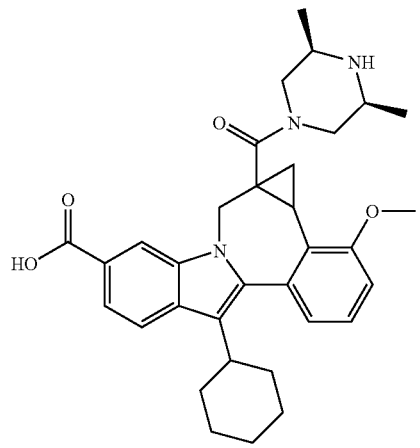 | | |
| 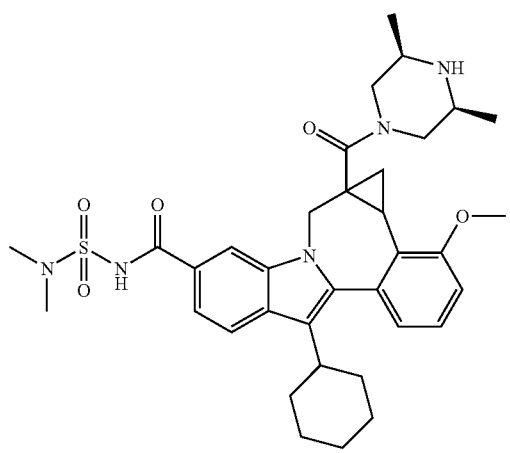 | B | B |
| 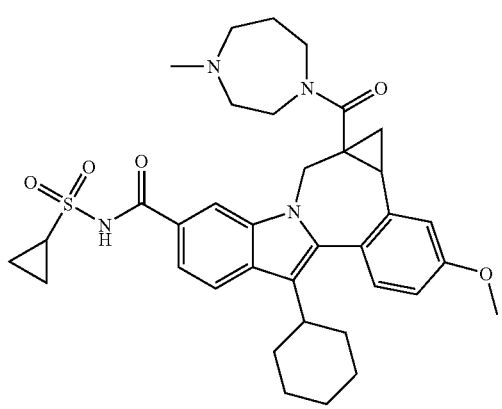 | B | B |

TABLE 1-continued
| Structure | IC$_{50}$ | EC$_{50}$ |
|---|---|---|
| 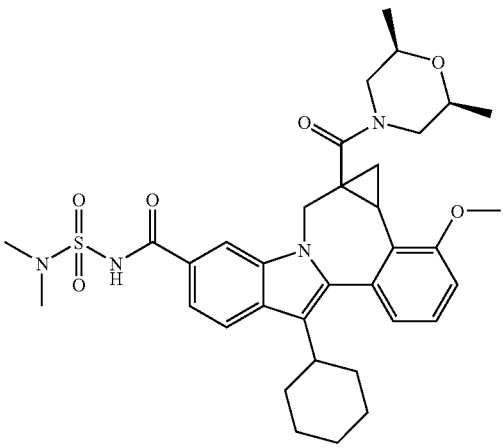 | B | B |
| 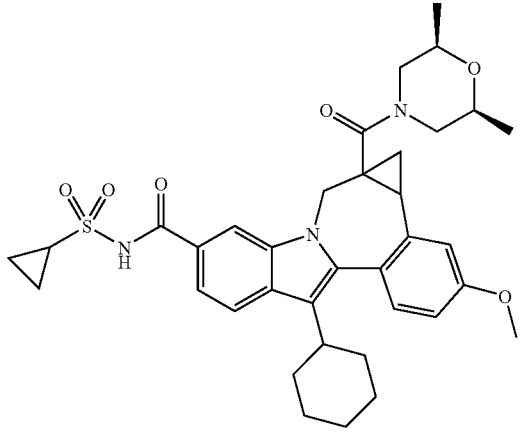 | B | B |
| 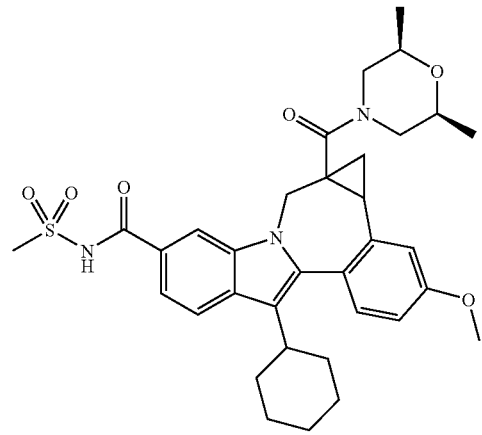 | B | B |

TABLE 1-continued
| Structure | IC$_{50}$ | EC$_{50}$ |
|---|---|---|
| 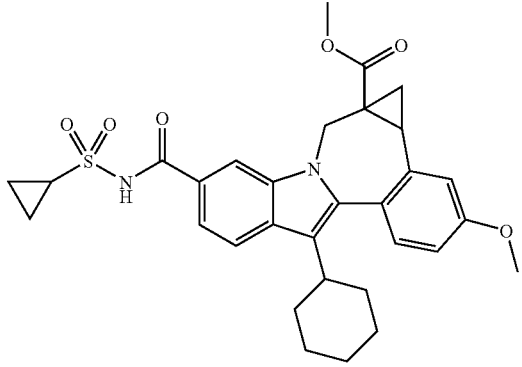 | | |
| 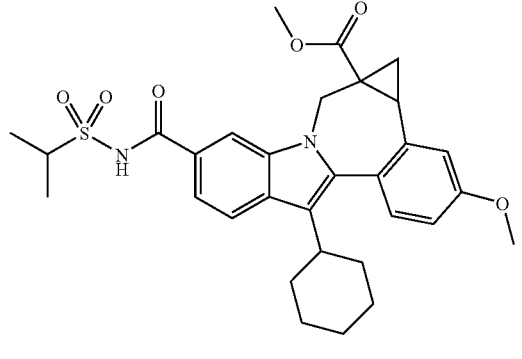 | B | |
| 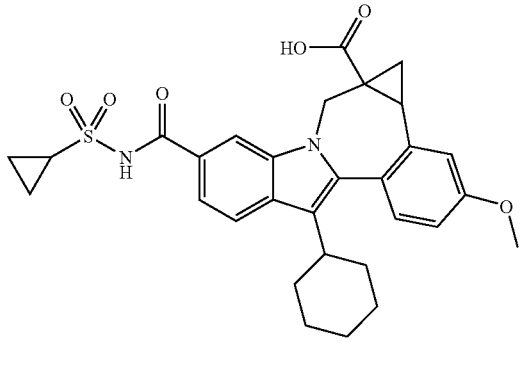 | B | |
| 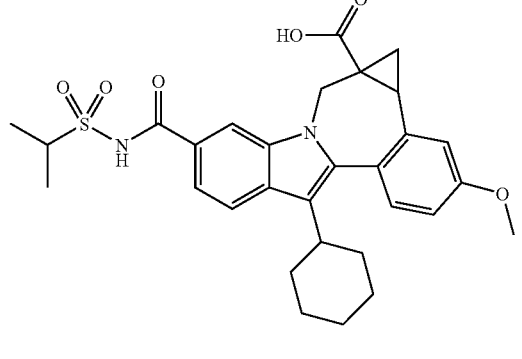 | B | |

TABLE 1-continued

| Structure | IC$_{50}$ | EC$_{50}$ |
|---|---|---|
| | | B |
| | | B |
| | | |
| | | |

TABLE 1-continued
| Structure | IC$_{50}$ | EC$_{50}$ |
|---|---|---|
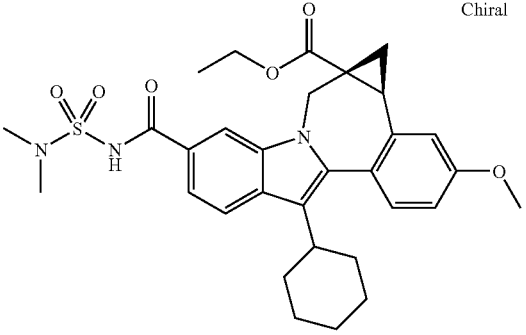
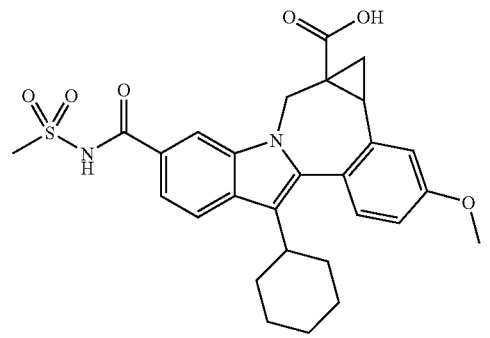
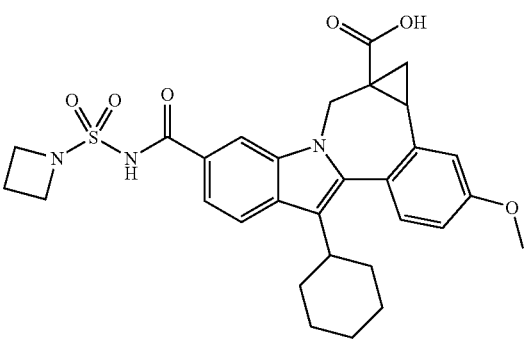
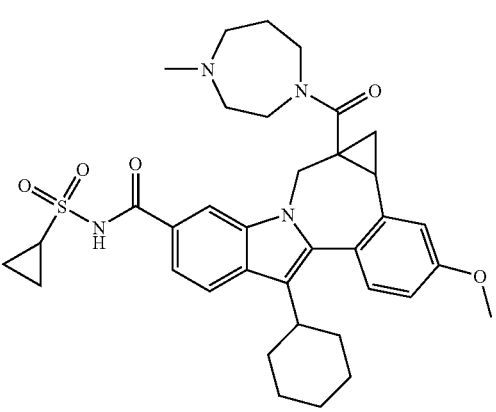

TABLE 1-continued

| Structure | IC$_{50}$ | EC$_{50}$ |
|---|---|---|
| | B | B |
| | B | B |

TABLE 1-continued

| Structure | IC$_{50}$ | EC$_{50}$ |
|---|---|---|
| | | |
| | | |
| 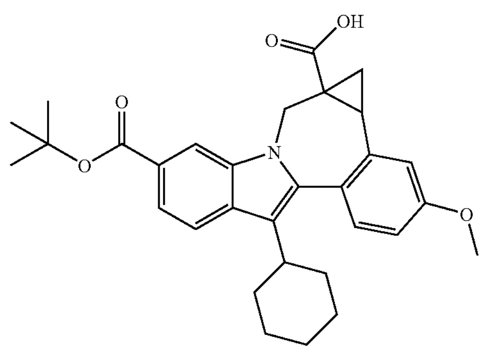 | D | |
| 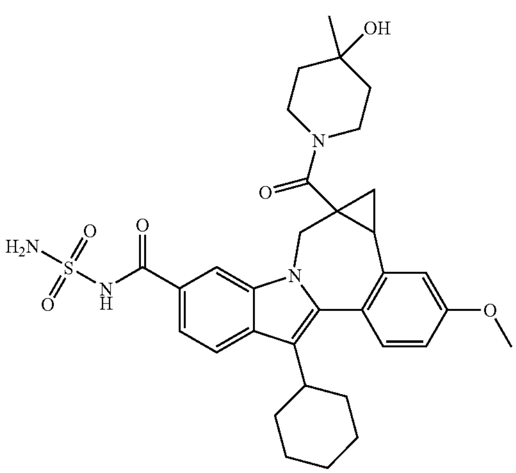 | B | B |

TABLE 1-continued

| Structure | IC$_{50}$ | EC$_{50}$ |
|---|---|---|
| | B | B |
| | B | F |
| | B | B |

TABLE 1-continued

| Structure | IC$_{50}$ | EC$_{50}$ |
|---|---|---|
| | B | B |
| | B | |
| | B | |

IC$_{50}$ A > 1 μM; B 0.097 μM-1 μM; EC$_{50}$: C > 10 μM; D 1 μM-10 μM; E 1.0 μM-0.02 μM; F > 0.12 μM. IC$_{50}$ values were determined using the preincubation protocal. EC$_{50}$ values were determined using the FRET assay.

Additionally, compounds disclosed in U.S. patent application Ser. No. 11/181,639, filed Jul. 14, 2005 were shown to have activity in these assays (see Table 2).

TABLE 2

Structure

TABLE 2-continued

Structure

TABLE 2-continued
Structure
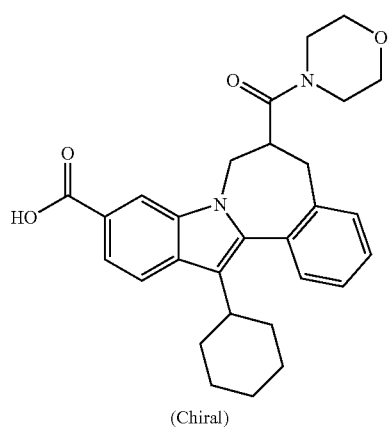
(Chiral)
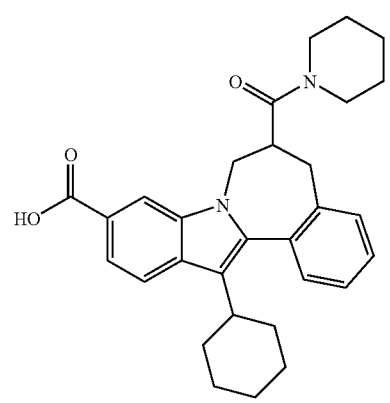
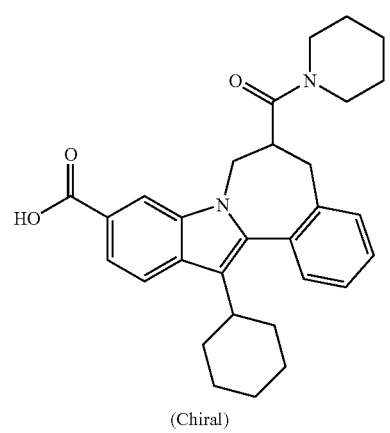
(Chiral)
TABLE 2-continued
Structure
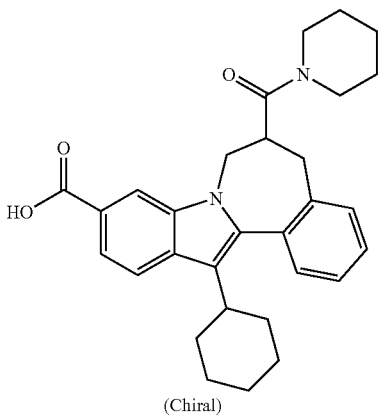
(Chiral)
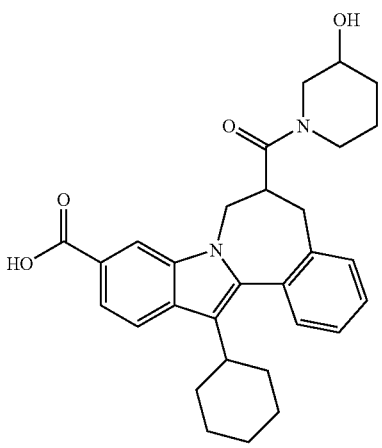
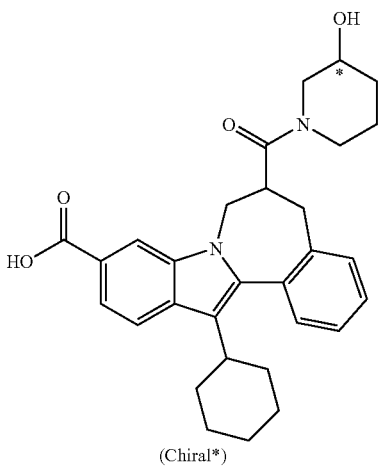
(Chiral*)

TABLE 2-continued
Structure
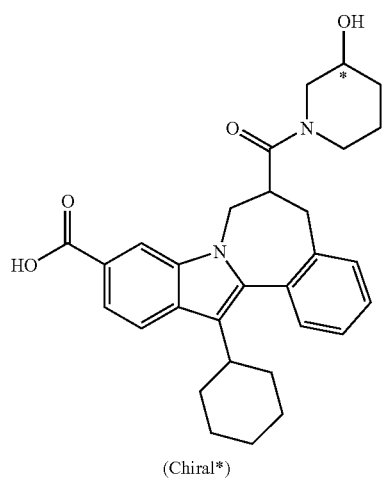
(Chiral*)
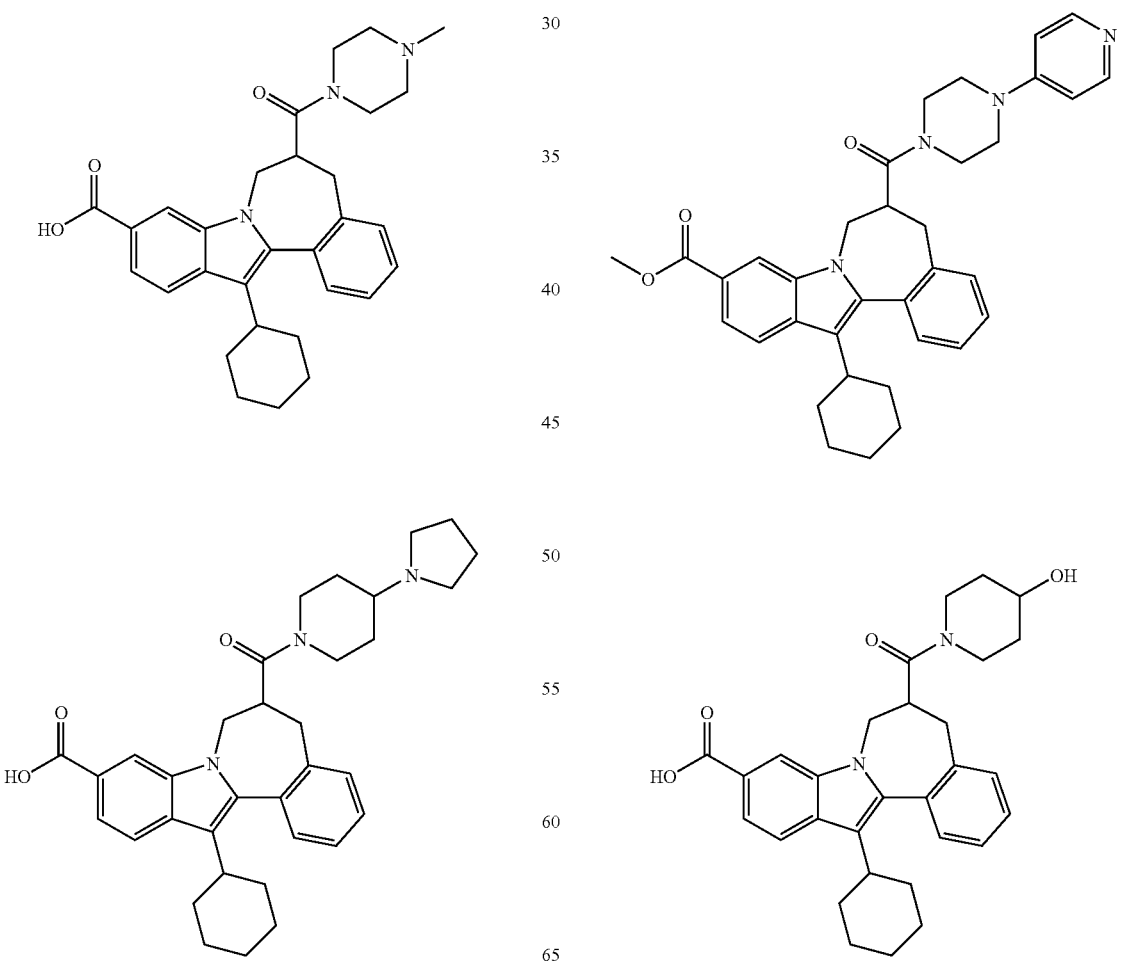

TABLE 2-continued
Structure
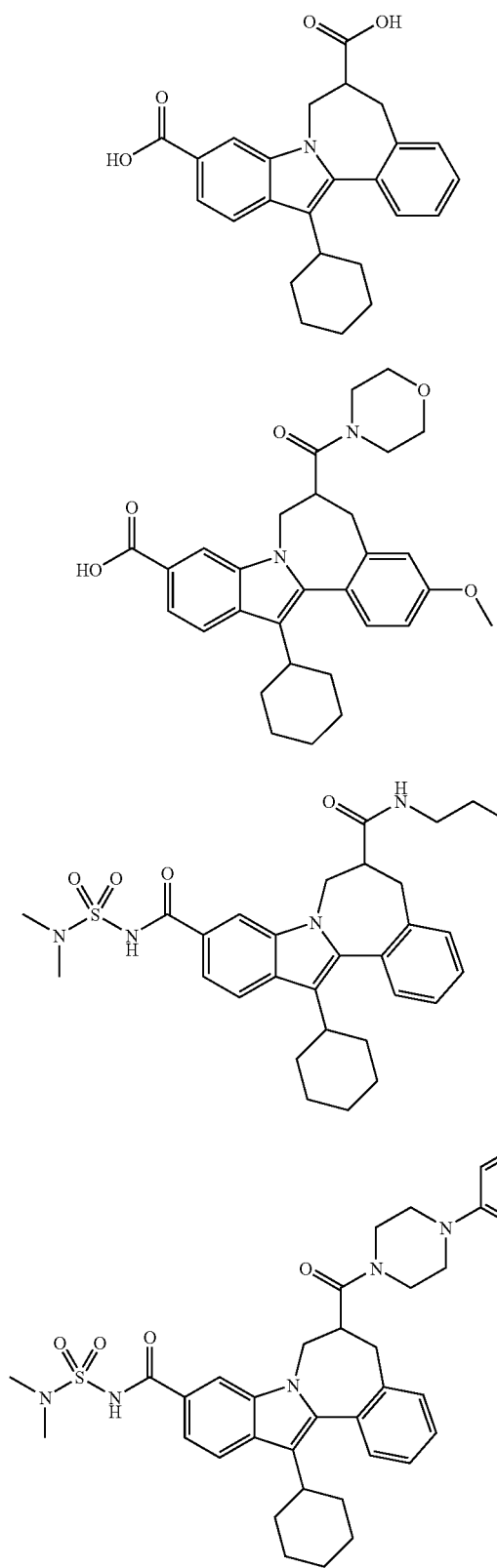
TABLE 2-continued
Structure
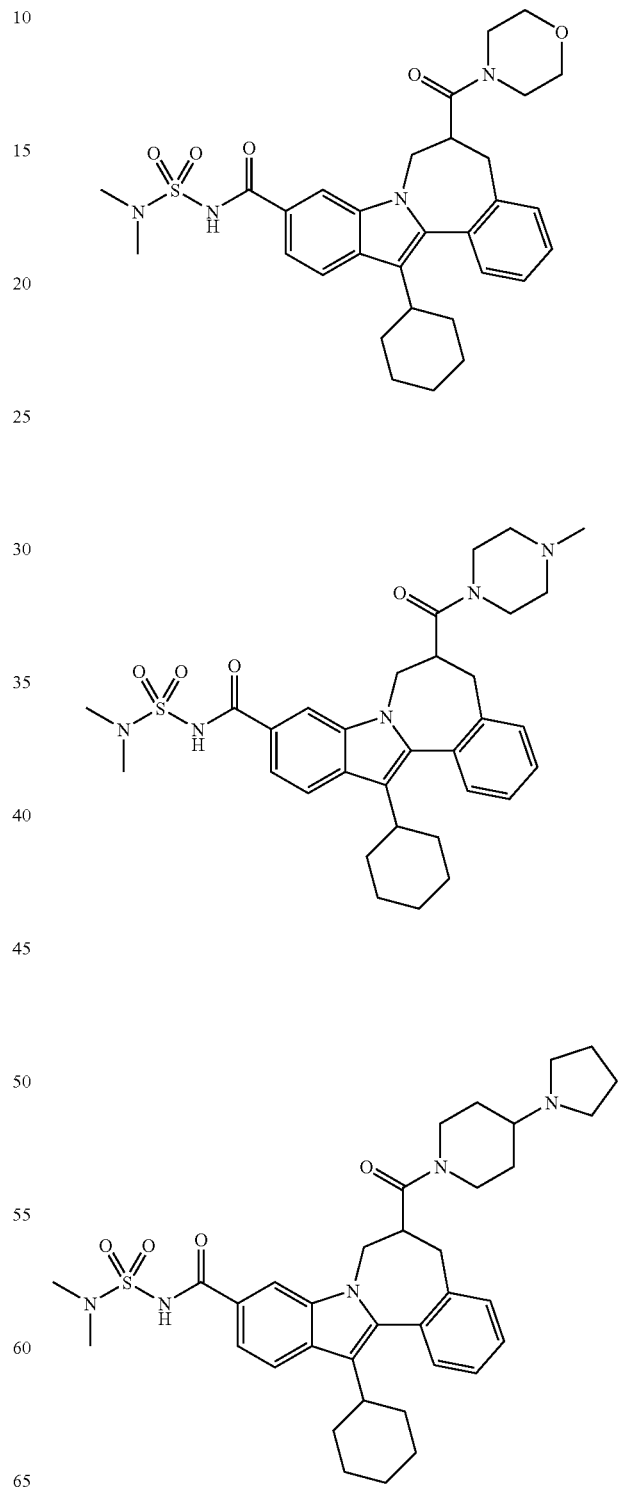

TABLE 2-continued
Structure
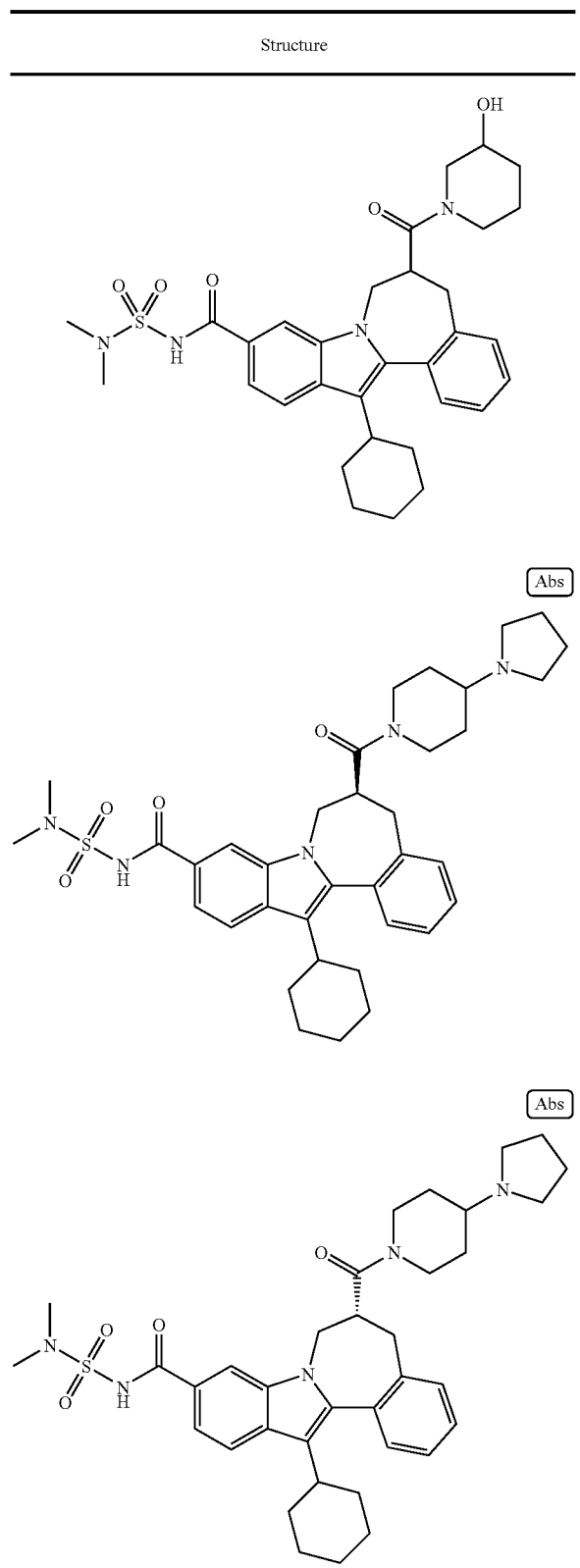
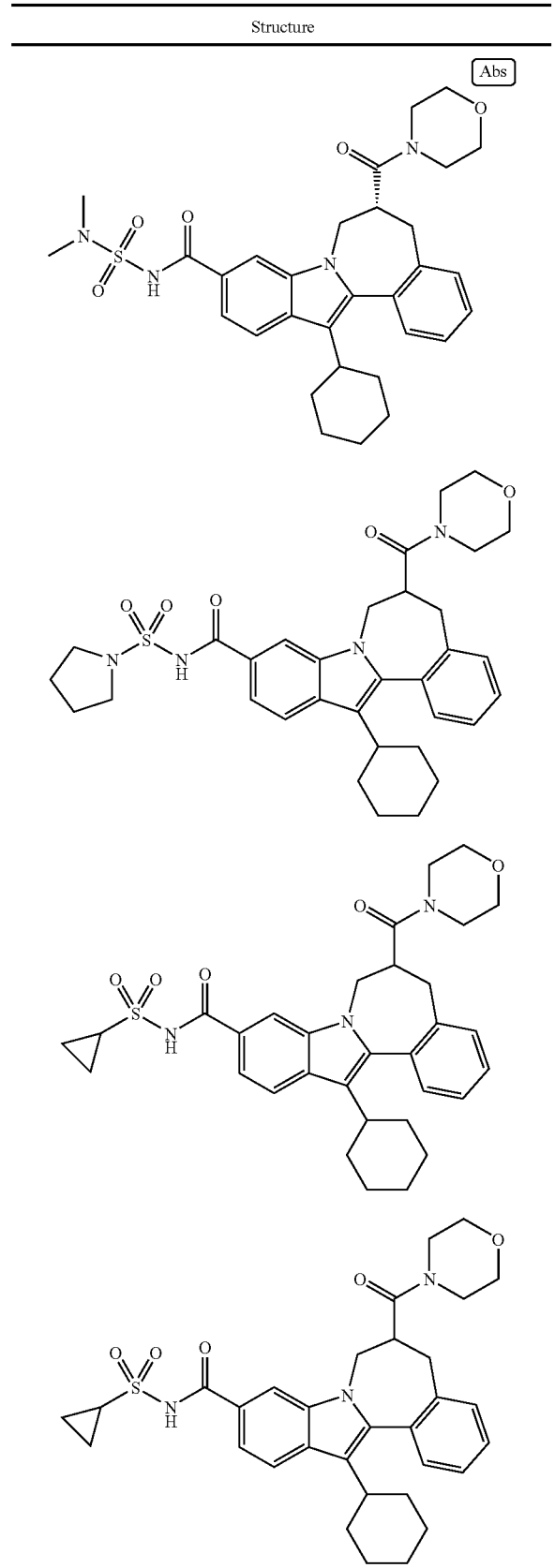

TABLE 2-continued
Structure
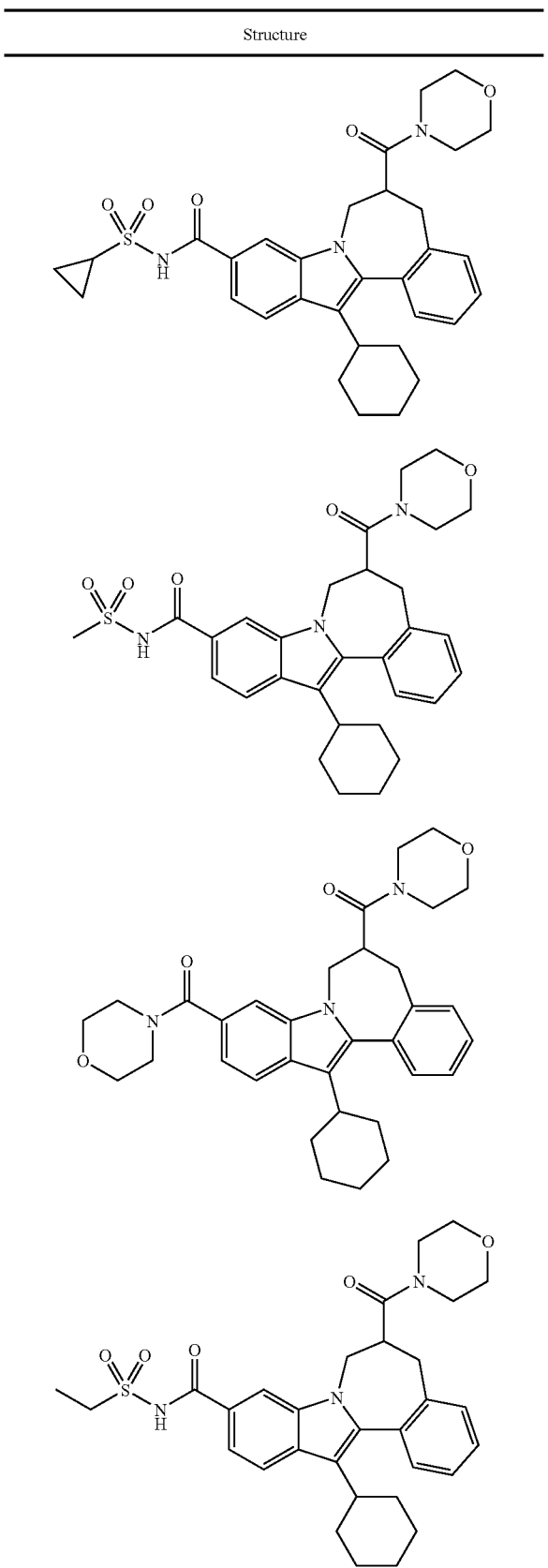
TABLE 2-continued
Structure
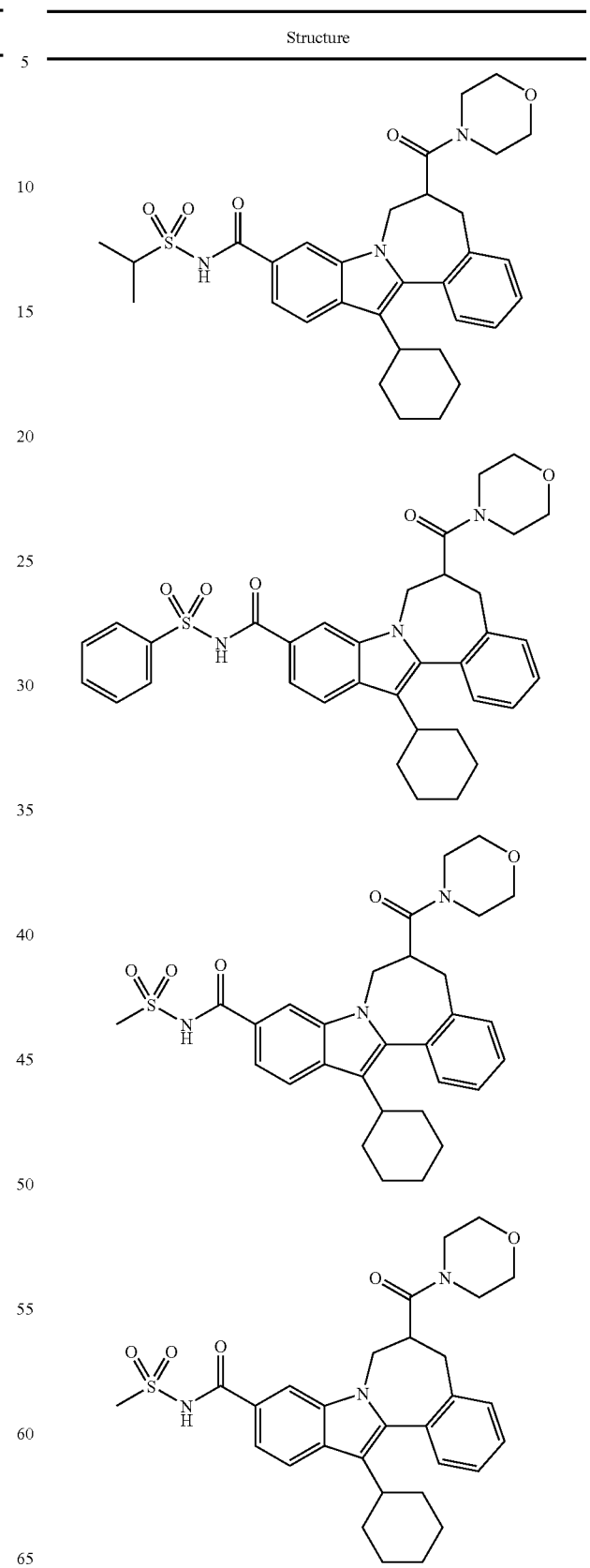

TABLE 2-continued
Structure
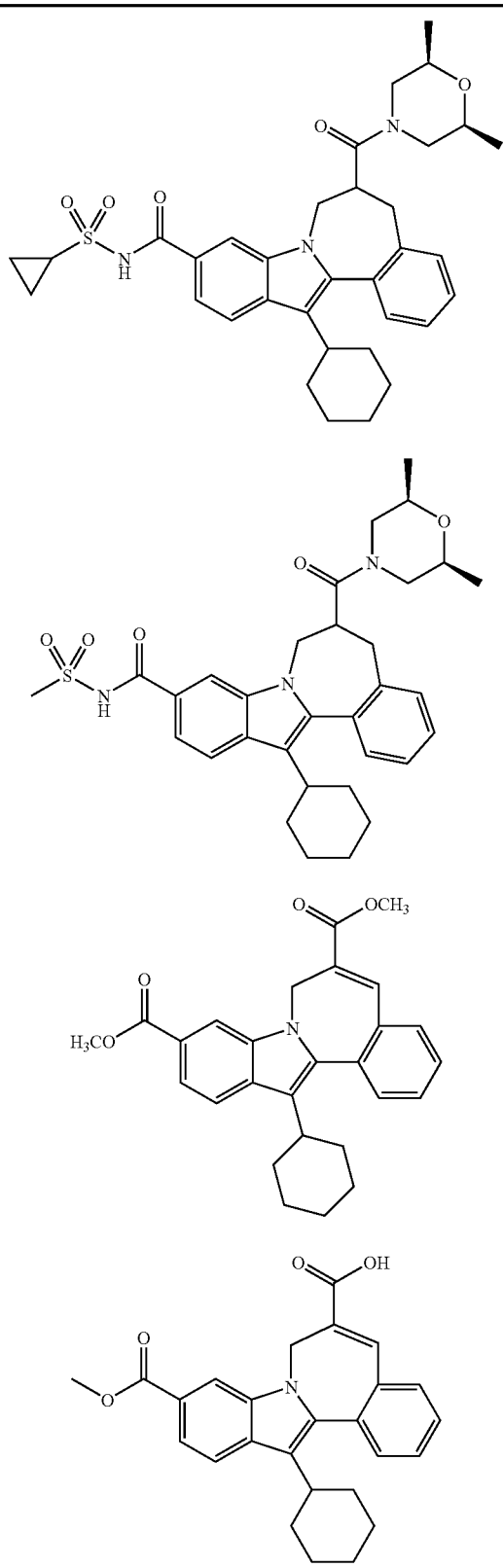
TABLE 2-continued
Structure
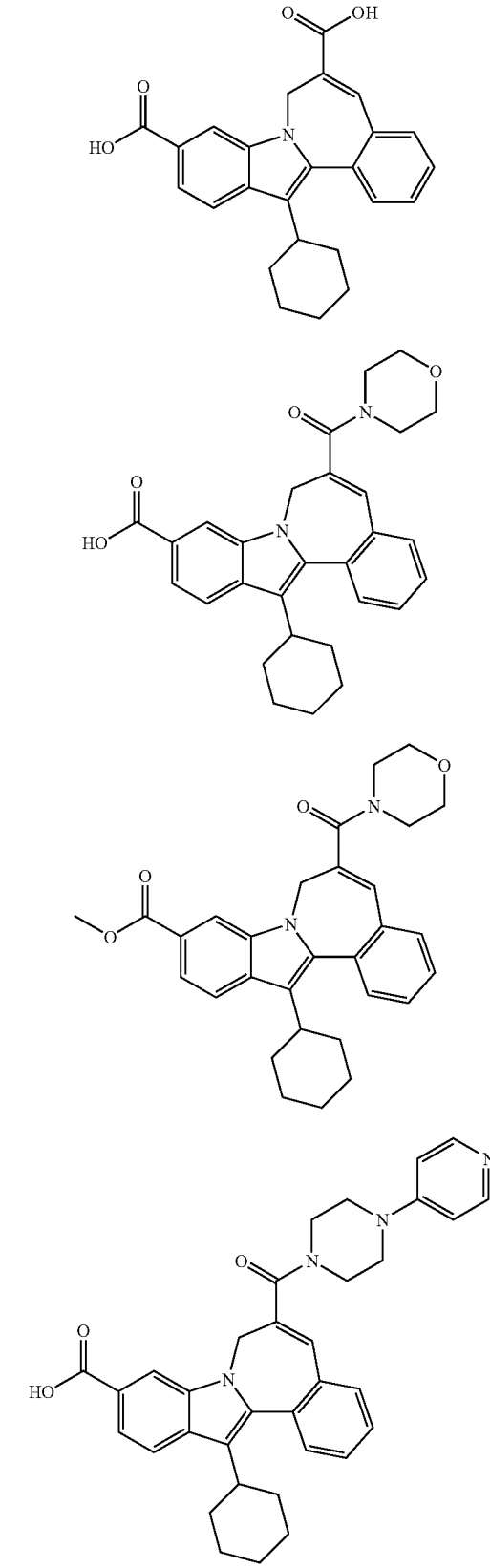

TABLE 2-continued
Structure
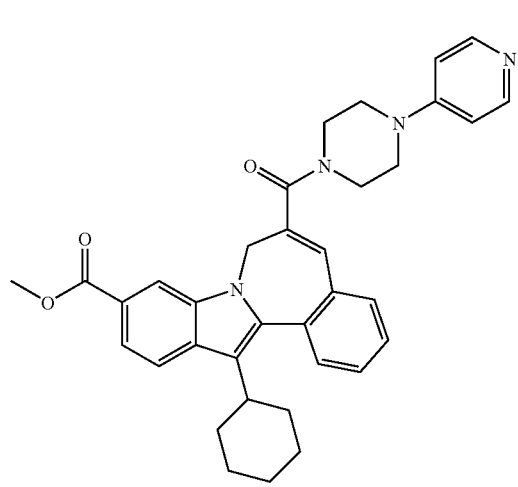
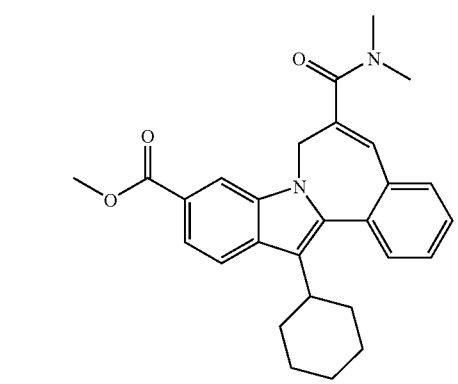
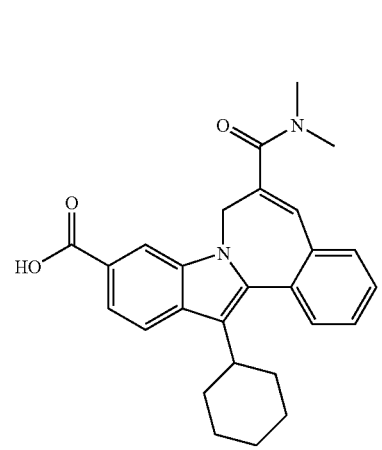
TABLE 2-continued
Structure
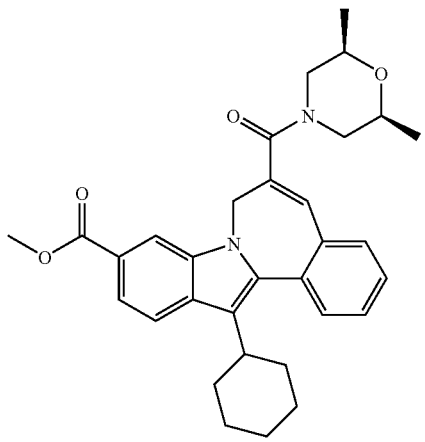
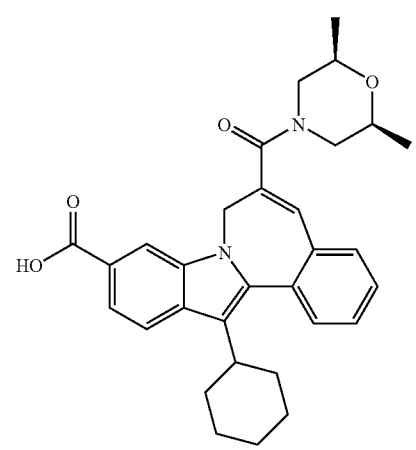
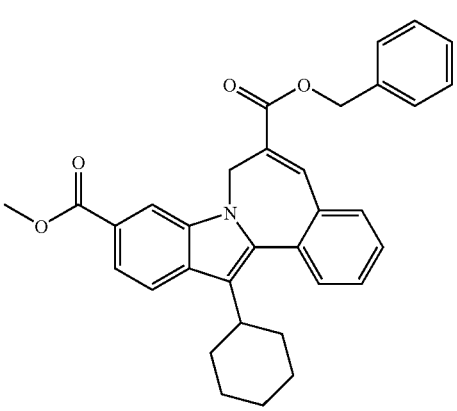

TABLE 2-continued
Structure
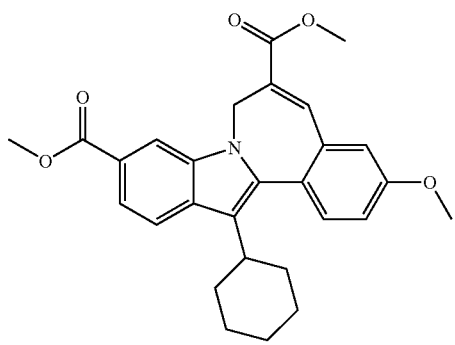
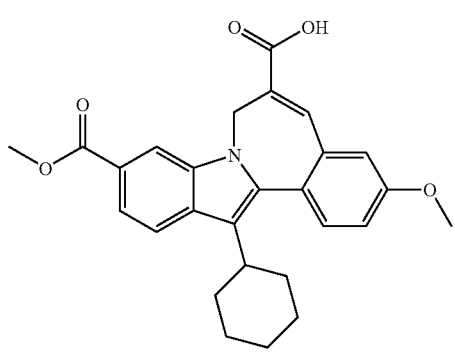
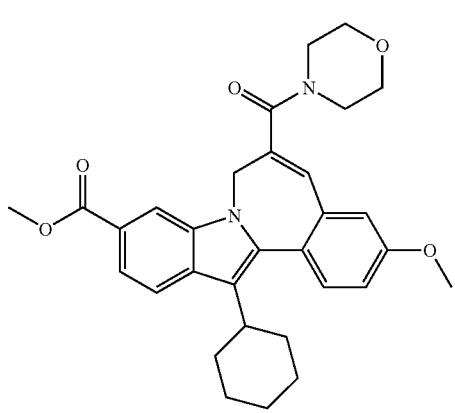
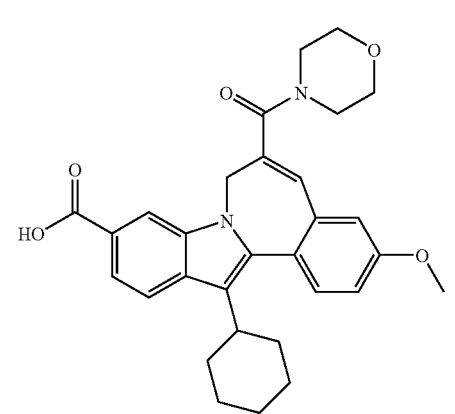
TABLE 2-continued
Structure
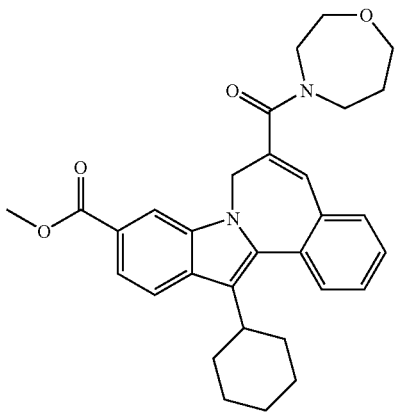
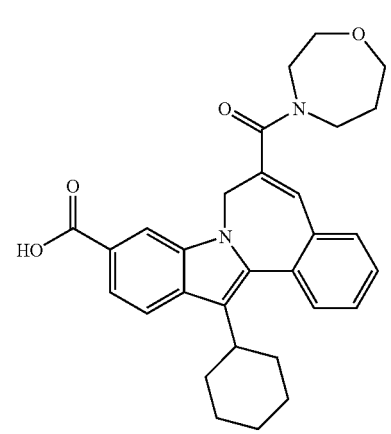
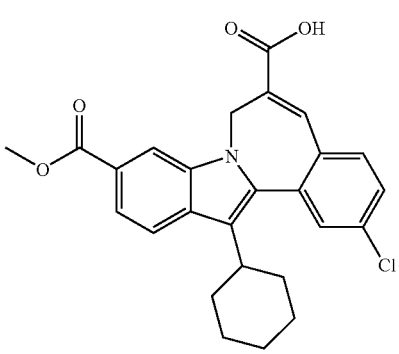
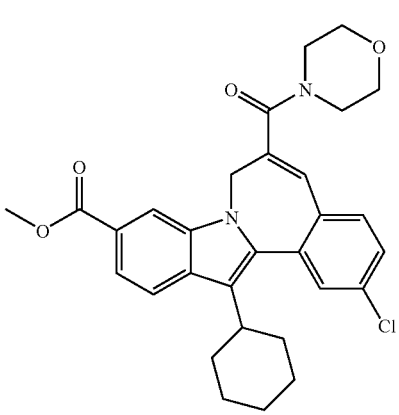

US 7,485,633 B2
TABLE 2-continued
Structure
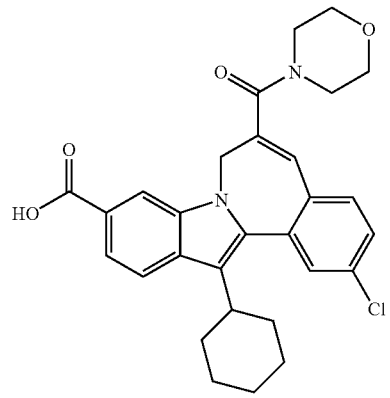
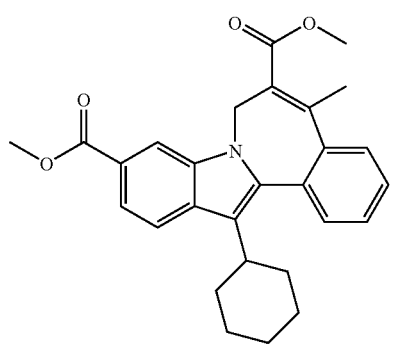
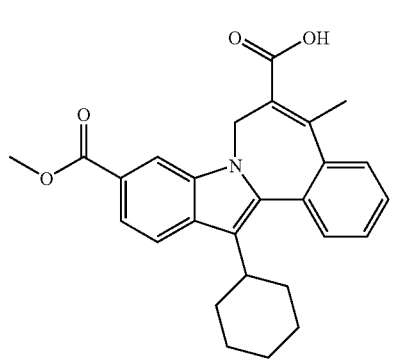
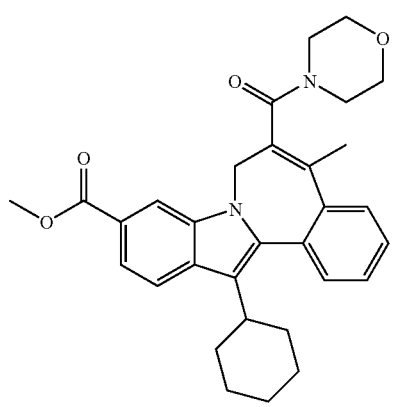
TABLE 2-continued
Structure
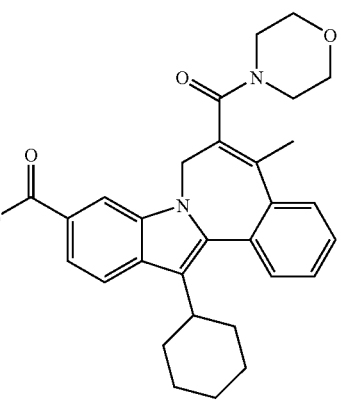
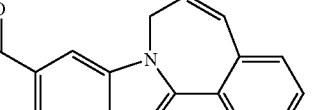
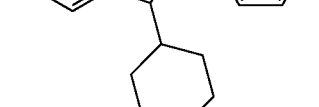

TABLE 2-continued
Structure
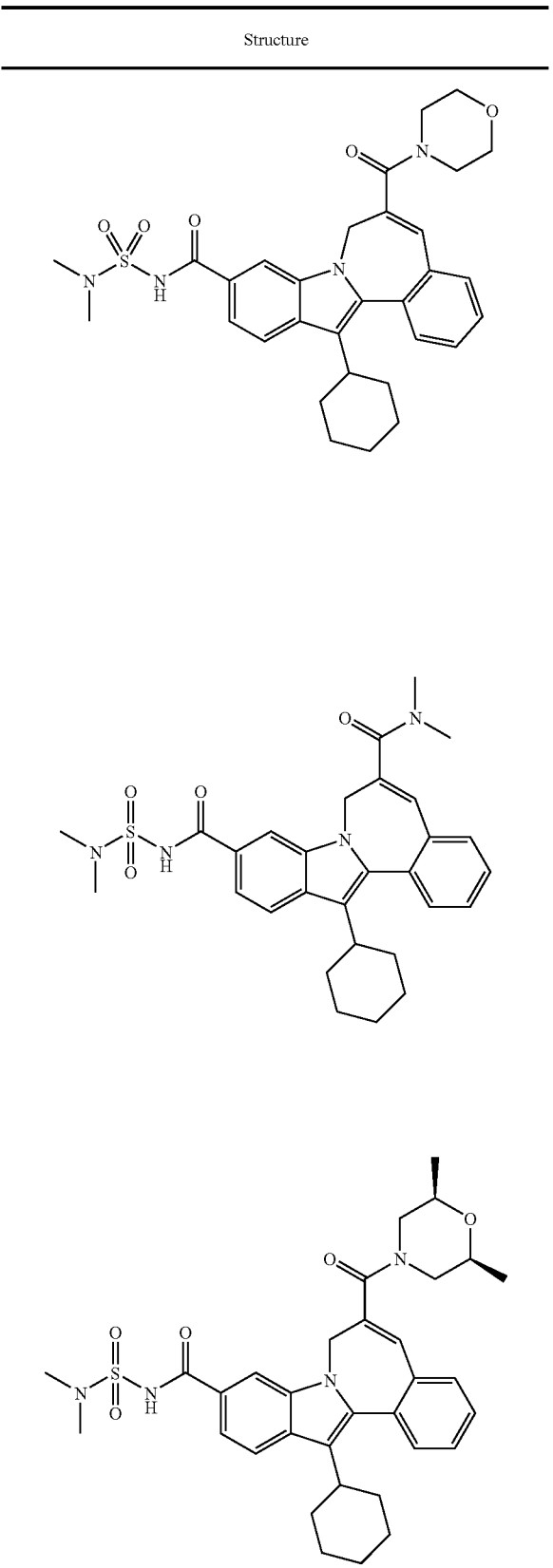
TABLE 2-continued
Structure
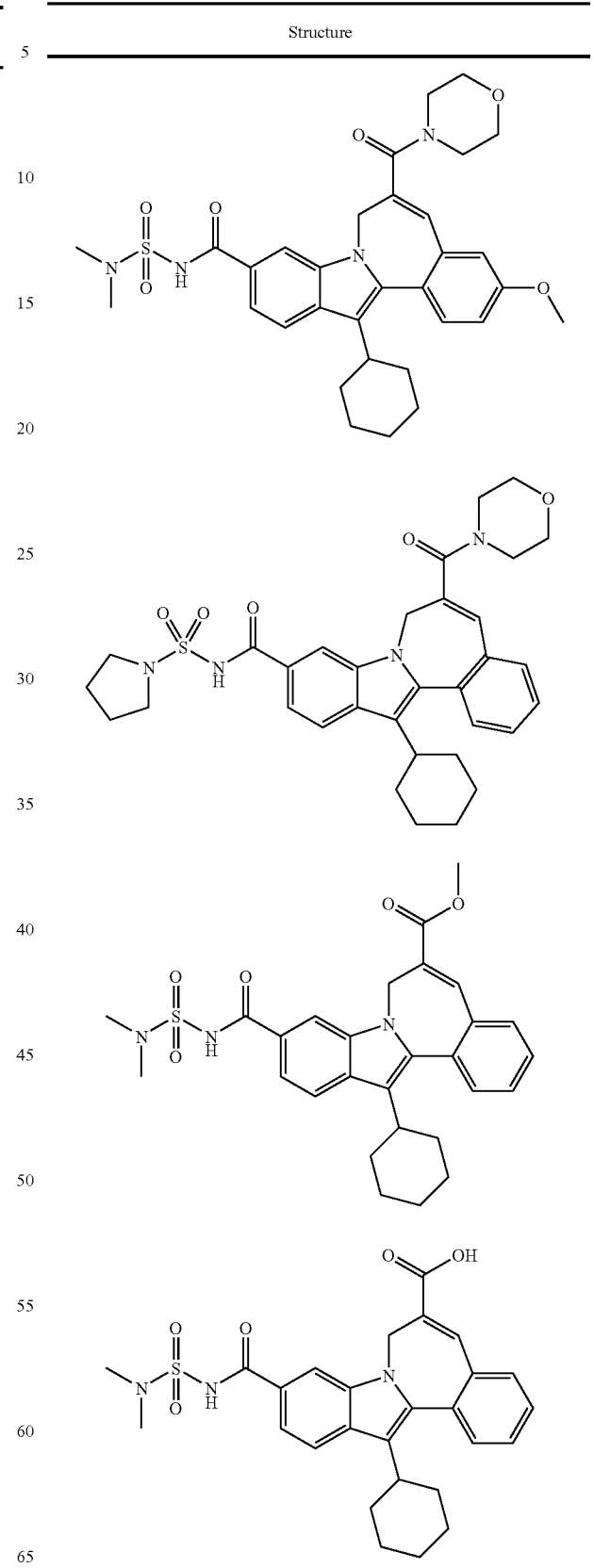

TABLE 2-continued
Structure
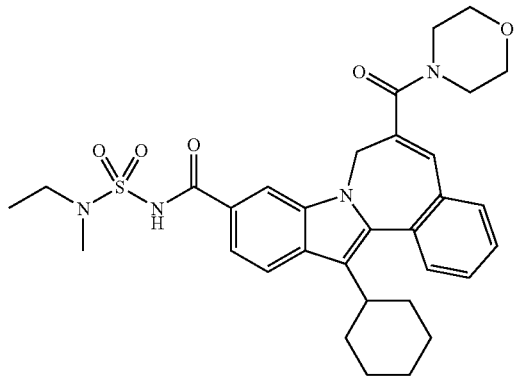
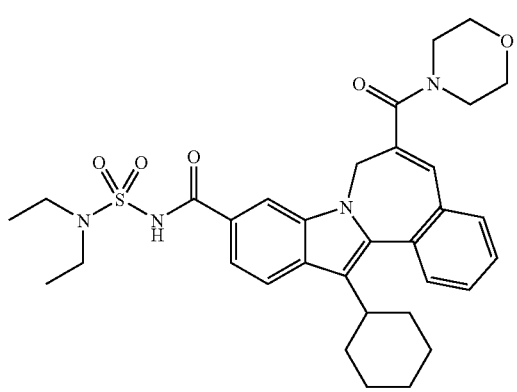
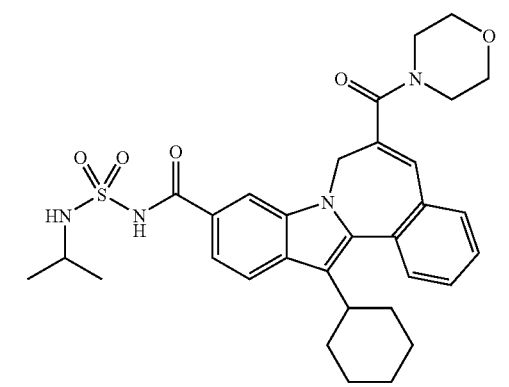
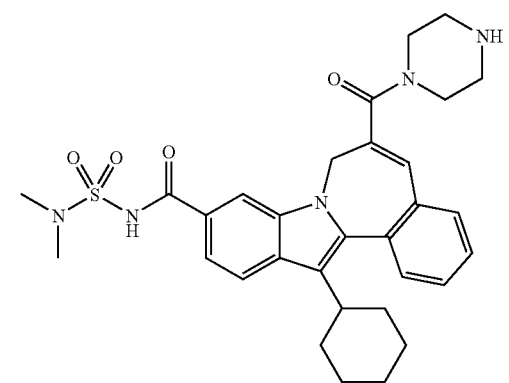
TABLE 2-continued
Structure
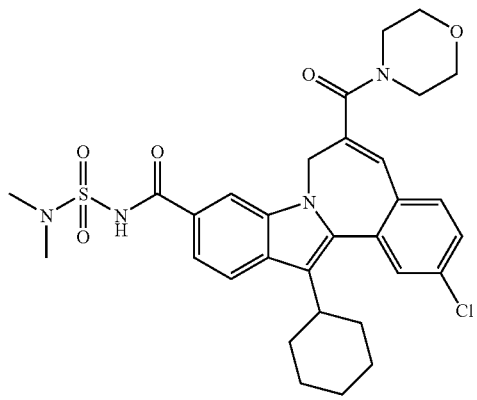
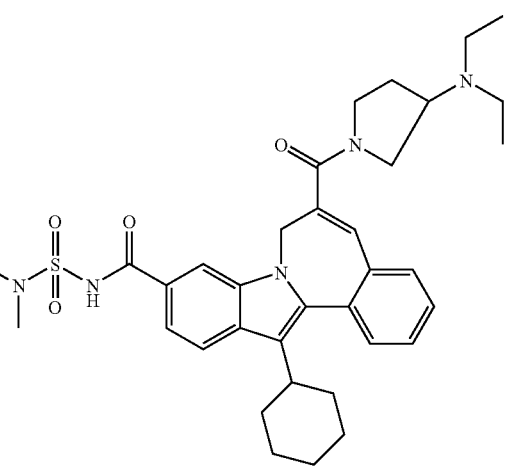
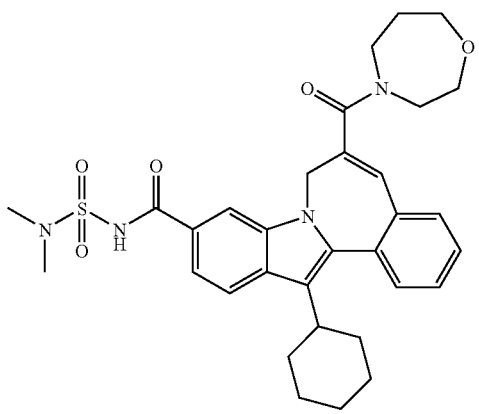

TABLE 2-continued
Structure
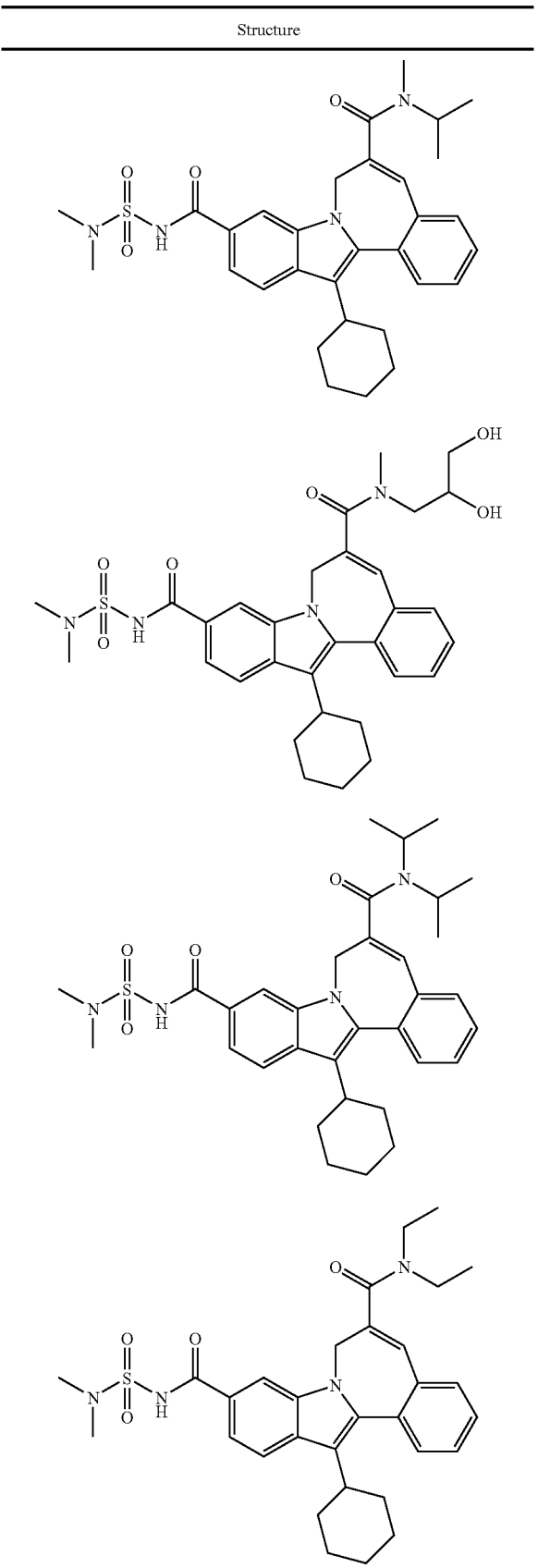
TABLE 2-continued
Structure
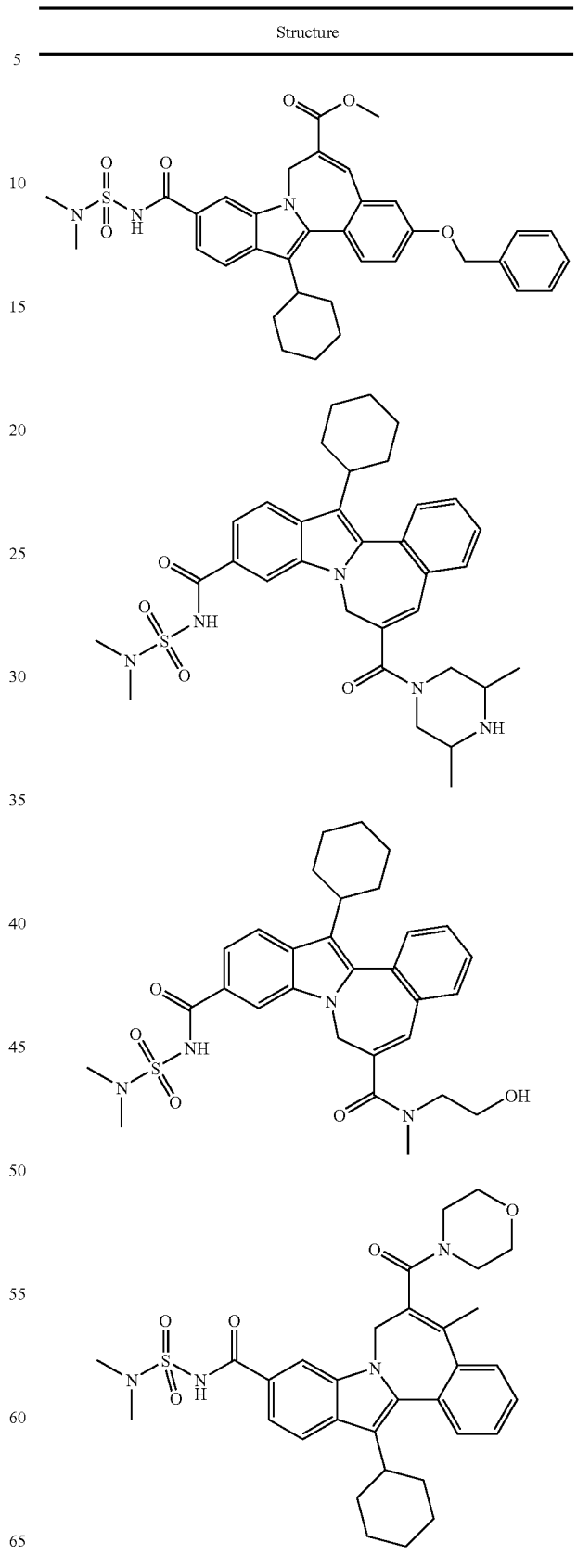

TABLE 2-continued
Structure
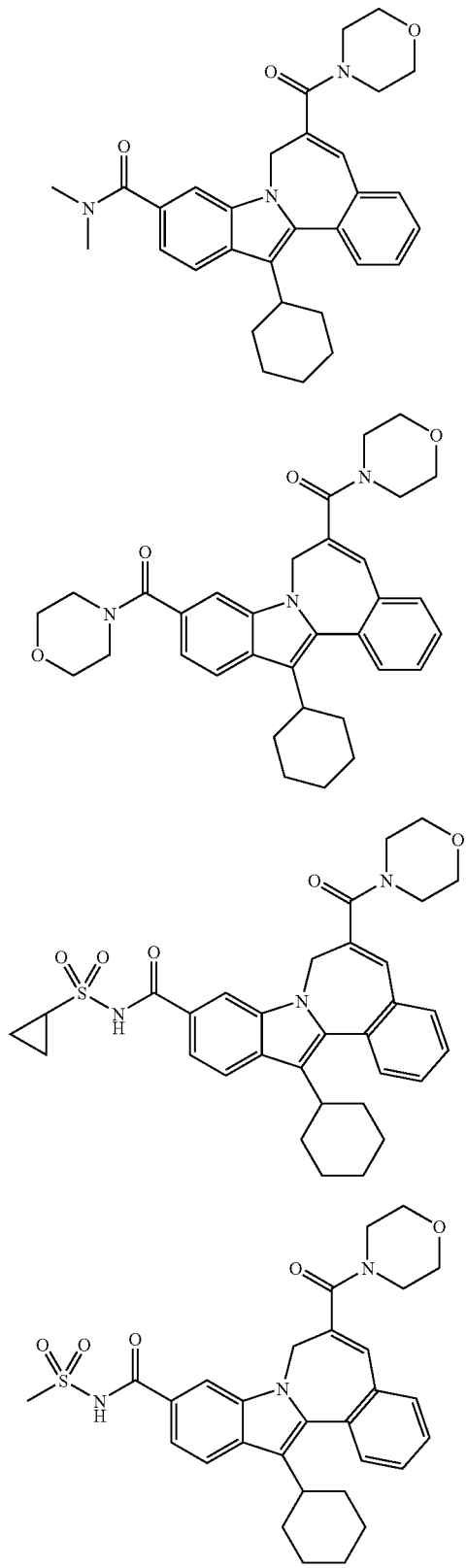
TABLE 2-continued
Structure
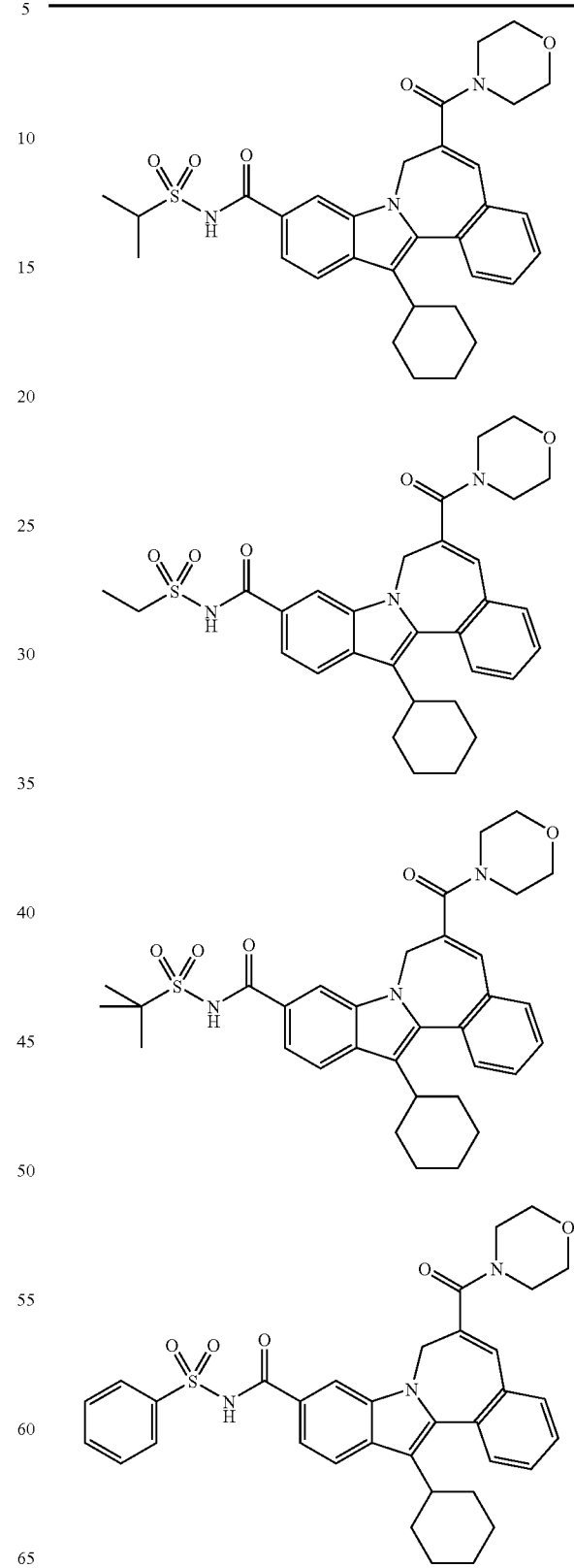

TABLE 2-continued

Structure

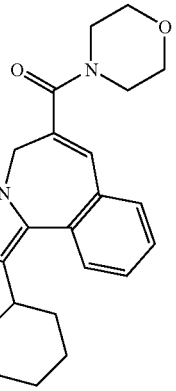

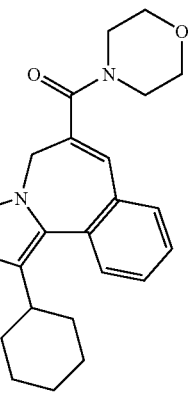

Pharmaceutical Compositions and Methods of Treatment

Formula I compounds demonstrate activity against HCV NS5B and can be useful in treating HCV and HCV infection. Therefore, another aspect of the invention is a composition comprising a compound of formula I, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of formula I, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula I or a pharmaceutically acceptable salt thereof.

Another aspect of the invention is a method of treating an HCV infection in a patient comprising administering to the patient a therapeutically effective amount of a compound of formula I or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of formula I, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 3.

TABLE 3

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |

TABLE 3-continued

| Brand Name | Type of Inhibitor or Target | Source Company |
|---|---|---|
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |

TABLE 3-continued

| Brand Name | Type of Inhibitor or Target | Source Company |
| --- | --- | --- |
| VX-950/LY-570310 | serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

DESCRIPTION OF SPECIFIC EMBODIMENTS

Formula I compounds illustrated in the preceding schemes can generally be purified by reverse phase chromatography using a preparative C-18 column employing gradients of methanol—water containing 0.1% of trifluoroacetic acid (TFA), and using a Shimadzu High Performance Liquid Preparative Chromatographic System employing an XTERRA 30×100 mm S5 column at 40 mL/min flow rate with a 12 min gradient. An Emrys Optimizer personal microwave reactor was used for the microwave assisted reactions. Molecular weights and purities were usually determined using a Shimadzu LCMS using a Phenomenex-Luna 3.0×50 mm S 10 reverse phase column employing a flow rate of 4 mL min using a 0.1% TFA in methanol/H$_2$O gradient [0-100% in 2 min, with 3 min run time]. NMR spectra were usually obtained on either a Bruker 500 or 300 MHz instrument. The preparative silicic acid plates were 20×20 cm with a 1000 micron layer of silica gel GF.

Intermediate 1

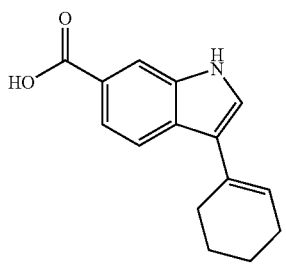

3-Cyclohexenyl-1H-indole-6-carboxylic acid. Cyclohexanone (96 mL, 0.926 mol) was added to a stirred solution of methyl indole-6-carboxylic acid (50.0 g, 0.335 mol) in methanol (920 mL) at 22° C. Methanolic sodium methoxide (416 mL of 25% w/w, 1.82 mol) was added in portions over 10 minutes. The mixture was stirred at reflux for 18 hours, cooled to room temperature, concentrated, diluted with cold water, and acidified with 36% HCl solution. The resulting precipitate was collected by filtration, washed with cold water, and dried over phosphorous pentoxide (0.1 mm) to provide the title compound as a tan colored solid (80.9 g, 97.5% yield).

Intermediate 2

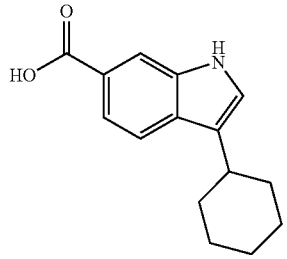

3-Cyclohexyl-1H-indole-6-carboxylic acid. 3-Cyclohexenyl-1H-indole-6-carboxylic acid (38 g) was added to a Parr bottle, followed by methanol (100 mL) and THF (100 mL). The bottle was flushed with argon and 10% palladium on carbon (1.2 g) was added. The flask was then evacuated and subsequently refilled with H$_2$ to a pressure of 55 psi, and the resultant mixture was shaken for 18 hours at RT. The catalyst was then removed by filtration through celite. Concentration of the filtrate provided the desired product as a pale purple solid (30.6 g, 79%). ESI-MS m/z 244 (MH$^+$).

Intermediate 3

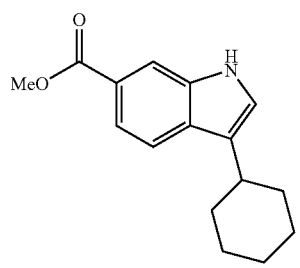

Methyl 3-cyclohexyl-1H-indole-6-carboxylate. Thionyl chloride (1 mL) was added to a stirred mixture of 3-cyclohexyl-1H-indole-6-carboxylic acid (30.4 g, 0.125 mol) in methanol (300 mL). The mixture was stirred at reflux for 18 hours, treated with decolorizing carbon, and filtered. The filtrate was concentrated to about 150 mL at which point crystallization occurred. The filtrate was cooled to room temperature and filtered. The solid was washed with cold methanol followed by diethyl ether to provide the desired product as a pale purple solid (22.2 g, 69% yield). ESI-MS m/z 258 (MH$^+$); $^1$H NMR (300 MHz, CDCl$_3$) δ 1.35 (m, 4H), 1.63 (s, 1H), 1.78 (m, 3H), 2.06 (d, J=8.05 Hz, 2H, 3.90 (m, 1H), 7.08 (d, J=1.83 Hz, 1H), 7.62 (s, 1H), 7.65 (s, 1H), 7.74 (d, J=1.46 Hz, 1H), 7.77 (d, J=1.46 Hz, 1H), 8.08 (s, 1H).

Intermediate 4

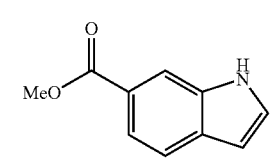

Methyl 1H-indole-6-carboxylate. An ethereal solution of diazomethane (620 mL) was added slowly to a cooled, (−15° C.) stirred suspension of 6-indole carboxylic acid (45 g, 0.27 mol.) in diethyl ether (250 mL). Upon addition, the reaction mixture was stirred for a further 1 h at −15° C., after which the reaction was quenched by the slow addition of acetic acid (50 mL). The resultant mixture was then concentrated under reduced pressure, and the residue purified using flash chromatography on silica (60-120), using DCM as eluant.

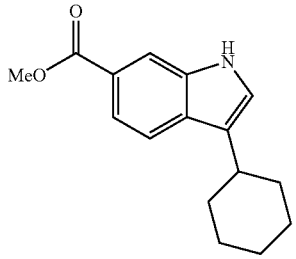

Intermediate 5

Methyl 3-cyclohexyl-1H-indole-6-carboxylate. Cyclohexanone (42.46 mL, 0.40 mol) was added in a single portion to a stirred solution of methyl indole-6-carboxylate (47.8 g, 0.27 m) in dry dichloromethane (500 mL). The reaction mixture was then cooled to 10° C. and trifluoroacetic acid (63.13 mL, 0.8 m) was added dropwise followed by triethyl silane (174.5 mL, 1.09 m). Upon addition, the temperature was allowed to rise to rt, after which it was stirred for a further 12 h. Dichloromethane (200 mL) was then added and the reaction mixture was washed successively with 10% sodium bicarbonate solution and brine. The organic layer dried over sodium sulfate, filtered and concentrated under vacuum. The resultant residue was purified by flash chromatography on silica (60-120) using hexane-ethyl acetate (9.5:0.5) mixture as eluant. Homogeneous fractions were combined and evaporated to give 60 g of the desired product (85%). Analytical data on this material was consistant with that observed with a sample prepared by the alternative route described above.

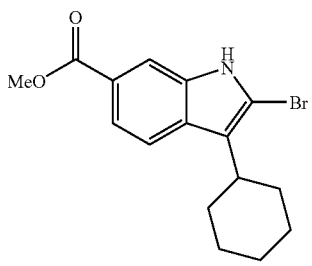

Intermediate 6

Methyl 2-bromo-3-cyclohexyl-2-1H-indole-6-carboxylate. Dry pyridinium tribromide (12.0 g, 38 mmol) was added in one portion to a stirred and cooled (ice/water bath) solution of methyl 3-cyclohexyl-1H-indole-6-carboxylate (7.71 g, 30 mmol) in a mixture of THF (80 mL) and chloroform (80 mL). The flask was removed from the cooling bath and stirring was continued for 2 hours at room temperature. The mixture was sequentially washed with 1M NaHSO$_3$ (2×50 mL) and 1N HCl (50 mL). It was then dried over anhydrous sodium sulfate, filtered, and concentrated. The concentrate was treated with hexanes and the resulting precipitate was collected by filtration to provide the desired product as an off-white solid (5.8 g, 58%). $^1$H NMR (300 MHz, CDCl$_3$) δ 1.38 (m, 3H), 1.85 (m, 7H), 2.81 (m, 1H), 7.71 (m, 2H), 8.03 (s, 1H), 8.47 (s, 1H).

The hexane mother liquor was concentrated and the residue was dissolved in hexane/ethyl acetate (5:1). The solution was passed through a pad of silica gel with the same solvents. Concentration of the eluate followed by the addition of hexane (10 mL) resulted in the precipitation of additional product which was collected by filtration to provide 2.8 g (28%) of the desired product.

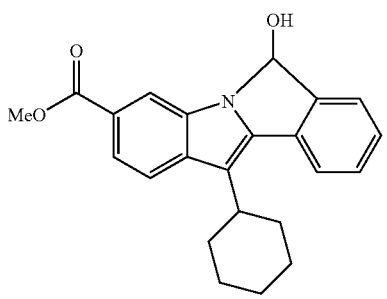

Intermediate 7

Methyl 11-cyclohexyl-6-hydroxy-6H-isoindolo[2,1-a]indole-3-carboxylate. A stirred mixture of methyl 2-bromo-3-cyclohexyl-1H-indole-6-carboxylate (10.1 g, 30 mmol), 2-formylphenylboronic acid (5.4 g, 36 mmol), LiCl (3.8 g (90 mmol) and Pd (PPh$_3$)$_4$ (1.6 g, 1.38 mmol) in 1M Na$_2$CO$_3$ (40 mL) and 1:1 EtOH-toluene (180 mL) was heated under nitrogen at 85° C. for 3 hours. The reaction mixture was then cooled to RT, and extracted with EtOAc (2×100 mL). The extracts were washed sequentially with water and brine, then dried (MgSO$_4$), filtered and concentrated in-vacuo to afforded 13.3 g of crude product. This material was triturated with DCM and hexanes to provide pure desired product (7.52 g, 70%). LC-MS: m/e 360 (M–H); 344 (M–17)$^+$. $^1$H NMR (400 MHz, CHLOROFORM-D) δ ppm 1.33-1.60 (m, 4H) 1.77-2.01 (m, 6H) 2.80 (d, J=11.83 Hz, 1H) 3.02-3.18 (m, 1H) 3.89 (s, 3H) 6.49 (d, J=11.33 Hz, 1H) 7.34 (t, J=7.55 Hz, 1H) 7.46 (t, J=7.55 Hz, 1H) 7.62 (d, J=7.30 Hz, 1H) 7.66-7.74 (m, 2H) 7.77 (d, J=7.81 Hz, 1H) 8.21 (s, 1H).

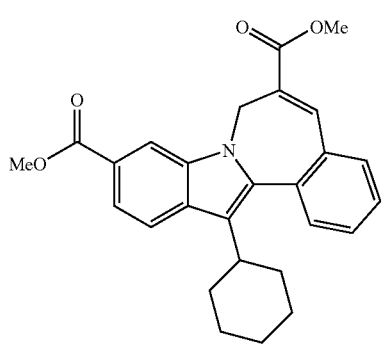

Intermediate 8

Methyl 13-cyclohexyl-6-(methoxycarbonyl)-7H-indolo[2,1-a][2]benzazepine-10-carboxylate. A stirred suspension of methyl 11-cyclohexyl-6-hydroxy-6H-isoindolo[2,1-a]indole-3-carboxylate (3.61 g, 10 mmol), Cs$_2$CO$_3$ (3.91 g, 12 mmol) and trimethyl 2-phosphonoacetate (2.86 g, 14 mmol) in an. DMF (40 mL) was heated at 60° C. under nitrogen for 3 h. The resultant yellow suspension was cooled to rt and water was added with vigorous stirring. A yellow precipitate formed which was collected by filtration. The filtrand was washed with water, and then air dried overnight to afford the title compound as a yellow powder (4.124 g, 96%). LC/MS: m/e 430 (MH$^+$); $^1$H NMR (400 MHz, CHLOROFORM-D) δ ppm 1.30-1.46 (m, J=14.86 Hz, 2H) 1.55 (s, 2H) 1.77 (s, 2H)

1.85-2.18 (m, 4H) 2.76-2.89 (m, 1H) 3.84 (s, 3H) 3.95 (s, 3H) 4.19 (s, 1H) 5.68 (s, 1H) 7.38-7.63 (m, 4H) 7.74 (dd, J=8.44, 1.39 Hz, 1H) 7.81-7.98 (m, 2H) 8.29 (d, J=1.01 Hz, 1H).

Intermediate 9

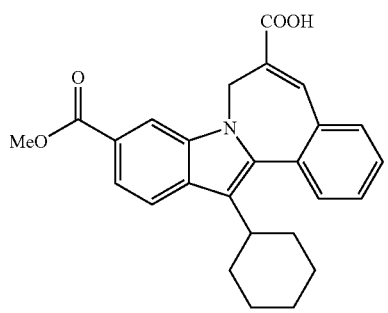

Methyl 13-cyclohexyl-6-(carboxy)-5H-indolo[2,1-a][2]benzazepine-10-carboxylate. Methyl 13-cyclohexyl-6-(methoxycarbonyl)-7H-indolo[2,1-a][2]benzazepine-10-carboxylate (308 mg, 0.72 mmol) was dissolved in N,N-dimethylformamide (5 mL) and treated with LiOH (173 mg, 7.2 mmol). The mixture was heated at 50° C. for 4 hr, after which the solvent was removed in vacuo. The residue was dissolved in H₂O (5 mL) and the resultant mixture was acidified by the addition of a 10% aqueous HCL solution. A precipitate formed which was collected by filtration and air dried to afford the title compound as a bright yellow solid (290 mg, 97%). ESI-MS m/z [M+1]=415.

Intermediate 10

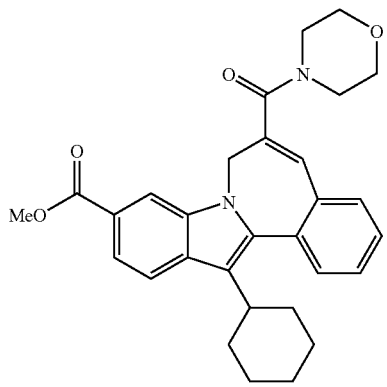

Methyl 13-cyclohexyl-6-(morpholinylcarbonyl)-5H-indolo[2,1-a][2]benzazepine-10-carboxylate. TBTU (145 mg, 0.45 mmol) was added to a stirred solution of Methyl 13-cyclohexyl-6-(carboxy)-5H-indolo[2,1-a][2]benzazepine-10-carboxylate (125 mg, 0.30 mmol), morpholine (26 μL, 0.30 mmol), and N,N-diisopropylethylamine 200 μL, 1.15 mmol) in DMF (2 mL). The mixture was stirred at 22° C. for 20 min. The resulting solution was then injected onto a Shimadzu reverse phase preparative HPLC. The product containing fraction was concentrated on a Speed Vac® to leave methyl 13-cyclohexyl-6-(morpholinylcarbonyl)-5H-indolo[2,1-a][2]benzazepine-10-carboxylic acid as a yellow solid (64 mg, 44%). ESI-MS m/z 487 (MH⁺); ¹H NMR (500 MHz, CDCl₃) δ 1.21 (m, 1H), 1.34-1.55 (m, 3H), 1.77 (m, 2H), 1.91 (m, 1H), 2.06 (m, 3H), 2.83 (m, 1H), 2.97-3.85 (m, 8H), 3.97 (s, 3H), 4.45 (m, 1H), 5.07 (m, 1H), 6.89 (s, 1H), 7.41 (d, 1H), 7.49 (m, 2H), 7.57 (m, 1H), 7.75 (m, 1H), 7.89 (d, J=8.55 Hz, 1H), 8.15 (s, 1H).

Intermediate 11

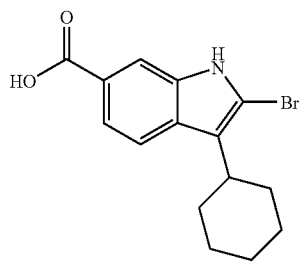

2-bromo-3-cyclohexyl-2-1H-indole-6-carboxylic acid. To a solution of methyl 2-bromo-3-cyclohexyl-2-1H-indole-6-carboxylate (8.0 g, 23.79 mmol) in THF/MeOH (30 mL/30 mL), 10 N solution of NaOH (23.8 mL, 238 mmol.) was added. The reaction mixture was stirred at 40° C. for 6 hrs, then at rt. for overnight. It was then concentrated and acidified with concentrated HCl solution to pH ~4. A brownish solid was collected as crude product. (7.6 g, 99% yield). MS m/322 (MH⁺), Retention time: 3.696 min.

Intermediate 12

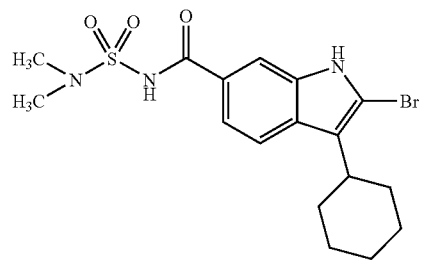

2-Bromo-3-cyclohexyl-N-[(dimethylamino)sulfonyl]-1H-indole-6-carboxamide. 1,1'-Carbonyldiimidazole (1.17 g, 7.2 mmol) was added to a stirred solution of 2-bromo-3-cyclohexyl-1H-indole-6-carboxylic acid (2.03 g, 6.3 mmol) in THF (6 mL) at 22° C. The evolution of CO₂ was instantaneous and when it slowed the solution was heated at 50° C. for 1 hr and then cooled to 22° C. N,N-Dimethylsulfamide (0.94 g, 7.56 mmol) was added followed by the dropwise addition of a solution of DBU (1.34 g, 8.8 mmol) in THF (4 mL). Stirring was continued for 24 hr. The mixture was partitioned between ethyl acetate and dilute HCl. The ethyl acetate layer was washed with water followed by brine and dried over Na₂SO₄. The extract was concentrated to dryness to leave the title product as a pale yellow friable foam, (2.0 g, 74%, >90% purity, estimated from NMR). ¹H NMR (300 MHz, DMSO-D6) δ ppm 1.28-1.49 (m, 3H) 1.59-2.04 (m, 7H) 2.74-2.82 (m, 1H) 2.88 (s, 6H) 7.57 (dd, J=8.42, 1.46 Hz, 1H) 7.74 (d, J=8.78 Hz, 1H) 7.91 (s, 1H) 11.71 (s, 1H) 12.08 (s, 1H).

Intermediate 13

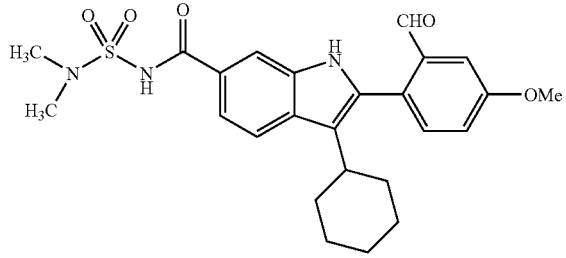

3-cyclohexyl-N—(N,N-dimethylsulfamoyl)-2-(2-formyl-4-methoxyphenyl)-1H-indole-6-carboxamide. A mixture of the 2-Bromo-3-cyclohexyl-N-[(dimethylamino)sulfonyl]-1H-indole-6-carboxamide (4.28 g, 0.01 mol), boronic acid (2.7 g, 0.015 mol), 2-dicyclohexylphosphino-2',6'-dimethoxy-biphenyl (41 mg, 0.0001 mol), palladium acetate (11.2 mg), and finely ground potassium carbonate (4.24 g, 0.02 mol) in toluene (30 mL) was stirred under reflux and under nitrogen for 30 min, at which time LC/MS analysis showed the reaction to be complete. The reaction mixture was then diluted with ethyl acetate and water, and then acidified with an excess of dilute HCl. The ethyl acetate layer was then collected and washed with dilute HCl, water and brine. The organic solution was then dried (magnesium sulfate), filtered and concentrated to give a gum. The gum was diluted with hexanes (250 ml) and ethyl acetate (25 mL), and the mixture was stirred for 20 hr at 22° C. during which time the product was transformed into a bright yellow granular solid (4.8 g) which was used directly without further purification.

Intermediate 14

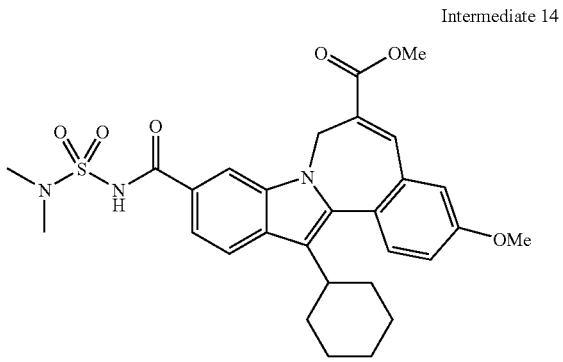

6-Carbomethoxy-13-cyclohexyl-N-[(dimethylamino)sulfonyl]-5H-indolo[2,1-a][2]benzazepine-10-carboxamide. A mixture of the 3-cyclohexyl-N—(N,N-dimethylsulfamoyl)-2-(2-formyl-4-methoxyphenyl)-1H-indole-6-carboxamide (4.8 g, 0.01 mol), and cesium carbonate (7.1 g, 0.02 mol) and the trimethyl 2-phosphonoacetate (2.86 g, 0.014 mol) in DMF (28 mL) was stirred for 20 hr at an oil bath temperature of 55° C. The mixture was poured into ice-water and acidified with dilute HCl to precipitate the crude product. The solid was collected, dried and flash chromatographed on $SiO_2$ (110 g) using an ethyl acetate and methylene chloride (1:10) solution containing 2% acetic acid. Homogeneous fractions were combined and evaporated to afford the title compound as a pale yellow solid (3.9 g, 71% yield). MS: 552 (M=H+).

Intermediate 15

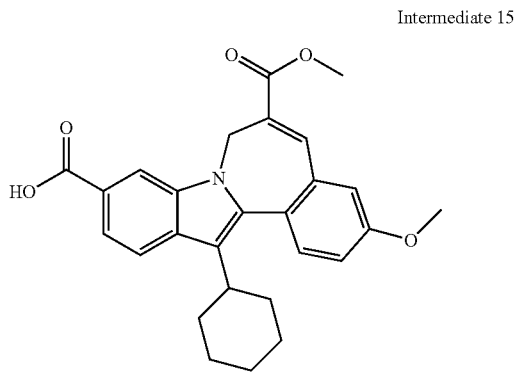

13-Cyclohexyl-3-methoxy-6-(methoxycarbonyl)-7H-indolo[2,1-a][2]benzazepine-10-carboxylic acid. Trifluoroacetic acid (30 mL) was added dropwise to a stirring slurry of 10-tert-butyl 6-methyl 13-cyclohexyl-3-methoxy-7H-indolo[2,1-a][2]benzazepine-6,10-dicarboxylate (10 g, 20 mmol) in dichloroethane (30 mL) under $N_2$. The clear dark green solution was stirred at rt for 2.5 h, concentrated to dryness and stirred with EtOAc (100 mL) overnight. The solids were collected by filtration, washed with EtOAc and $Et_2O$ to yield 13-cyclohexyl-3-methoxy-6-(methoxycarbonyl)-7H-indolo[2,1-a][2]benzazepine-10-carboxylic acid (8.35 g, 18.8 mmol, 94%) was as a yellow solid which was used without further purification. $^1$HNMR (300 MHz, $CDCl_3$) δ 1.13-2.16 (m, 10H), 2.74-2.88 (m, 1H), 3.84 (s, 3H), 3.89 (s, 3H), 4.06-4.29 (m, 1H), 5.54-5.76 (m, 1H), 6.98 (d, J=2.6 Hz, 1H), 7.08 (dd, J=8.4, 2.6 Hz, 1H), 7.52 (d, J=8.4 Hz, 1H), 7.78 (dd, J=8.8, 1.1 Hz, 1H), 7.80 (s, 1H), 7.86 (d, J=8.8 Hz, 1H), 8.34 (d, J=1.1 Hz, 1H). LCMS: m/e 446 (M+H)$^+$, ret time 3.21 min, column B, 4 minute gradient.

Intermediate 16

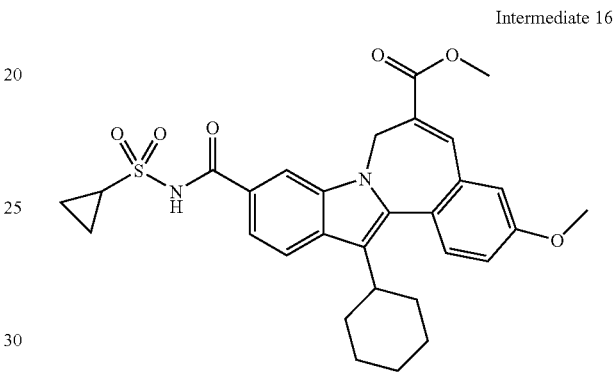

Methyl 13-cyclohexyl-10-((cyclopropylsulfonyl)carbamoyl)-3-methoxy-7H-indolo[2,1-a][2]benzazepine-6-carboxylate. 1,1'-Carbonyldiimidazole (1.82 g, 11.2 mmol) was added to a slurry of 13-cyclohexyl-3-methoxy-6-(methoxycarbonyl)-7H-indolo[2,1-a][2]benzazepine-10-carboxylic acid (3.85 g, 8.65 mmol) in THF (15 mL). The reaction mixture was heated at 60° C. for 1.5 h, cooled to rt, treated with cyclopropanesulfonamide (1.36 g, 11.2 mmol), stirred 10 min and then treated with the dropwise addition of a solution of DBU (2.0 mL, 13 mmol) in THF (3 mL). The reaction mixture was stirred at rt overnight, diluted with EtOAc (100 mL) and washed with $H_2O$ (~30 mL), 1N HCl (aq.) (2×50 mL) and brine (~30 mL). The combined aqueous layers were extracted with EtOAc (100 mL) and the organic layer was washed with 1N HCl (aq.) (~50 mL). The combined organic layers were washed with brine (~30 mL), dried ($MgSO_4$), filtered and concentrated. The residue was stirred with $Et_2O$ (~100 mL) for 2 h and the solids were collected by filtration, rinsed with $Et_2O$ and dried to yield methyl 13-cyclohexyl-10-((cyclopropylsulfonyl)carbamoyl)-3-methoxy-7H-indolo[2,1-a][2]benzazepine-6-carboxylate (4.24 g, 7.73 mmol, 89%) as a pale yellow solid which was used without further purification. $^1$HNMR (300 MHz, $CDCl_3$) δ 1.08-2.13 (m, 14H), 2.73-2.87 (m, 1H), 3.13-3.24 (m, 1H), 3.82 (s, 3H), 3.89 (s, 3H), 4.04-4.27 (m, 1H), 5.50-5.71 (m, 1H), 6.98 (d, J=2.6 Hz, 1H), 7.08 (dd, J=8.8, 2.6 Hz, 1H), 7.44 (dd, J=8.4, 1.1 Hz, 1H), 7.50 (d, J=8.8 Hz, 1H), 7.80 (s, 1H), 7.86 (d, J=8.4 Hz, 1H), 8.11 (br s, 1H), 8.78 (br s, 1H). LCMS: m/e 549 (M+H)$^+$, ret time 3.79 min, column B, 4 minute gradient.

Intermediate 17

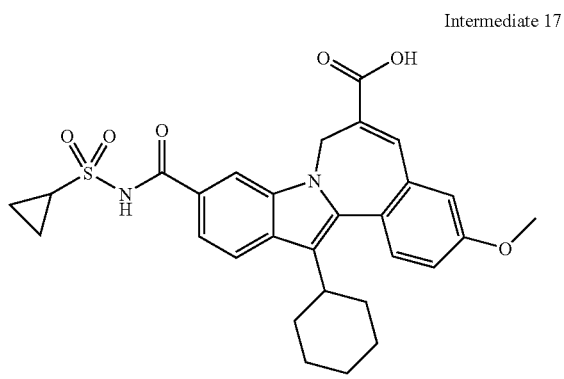

13-Cyclohexyl-10-((cyclopropylsulfonyl)carbamoyl)-3-methoxy-7H-indolo[2,1-a][2]benzazepine-6-carboxylic acid. Methyl 13-cyclohexyl-10-((cyclopropylsulfonyl)carbamoyl)-3-methoxy-7H-indolo[2,1-a][2]benzazepine-6-carboxylate (1.0 g, 1.8 mmol) was dissolved into MeOH//THF (1:1, 24 mL) and treated with 1M aqueous NaOH (5 mL). The reaction mixture was stirred and heated at 60° C. for 1.5 h and cooled to rt. The clear solution was neutralized with 1M aqueous HCl (5 mL) and concentrated to remove organic solvents. The resultant solids were collected by filtration, washed with $H_2O$ and dried under vacuum to yield 13-cyclohexyl-10-((cyclopropylsulfonyl)carbamoyl)-3-methoxy-7H-indolo[2,1-a][2]benzazepine-6-carboxylic acid (1.0 g, 1.7 mmol, 94%) as a bright yellow solid (with 0.75 equiv. of THF) which was used without further purification. $^1$HNMR (300 MHz, $CD_3OD$) δ 1.11-2.24 (m, 17H, 3H from THF), 2.81-2.96 (m, 1H), 3.17-3.28 (m, 1H), 3.69-3.79 (m, 3H, from THF), 3.94 (s, 3H), 4.07-4.33 (m, 1H), 5.55-5.81 (m, 1H), 7.14-7.24 (m, 2H), 7.55-7.64 (m, 2H), 7.88-7.94 (m, 2H), 8.20 (br s, 1H). LCMS: m/e 535 (M+H)$^+$, ret time 3.73 min, column B, 4 minute gradient.

Intermediate 18

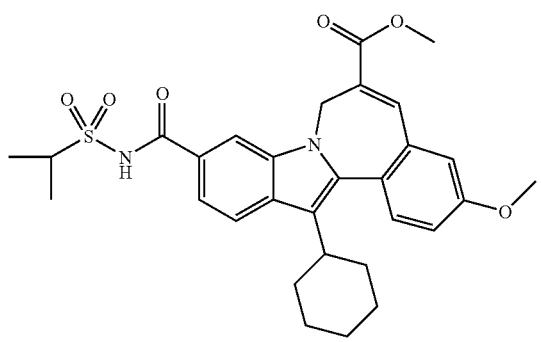

Methyl 13-cyclohexyl-10-((isopropylsulfonyl)carbamoyl)-3-methoxy-7H-indolo[2,1-a][2]benzazepine-6-carboxylate. 1,1'-Carbonyldiimidazole (262 mg, 1.62 mmol) was added to a slurry of 13-cyclohexyl-3-methoxy-6-(methoxycarbonyl)-7H-indolo[2,1-a][2]benzazepine-10-carboxylic acid (603 mg, 1.36 mmol) in THF (3 mL). The reaction mixture was heated at 60° C. for 1.5 h, cooled to rt, treated with propane-2-sulfonamide (200 mg, 1.62 mmol), stirred 10 min and then treated with the dropwise addition of a solution of DBU (0.27 mL, 1.8 mmol) in THF (0.75 mL). The reaction mixture was stirred at rt overnight, diluted with EtOAc (15 mL) and washed with $H_2O$ (~5 mL), 1N HCl (aq.) (2×10 mL) and brine (~5 mL). The combined aqueous layers were extracted with EtOAc (15 mL) and the organic layer was washed with 1N HCl (aq.) (~10 mL). The combined organic layers were washed with brine (~5 mL), dried ($MgSO_4$), filtered and concentrated. The residue was stirred with $Et_2O$ (~15 mL) for 2 h and the solids were collected by filtration, rinsed with $Et_2O$ and dried to yield methyl 13-cyclohexyl-10-((isopropylsulfonyl)carbamoyl)-3-methoxy-7H-indolo[2,1-a][2]benzazepine-6-carboxylate (640 mg, 1.2 mmol, 85%) as a bright yellow solid which was used without further purification. $^1$HNMR (300 MHz, $CDCl_3$) δ 1.12-2.13 (m, 10H), 1.47 (d, J=7.0 Hz, 6H), 2.73-2.86 (m, 1H), 3.82 (s, 3H), 3.89 (s, 3H), 4.06-4.26 (m, 1H), 4.09 (septet, J=7.0 Hz, 1H), 5.51-5.71 (m, 1H), 6.98 (d, J=2.6 Hz, 1H), 7.08 (dd, J=8.4, 2.6 Hz, 1H), 7.44 (dd, J=8.4, 1.5 Hz, 1H), 7.50 (d, J=8.4 Hz, 1H), 7.80 (s, 1H), 7.87 (d, J=8.4 Hz, 1H), 8.10 (d, J=1.5 Hz, 1H), 8.57 (s, 1H). LCMS: m/e 551 (M+H)$^+$, ret time 3.87 min, column B, 4 minute gradient.

Intermediate 19

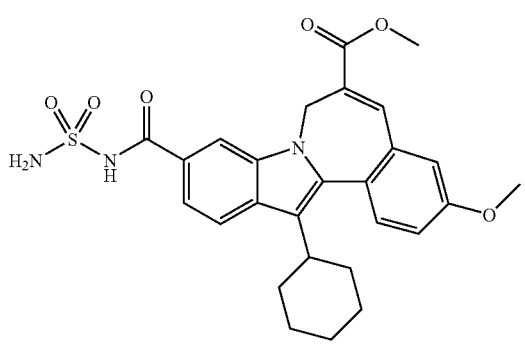

Methyl 10-((aminosulfonyl)carbamoyl)-13-cyclohexyl-3-methoxy-7H-indolo[2,1-a][2]benzazepine-6-carboxylate. 1,1'-Carbonyldiimidazole (1.23 g, 7.60 mmol) was added to a slurry of 13-cyclohexyl-3-methoxy-6-(methoxycarbonyl)-7H-indolo[2,1-a][2]benzazepine-10-carboxylic acid (2.6 g, 5.8 mmol) in THF (11 mL). The reaction mixture was heated at 60° C. for 1.5 h, cooled to rt, treated with sulfamide (1.12 g, 11.7 mmol), stirred 10 min and then treated with the dropwise addition of a solution of DBU (1.8 mL, 11.7 mmol) in THF (3 mL). The reaction mixture was stirred at rt for 3 h, diluted with EtOAc (80 mL) and $CH_2Cl_2$ (100 mL) and concentrated to dryness. The residue was diluted with $CH_2Cl_2$ (100 mL) and washed with 1N HCl (aq.) (2×100 mL). The combined aqueous layers were extracted with $CH_2Cl_2$ (100 mL) and the combined organic layers were washed with ½ saturated brine (~50 mL), dried ($MgSO_4$), filtered and concentrated. The residue was stirred with $Et_2O$ (~75 mL) for 1 h and the solids were collected by filtration, rinsed with $Et_2O$ and dried to yield methyl 10-((aminosulfonyl)carbamoyl)-13-cyclohexyl-3-methoxy-7H-indolo[2,1-a][2]benzazepine-6-carboxylate (2.8 g, 5.3 mmol, 91%) as a bright yellow solid which was used without further purification. $^1$HNMR (300 MHz, $CDCl_3$) δ 1.08-2.10 (m, 10H), 2.71-2.84 (m, 1H), 3.79 (s, 3H), 3.89 (s, 3H), 4.00-4.18 (m, 1H), 5.50-5.64 (m, 1H), 5.68 (s, 2H), 6.97 (d, J=2.6 Hz, 1H), 7.07 (dd, J=8.8, 2.6 Hz, 1H), 7.46 (dd, J=8.4, 1.5 Hz, 1H), 7.49 (d, J=8.8 Hz, 1H), 7.78 (s, 1H), 7.82 (d, J=8.4 Hz, 1H), 8.10 (br s, 1H), 9.49 (s, 1H). LCMS: m/e 524 (M+H)$^+$, ret time 3.60 min, column B, 4 minute gradient.

Intermediate 20

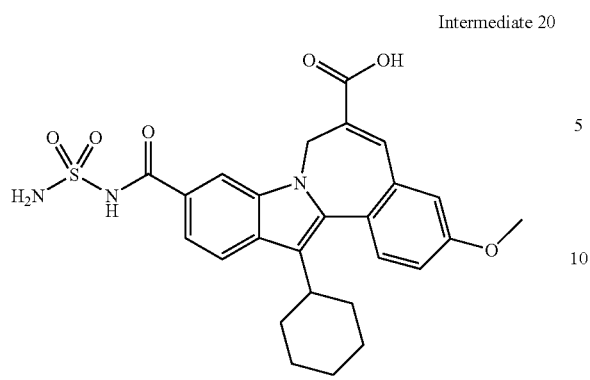

10-((Aminosulfonyl)carbamoyl)-13-cyclohexyl-3-methoxy-7H-indolo[2,1-a][2]benzazepine-6-carboxylic acid. Methyl 10-((aminosulfonyl)carbamoyl)-13-cyclohexyl-3-methoxy-7H-indolo[2,1-a][2]benzazepine-6-carboxylate (725 mg, 1.39 mmol) was dissolved into MeOH//THF (1:1, 16 mL) and treated with 1M aqueous NaOH (3 mL). The reaction mixture was stirred and heated at 60° C. for 0.5 h and cooled to rt. The reaction solution was diluted with MeOH/H$_2$O (2:1, 15 mL), neutralized with 1M aqueous HCl (3 mL) and concentrated to remove organic solvents. The resultant solids were collected by filtration, washed with H$_2$O and dried under vacuum to yield 10-((aminosulfonyl)carbamoyl)-13-cyclohexyl-3-methoxy-7H-indolo[2,1-a][2]benzazepine-6-carboxylic acid (650 g, 1.3 mmol, 92%) as a bright yellow solid which was used without further purification. $^1$HNMR (300 MHz, CDCl$_3$) δ 1.16-2.22 (m, 10H), 2.82-2.96 (m, 1H), 3.94 (s, 3H), 4.07-4.29 (m, 1H), 5.57-5.80 (m, 1H), 7.14-7.23 (m, 2H), 7.55-7.63 (m, 2H), 7.88-7.94 (m 2H), 8.18 (s, 1H). LCMS: m/e 510 (M+H)$^+$, ret time 2.85 min, column B, 4 minute gradient.

EXAMPLE 1

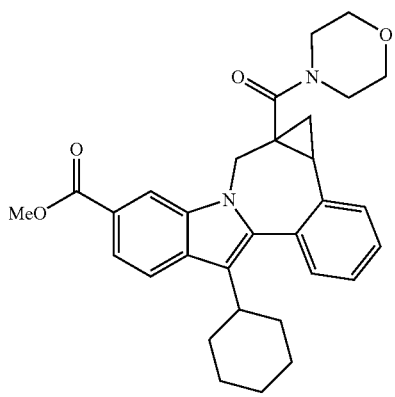

(+/−) 8-Cyclohexyl-1,1a,2,12b-tetrahydro-1a-(4-morpholinylcarbonyl)-cycloprop[d]indolo[2,1-a][2]benzazepine-5-carboxylic acid, methyl ester. Trimethylsulfoxonium iodide (660 mg, 3.0 mmol) was added to a suspension of NaH (124 mg in 60% oil dispersion, 3.1 mmol) in DMSO (20 mL). The reaction mixture was stirred at rt for 15 min., after which a solution of 13-cyclohexyl-6-(4-morpholinylcarbonyl)-7H-indolo[2,1-a][2]benzazepine-10-carboxylic acid, methyl ester (484 mg, 1.0 mmol) in DMSO (10 mL) was added. The reaction was then stirred at rt. for 3 hr. and then at 50° C. overnight. The reaction was quenched by the addition of water, whereupon an off-white precipitate formed which was collected by filtration. This material was then purified by preparative reverse phase HPLC to afford the product as a light yellow solid. (330 mg, 66% yield). MS m/z 499 (MH$^+$), Retention time: 3.818 min.

EXAMPLE 2

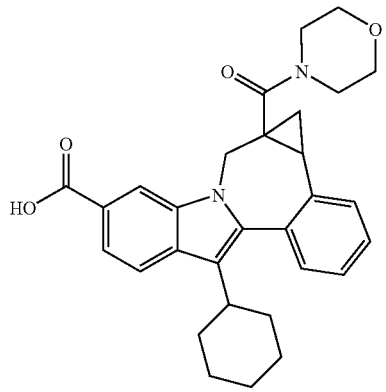

(+/−)-8-cyclohexyl-1,1a,2,12b-tetrahydro-1a-(4-morpholinylcarbonyl)-cycloprop[d]indolo[2,1-a][2]benzazepine-5-carboxylic acid. To a solution of (+/−)-8-cyclohexyl-1,1a,2,12b-tetrahydro-1a-(4-morpholinylcarbonyl)-cycloprop[d]indolo[2,1-a][2]benzazepine-5-carboxylic acid, methyl ester (235 mg, 0.471 mmol) in a THF/Methanol mixture (6.0 mL/6.0 mL), 2N NaOH solution (2.0 mL) was added. The reaction mixture was heated at 90° C. under microwave conditions for 15 min. It was then concentrated, acidified with 1N HCl solution and extracted with ethyl acetate (2×50 mL). The organic layers were combined, dried (MgSO$_4$), filtered and concentrated under reduced pressure. The residue was then purified by reverse phase preparative HPLC to give the product as an off-white solid, (165 mg, 72% yield). MS m/z 499 (MH$^+$), Retention time: 3.663 min; $^1$H NMR (500 MHz, CD$_3$OD) δ ppm. Compound was observed to exist as inter-converting rotamers, as evidenced from the compound's NMR spectrum.

EXAMPLES 3 AND 4

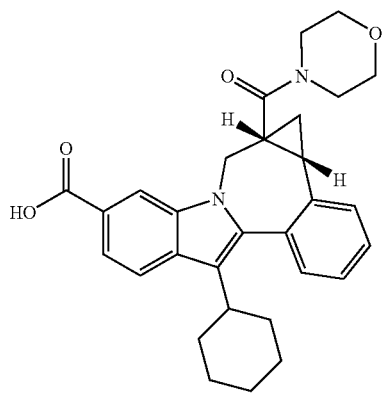

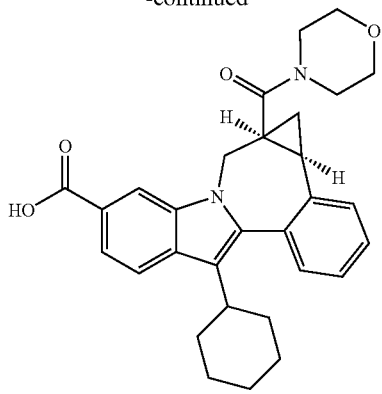

(+) 8-Cyclohexyl-1,1a, 2,12b-tetrahydro-1a-(4-morpholinylcarbonyl)-cycloprop[d]indolo[2,1-a][2]benzazepine-5-carboxylic acid, and (−) 8-cyclohexyl-1,1a,2,12b-tetrahydro-1a-(4-morpholinylcarbonyl)-cycloprop[d]indolo[2,1-a][2]benzazepine-5-carboxylic acid. (Only relative stereochemistry implied). Using the chiral reverse phase preparative HPLC procedure provided below, a racemic sample of (+/−) 8-cyclohexyl-1,1a,2,12b-tetrahydro-1a-(4-morpholinylcarbonyl)-cycloprop[d]indolo[2,1-a][2]benzazepine-5-carboxylic acid was resolved to provide samples of each of the enantiomers present. Method details: Chiralpak AD semiprep column, 20×250 mm, 10 μm; Mobile Phase: 0.05% TFA/EtOH; Temp: ambient; Flow rate: 7.0 mL/min. for 45 min; UV monitored @ 213 nm; Injection: 2 mL of ~15 mg/mL in ethanol.

EXAMPLE 5

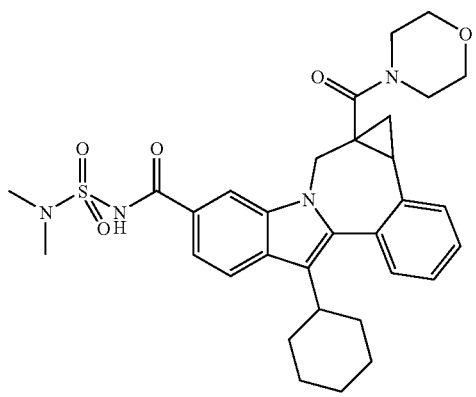

(+/−) 8-cyclohexyl-N-[(dimethylamino)sulfonyl]-1,1a,2,12b-tetrahydro-1a-(4-morpholinylcarbonyl)-cycloprop[d]indolo[2,1-a][2]benzazepine-5-carboxamide. A 2M solution of oxalyl chloride (0.093 mL, 0.186 mmol) in $CH_2Cl_2$ was added dropwise to a solution of (+/−)-8-cyclohexyl-1,1a,2,12b-tetrahydro-1a-(4-morpholinylcarbonyl)-cycloprop[d]indolo[2,1-a][2]benzazepine-5-carboxylic acid (45 mg, 0.093 mmol) in $CH_2Cl_2$ (10 mL), containing one drop of DMF. The reaction mixture was stirred at rt. for 2 hr., after which it was concentrated and dried under high vacuum. The residue was subsequently dissolved in THF (10 mL) and a solution of N,N-dimethylsulfonamide, (23 mg, 0.186 mmol) and DIPEA (0.049 mL, 0.279 mmol)) in THF (2 mL) was added. This was followed by the addition of DMAP (10 mg), after which the reaction was stirred at rt. for 10 min., and then at 50° C. overnight. It was then cooled, and the mixture concentrated under reduced pressure. The resultant residue was purified by preparative reverse phase HPLC to afford the product as a yellow solid, (5.0 mg, 9% yield). MS m/z 591 (MH+), Retention time: 3.525 min; $^1$H NMR (300 MHz, $CD_3OD$) δ ppm. Compound was observed to exist as interconverting rotamers, as evidenced from the compound's NMR spectrum.

EXAMPLE 6

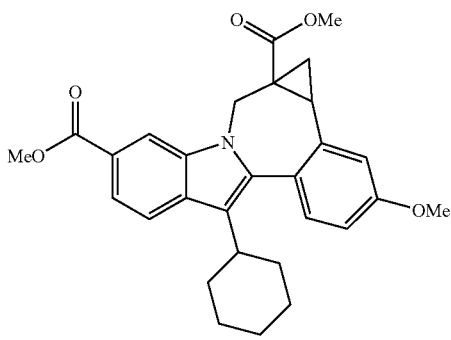

(+/−) 8-Cyclohexyl-1,12b-dihydro-11-methoxy-cycloprop[d]indolo[2,1-a][2]benzazepine-1a,5(2H)-dicarboxylic acid, dimethyl ester. Trimethylsulfoxonium iodide (1.44 g, 6.528 mmol) was added to a suspension of NaH (162 mg as 60% oil dispersion, 6.746 mmol) in DMSO (30 mL), and the reaction was stirred at rt for 30 min. A solution of 13-cyclohexyl-3-methoxy-7H-indolo[2,1-a][2]benzazepine-6,10-dicarboxylic acid, dimethyl ester (1.0 g, 2.176 mmol) in DMSO (10 mL) was then added, and the resultant mixture was stirred at rt. for 2 hr, and then at 50° C. overnight. The reaction was subsequently quenched by the addition of water, after which an off-white precipitate formed which was collected by filtration. This material was then purified using silica gel flash chromatography using hexanes to 25% ethyl acetate in hexanes as eluent. Homogeneous fractions where combined and evaporated in vacuo to give the product as an off-white solid, (815 mg, 79% yield). MS m/z 474 (MH+), Retention time: 4.161 min.

EXAMPLE 7

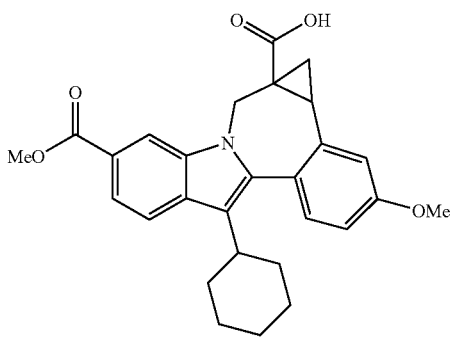

(+/−) 8-cyclohexyl-1,12b-dihydro-11-methoxy-cycloprop[d]indolo[2,1-a][2]benzazepine-1a,5(2H)-dicarboxylic acid, 5-methyl ester. To a solution of (+/−)-8-cyclohexyl-1,12b-dihydro-11-methoxy-cycloprop[d]indolo[2,1-a][2]benzazepine-1a,5(2H)-dicarboxylic acid, dimethyl ester (800, 1.69 mmol) in THF (25 mL), a 1M solution of n-$Bu_4NOH$ (2.5 mL, 2.5 mmol) in methanol was added. The reaction mixture was stirred at rt. for three days and then heated at 40° C. for 3 hr. It was concentrated, acidified with 1N HCl solution and extracted with ethyl acetate (2×30 mL). The organic layers were combined, dried ($MgSO_4$), filtered and concentrated under reduced pressure to give the product as a light-yellow colored solid, (750 mg, 97% yield). MS m/z 460 (MH+), Retention time: 4.001 min; $^1$H NMR (300 MHz, CD$_3$OD) δ ppm. Compound was observed to exist as inter-converting rotamers, as evidenced from the compound's NMR spectrum.

EXAMPLE 8

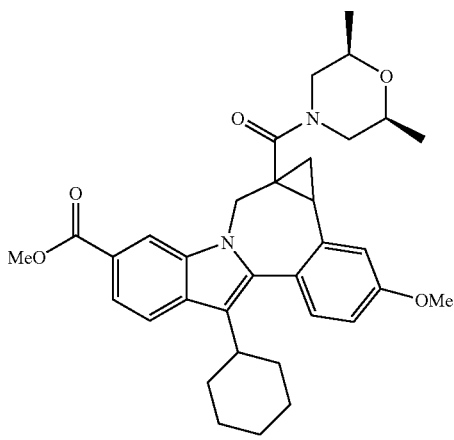

8-Cyclohexyl-1a-[[2,6-dimethyl-4-morpholinyl]carbonyl]-1,1a,2,12b-tetrahydro-11-methoxy-cycloprop[d]indolo[2,1-a][2]benzazepine-5-carboxylic acid, methyl ester. TBTU (105 mg, 0.326 mmol) and DIPEA (0.19 mL, 1.09 mmol) were added to a solution of (+/−)-8-cyclohexyl-1,12b-dihydro-11-methoxy-cycloprop[d]indolo[2,1-a][2]benzazepine-1a,5(2H)-dicarboxylic acid, 5-methyl ester (100 mg, 0.218 mmol) in DMSO (2.0 mL). The mixture was stirred at rt for 15 min. after which, cis-2,6-dimethylmorpholine (37.5 mg, 0.326 mmol) was added and the reaction was then stirred at rt. overnight. The resultant mixture was then concentrated and the residue purified by preparative reverse phase HPLC to give the title compound as a white solid, (76 mg, 63% yield). MS m/z 557 (MH$^+$), Retention time: 3.941 min; $^1$H NMR (500 MHz, CD$_3$OD) δ ppm. Compound was observed to exist as inter-converting rotamers, as evidenced from the compound's NMR spectrum.

EXAMPLE 9

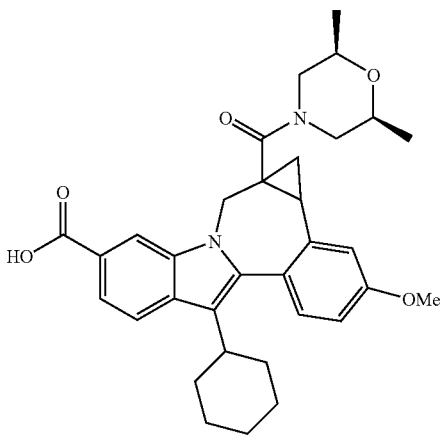

(+/−)-8-Cyclohexyl-1a-[[(cis)-2,6-dimethyl-4-morpholinyl]carbonyl]-1,1a,2,12b-tetrahydro-11-methoxy-cycloprop[d]indolo[2,1-a][2]benzazepine-5-carboxylic acid. A 2M NaOH solution (1.0 mL) was added to a solution of, rel-8-cyclohexyl-1a-[[(cis)-2,6-dimethyl-4-morpholinyl]carbonyl]-1,1a,2,12b-tetrahydro-11-methoxy-cycloprop[d]indolo[2,1-a][2]benzazepine-5-carboxylic acid, methyl ester (73 mg, 0.131 mmol) in a THF/Methanol mixture (2.0 mL/2.0 mL). The reaction was heated at 90° C. under microwave conditions for 10 min. It was then concentrated, acidified with 1N HCl solution and extracted with ethyl acetate (2×20 mL). The organic layers were combined, dried (MgSO$_4$), filtered and concentrated under reduced pressure to give the title compound as a light yellow colored solid, (70 mg, 98% yield). MS m/z 543 (MH$^+$), Retention time: 3.808 min; $^1$H NMR (500 MHz, CD$_3$OD) δ ppm. Compound was observed to exist as inter-converting rotamers, as evidenced from the compound's NMR spectrum.

EXAMPLE 10

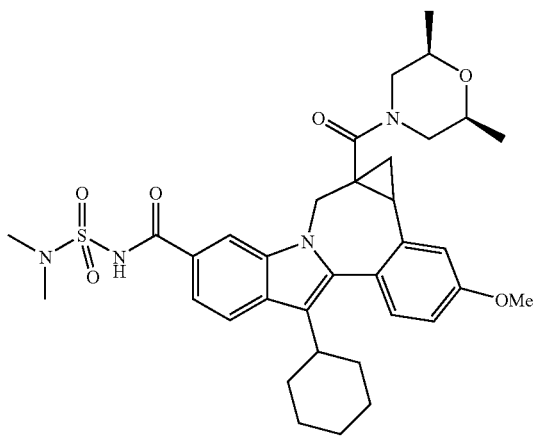

8-cyclohexyl-N-[(dimethylamino)sulfonyl]-1,1a,2,12b-tetrahydro-1a-[[(cis)-2,6-dimethyl-4-morpholinyl]carbonyl]-cycloprop[d]indolo[2,1-a][2]benzazepine-5-carboxamide. A 2M solution of oxalyl chloride (0.1 mL, 0.2 mmol) in CH$_2$Cl$_2$ was added dropwise to a solution of rel-8-cyclohexyl-1a-[[(cis)-2,6-dimethyl-4-morpholinyl]carbonyl]-1,1a,2,12b-tetrahydro-11-methoxy-cycloprop[d]indolo[2,1-a][2]benzazepine-5-carboxylic acid (54 mg, 0.1 mmol) in CH$_2$Cl$_2$ (10 mL) containing one drop of DMF. The reaction mixture was stirred at rt. for 2 h, after which it was concentrated and dried under high vacuum. The resultant residue was dissolved in THF (10 mL) and a solution of N,N-dimethylsulfonamide (24.8 mg, 0.2 mmol) and DIPEA (0.052 mL, 0.3 mmol)) in THF (2 mL) was added. This was followed by the addition of DMAP (10 mg), after which the reaction mixture was stirred at rt. for 10 min, and then at 50° C. overnight. It was then concentrated and the residue purified by preparative reverse phase HPLC to afford the title compound as a white solid, (19.0 mg, 31% yield). MS m/z 649 (MH$^+$), Retention time: 3.685 min; $^1$H NMR (500 MHz, CD$_3$OD) δ ppm. Compound was observed to exist as inter-converting rotamers, as evidenced from the compound's NMR spectrum.

EXAMPLE 11

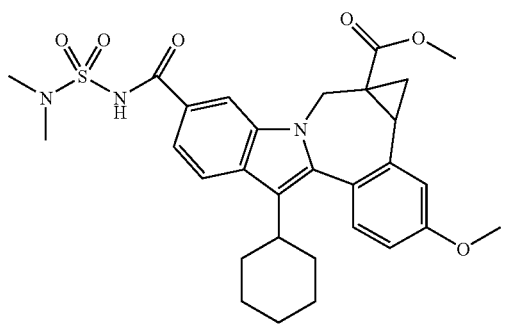

(+/−) Cycloprop[d]indolo[2,1-a][2]benzazepine-5-carboxylic acid, 8-cyclohexyl-1,1a,2,12b-tetrahydro-11-methoxy-1a-[(4-morpholinylcarbonyl)amino]-methyl ester. To slurry of sodium hydride (60% dispersion in mineral oil, 870 mg, 22 mmol) in DMSO (18 mL) stirring under $N_2$ was added trimethylsulfoxonium iodide (4.8 g, 22 mmol). The reaction mixture was stirred for 30 min and then methyl 13-cyclohexyl-N-[(dimethylamino)sulfonyl]-3-methoxy-7H-indolo[2,1-a][2]benzazepine-6-carboxylate-10-carboxamide (5.0 g, 9.1 mmol) in DMSO (20 mL) was added (flask rinsed with DMSO (2×6 mL)). The reaction mixture was stirred 10 min, poured into 0.1N HCl (225 mL), stirred 30 min and the solids were collected by filtration. The solids were dissolved into $CH_2Cl_2$ (120 mL) washed with $H_2O$ (50 mL), dried ($MgSO_4$), filtered and concentrated to dryness. The residue was purified by silica gel chromatography (Biotage Horizon, 40S, 0-5% MeOH/$CH_2Cl_2$) and the purified material was concentrated to dryness, dissolved into $Et_2O$ (50 mL) and crashed out with hexanes (50 mL). The slurry was stirred for 2 h and then the solids were collected by filtration to yield the product as a light yellow solid, (3.3 g, 5.9 mmol, 65%). Mixture of atrope isomers. $^1$HNMR (300 MHz, $CDCl_3$) δ 8.63 (s, 0.55H), 8.56 (s, 0.45H), 8.19 (d, J=1.5 Hz, 0.55H), 7.96 (d, J=1.1 Hz, 0.45H), 7.84 (d, J=8.4 Hz, 0.45H), 7.83 (d, J=8.4 Hz, 0.55H), 7.43-7.34 (m, 1H), 7.25 (d, J=8.4 Hz, 0.45H), 7.23 (d, J=8.4 Hz, 0.55H), 7.11 (d, J=2.6 Hz, 0.55H), 7.00 (d, J=2.6 Hz, 0.45H), 6.94-6.86 (m, 1H), 5.39 (d, J=15.0 Hz, 0.55H), 5.15 (d, J=15.0 Hz, 0.45H), 4.06 (d, J=15.0 Hz, 0.45H), 3.87 (s, 3H), 3.79 (s, 1.35H), 3.52 (s, 1.65H), 3.41 (d, J=15.0 Hz, 0.55H), 3.05 (s, 6H), 2.97-2.58 (m, 2H), 2.10-1.13 (m, 11.55H), 0.36 (t, J=6.2 Hz, 0.45H). LCMS: m/e 564 (M−H)⁻, ret time 3.11 min, column A, 4 minute gradient.

EXAMPLE 12

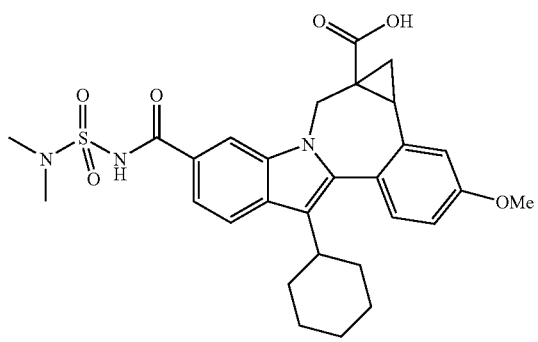

(+/−) Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-. To a solution of (+/−) Cycloprop[d]indolo[2,1-a][2]benzazepine-5-carboxylic acid, 8-cyclohexyl-1,1a,2,12b-tetrahydro-11-methoxy-1a-[(4-morpholinylcarbonyl)amino]-methyl ester (100 mg, 0.177 mmol) in THF/Methanol mixture (2.0 mL/2.0 mL), 2N NaOH solution (1.0 mL) was added. The reaction mixture was heated at 90° C. under microwave conditions for 5 min. It was then concentrated, acidified with 1N HCl solution and extracted with ethyl acetate (2×20 mL). The organic layers were combined, dried ($MgSO_4$), filtered and concentrated. The residue was purified by Prep. HPLC to afford the desired product as a light yellow solid, (59 mg, 60% yield). MS m/z 552 (MH⁺), Retention time: 3.850 min. 1H NMR (300 MHz, MeOD) δ ppm 0.25 (m, 0.38H) 1.14-2.22 (m, 11.62H) 2.69-2.98 (m, 2H) 3.02 (s, 2.28H) 3.02 (s, 3.72H) 3.41 (d, J=15.00 Hz, 0.62H) 3.88 (s, 3H) 4.01 (d, J=15.00 Hz, 0.38H) 5.26 (d, J=15.00 Hz, 0.38H) 5.45 (d, J=14.64 Hz, 0.62H) 6.94-7.02 (m, 1H) 7.13 (d, J=2.56 Hz, 0.38H) 7.21 (d, J=2.20 Hz, 0.62H) 7.26 (d, J=8.42 Hz, 0.62H) 7.30 (d, J=8.78 Hz, 0.38H) 7.53 (dd, J=8.42, 1.46 Hz, 0.62H) 7.61 (dd, J=8.60, 1.65 Hz, 0.38H) 7.85 (d, J=8.42 Hz, 0.62H) 7.89 (d, J=8.42 Hz, 0.38H) 8.10 (s, 0.38H) 8.28 (d, J=1.46 Hz, 0.62H).

EXAMPLE 13

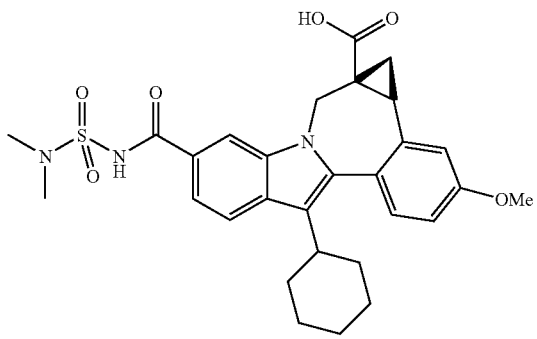

Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-, (1aR)-[partial]-. 10 N NaOH (2.0 mL, 20 mmol) solution and 4 mL of water were added to a solution of cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R,3S)-3-hydroxy-4,7,7-trimethylbicyclo[2.2.1]hept-2-yl]-11-methoxy-, (1aR)-[partial]-(160 mg, 0.228 mmol) in THF/MeOH (7 mL/7 mL). The reaction mixture was heated at 120° C. under microwave conditions for 1 hr. It was then concentrated, acidified with conc. HCl solution and extracted with ethyl acetate twice (2×30 mL). The organic layers were combined, dried ($MgSO_4$), filtered and concentrated in vacuo to an orange oil. The crude product was then purified by Prep. HPLC column to afford the product a light yellow solid, (80 mg, 64% yield). Average specific rotation −130.85°. Solvent MeOH; Wavelength 589 nm; 50 cm cell. MS m/552 (MH⁺), Retention time: 3.760 min. 1H NMR (500 MHz, MeOD) δ ppm 0.27 (m, 0.38H) 1.14-2.22 (m, 11.62H) 2.76 (m, 0.38H) 2.80-2.92 (m, 1H) 2.92-3.09 (m, 6.62H) 3.45 (d, J=14.95 Hz, 0.62H) 3.90 (s, 1.86H) 3.91 (s, 1.14H) 4.04 (d, J=15.26 Hz, 0.38H) 5.28 (d, J=15.26 Hz, 0.38H) 5.47 (d, J=15.26 Hz, 0.62H) 6.95-7.05 (m, 1H) 7.15 (d, J=2.75 Hz, 0.38H) 7.23 (d, J=1.83 Hz, 0.62H) 7.28 (d, J=8.55 Hz, 0.62H) 7.33 (d, J=8.54 Hz, 0.38H) 7.54 (dd, J=8.39, 1.68 Hz, 0.62H) 7.63 (dd, J=8.55, 1.53 Hz, 0.38H) 7.86 (d, J=8.55 Hz, 0.62H) 7.91 (d, J=8.55 Hz, 0.38H) 8.11 (d, J=1.22 Hz, 0.62H) 8.29 (d, J=1.22 Hz, 0.38H). The product was observed to exist as inter-converting rotamers, as evidenced from the compound's NMR spectrum.

EXAMPLE 14

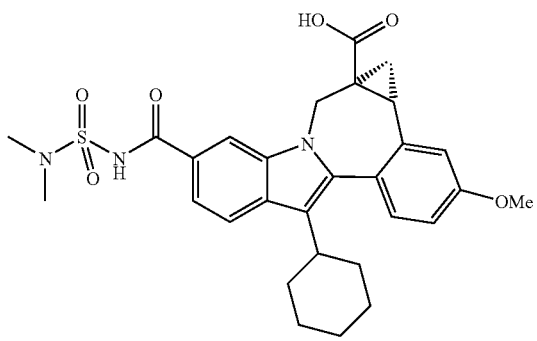

Cycloprop[d]indolo[2,1-a][2]benzazepine-1a(2H)-carboxylic acid, 8-cyclohexyl-5-[[[(dimethylamino)sulfonyl]

amino]carbonyl]-1,12b-dihydro-11-methoxy-, (1aS)-[partial]-. 10 N NaOH (1.8 mL, 18 mmol) solution and 4 mL of water were added to a solution of cycloprop[d]indolo[2,1-a][2]benzazepine-1a,5(2H)-dicarboxamide, 8-cyclohexyl-$N^5$-[(dimethylamino)sulfonyl]-1,12b-dihydro-$N^{1a}$-[(2R,3S)-3-hydroxy-4,7,7-trimethylbicyclo[2.2.1]hept-2-yl]-11-methoxy-, (1 aS)-[partial]-(130 mg, 0.185 mmol) in THF/MeOH (7 mL/7 mL). The reaction mixture was heated at 120° C. under microwave conditions for 1 hr. It was concentrated, acidified with conc. HCl solution and extracted with ethyl acetate twice (2×30 mL). The organic layers were combined, dried ($MgSO_4$), filtered and concentrated in vacuo to give an orange oil. The crude product was then purified by Prep. HPLC column to afford the product as a light yellow solid, (68 mg, 67% yield). MS m/552 ($MH^+$), Retention time: 3.773 min. 1H NMR (500 MHz, MeOD) δ ppm 0.27 (m, 0.38H) 1.14-2.22 (m, 11.62H) 2.76 (m, 0.38H) 2.80-2.92 (m, 1H) 2.92-3.09 (m, 6.62H) 3.45 (d, J=14.95 Hz, 0.62H) 3.90 (s, 1.86H) 3.91 (s, 1.14H) 4.04 (d, J=15.26 Hz, 0.38H) 5.28 (d, J=15.26 Hz, 0.38H) 5.47 (d, J=15.26 Hz, 0.62H) 6.95-7.05 (m, 1H) 7.15 (d, J=2.75 Hz, 0.38H) 7.23 (d, J=1.83 Hz, 0.62H) 7.28 (d, J=8.55 Hz, 0.62H) 7.33 (d, J=8.54 Hz, 0.38H) 7.54 (dd, J=8.39, 1.68 Hz, 0.62H) 7.63 (dd, J=8.55, 1.53 Hz, 0.38H) 7.86 (d, J=8.55 Hz, 0.62H) 7.91 (d, J=8.55 Hz, 0.38H) 8.11 (d, J=1.22 Hz, 0.62H) 8.29 (d, J=1.22 Hz, 0.38H). The product was observed to exist as inter-converting rotamers, as evidenced from the compound's NMR spectrum.

EXAMPLE 15

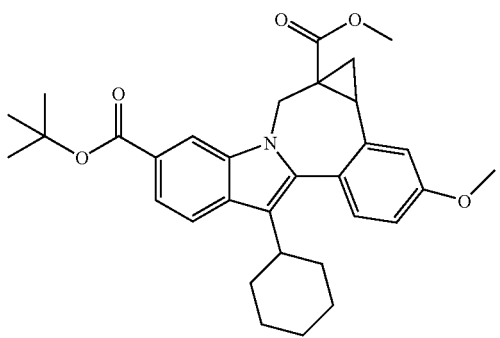

(+/−) Cycloprop[d]indolo[2,1-a][2]benzazepine-1a,5(2H)-dicarboxylic acid, 8-cyclohexyl-1,12b-dihydro-11-methoxy-, 5-(1,1-dimethylethyl) 1a-methyl ester. Sodium hydride (96 mg, 4 mmol) was added to a stirred suspension of trimethylsulfoxonium chloride (567 mg, 4.4 mmol) in anhydrous DMSO (10 mL) under nitrogen. The resultant mixture was stirred at rt for 30-45 min and then neat 7H-indolo[2,1-a][2]benzazepine-6,10-dicarboxylic acid, 13-cyclohexyl-3-methoxy-, 10-(1,1-dimethylethyl)6-methyl ester (1.0, 2 mmol) was added in small portions. The suspension was diluted with DMSO (5 mL) and heated at 50° C. for 3-4 h. The reaction mixture was allowed to cool to rt and water was added. A solid separated, which was collected by filtration and washed with water and then air dried overnight to afford 1.15 g of crude product. This material was purified by flash column chromatography (silica gel, 3% MeOH in DCM) to provide pure title compound (0.96 g): LC/MS: Retention time 3.816 min; m/e 516 ($MH^+$). $^1$H NMR (400 MHz, $CDCl_3$): The product was observed to exist as inter-converting rotamers, as evidenced from the compound's NMR spectrum.

EXAMPLE 16

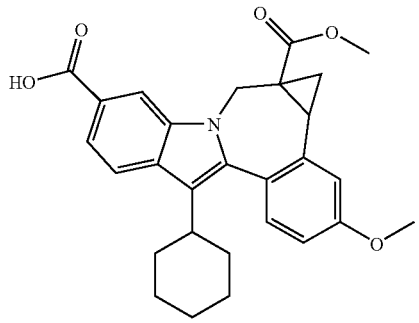

(+/−)-8-cyclohexyl-11-(methyloxy)-1a-((methyloxy)carbonyl)-1,1a,2,12b-tetrahydrocyclopropa[d]indolo[2,1-a][2]benzazepine-5-carboxylic acid. (+/−)-5-(1,1-Dimethylethyl) 1a-methyl 8-cyclohexyl-11-(methyloxy)-1,12b-dihydrocyclopropa[d]indolo[2,1-a][2]benzazepine-1a,5(2H)-dicarboxylate (0.60 g, 1.16 mMol) was dissolved in 1,2-dichloroethane (10 mL) and trifluoroacetic acid (10 mL) added and the reaction stirred at room temperature under nitrogen and monitored by HPLC until complete. Volatiles were removed in vacuo and benzene added to the residue azeotrope removal of trifluoroacetic acid in vacuo to yield product as a yellow foam. $^1$H NMR (500 MHz, CHLOROFORM-D) δ ppm 0.34-0.48 (m, 0.4H) 0.91 (s, 0.4H) 1.17-1.33 (m, 2H) 1.32-1.49 (m, 3H) 1.58 (d, J=13.12 Hz, 0.5H) 1.64-1.86 (m, 3.5H) 1.87-2.16 (m, 4.5H) 2.59-2.70 (m, 0.4H) 2.79 (t, J=12.51 Hz, 0.4H) 2.84-2.99 (m, 1.3H) 3.45 (d, J=15.26 Hz, 0.6H) 3.58 (d, J=1.53 Hz, 1.7H) 3.81 (d, J=1.53 Hz, 1.2H) 3.83-3.95 (m, 3H) 4.09 (d, J=15.26 Hz, 0.4H) 5.21 (d, J=14.95 Hz, 0.4H) 5.45 (d, J=14.95 Hz, 0.6H) 6.88-6.97 (m, 1H) 7.02 (d, J=2.44 Hz, 0.4H) 7.14 (s, 0.6H) 7.26-7.33 (m, 1H) 7.74-7.92 (m, 2H) 8.21 (s, 0.4H) 8.43 (s, 0.6H); MS m/z 460 ($MH^+$).

EXAMPLE 17

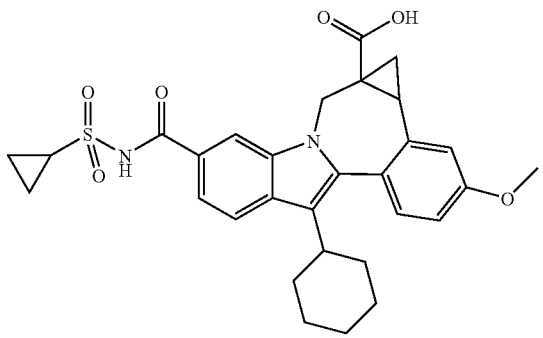

(+/−) 8-cyclohexyl-5-(cyclopropylsulfonylcarbamoyl)-1,1a,2,12b-tetrahydro-11-methoxy-cycloprop[d]indolo[2,1-a][2]benzazepine-1a-carboxylic acid. A mixture of (+/−) 8-cyclohexyl-1,1a,2,12b-tetrahydro-11-methoxy-1a-(methoxycarbonyl)-cycloprop[d]indolo[2,1-a][2]benzazepine-5-carboxylic acid (1 equiv), and carbonyldiimidazole (1.5 equiv) in anhydrous THF was heated at 50° C. for 30 min and allowed to cool to rt. Then 1 equiv of cyclopropanesulfonamide and 1,8-diazabicyclo[5.4.0]undec-7-ene (2 equiv) were added consecutively. The resultant mixture was stirred at rt overnight. After acidic aqueous workup, the isolated crude product was purified by prep. HPLC. The intermediate ester was then hydrolyzed using 1N NaOH in THF-MeOH to afford the title compound.

EXAMPLE 18

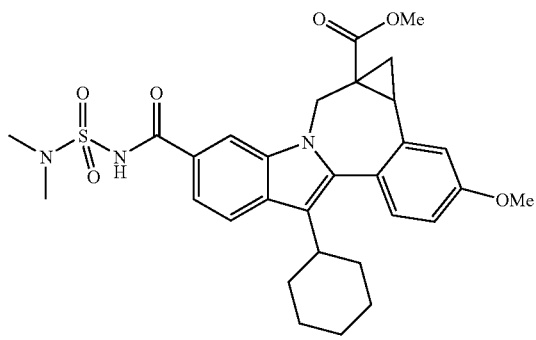

(+/−) Cycloprop[d]indolo[2,1-a][2]benzazepine-5-carboxylic acid, 8-cyclohexyl-1,1a,2,12b-tetrahydro-11-methoxy-1a-[(4-morpholinylcarbonyl)amino]-methyl ester. To a mixture of trimethylsulfoxonium iodide (199 mg, 0.906 mmol) and NaH (38 mg in 60% oil dispersion, 0.953 mmol) in a round-bottomed flask, DMSO (5 mL) was added. The reaction mixture was stirred at rt for 0.5 hr. Then 7H-Indolo[2,1-a][2]benzazepine-6-carboxylic acid, 13-cyclohexyl-10-[[[(dimethylamino)sulfonyl]amino]carbonyl]-3-(methoxy)-, methyl ester (125 mg, 0.227 mmol) was added. The reaction mixture was stirred at rt. for 3 hr. Then it was heated at 50° C. for 3 hr. The reaction was quenched with water and acidified with 1N HCl solution. A light yellow solid was collected as crude product. (106 mg, 83% yield) 6 mg of crude product was then purified by Prep. HPLC column to afford a light yellow solid as pure racemic compound. (1.8 mg). MS m/z 566 (MH$^+$), Retention time: 3.850 min. 1H NMR (500 MHz, MeOD) δ ppm 0.28 (m, 0.36H) 1.19-2.20 (m, 11.64H) 2.70-3.02 (m, 2H) 3.03 (s, 2.16H) 3.05 (s, 3.84H) 3.49 (d, J=15.26 Hz, 0.64H) 3.54 (s, 1.92H) 3.83 (s, 1.08H) 3.91 (s, 3H) 4.08 (d, J=15.26 Hz, 0.36H) 5.29 (d, J=15.26 Hz, 0.36H) 5.50 (d, J=14.95 Hz, 0.64H) 6.98-7.06 (m, 1H) 7.16 (d, J=2.44 Hz, 0.36H) 7.23 (d, J=2.44 Hz, 0.64H) 7.30 (d, J=8.55 Hz, 0.64H) 7.34 (d, J=8.55 Hz, 0.36H) 7.56 (dd, J=8.55, 1.53 Hz, 0.64H) 7.63 (dd, J=8.55, 1.53 Hz, 0.36H) 7.88 (d, J=8.55 Hz, 0.64H) 7.91 (d, J=8.55 Hz, 0.36H) 8.12 (s, 0.36H) 8.33 (d, J=1.53 Hz, 0.64H). The product was observed to exist as inter-converting rotamers, as evidenced from the compound's NMR spectrum.

EXAMPLE 19

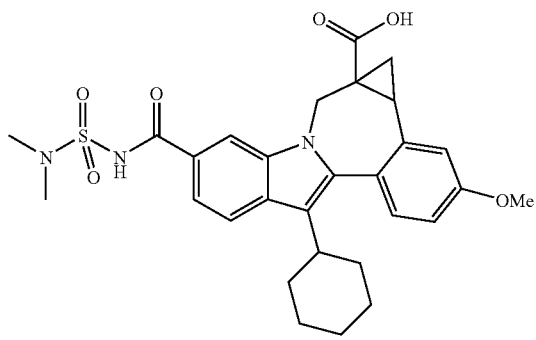

(+/−) Cycloprop[d]indolo[2,1-a][2]benzazepine-5-carboxylic acid, 8-cyclohexyl-1,1a,2,12b-tetrahydro-11-methoxy-1a-[(4-morpholinylcarbonyl)amino]-. To a solution of (+/−) Cycloprop[d]indolo[2,1-a][2]benzazepine-5-carboxylic acid, 8-cyclohexyl-1,1a,2,12b-tetrahydro-11-methoxy-1a-[(4-morpholinylcarbonyl)amino]-methyl ester (100 mg, 0.177 mmol) in THF/Methanol mixture (2.0 mL/2.0 mL), 2N NaOH solution (1.0 mL) was added. The reaction mixture was heated at 90° C. under microwave condition for 5 min. Then it was concentrated, acidified with 1N HCl solution and extracted with ethyl acetate (2×20 mL). The organic layers were combined, dried (MgSO$_4$) and concentrated. The residue was purified by Prep. HPLC to afford a light yellow solid as final product. (59 mg, 60% yield). MS m/z 552 (MH$^+$), Retention time: 3.850 min. 1H NMR (300 MHz, MeOD) δ ppm 0.25 (m, 0.38H) 1.14-2.22 (m, 11.62H) 2.69-2.98 (m, 2H) 3.02 (s, 2.28H) 3.02 (s, 3.72H) 3.41 (d, J=15.00 Hz, 0.62H) 3.88 (s, 3H) 4.01 (d, J=15.00 Hz, 0.38H) 5.26 (d, J=15.00 Hz, 0.38H) 5.45 (d, J=14.64 Hz, 0.62H) 6.94-7.02 (m, 1H) 7.13 (d, J=2.56 Hz, 0.38H) 7.21 (d, J=2.20 Hz, 0.62H) 7.26 (d, J=8.42 Hz, 0.62H) 7.30 (d, J=8.78 Hz, 0.38H) 7.53 (dd, J=8.42, 1.46 Hz, 0.62H) 7.61 (dd, J=8.60, 1.65 Hz, 0.38H) 7.85 (d, J=8.42 Hz, 0.62H) 7.89 (d, J=8.42 Hz, 0.38H) 8.10 (s, 0.38H) 8.28 (d, J=1.46 Hz, 0.62H). The product was observed to exist as inter-converting rotamers, as evidenced from the compound's NMR spectrum.

EXAMPLE 20

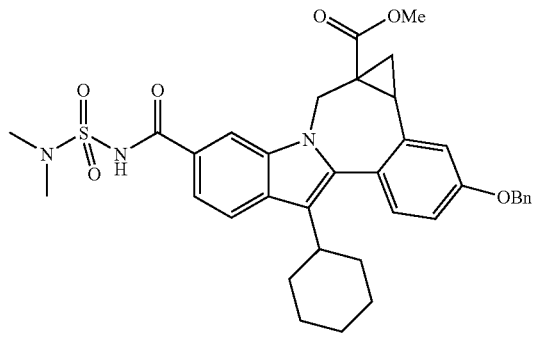

(+/−) Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-(phenylmethoxy)-, methyl ester. To a mixture of trimethylsulfoxonium iodide (687 mg, 3.122 mmol) and NaH (131 mg in 60% oil dispersion, 3.276 mmol) in a round-bottomed flask, DMSO (20 mL) was added. The reaction mixture was stirred at rt for 0.5 hr. Then 7H-Indolo[2,1-a][2]benzazepine-6-carboxylic acid, 13-cyclohexyl-10-[[[(dimethylamino)sulfonyl]amino]carbonyl]-3-(phenylmethoxy)-, methyl ester (490 mg, 0.78 mmol) was added. The reaction mixture was stirred at rt. for 3 hr. Then it was heated at 50° C. for overnight. The reaction was quenched with water and acidified with 1N HCl solution. A light yellow solid was collected as crude product. 10 mg of crude product was then purified by Prep. HPLC column to afford a yellow solid as pure racemic compound. (8.3 mg). MS m/z 642 (MH$^+$), Retention time: 4.085 min. 1H NMR (500 MHz, MeOD) δ ppm 0.27 (m, 0.35H) 1.18-2.20 (m, 11.65H) 2.73 (m, 0.35H) 2.79-3.01 (m, 1.65H) 3.03 (s, 2.1H) 3.05 (s, 3.9H) 3.47 (d, J=15.26 Hz, 0.65H) 3.53 (s, 1.95H) 3.82 (s, 1.05H) 4.07 (d, J=15.26 Hz, 0.35H) 5.19 (s, 2H) 5.28 (d, J=15.26 Hz, 0.35H) 5.48 (d, J=14.95 Hz, 0.65H) 7.04-7.12 (m, 1H) 7.23 (d, J=2.44 Hz, 0.35H) 7.25-7.38 (m, 2.65H) 7.39-7.45 (m, 2H) 7.48-7.52 (m, 2H) 7.56 (d, J=8.55 Hz, 0.65H) 7.63 (d, J=8.55 Hz, 0.35H) 7.87 (d, J=8.55 Hz, 0.65H) 7.91 (d, J=8.55 Hz, 0.35H) 8.11 (s, 0.35H) 8.32 (s, 0.65H).

The product was observed to exist as inter-converting rotamers, as evidenced from the compound's NMR spectrum.

EXAMPLE 21

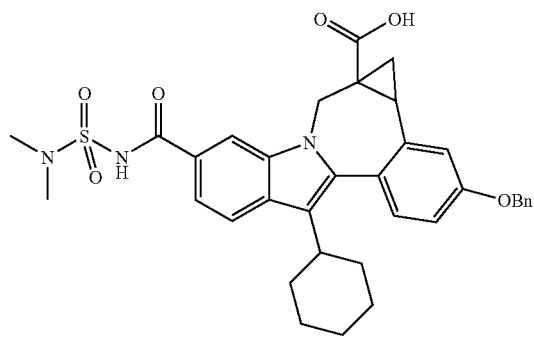

(+/−) Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-(phenylmethoxy)-.
To a solution of crude (+/−) Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-(phenylmethoxy)-, methyl ester in THF/Methanol mixture (8.0 mL/8.0 mL), 2N NaOH solution (4.0 mL) was added. The reaction mixture was heated at 85° C. under microwave condition for 10 min. Then it was concentrated and acidified with 1N HCl solution. A light orange solid was collected as crude acid. (480 mg, 98% yield) 10 mg of crude product was then purified by Prep. HPLC column to afford a light yellow solid as pure racemic compound. (8.5 mg). MS m/z 628 (MH+), Retention time: 4.055 min. 1H NMR (500 MHz, MeOD) δ ppm 0.28 (m, 0.38H) 1.17-2.23 (m, 11.62H) 2.76 (m, 0.38H) 2.81-2.91 (m, 1H) 2.93-3.01 (m, 0.62H) 3.03 (s, 2.28H) 3.04 (s, 3.72H) 3.46 (d, J=14.96 Hz, 0.62H) 4.06 (d, J=15.26 Hz, 0.38H) 5.21 (s, 2H) 5.29 (d, J=15.26 Hz, 0.38H) 5.48 (d, J=14.95 Hz, 0.62H) 7.05-7.12 (m, 1H) 7.24 (d, J=2.44 Hz, 0.38H) 7.27-7.39 (m, 2.62H) 7.39-7.46 (m, 2H) 7.48-7.57 (m, 2.62H) 7.63 (dd, J=8.55, 1.22 Hz, 0.38H) 7.87 (d, J=8.55 Hz, 0.62H) 7.91 (d, J=8.54 Hz, 0.38H) 8.12 (s, 0.38H) 8.30 (s, 0.62H).

EXAMPLE 22

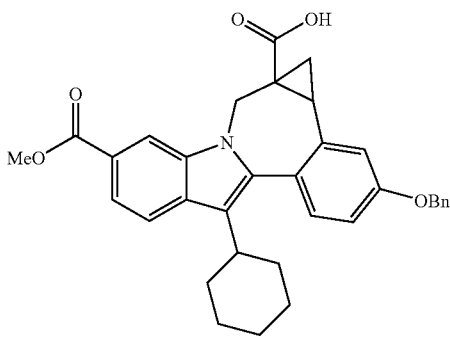

(+/−) Cycloprop[d]indolo[2,1-a][2]benzazepine-1a,5(2H)-dicarboxylic acid, 8-cyclohexyl-1,12b-dihydro-11-(phenylmethoxy)-, 5-methyl ester. To a mixture of trimethylsulfoxonium iodide (1196 mg, 5.433 mmol) and NaH (225 mg in 60% oil dispersion, 5.614 mmol) in a round-bottomed flask, DMSO (20 mL) was added. The reaction mixture was stirred at rt for 0.5 hr. Then 7H-Indolo[2,1-a][2]benzazepine-6,10-dicarboxylic acid, 13-cyclohexyl-3-(phenylmethoxy)-, dimethyl ester (970 mg, 1.811 mmol) was added. The reaction mixture was stirred at rt. for 3 hr. Then it was heated at 50° C. for 2 days. The reaction was quenched with water and acidified with 1N HCl solution. A yellow solid was collected. (975 mg, 98% yield). MS m/z 550 (MH+), Retention time: 4.580 min.

To a solution of (+/−) cycloprop[d]indolo[2,1-a][2]benzazepine-1a,5(2H)-dicarboxylic acid, 8-cyclohexyl-1,12b-dihydro-11-(phenylmethoxy)-, di-methyl ester (210 mg, 0.382 mmol) in THF (10 mL), 1M solution of Bu4NOH (0.46 mL, 0.46 mmol) in methanol was added. The reaction mixture was heated at 40° C. for 3 hr. Then it was concentrated, acidified with 1N HCl solution and extracted with ethyl acetate (2×30 mL). The organic layers were combined, dried (MgSO4) and concentrated to give a brownish solid as product. (200 mg, 98% yield). MS m/z 536 (MH+), Retention time: 4.361 min. 1H NMR (300 MHz, MeOD) δ ppm 0.24 (m, 0.38H) 0.91 (m, 0.38H) 1.15-2.23 (m, 11.24H) 2.69-3.05 (m, 2H) 3.41 (d, J=15.00 Hz, 0.62H) 3.93 (s, 1.86H) 3.95 (s, 1.14H) 4.01 (d, J=15.01 Hz, 0.38H) 5.14-5.28 (m, 2.38H) 5.43 (d, J=15.00 Hz, 0.62H) 7.04 (d, J=2.56 Hz, 0.38H) 7.07 (d, J=1.83 Hz, 0.62H) 7.18-7.46 (m, 5H) 7.46-7.54 (m, 2H) 7.65 (d, J=8.78 Hz, 0.62H) 7.73 (d, J=8.78 Hz, 0.38H) 7.82 (d, J=8.42 Hz, 0.62H) 7.87 (d, J=8.78 Hz, 0.38H) 8.11 (s, 0.38H) 8.38 (s, 0.62H).

EXAMPLE 23

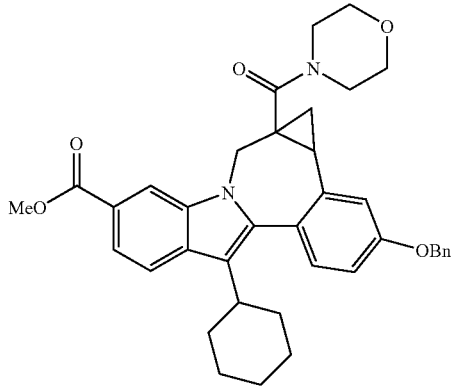

(+/−) Cycloprop[d]indolo[2,1-a][2]benzazepine-5-carboxylic acid, 8-cyclohexyl-1,1a,2,12b-tetrahydro-1a-(4-morpholinylcarbonyl)-11-(phenylmethoxy)-, methyl ester. To a solution of (+/−) cycloprop[d]indolo[2,1-a][2]benzazepine-1a,5(2H)-dicarboxylic acid, 8-cyclohexyl-1,12b-dihydro-11-(phenylmethoxy)-, 5-methyl ester (345 mg, 0.644 mmol) in DMSO (10.0 mL), TBTU (310 mg, 0.966 mmol) and DIPEA (0.56 mL, 3.22 mmol) were added. The reaction mixture was stirred at rt for 15 min. Then morpholine (0.084 mL, 0.966 mmol) was added and the reaction mixture was stirred at rt for 3 hr. It was then added water and acidified with 1N HCl solution. A light yellow solid was collected as product. (360 mg, 92% yield). MS m/z 605 (MH+), Retention time: 4.168 min. 1H NMR (500 MHz, CHLOROFORM-D) δ ppm 0.35 (m, 0.34H) 0.95 (m, 0.34H) 1.07-1.54 (m, 5.32H) 1.62-2.10 (m, 6H) 2.31-2.42 (m, 0.34H) 2.43-2.51 (m, 0.66H) 2.73 (m, 0.34H) 2.81-2.94(m, 0.66H) 2.96-3.16(m, 5H) 3.48-3.76(m, 3.66H) 3.88(s, 3H) 4.11 (d, J=14.95 Hz, 0.34H) 4.63 (d, J=14.95 Hz, 0.34H) 4.95-5.14 (m, 2.66H) 6.92 (dd, J=8.24, 2.44 Hz, 0.34H) 6.94-6.99 (m, 0.66H) 7.10 (s, 0.34H) 7.13 (s, 0.66H) 7.17-7.44 (m, 6H) 7.64-7.71 (m, 1H) 7.73-7.83 (m, 1H) 7.96 (s, 0.34H) 7.99 (s, 0.66H).

EXAMPLE 24

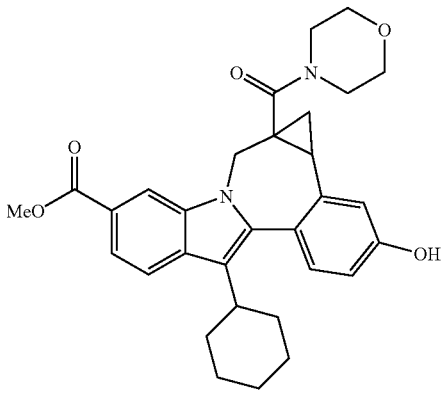

(+/−) Cycloprop[d]indolo[2,1-a][2]benzazepine-5-carboxylic acid, 8-cyclohexyl-1,1a,2,12b-tetrahydro-1a-(4-morpholinylcarbonyl)-11-hydroxy-, methyl ester. To a solution of cycloprop[d]indolo[2,1-a][2]benzazepine-5-carboxylic acid, 8-cyclohexyl-1,1a,2,12b-tetrahydro-1a-(4-morpholinylcarbonyl)-11-(phenylmethoxy)-, methyl ester (270 mg, 0.446 mmol) in ethyl acetate (15 mL), 10% Pd on carbon (15 mg) was added. The reaction mixture was stirred under a hydrogen balloon for overnight. Catalyst was filtered from celite and washed with methanol/ethyl acetate. The filtrate was concentrated to give an orange solid as product. (210 mg, 91% yield). MS m/z 515 (MH$^+$), Retention time: 3.693 min. 1H NMR (500 MHz, MeOD) δ ppm 0.22 (m, 0.22H) 1.05 (m, 0.22H) 1.19-1.66 (m, 5.56H) 1.75-2.20 (m, 6H) 2.45 (m, 0.22H) 2.60 (m, 0.78H) 2.81-3.08 (m, 1H) 3.18-3.27 (m, 2H) 3.40-3.87 (m, 6.78H) 3.95 (s, 2.34H) 3.98-4.05 (m, 0.88H) 4.15 (d, J=14.95 Hz, 0.22H) 5.11 (d, J=15.26 Hz, 0.78H) 6.81-6.91 (m, 1H) 7.03 (d, J=2.44 Hz, 0.22H) 7.07 (d, J=2.44 Hz, 0.78H) 7.24 (d, J=8.24 Hz, 1H) 7.68-7.77 (m, 1H) 7.85-7.91 (m, 1H) 8.11 (s, 0.78H) 8.17 (s, 0.22H).

EXAMPLE 25

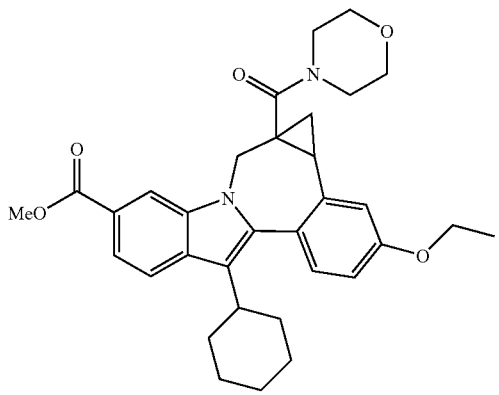

(+/−) Cycloprop[d]indolo[2,1-a][2]benzazepine-5-carboxylic acid, 8-cyclohexyl-11-ethoxy-1,1a,2,12b-tetrahydro-1a-(4-morpholinylcarbonyl)-, methyl ester. To a solution of (+/−) cycloprop[d]indolo[2,1-a][2]benzazepine-5-carboxylic acid, 8-cyclohexyl-1,1a,2,12b-tetrahydro-1a-(4-morpholinylcarbonyl)-11-hydroxy-, methyl ester (50 mg, 0.0972 mmol) in DMF (2 mL), NaH (4.7 mg in 60% oil dispersion, 0.117 mmol) was added. The reaction mixture was stirred at rt for 0.5 hr. Then iodoethane (0.012 mL, 0.146 mmol) was added. The reaction mixture was stirred at rt for an hour. It was quenched with water and acidified with 1N HCl solution. A yellowish solid was collected as product. (50 mg, 95% yield). MS m/z 543 (MH$^+$), Retention time: 3.995 min. 1H NMR (500 MHz, MeOD) δ ppm 0.22 (m, 0.3H) 1.06 (m, 0.3H) 1.19-1.65 (m, 8.4H) 1.71-2.19 (m, 6H) 2.51 (m, 0.3H) 2.62 (m, 0.7H) 2.78-3.88 (m, 9.7H) 3.95 (s, 2.1H) 4.00 (s, 0.9H) 4.09-4.20 (m, 2.3H) 4.85 (m, 0.3H) 5.09 (d, J=15.26 Hz, 0.7H) 6.97 (dd, J=8.39, 2.59 Hz, 0.3H) 7.00 (dd, J=8.55, 2.75 Hz, 0.7H) 7.16 (d, J=2.75 Hz, 0.3H) 7.18 (d, J=2.75 Hz, 0.7H) 7.31 (d, J=8.55 Hz, 1H) 7.68-7.76 (m, 1H) 7.85-7.92 (m, 1H) 8.10 (s, 0.7H) 8.15 (s, 0.3H).

EXAMPLE 26

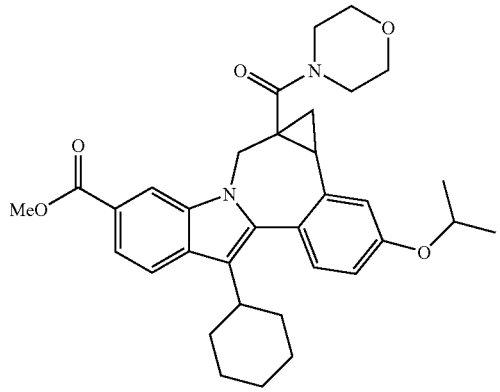

(+/−) Cycloprop[d]indolo[2,1-a][2]benzazepine-5-carboxylic acid, 8-cyclohexyl-1,1a,2,12b-tetrahydro-11-(1-methylethoxy)-1a-(4-morpholinylcarbonyl)-, methyl ester. To a solution of (+/−) cycloprop[d]indolo[2,1-a][2]benzazepine-5-carboxylic acid, 8-cyclohexyl-1,1a,2,12b-tetrahydro-1a-(4-morpholinylcarbonyl)-11-hydroxy-, methyl ester (50 mg, 0.0972 mmol) in DMF (2 mL), NaH (4.7 mg in 60% oil dispersion, 0.117 mmol) was added. The reaction mixture was stirred at rt for 0.5 hr. Then 2-iodopropane (24.8 mg, 0.146 mmol) was added. The reaction mixture was stirred at rt for overnight. It was quenched with water and acidified with 1N HCl solution. A yellowish solid was collected as product. (46 mg, 85% yield). MS m/z 557 (MH$^+$), Retention time: 4.043 min. 1H NMR (500 MHz, MeOD) δ ppm 0.24 (m, 0.28H) 1.07 (m, 0.28H) 1.23-1.66 (m, 11.56H) 1.73-2.20 (m, 6H) 2.51 (m, 0.28H) 2.63 (m, 0.72H) 2.80-3.87 (m, 9.72H) 3.96 (s, 2.16H) 4.00 (s, 0.84H) 4.15 (d, J=15.26 Hz, 0.28H) 4.69-4.75 (m, 1.28H) 5.11 (d, J=15.26 Hz, 0.72H) 6.97 (dd, J=8.55, 2.75 Hz, 0.28H) 7.00 (dd, J=8.70, 2.59 Hz, 0.72H) 7.15 (d, J=2.44 Hz, 0.28H) 7.17 (d, J=2.44 Hz, 0.72H) 7.31 (d, J=8.54 Hz, 1H) 7.66-7.78 (m, 1H) 7.82-7.93 (m, 1H) 8.12 (s, 0.72H) 8.17 (s, 0.28H).

EXAMPLE 27

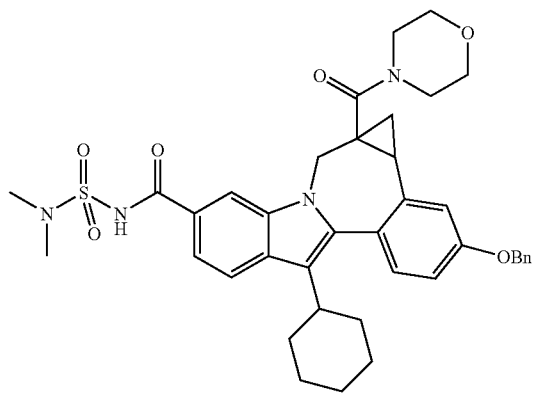

(+/−) Cycloprop[d]indolo[2,1-a][2]benzazepine-5-carboxamide, 8-cyclohexyl-N-[(dimethylamino)sulfonyl]-1,1a, 2,12b-tetrahydro-1a-(4-morpholinylcarbonyl)-11-(phenyl-methoxy)-. To a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-(phenylmethoxy)-(470 mg, 0.749 mmol) in DMSO (15.0 mL), TBTU (360 mg, 1.123 mmol) and DIPEA (0.65 mL, 3.745 mmol) were added. The reaction mixture was stirred at rt for 15 min. Then morpholine (0.098 mL, 1.123 mmol) was added and the reaction mixture was stirred at rt for 3 hr. It was then added water and acidified with 1N HCl solution. A light yellow solid was collected as crude product. It was purified by Prep. HPLC column to give an orange solid as final product. (180 mg, 34% yield). MS m/z 697 (MH+), Retention time: 3.935 min. 1H NMR (300 MHz, MeOD) δ ppm 0.16 (m, 0.28H) 1.06 (m, 0.28H) 1.15-1.64 (m, 5.44H) 1.67-2.20 (m, 6H) 2.49 (m, 0.28H) 2.62 (m, 0.72H) 2.75-3.81 (m, 15.72H) 4.11 (d, J=15.00 Hz, 0.28H) 4.90 (m, 0.28H) 5.09 (d, J=15.37 Hz, 0.72H) 5.19 (s, 1.44H) 5.21 (s, 0.56H) 7.02-7.14 (m, 1H) 7.18-7.54 (m, 7H) 7.56-7.66 (m, 1H) 7.90 (d, J=8.42 Hz, 0.28H) 7.92 (d, J=8.78 Hz, 0.72H) 8.02 (s, 0.72H) 8.07 (s, 0.28H).

EXAMPLE 28

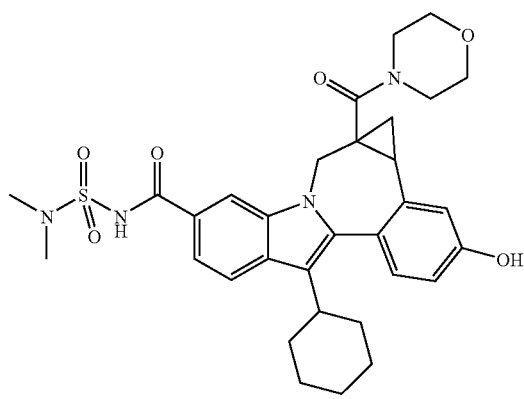

(+/−) Cycloprop[d]indolo[2,1-a][2]benzazepine-5-carboxamide, 8-cyclohexyl-N-[(dimethylamino)sulfonyl]-1,1a,2,12b-tetrahydro-11-hydroxy-1a-(4-morpholinylcarbonyl)-. To a solution of (+/−) Cycloprop[d]indolo[2,1-a][2]benzazepine-5-carboxamide, 8-cyclohexyl-N-[(dimethylamino)sulfonyl]-1,1a,2,12b-tetrahydro-1a-(4-morpholinylcarbonyl)-11-(phenylmethoxy)-(160 mg, 0.23 mmol) in methanol (20 mL), 10% Pd on carbon (50 mg) was added. The reaction mixture was stirred under a hydrogen balloon for overnight. Catalyst was filtered from celite and washed with methanol. The filtrate was concentrated to give a yellow solid as product. (114 mg, 82% yield). MS m/z 607 (MH+), Retention time: 3.420 min. 1H NMR (500 MHz, MeOD) δ ppm 0.17 (m, 0.26H) 1.07 (m, 0.26H) 1.20-1.65 (m, 5.48H) 1.73-2.20 (m, 6H) 2.45 (m, 0.26H) 2.61 (m, 0.74H) 2.80-3.86 (m, 15.74H) 4.15 (d, J=14.95 Hz, 0.26H) 4.71-4.76 (m, 0.26H) 5.12 (d, J=14.95 Hz, 0.74H) 6.83-6.90 (m, 1H) 7.03 (d, J=2.44 Hz, 0.26H) 7.08 (d, J=2.44 Hz, 0.74H) 7.22-7.27 (m, 1H) 7.59-7.64 (m, 1H) 7.88-7.95 (m, 1H) 8.03 (s, 0.74H) 8.09 (s, 0.26H).

EXAMPLE 29

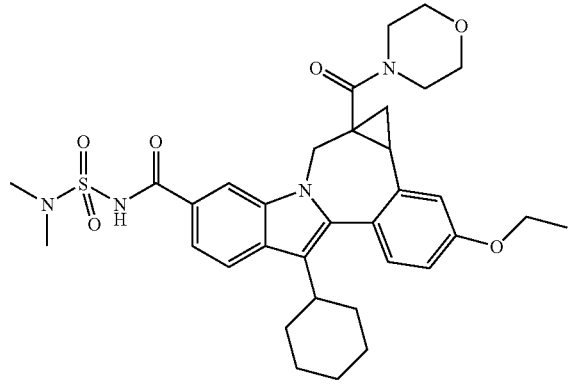

(+/−) Cycloprop[d]indolo[2,1-a][2]benzazepine-5-carboxamide, 8-cyclohexyl-N-[(dimethylamino)sulfonyl]-11-ethoxy-1,1a,2,12b-tetrahydro-1a-(4-morpholinylcarbonyl)-. To a solution of (+/−) Cycloprop[d]indolo[2,1-a][2]benzazepine-5-carboxamide, 8-cyclohexyl-N-[(dimethylamino)sulfonyl]-1,1a,2,12b-tetrahydro-11-hydroxy-1a-(4-morpholinylcarbonyl)-(30 mg, 0.0494 mmol) in DMF (1 mL), NaH (4.4 mg in 60% oil dispersion, 0.109 mmol) was added. The reaction mixture was stirred at rt for 0.5 hr. Then iodoethane (0.004 mL, 0.0494 mmol) was added. The reaction mixture was stirred at rt for overnight. It was quenched with water and acidified with 1N HCl solution. A yellowish solid was collected as crude product which was purified by Prep. HPLC column to afford a light yellow solid as final product. (16 mg, 51% yield). MS m/z 635 (MH+), Retention time: 3.741 min. 1H NMR (500 MHz, MeOD) δ ppm 0.19 (m, 0.25H) 1.09 (m, 0.25H) 1.20-1.65 (m, 8.5H) 1.71-2.21 (m, 6H) 2.52 (m, 0.25H) 2.64 (m, 0.75H) 2.79-3.88 (m, 15.75H) 4.11-4.24 (m, 2H) 4.80-4.84 (m, 0.25H) 5.13 (d, J=15.26 Hz, 0.75H) 6.95-7.05 (m, 1H) 7.16 (d, J=2.44 Hz, 0.25H) 7.19 (d, J=2.75 Hz, 0.75H) 7.30-7.38 (m, 1H) 7.62 (d, J=8.55 Hz, 1H) 7.89-7.97 (m, 1H) 8.04 (s, 0.75H) 8.09 (s, 0.25H).

EXAMPLE 30

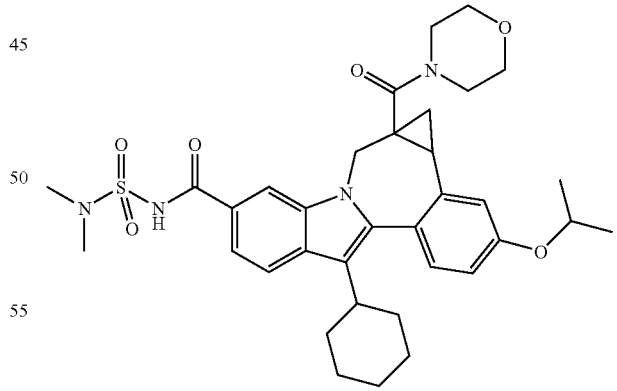

(+/−) Cycloprop[d]indolo[2,1-a][2]benzazepine-5-carboxamide, 8-cyclohexyl-N-[(dimethylamino)sulfonyl]-11-(1-methylethoxy)-1a,2,12b-tetrahydro-1a-(4-morpholinylcarbonyl)-. To a solution of (+/−) Cycloprop[d]indolo[2,1-a][2]benzazepine-5-carboxamide, 8-cyclohexyl-N-[(dimethylamino)sulfonyl]-1,1a,2,12b-tetrahydro-11-hydroxy-1a-(4-morpholinylcarbonyl)-(30 mg, 0.0494 mmol) in DMF (1 mL), NaH (4.4 mg in 60% oil dispersion, 0.109 mmol) was added. The reaction mixture was stirred at rt for 0.5 hr. Then 2-iodopropane (8.4 mg, 0.04948 mmol) was added. The reaction mixture was stirred at rt for overnight. It was quenched with water and acidified with 1N HCl solution. A yellowish solid was collected as crude product which was purified by Prep. HPLC column to afford a light yellow solid as final product. (23.2 mg, 72% yield). MS m/z 649 (MH+), Retention time: 3.836 min. 1H NMR (500 MHz, MeOD) δ ppm 0.19 (m, 0.27H) 1.08 (m, 0.27H) 1.20-1.65 (m, 11.46H) 1.73-2.21 (m, 6H) 2.51 (m, 0.27H) 2.63 (m, 0.73H) 2.78-3.85 (m, 15.73H) 4.15 (d, J=14.95 Hz, 0.27H) 4.69-4.80 (m, 1.27H) 5.11 (d, J=15.26 Hz, 0.73H) 6.94-7.03 (m, 1H) 7.15 (d, J=2.75 Hz, 0.27H) 7.17 (d, J=2.44 Hz, 0.73H) 7.31 (d, J=8.55 Hz, 1H) 7.58-7.66 (m, 1H) 7.88-7.95 (m, 1H) 8.03 (s, 0.73H) 8.09 (s, 0.27H).

EXAMPLE 31

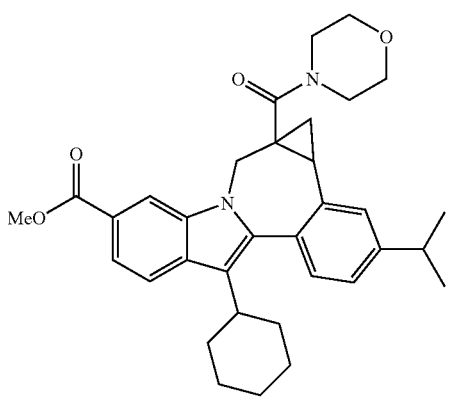

(+/−) Cycloprop[d]indolo[2,1-a][2]benzazepine-5-carboxylic acid, 8-cyclohexyl-1,1a,2,12b-tetrahydro-11-(1-methylethyl)-1a-(4-morpholinylcarbonyl)-, methyl ester. A microwave reaction tube was charged with InCl3 (77 mg, 0.155 mmol) under nitrogen. Then it was sealed and added THF (3 mL). A solution of isopropyl magnesium bromide (0.47 mL, 1.0 M solution, 0.47 mmol) in THF was added at −78° C. and stirred for 0.5 hr. The reaction mixture was then warmed to rt and a solution of (+/−)-cycloprop[d]indolo[2,1-a][2]benzazepine-5-carboxylic acid, 8-cyclohexyl-1,1a,2,12b-tetrahydro-1a-(4-morpholinylcarbonyl)-11-[[(trifluoromethyl)sulfonyl]oxy]-, methyl ester (100 mg, 0.155 mmol) and PdCl2(PPh3)2 (10.9 mg, 0.0155 mmol) in THF (2 mL) was added. The reaction mixture was heated at 100° C. under microwave condition for 2 hr. Then it was quenched with methanol and concentrated. The residue was purified by Prep. HPLC column to afford a light yellow solid as product. (12 mg, 14% yield). MS m/z 541 (MH+), Retention time: 4.188 min. 1H NMR (500 MHz, METHANOL-D4) δ ppm 0.19 (m, 0.28H) 1.02 (m, 0.28H) 1.15-1.62 (m, 11.44H) 1.64-2.18 (m, 6H) 2.51 (m, 0.28H) 2.59 (m, 0.72H) 2.63-2.70 (m, 1H) 2.83-3.85 (m, 9.72H) 3.92 (s, 3H) 4.08 (d, J=15.26 Hz, 0.28H) 4.77-4.81 (m, 0.28H) 5.06 (d, J=15.26 Hz, 0.72H) 7.19-7.31 (m, 2H) 7.40 (s, 0.28H) 7.45 (s, 0.72H) 7.67-7.73 (m, 1H) 7.87 (d, J=8.55 Hz, 1H) 8.08 (s, 0.72H) 8.13 (s, 0.28H).

EXAMPLE 32

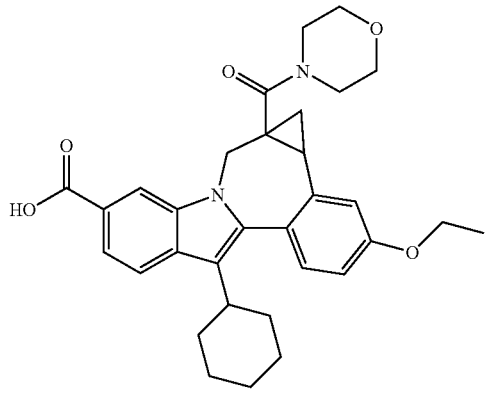

(+/−) Cycloprop[d]indolo[2,1-a][2]benzazepine-5-carboxylic acid, 8-cyclohexyl-1,1-ethoxy-1,1a,2,12b-tetrahydro-1a-(4-morpholinylcarbonyl)-. To a solution of (+/−) Cycloprop[d]indolo[2,1-a][2]benzazepine-5-carboxylic acid, 8-cyclohexyl-11-ethoxy-1,1a,2,12b-tetrahydro-1a-(4-morpholinylcarbonyl)-, methyl ester (40 mg, 0.074 mmol) in THF/Methanol mixture (2.0 mL/2.0 mL), 2N NaOH solution (1.0 mL) was added. The reaction mixture was heated at 85° C. under microwave condition for 5 min. Then it was concentrated, acidified with 1N HCl solution and extracted with ethyl acetate (2×20 mL). The organic layers were combined, dried (MgSO4) and concentrated. The residue was purified by Prep. HPLC to afford a yellow solid as final product. (28 mg, 72% yield). MS m/z 529 (MH+), Retention time: 3.865 min. 1H NMR (500 MHz, MeOD) δ ppm 0.23 (m, 0.28H) 1.05 (m, 0.28H) 1.18-1.64 (m, 8.44H) 1.71-2.19 (m, 6H) 2.50 (m, 0.28H) 2.61 (m, 0.72H) 2.76-3.87 (m, 9.72H) 4.07-4.20 (m, 2.28H) 4.85 (m, 0.28H) 5.07 (d, J=15.26 Hz, 0.72H) 6.96 (dd, J=8.39, 2.59 Hz, 0.28H) 6.99 (dd, J=8.55, 2.75 Hz, 0.72H) 7.15 (d, J=2.44 Hz, 0.28H) 7.17 (d, J=2.44 Hz, 0.72H) 7.29 (d, J=8.55 Hz, 1H) 7.70-7.77 (m, 1H) 7.87 (d, J=8.24 Hz, 1H) 8.11 (s, 0.72H) 8.15 (s, 0.28H).

EXAMPLE 33

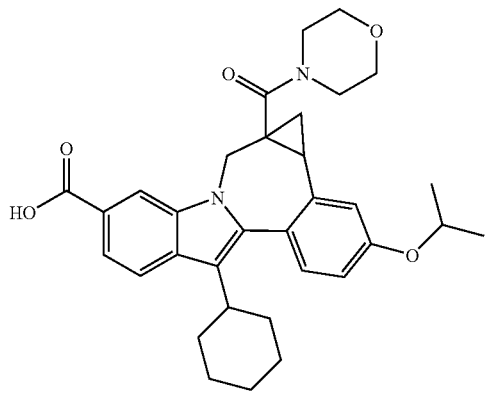

(+/−) Cycloprop[d]indolo[2,1-a][2]benzazepine-5-carboxylic acid, 8-cyclohexyl-11-(1-methyl ethoxy)-1,1a,2,12b-tetrahydro-1a-(4-morpholinylcarbonyl)-. To a solution of (+/−) cycloprop[d]indolo[2,1-a][2]benzazepine-5-carboxylic acid, 8-cyclohexyl-1,1a,2,12b-tetrahydro-11-(1-methylethoxy)-1a-(4-morpholinylcarbonyl)-, methyl ester (36 mg, 0.065 mmol) in THF/Methanol mixture (2.0 mL/2.0 mL), 2N NaOH solution (1.0 mL) was added. The reaction mixture was heated at 850° C. under microwave condition for 5 min. Then it was concentrated, acidified with 1N HCl solution and extracted with ethyl acetate (2×20 mL). The organic layers were combined, dried (MgSO$_4$) and concentrated. The residue was purified by Prep. HPLC to afford a yellow solid as final product. (24 mg, 68% yield). MS m/z 543 (MH$^+$), Retention time: 3.931 min. 1H NMR (300 MHz, MeOD) δ ppm 0.24 (m, 0.27H) 1.06 (m, 0.27H) 1.11-2.23 (m, 17.46H) 2.52 (m, 0.27H) 2.62 (m, 0.73H) 2.70-3.90 (m, 9.73H) 4.15 (d, J=15.00 Hz, 0.27H) 4.68-4.78 (m, 1.27H) 5.11 (d, J=15.00 Hz, 0.73H) 6.92-7.04 (m, 1H) 7.13-7.21 (m, 1H) 7.31 (d, J=8.42 Hz, 1H) 7.67-7.79 (m, 1H) 7.89 (d, J=8.42 Hz, 1H) 8.13 (s, 0.73H) 8.18 (s, 0.27H).

EXAMPLE 34

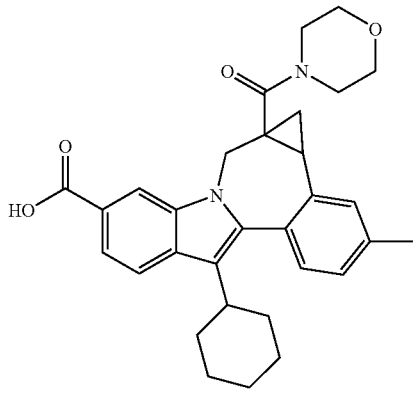

(+/−) Cycloprop[d]indolo[2,1-a][2]benzazepine-5-carboxylic acid, 8-cyclohexyl-11-methyl-1,1a,2,12b-tetrahydro-1a-(4-morpholinylcarbonyl)-. To a solution of (+/−) cycloprop[d]indolo[2,1-a][2]benzazepine-5-carboxylic acid, 8-cyclohexyl-11-methyl-1,1a,2,12b-tetrahydro-1a-(4-morpholinylcarbonyl)-methyl ester (14 mg, 0.027 mmol) in THF/Methanol mixture (2.0 mL/2.0 mL), 2N NaOH solution (0.3 mL) was added. The reaction mixture was heated at 85° C. under microwave condition for 3 min. Then it was concentrated, acidified with 1N HCl solution and extracted with ethyl acetate (2×20 mL). The organic layers were combined, dried (MgSO$_4$) and concentrated. The residue was purified by Prep. HPLC to afford a light yellow solid as final product. (7.5 mg, 56% yield). MS m/z 499 (MH$^+$), Retention time: 3.855 min. 1H NMR (500 MHz, MeOD) δ ppm 0.22 (m, 0.24H) 1.06 (m, 0.24H) 1.20-1.65 (m, 5.52H) 1.74-2.21 (m, 6H) 2.44 (s, 2.28H) 2.46 (s, 0.72H) 2.52 (m, 0.24H) 2.61 (m, 0.76H) 2.80-3.87 (m, 9.76H) 4.13 (d, J=14.95 Hz, 0.24H) 4.76-4.83 (m, 0.24H) 5.10 (d, J=15.26 Hz, 0.76H) 7.22-7.32 (m, 2H) 7.43 (s, 0.24H) 7.48 (s, 0.76H) 7.71-7.78 (m, 1H) 7.89 (d, J=8.55 Hz, 1H) 8.14 (s, 0.76H) 8.18 (s, 0.24H).

EXAMPLE 35

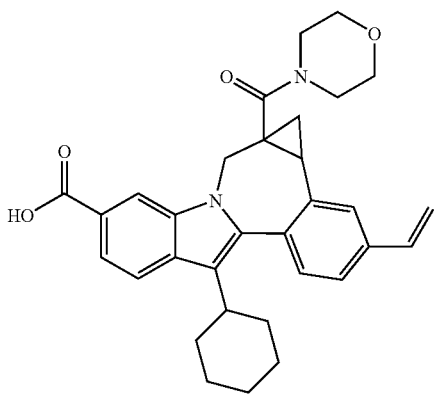

(+/−) 8-cyclohexyl-1a-(4-morpholinylcarbonyl)-11-vinyl-1,1a,2,12b-tetrahydrocyclopropa[d]indolo[2,1-a][2]benzazepine-5-carboxylic acid. To a solution of (+/−) cycloprop[d]indolo[2,1-a][2]benzazepine-5-carboxylic acid, 8-cyclohexyl-11-ethenyl-1,1a,2,12b-tetrahydro-1a-(4-morpholinylcarbonyl)-, methyl ester (51 mg, 0.097 mmol) in a THF/Methanol mixture (2.0 mL/2.0 mL), 2N NaOH solution (0.5 mL) was added. The reaction mixture was heated at 85° C. under microwave condition for 3 min. Then it was concentrated, acidified with 1N HCl solution and extracted with ethyl acetate (2×20 mL). The organic layers were combined, dried (MgSO$_4$) and concentrated to give a yellow solid as final product. (39 mg, 79% yield). MS m/z 511 (MH$^+$), Retention time: 3.903 min. 1H NMR (500 MHz, MeOD) δ ppm 0.25 (m, 0.28H) 1.07 (m, 0.28H) 1.19-1.67 (m, 5.44H) 1.74-2.22 (m, 6H) 2.58 (m, 0.28H) 2.64 (m, 0.72H) 2.79-3.87 (m, 9.72H) 4.14 (d, J=15.26 Hz, 0.28H) 4.78-4.82 (m, 0.28H) 5.08 (d, J=15.26 Hz, 0.72H) 5.36 (d, J=10.99 Hz, 0.72H) 5.37 (d, J=10.99 Hz, 0.28H) 5.93 (d, J=17.70 Hz, 0.72H) 5.95 (d, J=17.71 Hz, 0.28H) 6.78-6.88 (m, 1H) 7.35 (d, J=7.93 Hz, 1H) 7.50 (d, J=7.93 Hz, 0.28H) 7.53 (d, J=8.24 Hz, 0.72H) 7.64-7.79 (m, 2H) 7.90 (d, J=8.55 Hz, 1H) 8.13 (s, 0.72H) 8.17 (s, 0.28H).

EXAMPLE 36

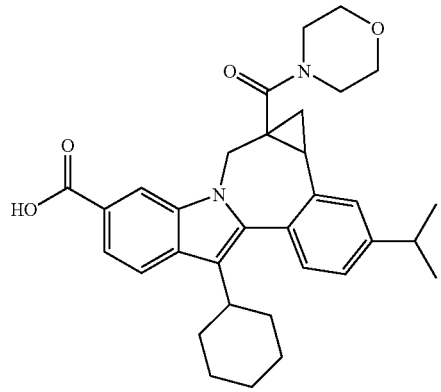

(+/−) Cycloprop[d]indolo[2,1-a][2]benzazepine-5-carboxylic acid, 8-cyclohexyl-11-(2-methyl ethyl)-1,1a,2,12b-tetrahydro-1a-(4-morpholinylcarbonyl)-. To a solution of (+/−) cycloprop[d]indolo[2,1-a][2]benzazepine-5-carboxylic acid, 8-cyclohexyl-11-(2-methyl ethyl)-1,1a,2,12b-tetrahydro-1a-(4-morpholinylcarbonyl)-methyl ester (10 mg, 0.0185 mmol) in THF/Methanol mixture (2.0 mL/2.0 mL), 2N NaOH solution (0.4 mL) was added. The reaction mixture was heated at 85° C. under microwave condition for 3 min. Then it was concentrated, acidified with 1N HCl solution and extracted with ethyl acetate (2×20 mL). The organic layers were combined, dried (MgSO$_4$) and concentrated. The residue was purified by Prep. HPLC to afford an off-white solid as final product. (5.0 mg, 51% yield). MS m/z 527 (MH$^+$), Retention time: 4.023 min. 1H NMR (500 MHz, MeOD) δ ppm 0.21 (m, 0.28H) 1.04 (m, 0.28H) 1.13-1.63 (m, 11.44H) 1.63-2.20 (m, 6H) 2.52 (m, 0.28H) 2.61 (m, 0.72H) 2.63-2.72 (m, 1H) 2.77-3.86 (m, 9.72H) 4.11 (d, J=15.26 Hz, 0.28H) 4.86-4.93 (m, 0.28H) 5.08 (d, J=15.26 Hz, 0.72H) 7.18-7.34 (m, 2H) 7.38-7.53 (m, 1H) 7.67-7.76 (m, 1H) 7.87 (d, J=8.24 Hz, 1H) 8.11 (s, 0.72H) 8.16 (s, 0.28H).

EXAMPLE 37

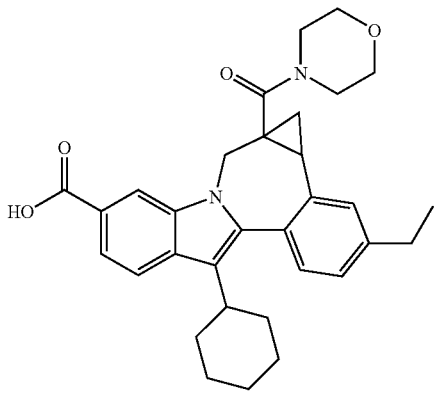

(+/−) Cycloprop[d]indolo[2,1-a][2]benzazepine-5-carboxylic acid, 8-cyclohexyl-11-ethyl-1,1a,2,12b-tetrahydro-1a-(4-morpholinylcarbonyl)-. To a solution of (+/−) Cycloprop[d]indolo[2,1-a][2]benzazepine-5-carboxylic acid, 8-cyclohexyl-11-vinyl-1,1a,2,12b-tetrahydro-1a-(4-morpholinylcarbonyl)-methyl ester (35 mg, 0.0685 mmol) in methanol/ethyl acetate (8 mL/8 mL), 10% Pd on carbon (5 mg) was added. The reaction mixture was stirred under a hydrogen balloon for overnight. Catalyst was filtered from celite and washed with methanol/ethyl acetate. The filtrate was concentrated to give a light yellow solid as product. (35 mg, 99% yield). MS m/z 513 (MH+), Retention time: 3.933 min. 1H NMR (500 MHz, MeOD) δ ppm 0.22 (m, 0.25H) 1.04 (m, 0.25H) 1.16-1.64 (m, 8.5H) 1.72-2.19 (m, 6H) 2.53 (m, 0.25H) 2.61 (m, 0.75H) 2.69-2.79 (m, 2H) 2.80-3.86 (m, 9.75H) 4.09 (d, J=14.95 Hz, 0.25H) 4.81 (d, J=15.26 Hz, 0.25H) 5.06 (d, J=15.26 Hz, 0.75H) 7.22-7.32 (m, 2H) 7.44 (s, 0.25H) 7.49 (s, 0.75H) 7.70-7.78 (m, 1H) 7.88 (d, J=8.55 Hz, 1H) 8.12 (s, 0.75H) 8.16 (s, 0.25H).

EXAMPLE 38

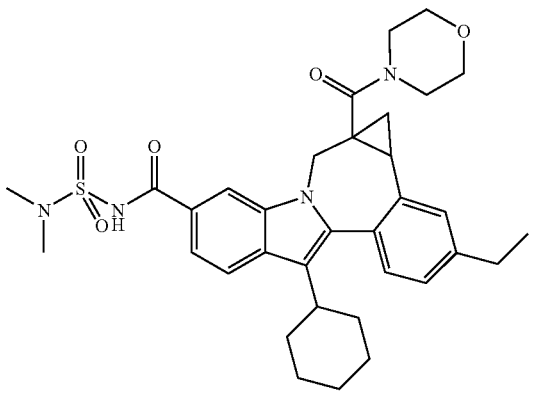

(+/−) Cycloprop[d]indolo[2,1-a][2]benzazepine-5-carboxamide, 8-cyclohexyl-N-[(dimethylamino)sulfonyl]-11-ethyl-1,1a,2,12b-tetrahydro-1a-(4-morpholinylcarbonyl)-. To a solution of (+/−) Cycloprop[d]indolo[2,1-a][2]benzazepine-5-carboxylic acid, 8-cyclohexyl-11-ethyl-1,1a,2,12b-tetrahydro-1a-(4-morpholinylcarbonyl)- (30 mg, 0.0585 mmol) in CH$_2$Cl$_2$ (5 mL), one drop of DMF was added. Then 2M solution of oxalyl chloride (0.059 mL, 0.117 mmol) in CH$_2$Cl$_2$ was added dropwise. The reaction mixture was stirred at rt. for 2 hr. Then it was concentrated and dried under high vacuum. It was then dissolved in THF (5 mL) and a pre-mixed solution of N,N-dimethylsulfonamide (18 mg, 0.146 mmol) and BEMP (0.034 mL, 0.117 mmol)) in THF (2 mL) was added. DMAP (10 mg) and DIPEA (0.4 mL) were added after the reaction mixture was stirred at rt. for 10 min. It was continued stirring at rt. for overnight. Then it was concentrated and the residue was purified by Prep. HPLC column to afford a yellow solid as final compound. (11 mg, 30% yield). MS m/z 619 (MH+), Retention time: 3.823 min. 1H NMR (500 MHz, MeOD) δ ppm 0.18 (m, 0.28H) 1.09 (m, 0.28H) 1.22-1.66 (m, 8.44H) 1.74-2.20 (m, 6H) 2.55 (m, 0.28H) 2.64 (m, 0.72H) 2.70-2.81 (m, 2H) 2.83-3.85 (m, 15.72H) 4.15 (d, J=15.26 Hz, 0.28H) 4.87-4.91 (m, 0.28H) 5.13 (d, J=15.56 Hz, 0.72H) 7.26-7.35 (m, 2H) 7.46 (s, 0.28H) 7.51 (s, 0.72H) 7.62 (dd, J=8.24, 1.22 Hz, 0.72H) 7.63 (dd, J=8.55, 1.53 Hz, 0.28H) 7.93 (d, J=8.24 Hz, 0.28H) 7.94 (d, J=8.85 Hz, 0.72H) 8.05 (d, J=1.22 Hz, 0.72H) 8.10 (s, 0.28H).

EXAMPLE 39

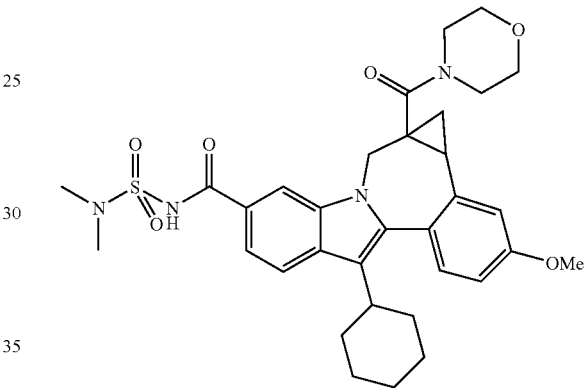

(+/−) Cycloprop[d]indolo[2,1-a][2]benzazepine-5-carboxamide, 8-cyclohexyl-N-[(dimethylamino)sulfonyl]-11-methoxy-1,1a,2,12b-tetrahydro-1a-(4-morpholinylcarbonyl)-. To a solution of (+/−) Cycloprop[d]indolo[2,1-a][2]benzazepine-5-carboxylic acid, 8-cyclohexyl-11-methoxy-1,1a,2,12b-tetrahydro-1a-(4-morpholinylcarbonyl)- (40 mg, 0.078 mmol) in CH$_2$Cl$_2$ (5 mL), one drop of DMF was added. Then 2M solution of oxalyl chloride (0.078 mL, 0.155 mmol) in CH$_2$Cl$_2$ was added dropwise. The reaction mixture was stirred at rt. for 2 hr. Then it was concentrated and dried under high vacuum. It was then dissolved in THF (5 mL) and a pre-mixed solution of N,N-dimethylsulfonamide (29 mg, 0.234 mmol) and BEMP (0.056 mL, 0.195 mmol)) in THF (2 mL) was added. DMAP (10 mg) was added after the reaction mixture was stirred at rt. for 10 min. It was continued stirring at rt. for overnight. Then it was concentrated and the residue was purified by Prep. HPLC column to afford an off-white solid as final compound. (10 mg, 21% yield). MS m/z 621 (MH+), Retention time: 3.633 min. 1H NMR (500 MHz, Acetone) δ ppm 0.25 (m, 0.38H) 1.12 (m, 0.38H) 1.16-2.24 (m, 11.24H) 2.55 (m, 0.38H) 2.64 (m, 0.62H) 2.94-3.05 (m, 3H) 3.02 (s, 3.72H) 3.03 (s, 2.28H) 3.24-3.82 (m, 6.62H) 3.92 (s, 1.86H) 3.93 (s, 1.14H) 4.20 (d, J=14.95 Hz, 0.38H) 4.94 (d, J=14.95 Hz, 0.38H) 5.19 (d, J=14.95 Hz, 0.62H) 7.03 (dd, J=8.39, 2.59 Hz, 0.38H) 7.06 (dd, J=8.55, 2.75 Hz, 0.62H) 7.20 (d, J=2.75 Hz, 0.62H) 7.22 (d, J=2.75 Hz, 0.38H) 7.38 (d, J=8.55 Hz, 1H) 7.73 (dd, J=8.55, 1.53 Hz, 0.62H) 7.76 (dd, J=8.24, 1.53 Hz, 0.38H) 7.92-8.00 (m, 1H) 8.26 (s, 0.62H) 8.30 (s, 0.38H).

EXAMPLE 40

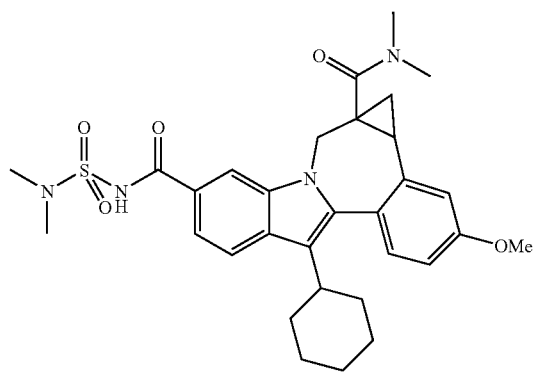

(+/−) Cycloprop[d]indolo[2,1-a][2]benzazepine-5-carboxamide, 8-cyclohexyl-N-[(dimethylamino)sulfonyl]-1a-[[N,N-dimethyl]-carbonyl]-1,1a,2,12b-tetrahydro-11-methoxy-. MS m/z 579 (MH$^+$), Retention time: 3.725 min. 1H NMR (500 MHz, MeOD) δ ppm 0.19 (m, 0.4H) 1.08 (m, 0.4H) 1.18-1.70 (m, 5.2H) 1.72-2.19 (m, 6H) 2.52 (m, 0.4H) 2.60-3.26 (m, 13.6H) 3.64 (d, J=15.56 Hz, 0.6H) 3.90 (s, 1.8H) 3.92 (s, 1.2H) 4.17 (d, J=14.95 Hz, 0.4H) 4.78-4.83 (m, 0.4H) 5.09 (d, J=14.95 Hz, 0.6H) 6.98-7.05 (m, 1H) 7.20 (d, J=1.53 Hz, 1H) 7.33 (d, J=8.54 Hz, 0.6H) 7.34 (d, J=8.54 Hz, 0.4H) 7.58 (dd, J=8.55, 1.53 Hz, 0.6H) 7.62 (dd, J=8.55, 1.53 Hz, 0.4H) 7.87-7.94 (m, 1.6H) 8.13 (s, 0.4H).

EXAMPLE 41

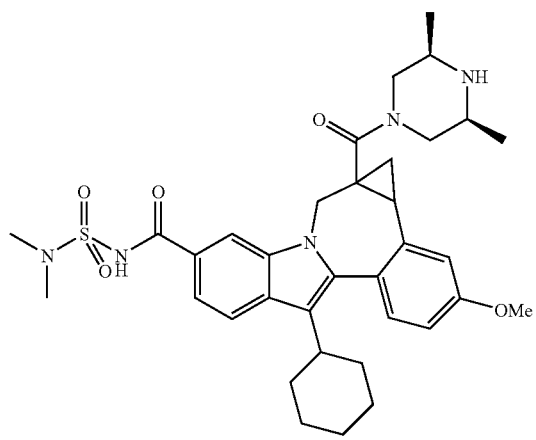

(+/−) Cycloprop[d]indolo[2,1-a][2]benzazepine-5-carboxamide, 8-cyclohexyl-N-[(dimethylamino)sulfonyl]-1a-[[(3a,5a)-3,5-dimethyl-1-piperazinyl]carbonyl]-1,1a,2,12b-tetrahydro-11-methoxy-. MS m/z 648 (MH$^+$), Retention time: 3.370 min. 1H NMR (500 MHz, MeOD) δ ppm 0.21 (m, 0.34H) 1.11 (m, 0.34H) 1.16-1.59 (m, 10.32H) 1.66-2.18 (m, 7H) 2.56 (m, 0.34H) 2.64 (m, 0.66H) 2.78-3.12 (m, 9H) 3.35-3.74 (m, 2.66H) 3.90 (s, 1.98H) 3.92 (s, 1.02H) 4.04-4.61 (m, 2.34H) 4.90-4.94 (m, 0.34H) 5.09 (d, J=15.26 Hz, 0.66H) 7.00-7.06 (m, 1H) 7.18 (d, J=2.44 Hz, 0.34H) 7.20 (d, J=2.44 Hz, 0.66H) 7.34 (d, J=8.54 Hz, 1H) 7.57 (d, J=8.55 Hz, 0.66H) 7.62 (d, J=7.63 Hz, 0.34H) 7.89 (d, J=8.55 Hz, 0.66H) 7.92 (d, J=8.55 Hz, 0.34H) 7.97 (s, 0.66H) 8.09 (s, 0.34H).

EXAMPLE 42

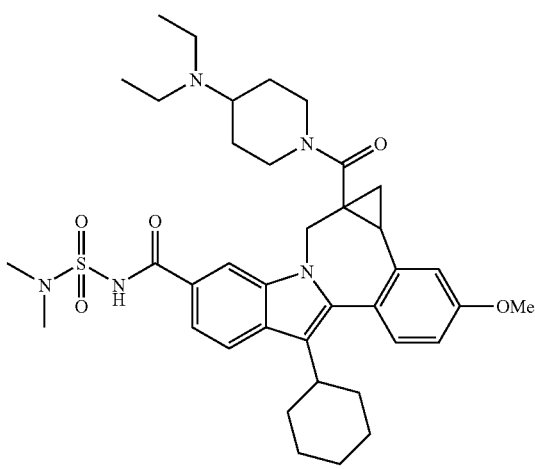

(+/−) Cycloprop[d]indolo[2,1-a][2]benzazepine-5-carboxamide, 8-cyclohexyl-1a-[[4-(diethylamino)-1-piperidinyl]carbonyl]-N-[(dimethylamino)sulfonyl]-1,1a,2,12b-tetrahydro-11-methoxy-. To a mixture of the (+/−)-cycloprop[d]indolo[2,1-a][2]benzazepine-5-carboxylic acid, 8-cyclohexyl-1,1a,2,12b-tetrahydro-11-methoxy-1a-[(4-morpholinylcarbonyl)amino]- (109.7 mg, 0.20 mmol), N,N,N',N'-tetramethyluronium tetrafluoroborate (TBTU, 302 mg, 0.94 mmol) and 4-diethylaminopiperidine (47 mg, 0.30 mmol) in DMF (2 ml) at r.t. under N$_2$ was added N,N-diisopropylethylamine (0.21 ml, 1.21 mmol). The reaction mixture was stirred at r.t. for 3 hr. 15 min., and then concentrated. The residue was diluted with water (5 ml). The precipitates were filtered, washed with water (2×2 ml) and dried. The solid residue was purified by Shimadzu-VP preparative reverse phase HPLC with separation method: Solvent A=10% MeOH-90% H$_2$O-0.1% TFA, Solvent B=90% MeOH-10% H$_2$O-0.1% TFA, Start % B=0, Final % B=100, Gradient time=6 min, Flow Rate=30 mL/min, Column: Xterra Prep MS C18 5 u 30×50 mm, Fraction Collection: 5.98-6.52 min. to give the title compound (93 mg) as a light yellow solid; Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=690.50, HPLC R$_t$=2.118 min. Analytical HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Flow Rate=5 ml/min, Column: Phenomenex Lina C18 5 um 3.0×50 mm; LC/MS: (ES+) m/z (M+H)$^+$=690.47, HPLC R$_t$=1.263 min.

EXAMPLE 43

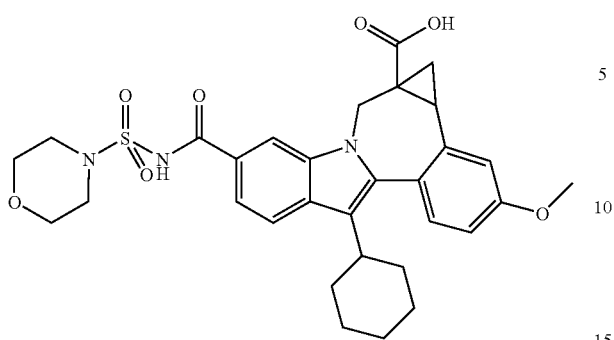

(+/−) 8-cyclohexyl-5-(morpholinosulfonylcarbamoyl)-1,1a,2,12b-tetrahydro-11-methoxy-cycloprop[d]indolo[2,1-a][2]benzazepine-1a-carboxylic acid. LC/MS: Retention time: 1.968 min; m/e 460 (MH+). 1H NMR (400 MHz, CDCl3): Compound was observed to exist as inter-converting rotamers, as evidenced from the compounds NMR spectrum.

EXAMPLE 44

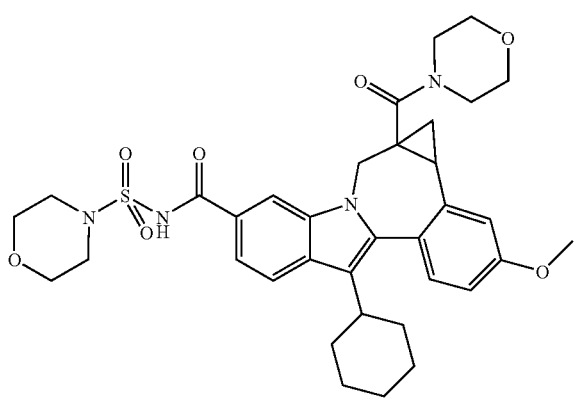

(+/−) 8-cyclohexyl-N-4-(morpholinosulfonyl)-1,1a,2,12b-tetrahydro-11-methoxy-1a-(morpholine-4-carbonyl)-cycloprop[d]indolo[2,1-a][2]benzazepine-5-carboxamide. LC/MS: Retention time: 1.982 min; m/e 663 (MH+). Compound was observed to exist as inter-converting rotamers, as evidenced from the compounds NMR spectrum. 1H NMR (400 MHz, CHLOROFORM-D) δ ppm 0.36-1.61 (m, 7H) 1.90 (d, J=97.20 Hz, 6H) 2.38-3.82 (m, 17H) 3.88-3.91 (m, 3H) 3.96-4.24 (m, 1H) 4.63-5.20 (m, 1H) 6.90-6.99 (m, 1H) 7.01-7.13 (m, 1H) 7.25-7.32 (m, 1H) 7.40-7.56 (m, 1H) 7.84-8.02 (m, 2H).

EXAMPLE 45

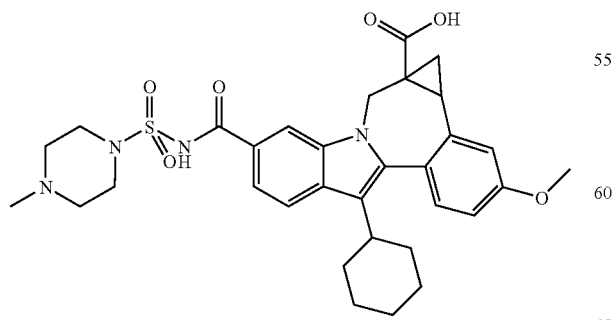

(+/−) 8-cyclohexyl-5-(4-methylpiperazin-1-ylsulfonylcarbamoyl)-1,1a,2,12b-tetrahydro-11-methoxy-cycloprop[d][2]benzazepine-1a-carboxylic acid. LC/MS: Retention time: 1.687 min; m/e 607 (MH+). 1H NMR (400 MHz, CDCl3). Compound was observed to exist as inter-converting rotamers, as evidenced from the compound's NMR spectrum.

EXAMPLE 46

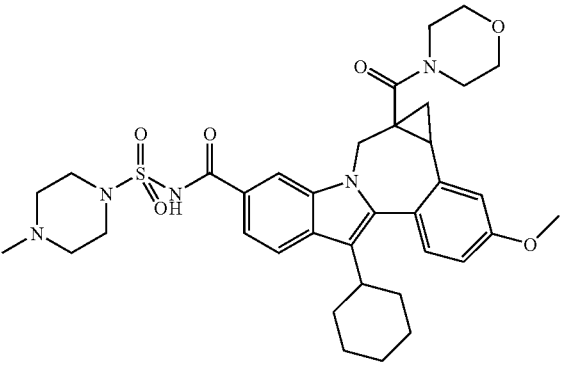

(+/−) 8-cyclohexyl-N-(4-methylpiperazin-1-ylsulfonyl)-1,1a,2,12b-tetrahydro-11-methoxy-1a-(morpholine-4-carbonyl)-cycloprop[d]indolo[2,1-a][2]benzazepine-5-carboxamide. LC/MS: Retention time: 1.738 min; m/e 676 (MH+). Compound was observed to exist as inter-converting rotamers, as evidenced from the compound's NMR spectrum. 1H NMR (400 MHz, CHLOROFORM-D) δ ppm 0.31-1.14 (m, 1H) 1.11-2.19 (m, 11H) 2.34-2.58 (m, 2H) 2.80-2.86 (m, 3H) 2.87-3.85(m, 14H) 3.87-3.91 (m, 3H) 4.02-4.23 (m, 3H) 4.68-5.17 (m, 1H) 6.90-6.99 (m, 1H) 6.99-7.12 (m, 1H) 7.27-7.32 (m, 1H) 7.46-7.59 (m, 1H) 7.85-7.98 (m, 2H).

EXAMPLE 47

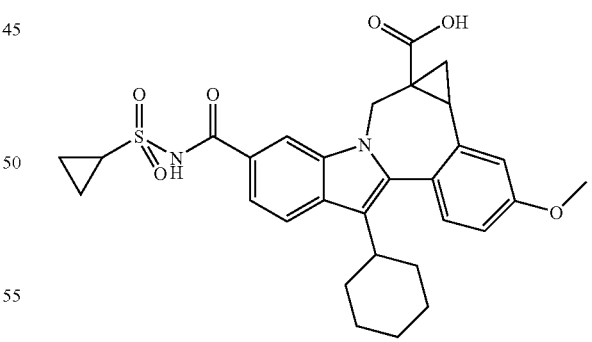

(+/−) 8-cyclohexyl-5-(cyclopropylsulfonylcarbamoyl)-1,1a,2,12b-tetrahydro-11-methoxy-cycloprop[d]indolo[2,1-a][2]benzazepine-1a-carboxylic acid. LC/MS: Retention time: 2.030 min; m/e 549 (MH+). 1H NMR (400 MHz, CDCl3). Compound was observed to exist as inter-converting rotamers, as evidenced from the compound's NMR spectrum.

EXAMPLE 48

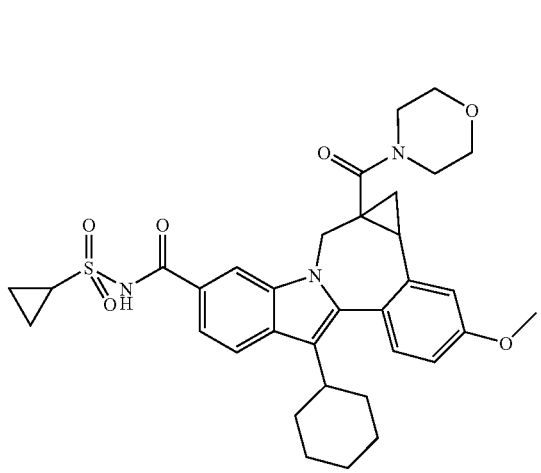

(+/−) 8-cyclohexyl-N-(cyclopropylsulfonyl)-1,1a,2,12b-tetrahydro-11-methoxy-1a-(morpholine-4-carbonyl)-cycloprop[d]indolo[2,1-a][2]benzazepine-5-carboxamide. LC/MS: Retention time: 1.962 min; m/e 618 (MH+). Compound was observed to exist as inter-converting rotamers, as evidenced from the compound's NMR spectrum. ¹H NMR (400 MHz, CHLOROFORM-D) δ ppm 0.33-1.58 (m, 10H) 1.66-1.83 (m, 2H) 1.86-2.15 (m, 4H) 2.35-2.63 (m, 1H) 2.72-3.84 (m, 10H) 3.84-3.92 (m, 3H) 3.93-4.25 (m, 1H) 4.65-5.18 (m, 1H) 6.88-7.15 (m, 2H) 7.22-7.31 (m, 1H) 7.49-7.65 (m, 1H) 7.82-8.04 (m, 2H).

EXAMPLE 49

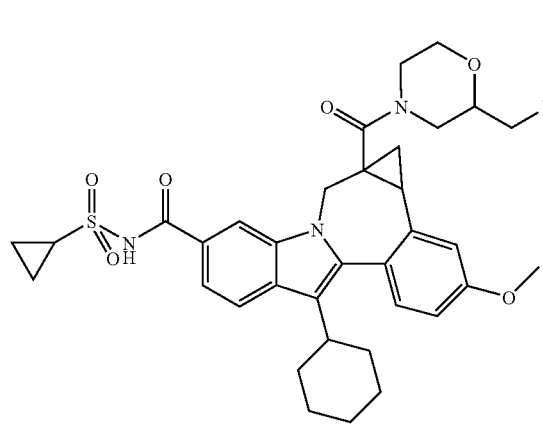

8-cyclohexyl-N-(cyclopropylsulfonyl)-1,1a,2,12b-tetrahydro-11-methoxy-1a-[2-[(dimethylamino)methyl]morpholine-4-carbonyl]-cycloprop[d]indolo[2,1-a][2]benzazepine-5-carboxamide. LC/MS: Retention time: 3.041 min; m/e 675 (MH+). ¹H NMR (400 MHz, CDCl₃). Compound was observed to exist as inter-converting rotamers, as evidenced from the compound's NMR spectrum.

EXAMPLE 50

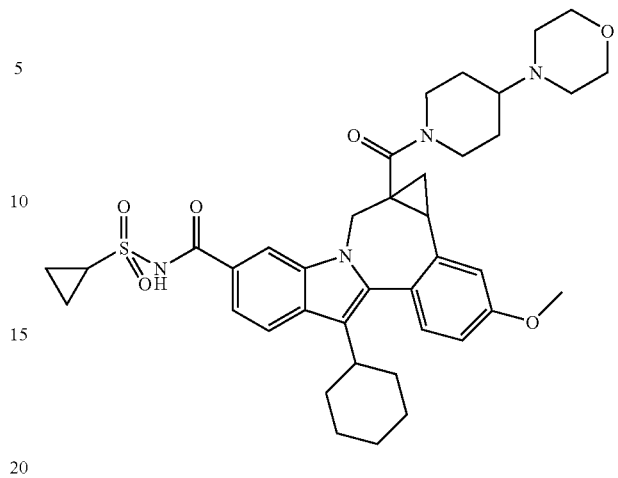

(+/−) 8-cyclohexyl-N-(cyclopropylsulfonyl)-1,1a,2,12b-tetrahydro-11-methoxy-1a-(4-morpholinopiperidine-1-carbonyl)-cycloprop[d]indolo[2,1-a][2]benzazepine-5-carboxamide. LC/MS: Retention time: 1.717 min; m/e 701 (MH+). Compound was observed to exist as inter-converting rotamers, as evidenced from the compound's NMR spectrum. ¹H NMR (400 MHz, CHLOROFORM-D) δ ppm 0.43-1.68 (m, 12H) 1.70-2.11 (m, 6H) 2.18-4.13 (m, 19H) 3.86-3.90 (m, 3H) 4.22-4.69 (m, 1H) 6.83-7.01 (m, 1H) 7.04-7.11 (m, J=6.92, 2.39 Hz, 1H) 7.20-7.31 (m, 1H) 7.36-7.80 (m, J=87.88 Hz, 1H) 7.86-8.20 (m, 2H).

EXAMPLE 51

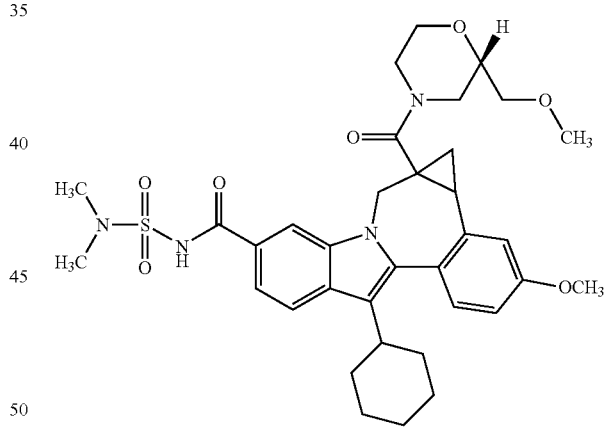

(+/−)-8-cyclohexyl-N-[(dimethylamino)sulfonyl]-1,1a,2,12b-tetrahydro-1a-[[(cis)-(S)-2-methoxymethyl-4-morpholinyl]carbonyl]-cycloprop[d]indolo[2,1-a][2]benzazepine-5-carboxamide. TBTU (120 mg, 0.374 mmol) was added to a stirred solution at 22° C. of (+/−)-8-cyclohexyl-5-[[[[(dimethylamino)sulfonyl]amino]carbonyl]-1,12b-dihydro-11-methoxy cycloprop[d]indolo[2,1-a][2]benzazepine-1a(2H)-carboxylic acid, (164.4 mg, 0.298 mmol), (2S)-2-(methoxymethyl)morpholine hydrochloride (63 mg, 0.376 mmol), and TEA (152 mg, 1.50 mmol) in DMSO (1 mL). The mixture was stirred for 1 hr and was diluted with water. The solution was acidified with dilute HCl to precipitate the product which was collected, washed with cold water, and dried in vacuo over phosphorous pentoxide to afford a mixture of diastereoisomers (162 mg, 82% yield). A portion of this material was purified on a Shimadzu preparative liquid chromatograph using an XTerra® 30×100 mm reverse phase column and a gradient of methanol-water containing 1% TFA. The methanol was removed from the product containing fractions. The precipitated product was extracted into ethyl acetate. The organic layer was washed (water, brine), dried (sodium sulfate), and concentrated to a pale yellow solid. LC/MS: m/z 665 (MH+), rt 2.382 min. Phenomenex-Luna 4.6×50 mm S10 column. Gradient conditions: 10% MeOH-90% HOH-0.1% TFA to 90% MeOH-10% HOH-0.1% TFA in 2 min. $^1$H NMR (300 MHz, DMSO-D6) δ ppm 0.72-2.07 (m, 13H) 2.18-2.34 (m, 1H) 2.90 (d, J=3.66 Hz, 6H) 3.12-3.67 (m, 7H) 3.84 (s, 3H) 3.93-4.46 (m, 6H) 6.93-7.36 (m, 3H) 7.54-7.71 (m, J=8.42 Hz, 1H) 7.76-7.97 (m, 1H) 8.27 (d, J=47.94 Hz, 1H) 11.51-11.78 (m, 1H).

EXAMPLE 52

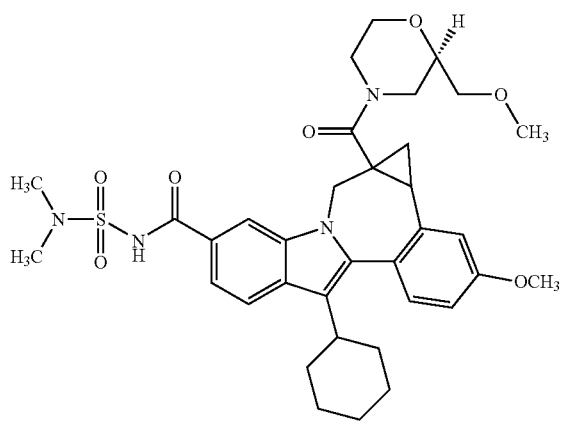

8-cyclohexyl-N-[(dimethylamino)sulfonyl]-1,1a,2,12b-tetrahydro-1a-[[(cis)-(R)-2-methoxymethyl-4-morpholinyl]carbonyl]-cycloprop[d]indolo[2,1-a][2]benzazepine-5-carboxamide. TBTU (110 mg, 0.342 mmol) was added to a stirred solution at 22° C. of (+/−)-8-cyclohexyl-5-[[[(dimethylamino)sulfonyl]amino]carbonyl]-1,12b-dihydro-11-methoxy cycloprop[d]indolo[2,1-a][2]benzazepine-1a(2H)-carboxylic acid (157.4 mg, 0.285 mmol), (2R)-2-(methoxymethyl)morpholine hydrochloride (67 mg, 0.399 mmol), and TEA (15 mg, 1.14 mmol) in DMSO (1.5 mL). The mixture was stirred for 2 hr and was diluted with water. The solution was acidified with dilute HCl to precipitate the product which was extracted into chloroform. The chloroform solution was washed (water (2×), brine), dried (magnesium sulfate), and concentrated to leave the product as a gum (298 mg). The product was purified on a silicic acid preparative plate. The plate was eluted with methylene chloride—2% acetic acid. The product containing bands were combined and extracted with methylene chloride—10% MeOH. Removal of the solvents left the titled compound as a mixture of diastereoisomers. LC/MS: m/z 665 (MH+), rt 2.382 min. Phenomenex-Luna 4.6×50 mm S10 column. Gradient conditions: 10% MeOH-90% HOH-0.1% TFA to 90% MeOH-10% HOH-0.1% TFA in 2 min. $^1$H NMR (500 MHz, DMSO-D6) δ ppm 0.75-2.15 (m, 13H) 2.88 (s, 6H) 3.12-3.29 (m, 5H) 3.31 (s, 3H) 3.83-3.93 (m, 5H) 4.55-5.34 (m, J=90.95 Hz, 1H) 6.96-7.09 (m, 1H) 7.11-7.22 (m, 1H) 7.24-7.31 (m, 1H) 7.57-7.71 (m, 1H) 7.77-7.91 (m, 1H) 8.10-8.38 (m, 1H) 11.21-12.22 (1H).

EXAMPLE 53

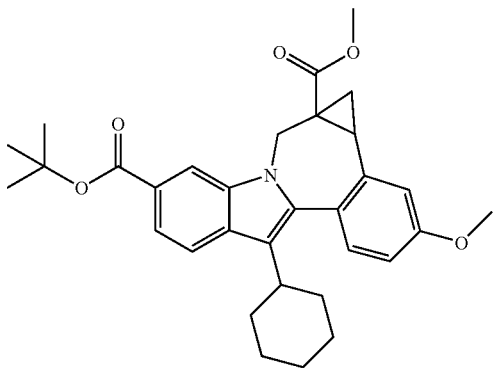

(+/−)-5-(1,1-dimethylethyl) 1a-methyl 8-cyclohexyl-11-(methyloxy)-1,12b-dihydrocyclopropa[d]indolo[2,1-a][2]benzazepine-1a,5(2H)-dicarboxylate. Trimethylsulfoxonium Iodide (7.20 g, 32.7 mMol) was suspended in 90 mL of anhydrous DMSO, blanketed in nitrogen and 95% sodium hydride (789 mg, 31.2 mMol) added. The reaction was stirred under nitrogen for 25 minutes until the solution was clear. 10-(1,1-dimethylethyl) 6-methyl 13-cyclohexyl-3-(methyloxy)-7H-indolo[2,1-a][2]benzazepine-6,10-dicarboxylate (9.00 g, 17.9 mMol) was added to the reaction and the reaction heated to 65 C for 4.5 hours. The reaction was partitioned between dichloromethane and 0.1N hydrochloric acid. The aqueous phase was extracted with dichloromethane. The dichloromethane fractions combined and washed 3× with 1.0N hydrochloric acid, dried over sodium sulfate and volatiles removed in vacuo to yield 10.9 g of a brown foam. The reaction was combined with a previous experiment and the product chromatographed on silica gel eluting with dichloromethane to yield 8.3 g of product as a light colored amorphous solid. $^1$H NMR (500 MHz, CHLOROFORM-D) δ ppm 0.40 (t, J=6.10 Hz, 0.5H) 1.17-1.30 (m, 2H) 1.30-1.46 (m, 3H) 1.49-1.61 (m, 3H) 1.63 (d, J=4.27 Hz, 9H) 1.65-1.71 (m, 1H) 1.71-1.83 (m, 3H) 1.91 (d, J=9.16 Hz, 1H) 1.94-2.15 (m, 3H) 2.64 (dd, J=9.77, 7.02 Hz, 0.5H) 2.77 (t, J=12.05 Hz, 0.5H) 2.85-2.97 (m, 1H) 3.42 (d, J=14.95 Hz, 0.6H) 3.57 (d, J=1.53 Hz, 1.5H) 3.79 (d, J=1.53 Hz, 1.5H) 3.88 (s, 3H) 4.02-4.09 (m, 0.6H) 5.19 (d, J=14.95 Hz, 0.5H) 5.42 (d, J=14.65 Hz, 0.5H) 6.86-6.95 (m, 1H) 7.01 (d, J=2.44 Hz, 0.5H) 7.12 (d, J=1.53 Hz, 0.5H) 7.26-7.30 (m, 0.8H) 7.63-7.75 (m, 1H) 7.80 (t, J=8.39 Hz, 1H) 8.08 (s, 0.5H) 8.27 (s, 0.5H); MS m/z 516 (MH+).

EXAMPLE 54

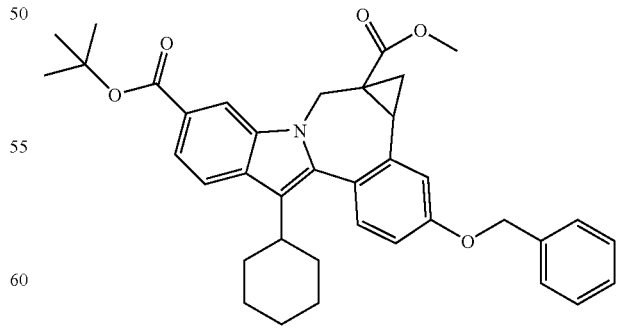

(+/−)-5-(1,1-dimethylethyl) 1a-methyl 8-cyclohexyl-11-((phenylmethyl)oxy)-1,12b-dihydrocyclopropa[d]indolo[2,1-a][2]benzazepine-1a,5(2H)-dicarboxylate. Trimethylsulfoxonium iodide (8.51 g, 38.7 mMol) was suspended in 100 ml of anhydrous DMSO and sodium hydride (95%, 937 mg, 37.1 mMol) was added and stirred under nitrogen for 30 minutes until the reaction appeared clear and homogenous. 10-(1,1-dimethylethyl) 6-methyl 13-cyclohexyl-3-((phenylmethyl)oxy)-7H-indolo[2,1-a][2]benzazepine-6,10-dicarboxylate (10.6 g, 18.4 mMol) was added and the reaction heated under a nitrogen atmosphere to 65° C. for 18 hrs. The reaction was partitioned between dichloromethane and 1N hydrochloric acid. The aqueous phase was extracted with dichloromethane and the organic phases combined, washed 3× with 1N hydrochloric acid and dried over sodium sulfate. Solvent was removed in vacuo to yield 11.2 g of crude product which was then combined with product from a previous experiment. The pure product was isolated by silica gel chromatography eluting with dichloromethane to yield 11.9 g. $^1$H NMR (500 MHz, CHLOROFORM-D) δ ppm 0.40 (t, J=6.10 Hz, 0.5H) 1.09-1.31 (m, 2.1H) 1.32-1.48 (m, 2.8H) 1.48-1.61 (m, 2.1H) 1.61-1.66 (m, 9H) 1.66-1.85 (m, 3.5H) 1.86-2.18 (m, 4.3H) 2.63 (t, J=8.39 Hz, 0.5H) 2.78 (m, 0.5H) 2.84-2.97 (m, 1.1H) 3.42 (d, J=14.95 Hz, 0.5H) 3.49-3.63 (m, 1.5H) 3.73-3.86 (m, 1.4H) 4.06 (d, J=15.26 Hz, 0.5H) 5.06-5.24 (m, 2.6H) 5.42 (d, J=14.95 Hz, 0.5H) 6.93-7.04 (m, 1H) 7.10 (s, 0.5H) 7.22 (s, 0.6H) 7.26-7.31 (m, 0.9H) 7.31-7.39 (m, 1.1H) 7.39-7.53 (m, 4.2H) 7.68 (dd, J=20.29, 8.39 Hz, 1.1H) 7.80 (t, J=8.39 Hz, 1H) 8.02-8.13 (m, 0.5H) 8.18-8.32 (m, 0.5H); MS m/z 592 (MH$^+$).

EXAMPLE 55

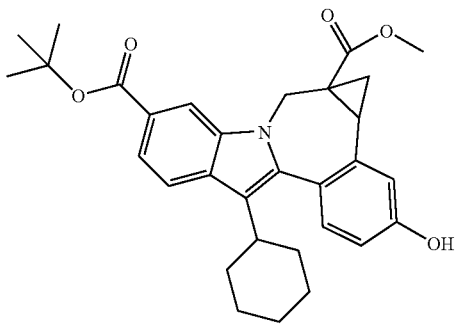

(+/−)-5-(1,1-dimethylethyl) 1a-methyl 8-cyclohexyl-11-hydroxy-1,12b-dihydrocyclopropa[d]indolo[2,1-a][2]benzazepine-1a,5(2H)-dicarboxylate. 5-(1,1-dimethylethyl) (+/−)-1a-methyl 8-cyclohexyl-11-((phenylmethyl)oxy)-1,12b-dihydrocyclopropa[d]indolo[2,1-a][2]benzazepine-1a,5(2H)-dicarboxylate (3.00 g, 5.1 mMol) was dissolved in 75 ml of inhibitor free THF and 70 mL of methanol added. The contents were placed under nitrogen and 304 mg of 10% palladium on carbon added to the reaction. The reaction was placed under hydrogen (1 atm, balloon) and stirred at room temperature for 18 hrs. An additional 200 mg of 10% palladium on carbon was added to the reaction and the reaction stirred an additional 21 hrs under hydrogen (1 atm, balloon). The reaction was filtered through celite and volatiles removed in vacuo to yield 2.7 g of product. $^1$H NMR (500 MHz, CHLOROFORM-D) δ ppm 0.32-0.44 (m, 0.5H) 1.11-1.29 (m, 2.2H) 1.29-1.46 (m, 3.5H) 1.47-1.61 (m, 2.5H) 1.63 (d, J=4.88 Hz, 9H) 1.65-1.83 (m, 3.6H) 1.85-2.13 (m, 4.1H) 2.59 (dd, J=10.07, 7.02 Hz, 0.5H) 2.76 (t, J=12.21 Hz, 0.5H) 2.81-2.95 (m, 1H) 3.36-3.45 (m, 0.6H) 3.49 (s, 2.4H) 3.56 (s, 1.4H) 3.79 (s, 1.2H) 4.05 (d, J=15.26 Hz, 0.5H) 5.18 (d, J=15.26 Hz, 0.6H) 5.25 (s, 0.7H) 5.41 (d, J=15.26 Hz, 0.5H) 6.77-6.88 (m, 1H) 6.95 (d, J=2.44 Hz, 0.5H) 7.08 (d, J=2.14 Hz, 0.5H) 7.21 (t, J=8.39 Hz, 1.1H) 7.63-7.74 (m, 1H) 7.80 (t, J=8.24 Hz, 1H) 8.04-8.10 (m, 0.5H) 8.19-8.29 (m, 0.5H); MS m/z 502 (MH$^+$); MS m/z 500 (M−H)$^-$.

EXAMPLE 56

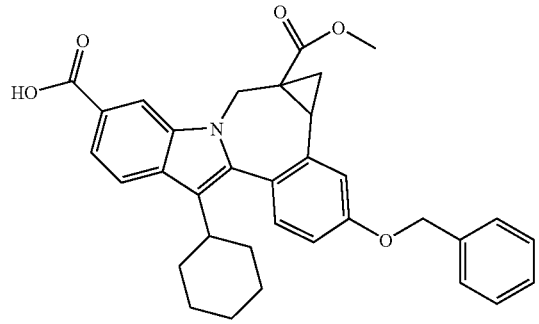

(+/−)-8-cyclohexyl-1a-((methyloxy)carbonyl)-11-((phenylmethyl)oxy)-1,1a,2,12b-tetrahydrocyclopropa[d]indolo[2,1-a][2]benzazepine-5-carboxylic acid. 5-(1,1-dimethylethyl) (+/−)-1a-methyl 8-cyclohexyl-11-((phenylmethyl)oxy)-1,12b-dihydrocyclopropa[d]indolo[2,1-a][2]benzazepine-1a,5(2H)-dicarboxylate (3.00 g, 5.07 mMol) was dissolved in 50 mL of 1,2-dichloroethane and 50 mL of trifluoroacetic acid was added to the reaction via addition funnel over 5 minutes. The reaction was stirred at room temperature for 1 hr and the volatiles were removed in vacuo. Residual trifluoroacetic acid was removed by azetrope with benzene and the off white solid was dried in vacuo to yield 2.8 g of product. $^1$H NMR (500 MHz, CHLOROFORM-D) δ ppm 0.43 (t, J=6.26 Hz, 0.4H) 1.06-1.16 (m, 0.3H) 1.18-1.33 (m, 2.4H) 1.33-1.50 (m, 2.7H) 1.58 (d, J=13.12 Hz, 0.5H) 1.65-1.72 (m, 0.7H) 1.71-1.85 (m, 2.7H) 1.93 (d, J=7.63 Hz, 1.3H) 1.96-2.18 (m, 2.9H) 2.61-2.70 (m, 0.4H) 2.80 (t, J=12.21 Hz, 0.4H) 2.86-2.99 (m, 1.2H) 3.45 (d, J=15.26 Hz, 0.6H) 3.53-3.64 (m, 1.8H) 3.76-3.86 (m, 1.1H) 4.10 (d, J=15.26 Hz, 0.4H) 5.09-5.19 (m, 2H) 5.22 (d, J=15.26 Hz, 0.4H) 5.38-5.51 (m, 0.6H) 6.95-7.05 (m, 1H) 7.11 (d, J=2.14 Hz, 0.4H) 7.26-7.31 (m, 0.7H) 7.33-7.40 (m, 1H) 7.43 (q, J=7.43 Hz, 2H) 7.44-7.50 (m, 2H) 7.72-7.93 (m, 2H) 8.21 (s, 0.4H) 8.37-8.50 (m, 0.6H); MS m/z 536 (MH$^+$); MS m/z 534 (M−H)$^-$.

EXAMPLE 57

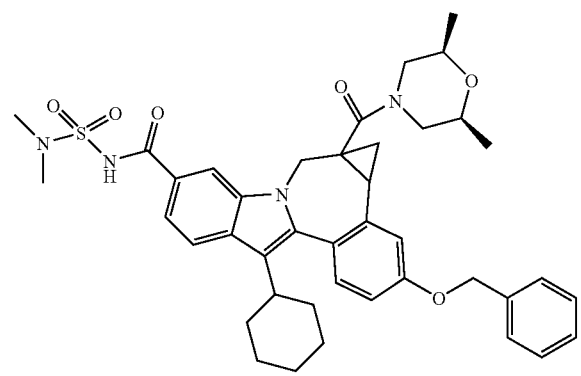

(+/−)-8-cyclohexyl-N-((dimethylamino)sulfonyl)-1a-(((cis)-2,6-dimethyl-4-morpholinyl)carbonyl)-11-((phenylmethyl)oxy)-1,1a,2,12b-tetrahydrocyclopropa[d]indolo[2,1-a][2]benzazepine-5-carboxamide. To a stirred solution of (+/−) Cycloprop[d]indolo[2,1-a][2]benzazepine-1a(2H)-carboxylic acid, 8-cyclohexyl-5-[[[(dimethylamino)sulfonyl] amino]carbonyl]-1,12b-dihydro-11-(phenylmethoxy)-, (1.01 g, 1.61 mMol) in 16 mL of DMF was added TBTU (647 mg, 2.01 mMol) The reaction was stirred at room temperature under a nitrogen atmosphere for 20 minutes then DMAP (600 mg, 4.91 mMol) was added followed by cis-2,6-dimethyl-morpholine (0.30 mL, 2.45 mMol). The reaction was stirred for 38 hrs at room temperature under nitrogen then poured into 50 mL of water. Hydrochloric acid (20 ml of 0.1N) was added to the aqueous suspension and a pale yellow solid collected by filtration and rinsed with 0.1N hydrochloric acid. The precipitate was dissolved in dichloromethane and washed 2× with 0.1N hydrochloric acid, dried over sodium sulfate and solvent removed in vacuo to yield 1.02 g of crude product. The aqueous phase was back extracted with dichloromethane and dried over sodium sulfate to yield 0.25 g of an oil which partially crystallized on standing. The organic isolates were combined and chromatographed on silica gel eluting with 5% ethyl acetate, 1% acetic acid in dichloromethane to yield 0.79 g (68%) of a very pale yellow solid. $^1$H NMR (500 MHz, CHLOROFORM-D) δ ppm 0.37 (t, J=5.34 Hz, 0.5H) 0.89 (s, 1H) 0.96-1.11 (m, 2.4H) 1.12-1.32 (m, 5.2H) 1.32-1.50 (m, 2.8H) 1.50-1.70 (m, 2.2H) 1.69-1.87 (m, 3.7H) 1.87-2.08 (m, 4.6H) 2.09 (s, 1.4H) 2.34-2.46 (m, 0.6H) 2.54-2.64 (m, 0.8H) 2.73-2.85 (m, 0.8H) 2.85-2.96 (m, 1.3H) 2.99 (d, J=20.75 Hz, 0.7H) 3.05 (s, 5.1H) 3.44-3.77 (m, 1.5H) 4.04-4.24 (m,1H) 4.68 (d, J=14.95 Hz, 0.5H) 5.04 (d, J=16.48 Hz, 0.4H) 5.09-5.19 (m, 1.8H) 6.92-7.06 (m, 1H) 7.09-7.23 (m, 1.2H) 7.26-7.33 (m, 1H) 7.33-7.52 (m, 5.5H) 7.80-7.91 (m, 1H) 7.92-8.05 (m, 1H) 8.81 (s, 0.5H) 9.05 (s, 0.3H); MS m/z 725 (MH$^+$); MS m/z 723 (M–H)$^-$.

EXAMPLE 58

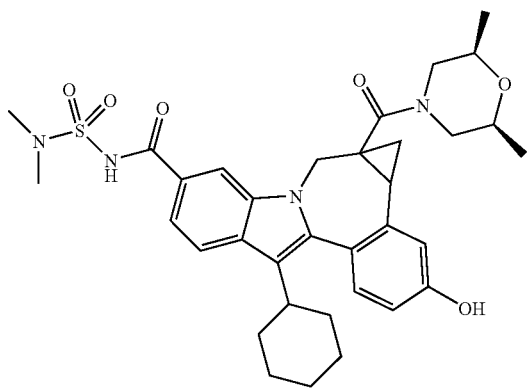

(+/−)-8-cyclohexyl-N-((dimethylamino)sulfonyl)-1a-(((cis)-2,6-dimethyl-4-morpholinyl)carbonyl)-11-hydroxy-1,1a,2,12b-tetrahydrocyclopropa[d]indolo[2,1-a][2]benzazepine-5-carboxamide. (+/−)-8-cyclohexyl-N-((dimethylamino)sulfonyl)-1a-(((cis)-2,6-dimethyl-4-morpholinyl)carbonyl)-11-((phenylmethyl)oxy)-1,1a,2,12b-tetrahydrocyclopropa[d]indolo[2,1-a][2]benzazepine-5-carboxamide (1.35 g, 1.87 mMol) was dissolved in a mixture of 75 ml of methanol and 35 ml of anhydrous inhibitor free THF. The reaction mixture was placed under nitrogen and 10% palladium on carbon (208 mg) was added. The reaction was placed under hydrogen (1 atm balloon) and stirred at room temperature for 17 hours. The reaction was filtered through celite, rinsed with methanol and filtrate volatiles removed in vacuo to yield 1.18 g (97%) of product. $^1$H NMR (500 MHz, CHLOROFORM-D) δ ppm 0.29-0.48 (m, 0.8H) 0.88 (s, 1.5H) 0.94-1.10 (m, 2.5H) 1.12-1.65 (m, 9.6H) 1.62-1.85 (m, 3.9H) 1.83-2.07 (m, 5H) 2.28-2.64 (m, 2H) 2.69-2.86 (m, 1.3H) 2.85-2.98 (m, 1.6H) 3.05 (s, 6H) 3.59 (d, J=14.95 Hz, 0.9H) 3.67-4.02 (m, 1.1H) 4.12 (d, J=14.34 Hz, 0.8H) 4.37 (s, 0.5H) 4.64 (d, J=14.65 Hz, 0.6H) 5.02 (d, J=13.12 Hz, 0.3H) 6.77-6.93 (m, 1.1H) 6.96-7.09 (m, 1.2H) 7.15 (d, J=8.24 Hz, 0.8H) 7.23 (d, J=9.16 Hz, 0.6H) 7.40 (d, J=8.55 Hz, 0.6H) 7.44-7.53 (m, 0.3H) 7.85 (d, J=8.55 Hz, 1.1H) 7.98 (t, J=17.70 Hz, 0.9H) 8.86 (s, 0.6H) 9.28 (s, 0.2H); MS m/z 635 (MH$^+$).

EXAMPLES 59 AND 60

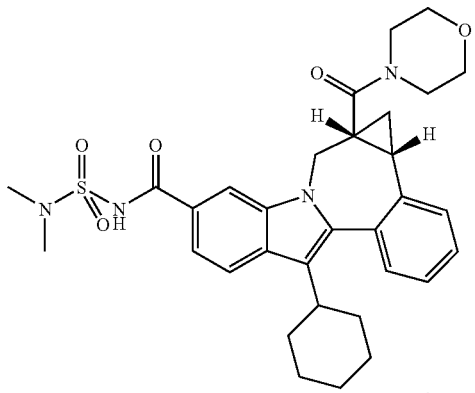

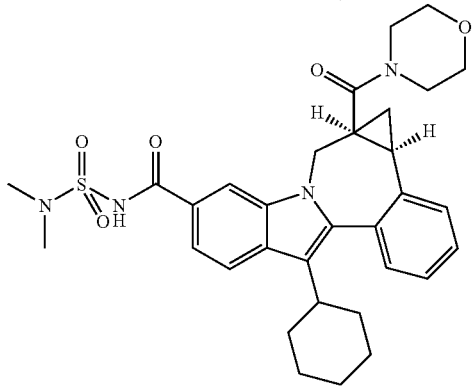

(+)-Cycloprop[d]indolo[2,1-a][2]benzazepine-5-carboxamide, 8-cyclohexyl-N-[(dimethylamino)sulfonyl]-1,1a,2,12b-tetrahydro-1a-(4-morpholinylcarbonyl)- and (−) and Cycloprop[d]indolo[2,1-a][2]benzazepine-5-carboxamide, 8-cyclohexyl-N-[(dimethylamino)sulfonyl]-1,1a,2,12b-tetrahydro-1a-(4-morpholinylcarbonyl)-. A 2M solution of oxalyl chloride (0.113 mL, 0.227 mmol) in CH$_2$Cl$_2$ was added dropwise to a solution of (+) or (−)cycloprop[d]indolo [2,1-a][2]benzazepine-5-carboxylic acid, 8-cyclohexyl-1,1a,2,12b-tetrahydro-1a-(4-morpholinylcarbonyl)- (55 mg, 0.113 mmol) in CH$_2$Cl$_2$ (10 mL), containing one drop of DMF. The reaction mixture was stirred at rt. for 2 hr., after which it was concentrated and dried under high vacuum. The residue was subsequently dissolved in THF (10 mL) and a solution of N,N-dimethylsulfonamide, (28 mg, 0.227 mmol) and DIPEA (0.059 mL, 0.339 mmol)) in THF (2 mL) was added. This was followed by the addition of DMAP (10 mg), after which the reaction was stirred at rt. for 10 min., and then at 50° C. overnight. It was then cooled, and the mixture concentrated under reduced pressure. The resultant residue was purified by preparative reverse phase HPLC to afford the product as (+) or (−) isomer. First isomer (synthesized from acid which came out first from chiral AD column): (off-white solid, 10 mg, 15% yield); MS m/z 591 (MH$^+$), Retention time: 3.585 min. Second isomer (synthesized from acid which came out second from chiral AD column): (light yellow solid, 19 mg, 28% yield); MS m/z 591 (MH$^+$), Retention time: 3.553 min. 1H NMR (500 MHz, Solvent) δ ppm 0.18 (m, 0.28H) 1.10 (dd, J=9.92, 5.95 Hz, 0.28H) 1.22-1.65 (m, 5.44H) 1.76-1.88 (m, 2H) 1.93-2.22 (m, 4H) 2.58 (dd, J=9.92, 6.26 Hz, 0.28H) 2.68 (m, 0.72H) 2.84-3.05 (m, 1H) 3.03 (s, 4.32H) 3.04 (s, 1.68H) 3.25-3.83 (m, 8.72H) 4.16 (d, J=14.95 Hz, 0.28H) 4.91 (m, 0.28H) 5.14 (d, J=15.26 Hz, 0.72H) 7.39-7.52 (m, 3H) 7.59-7.69 (m, 2H) 7.96 (m, 1H) 8.06 (d, J=1.22 Hz, 0.72H) 8.12 (s, 0.28H).

EXAMPLE 61

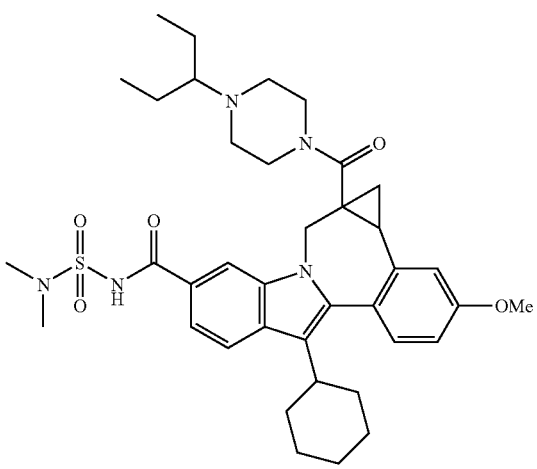

Cycloprop[d]indolo[2,1-a][2]benzazepine-5-carboxamide, 8-cyclohexyl-N-[(dimethylamino)sulfonyl]-1a-[[4-(1-ethylpropyl)-1-piperazinyl]carbonyl]-1,1a,2,12b-tetrahydro-11-methoxy-. To a mixture of the acid, 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid, (50 mg, 90.6 μmol), N,N,N',N'-tetramethyluronium tetrafluoroborate (TBTU, 150 mg, 467 μmol) and 1-(3-pentyl)piperazine (24 mg, 153 μmol) in DMF (2 ml) at r.t. under N$_2$ was added N,N-diisopropylethylamine (0.11 ml, 631 μmol). The reaction mixture was stirred at r.t. for 4 hr. 5 min., and then concentrated. The residue was diluted with MeOH (4 ml), and purified by Shimadzu-VP preparative reverse phase HPLC with separation method: Solvent A=10% MeOH-90% H$_2$O-0.1% TFA, Solvent B=90% MeOH-10% H$_2$O-0.1% TFA, Start % B=0, Final % B=100, Gradient time=6 min, Flow Rate=30 mL/min, Column: Xterra Prep MS C18 5 u 30×50 mm, Fraction Collection: 6.23-6.82 min. (UV detection at 220 nm) to give the trifluoroacetic acid salt (48.3 mg) as an off white solid; Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=690.56, HPLC R$_t$=1.675 min. Analytical HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Flow Rate=5 ml/min, Column: Phenomenex Lina C18 5 um 3.0×50 mm; LC/MS: (ES+) m/z (M+H)$^+$=690.49, HPLC R$_t$=1.690 min. LC/MS were performed by using Shimadzu-VP instrument with UV detection at 220 nm and Waters Micromass.

EXAMPLE 62

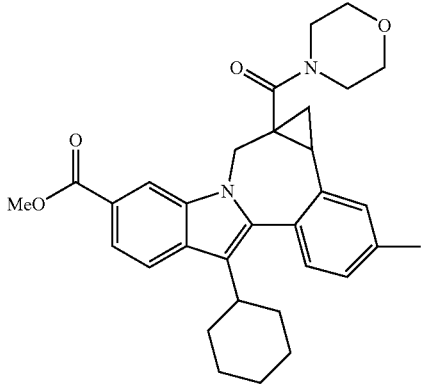

(+/−) Cycloprop[d]indolo[2,1-a][2]benzazepine-5-carboxylic acid, 8-cyclohexyl-11-methyl-1,1a,2,12b-tetrahydro-1a-(4-morpholinylcarbonyl)-, methyl ester. A microwave reaction tube was charged with InCl$_3$ (19.5 mg, 0.039 mmol) under nitrogen. Then it was sealed and added THF (2 mL). A solution of methyl lithium (0.074 mL, 1.6 M solution, 0.1185 mmol) in ether was added at −78° C. and stirred for 0.5 hr. The reaction mixture was then warmed to rt and a solution of (+/−) cycloprop[d]indolo[2,1-a][2]benzazepine-5-carboxylic acid, 8-cyclohexyl-1,1a,2,12b-tetrahydro-1a-(4-morpholinylcarbonyl)-11-[[(trifluoromethyl)sulfonyl]oxy]-, methyl ester (51 mg, 0.079 mmol) and PdCl$_2$(PPh$_3$)$_2$ (2.7 mg, 0.0039 mmol) in THF (1 mL) was added. The reaction mixture was heated at 100° C. under microwave condition for 2 hr. Then it was quenched with methanol and concentrated. The residue was purified by Prep. HPLC column to afford an off-white solid as product. (17 mg, 42% yield). MS m/z 513(MH$^+$), Retention time: 3.978 min. $^1$H NMR (500 MHz, MeOD) δ ppm 0.21 (m, 0.25H) 1.06 (m, 0.25H) 1.18-1.65 (m, 5.5H) 1.72-2.20 (m, 6H) 2.44 (s, 2.25H) 2.46 (s, 0.75H) 2.52 (m, 0.25H) 2.61 (m, 0.75H) 2.79-3.88 (m, 9.75H) 3.96 (s, 3H) 4.13 (d, J=14.95 Hz, 0.25H) 4.87-4.91 (m, 0.25H) 5.10 (d, J=15.26 Hz, 0.75H) 7.21-7.32 (m, 2H) 7.43 (s, 0.25H) 7.49 (s, 0.75H) 7.70-7.78 (m, 1H) 7.90 (d, J=8.55 Hz, 1H) 8.12 (s, 0.75H) 8.17 (s, 0.25H).

EXAMPLE 63

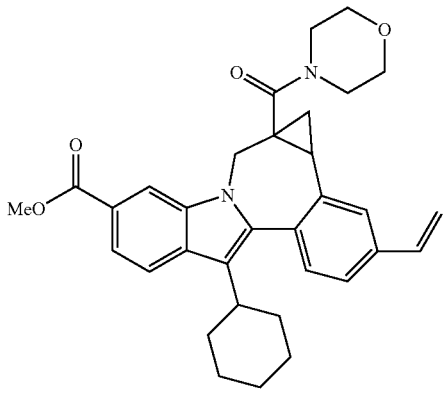

(+/−) 8-cyclohexyl-1a-(4-morpholinylcarbonyl)-11-vinyl-1,1a,2,12b-tetrahydrocyclopropa[d]indolo[2,1-a][2]benzazepine-5-carboxylic acid, methyl ester. To a solution of (+/−) cycloprop[d]indolo[2,1-a][2]benzazepine-5-carboxylic acid, 8-cyclohexyl-1,1a,2,12b-tetrahydro-1a-(4-morpholinylcarbonyl)-11-[[(trifluoromethyl)sulfonyl]oxy]-, methyl ester (125 mg, 0.195 mmol) in DMF (3 mL), LiCl (24.8 mg, 0.585 mmol), tributyl(vinyl)tin (74 mg, 0.234 mmol) and $PdCl_2$ $(PPh_3)_2$ (6.8 mg, 0.0098 mmol) were added. The reaction mixture was heated at 100° C. under $N_2$ atmosphere for overnight. It was then quenched with water and extracted with $CH_2Cl_2$ (2×20 mL). The organic layers were combined, dried ($MgSO_4$) and concentrated to give a brownish oil. It was then purified by Prep. HPLC to afford an orange solid as final product. (54 mg, 53% yield). MS m/z 525 (MH$^+$), Retention time: 4.090 min. $^1$H NMR (500 MHz, MeOD) δ ppm 0.21 (m, 0.26H) 1.05 (m, 0.26H) 1.19-1.64 (m, 5.48H) 1.73-1.85 (m, 2H) 1.89-2.16 (m, 4H) 2.56 (m, 0.26H) 2.62 (m, 0.74H) 2.77-3.86 (m, 9.74H) 3.94 (s, 3H) 4.08 (d, J=15.26 Hz, 0.26H) 4.76-4.80 (m, 0.26H) 5.03 (d, J=15.26 Hz, 0.74H) 5.36 (d, J=10.68 Hz, 0.74H) 5.37 (d, J=10.99 Hz, 0.26H) 5.93 (d, J=17.71 Hz, 0.74H) 5.95 (d, J=17.70 Hz, 0.26H) 6.77-6.87 (m, 1H) 7.32 (d, J=8.24 Hz, 1H) 7.46-7.53 (m, 1H) 7.63-7.75 (m, 2H) 7.88 (d, J=8.55 Hz, 1H) 8.08 (s, 0.74H) 8.12 (s, 0.26H).

Analytical data for some compounds is disclosed in Table 4.

TABLE 4

| Structure | Spectra data |
|---|---|
|  | MS m/z 499(MH+), Retention time: 3.818 min<br>1 H NMR (500 MHz, DMSO-D6) δ ppm −0.01 (m, 0.38 H) 1.05 (dd, J = 9.77, 5.80 Hz, 0.38 H) 1.09–1.54 (m, 5.24 H) 1.67–2.09 (m, 6 H) 2.74 (m, 0.38 H) 2.89 (m, 0.62 H) 2.97–3.09 (m,1 H) 3.42–3.78 (m, 8.62 H) 3.89 (s, 3 H) 4.02 (d, J = 15.26 Hz, 0.38 H) 5.00 (d, J = 15.26 Hz, 0.38 H) 5.10 (d, J = 15.56 Hz, 0.62 H) |
|  | 7.36 (m, 1 H)<br>7.42-7.51 (m, 2 H) 7.58-7.69 (m, 2 H) 7.92 (m, 1 H ) 8.10 (s, 0.62 H) 8.20 (s, 0.38 H)<br><br>MS m/z 485 (MH$^+$), Retention time: 3.663 min. |
|  | MS m/z 591 (MH$^+$), Retention time: 3.525 min. |

| Structure | Spectra data |
|---|---|
| 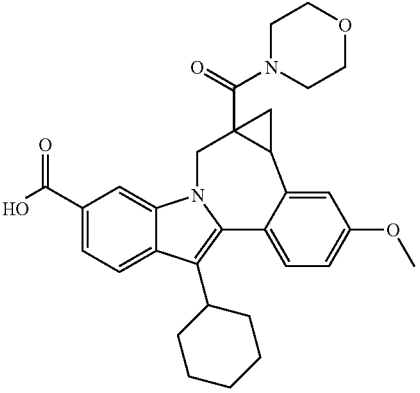 | MS m/z 515 (MH⁺), Retention time: 4.001 min.
1H NMR (500 MHz, DMSO-D6) δ ppm 0.02 (m, 0.38 H) 1.03 (dd, J = 9.77, 5.80 Hz, 0.38 H) 1.08-1.54 (m, 5.24 H) 1.66-2.10 (m, 6 H) 2.72 (m, 0.38 H) 2.87 (m, 0.62 H) 2.99 (m, 1 H) 3.28-3.78 (m, 8.62 H) 3.85 (s, 1.86 H) 3.86 (s, 1.14 H) 4.00 (d, J = 15.26 Hz, 0.38 H) 4.96 (d, J = 14.95 |
| 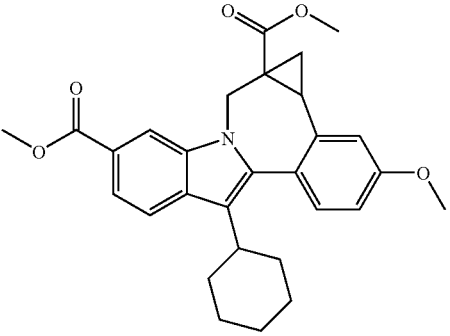 | Hz, 0.38 H) .06 (d, J = 15.26 Hz, 0.62 H) 7.02 (dd, J = 8.54, 2.75 Hz, 0.38 H) 7.06 (dd, J = 8.54, 2.44 Hz, 0.62 H) 7.13 (d, J = 2.44 Hz, 0.62 H) 7.20 (d, J = 2.44 Hz, 0.38 H) 7.28 (m, 1 H) 7.60 (dd, J = 8.54, 1.22 Hz, 0.62 H) 7.64 (m, 0.38 H) 7.82-7.89 (m, 1 H) 8.04 (s, 0.62 H) 8.14 (s, 0.38 H) 12.55 (s, br, 1 H)
1 H NMR (300 MHz, CD₃OD) δ ppm 0.25 (m, 0.3 H) 1.21-2.21 (m, 11.7 H) 2.70-3.02 (m, 2 H) 3.45 (d, J = 15.00 Hz, 0.7 H) 3.51 (s, 2.1 H) 3.81 (s, 0.9 H) 3.90 (s, 3 H) 3.95 (s, 0.9 H) 3.96 (s, 2.1 H) 4.03 (d, J = 15.00 Hz, 0.3 H) 522 (d, J = 15.00 Hz, 0.3 H) 5.45 (d, J = 15.00 Hz, 0.3 H) 5.45 (d, J = 15.00 Hz, 0.7 H) 6.95-7.03 (m, 1 H) 7.14 (d, J = 2.56 |
| 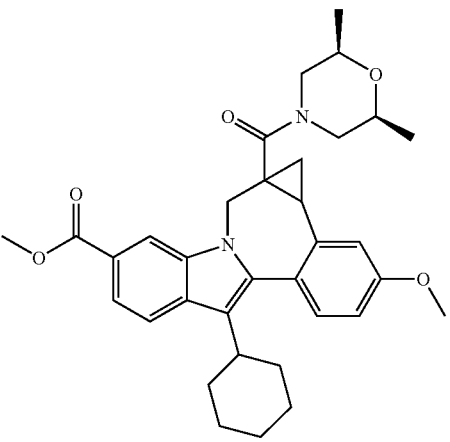 | Hz, 0.3 H) 7.21 (d, J = 1.83 Hz, 0.7 H) 7.25-7.34 (m, 1 H) 7.67 (m, 0.7 H) 7.72 (m, 0.3 H) 7.79-7.89 (m, 1 H) 8.11 (s, 0.3 H) 8.37 (s, 0.7 H).
MS m/z 557(MH⁺), Retention time: 3.941 min. |

| Structure | Spectra data |
| --- | --- |
| 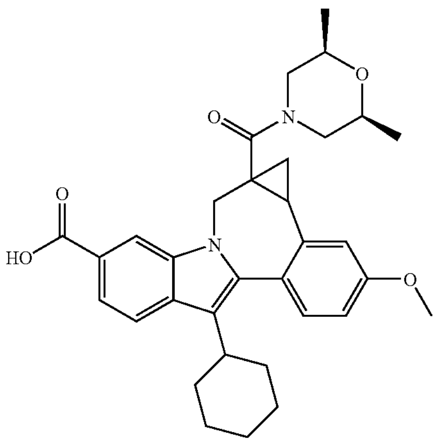 | MS m/z 543(MH+), Retention time: 3.808 min. |
| | MS m/z 612(MH+), Retention time: 3.516 min.<br>1 H NMR(500 MHz, DMSO-D6) δ ppm 0.01 (m, 0.44 H) 1.01 (dd, J = 9.61, 5.65 Hz, 0.44 H) 1.09-3.04 (m, 22.12 H) 3.44-3.64 (m, 5.56 H) 3.78-4.07(m, 9.44 H) 4.90 (d, J = 14.65 Hz, 0.44 H) 5.02 (d, J = 14.95 Hz, 0.56 H) 7.00-7.07 (m, 1 H) 7.13 (d, J = 2.44 Hz, 0.56 H) 7.20 (d, J = 2.44 Hz, 0.44 H) 7.28 (d, J = 8.54 Hz, 1 H) 7.58 (d, J = 8.55 Hz, 0.56 H) 7.66 (dd, J = 8.54, 1.22 Hz, 0.44 H) 7.89 (m, 1 H) 7.97 (s, 0.56 H) 8.18 (s, 0.44 H) |
| 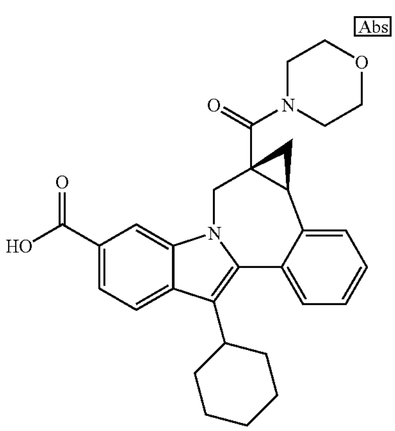 | MS m/z 485 (MH+), Retention time: 3.718 min. |

| Structure | Spectra data |
|---|---|
| 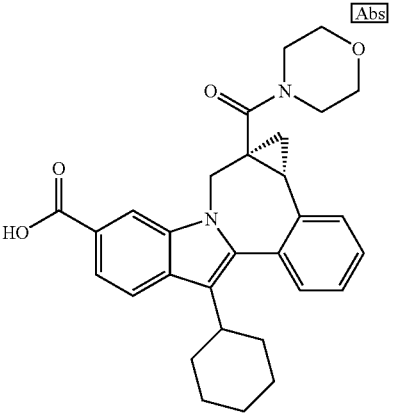 | MS m/z 485 (MH+), Retention time: 3.728 min.<br>1 H NMR (300 MHz, Solvent) δ ppm 0.22 (m, 0.23 H) 1.06 (dd, J = 9.88, 5.86 Hz, 0.23 H) 1.18-1.67 (m, 5.54 H) 1.69-2.21(m, 6H) 2.56 (dd, J = 9.88, 6.22 Hz, 0.23 H) 2.64 (dd, J = 9.15, 5.86 Hz, 0.77 H) 2.76-3.14 (m, 3 H) 3.30-3.88 (m, 6.77 H) 4.12 (d, J = 15.00 Hz, 0.23 H) 4.86 (d, J = 15.00 Hz, 0.23 H) 5.09 (d, J = 15.00 Hz, 0.77 H) 7.36-7.51 (m, 3 H) 7.56-7.68 (m, 1 H) 7.69  7.79 (m, 1 H) 7.90 (m, 1 H) 8.13 (s, 0.77 H) 8.18 (s, 0.23 H) |
| 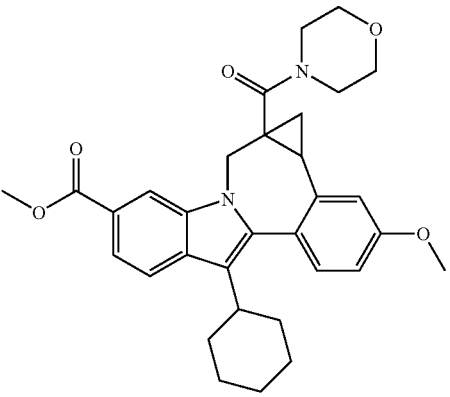 | MS m/z 529 (MH+), Retention time: 3.816 min.<br>1 H NMR (500 MHz, Solvent) δ ppm 0.24 (m, 0.25 H) 1.09 (m, 0.25 H) 1.22-1.65 (m, 5.5 H) 1.77-2.20 (m, 6 H) 2.54 (m, 0.25 H) 2.65 (m, 0.75 H) 2.80-3.87 (m, 9.75 H) 3.91 (s, 2.25 H) 3.92 (s, 0.75 H) 3.96 (s, 3 H) 4.16 (d, J = 14.95 Hz, 0.25 H) 4.88 (m, 0.25 H) 5.13 (d, J = 15.26 Hz, 0.75 H) 7.00 (dd, J = 8.54, 2.75 Hz, 0.25 H) 7.04 (dd, J = 8.55, 2.75 Hz, 0.75 H) 7.19 (d, J = 2.75 Hz, 0.25 H) 7.21 (d, J = 2.44 Hz, 0.75 H) 7.34 (d, J = 8.85 Hz, 1 H) 7.70-7.76 (m, 1 H) 7.90 (m, 1 H) 8.13 (s, 0.75 H) 8.18 (s, 0.25 H) |
| 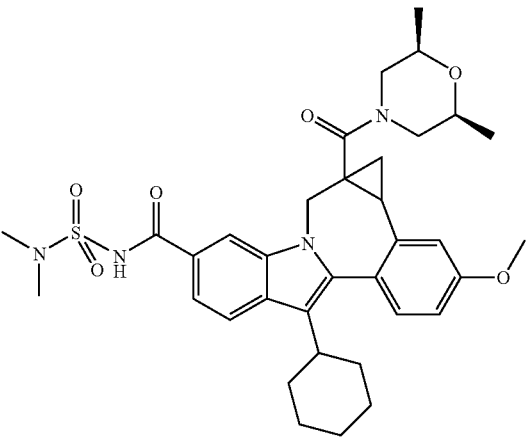 | MS m/z 649 (MH+), Retention time: 3.685 min. |

TABLE 4-continued
| Structure | Spectra data |
|---|---|
| 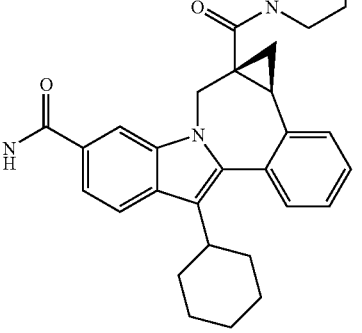 | MS m/z 591 (MH⁺), Retention time: 3.885 min. |
| 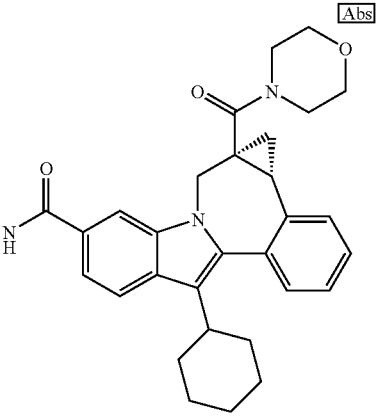 | MS m/z 591 (MH⁺), Retention time: 3.553 min.<br>1 H NMR (500 MHz, Solvent) δ ppm 0.18 (m, 0.28 H) 1.10 (dd, J = 9.92, 5.95 Hz, 0.28 H) 1.22-1.65 (m, 5.44 H) 1.76-1.88 (m, 2 H) 1.93-2.22 (m, 4 H) 2.58 (dd, J = 9.92, 6.26 Hz, 0.28 H) 2.68 (m, 0.72 H) 2.84-3.05 (m, 1 H) 3.03 (s, 4.32 H) 3.04 (s, 1.68 H) 3.25-3.83 (m, 8.72 H) 4.16 (d, J = 14.95 Hz, 0.28 H) 4.91 (m, 0.28 H) 5.14 (d, J = 15.26 Hz, 0.72 H) 7.39-7.52 (m, 3 H) 7.59-7.69 (m, 2 H) 7.96 (m, 1 H) 8.06 (d, J = 1.22 Hz, 0.72 H) 8.12 (s, 0.28 H) |
| 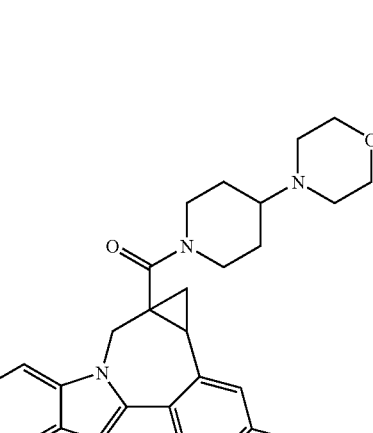 | MS m/z 598 (MH⁺), Retention time: 3.530 min. ¹H NMR (300 MHz, MeOD) δ ppm 0.27 (m, 0.3 H) 1.04 (m, 0.3 H) 1.14-2.23 (m,15.4 H) 2.43-3.09 (m, 3 H) 3.90 (s, 2.1 H) 3.91 (s, 0.9 H) 3.5-4.5 (m, 12 H) 4.9-5.2 (m, 1 H) 6.93-7.09 (m, 1 H) 7.15-7.22 (m, 1 H) 7.30 (s, 0.7 H) 7.33 (s, 0.3 H) 7.70 (d, J = 8.42 Hz, 0.7 H) 7.76 (d, J = 8.42 Hz, 0.3 H) 7.84-7.95 (m, 1 H) 8.08 (s, 0.7 H) 8.21 (s, 0.3 H) |

TABLE 4-continued

| Structure | Spectra data |
|---|---|
| 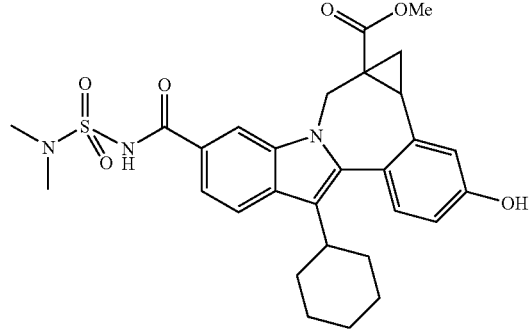 | MS m/z 552 (MH+), Retention time: 3.541 min. ¹H NMR (500 MHz, MeOD) δ ppm 0.23 (m, 0.35 H) 1.24-2.17 (m, 11.65 H) 2.61 (m, 0.35 H) 2.77-2.84 (m, 1 H) 2.95 (m, 0.65 H) 3.00 (s, 2.1 H) 3.02 (s, 3.9 H) 3.46 (d, J = 14.95 Hz, 0.65 H) 3.50 (s, 1.95 H) 3.79 (s, 1.05 H) 4.04 (d, J = 14.95 Hz, 0.35 H) 5.24 (d, J = 14.95 Hz, 0.35 H) 5.45 (d, J = 14.95 Hz, 0.65 H) 6.79-6.85 (m, 1 H) 6.96 (d, J = 2.44 Hz, 0.35 H) 7.07 (d, J = 2.44 Hz, 0.65 H) 7.17 (d, J = 8.24 Hz, 0.65 H) 7.21 (d, J = 8.24 Hz, 0.35 H) 7.53 (d, J = 8.24 Hz, 0.65 H) 7.60 (d, J = 8.55 Hz, 0.35 H) 7.83 (d, J = 8.24 Hz, 0.65 H) 7.87 (d, J = 8.54 Hz, 0.35 H) 8.07 (s, 0.35 H) 8.29 (s, 0.65 H) |
| 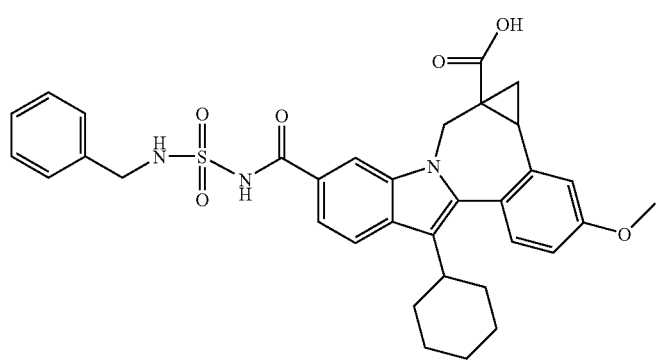 | ESI-MS m/e 613 (MH+), 1 H NMR (500 MHz, MeOD) δ ppm 1.22-2.20 (m, 13 H) 3.27-3.31 (m, 1 H) 3.47 (d, J = 14.95 Hz, 0.6 H) 3.92 (d, J = 2.44 Hz, 3 H) 4.04 (d, 0.4 H) 4.31 (d, J = 2.75 Hz, 2 H) 5.24 (d, 0.4 H) 5.48 (d, 0.6 H) 7.02 (d, 1 H) 7.17 (d, J = 2.75 Hz, 1 H) 7.19-7.35 (m, 5 H) 7.39 (t, J = 7.48 Hz, 2 H) 7.45-7.52 (m, 1 H) 7.80 (d, J = 1.53 Hz, 0.4 H) 7.85 (dd, J = 8.39, 6.87 Hz, 1 H) 8.22 (d, J = 1.53 Hz, 0.6 H) |

EXAMPLE 64

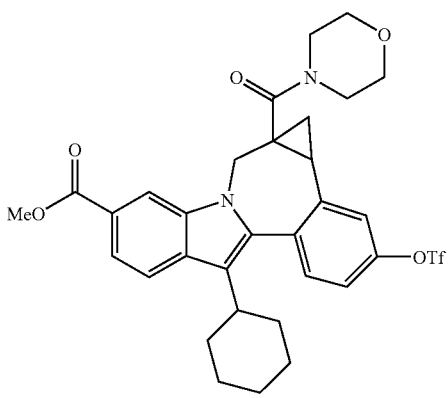

(+/−) Cycloprop[d]indolo[2,1-a][2]benzazepine-5-carboxylic acid, 8-cyclohexyl-1,1a,2,12b-tetrahydro-1a-(4-morpholinylcarbonyl)-11-[[(trifluoromethyl)sulfonyl]oxy]-, methyl ester. To a solution of (+/−) Cycloprop[d]indolo[2,1-a][2]benzazepine-5-carboxylic acid, 8-cyclohexyl-1,1a,2,12b-tetrahydro-1a-(4-morpholinylcarbonyl)-11-hydroxy-, methyl ester (250 mg, 0.486 mmol) in methylene chloride (20 mL), triethylamine (0.074 mL, 0.534 mmol) was added. Then trifluoromethanesulfonic anhydride (151 mg, 0.534 mmol) in CH₂Cl₂ (2 mL) was added dropwise at 0° C. The reaction mixture was warmed to rt and stirred for overnight. The reaction mixture was quenched with saturated NaHCO₃ solution and the organic layer was separated. It was then washed with brine and dried (MgSO₄). Evaporation of solvent gave a yellowish solid as product. (250 mg, 80% yield). MS m/z 647 (MH+), Retention time: 3.980 min.

EXAMPLE 65

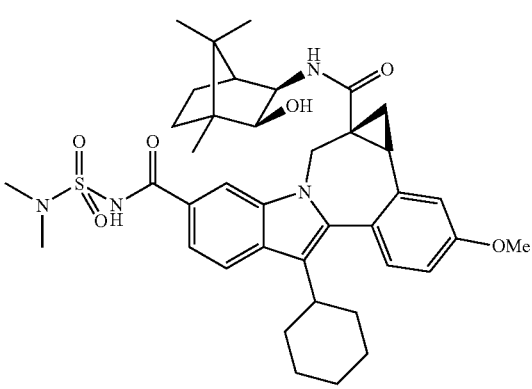

Cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aR)-[partial]-. TBTU (437 mg, 1.36 mmol) and DIPEA (0.95 mL, 5.436 mmol) were added to a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-(500 mg, 0.906 mmol) in DMSO (20.0 mL). The reaction mixture was stirred at rt for 15 min. (2S,3R)-3-Amino-1,7,7-trimethylbicyclo[2.2.1]heptan-2-ol (280 mg, 1.36 mmol) was then added and the reaction mixture was stirred at rt overnight. The reaction mixture was quenched with water and acidified with 1N HCl solution. A brown solid separated which was collected by filtration. This material was then fractionated by Prep. HPLC under the following conditions. Column: Waters Sunfire 19 mm×100 mm; Solvent A: 10% CH3CN-90% H2O-0.1% TFA; Solvent B: 90% CH3CN-10% H2O-0.1% TFA; Program: Start with 65% solvent B, initial hold time for 5 min, then gradually increase to 90% solvent B in 30 min with flow rate 25 mL/min. Load: 50-60 mg/run.

Cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aR)-[partial]-elutes before Cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aS)-[partial]- under the HPLC conditions described above. Product obtained as a light yellow solid, 230 mg, 36% yield). MS m/703 (MH$^+$), Retention time: 3.936 min. 1H NMR (500 MHz, MeOD) δ ppm 0.14-0.24 (m, 2.64H) 0.51 (s, 2.46H) 0.72-2.21 (m, 20.9H) 2.49 (m, 0.18H) 2.62 (m, 0.82H) 2.85 (m, 0.18H) 2.96 (m, 0.82H) 3.03 (s, 6H) 3.39 (m, 0.82H) 3.49-3.58 (m, 1.64H) 3.71-3.80 (m, 0.36H) 3.90 (s, 3H) 4.17 (d, J=14.65 Hz, 0.18H) 5.06 (d, J=14.65 Hz, 0.18H) 5.37 (d, J=14.95 Hz, 0.82H) 6.73 (d, J=5.49 Hz, 0.82H) 6.98-7.05 (m, 1H) 7.08 (d, J=4.58 Hz, 0.18H) 7.10 (d, J=2.44 Hz, 0.18H) 7.21 (d, J=2.44 Hz, 0.82H) 7.31 (d, J=8.55 Hz, 0.82H) 7.34 (d, J=8.55 Hz, 0.18H) 7.59-7.64 (m, 1H) 7.87-7.93 (m, 1H) 7.99 (s, 0.18H) 8.09 (d, J=1.22 Hz, 0.82H).

EXAMPLE 66

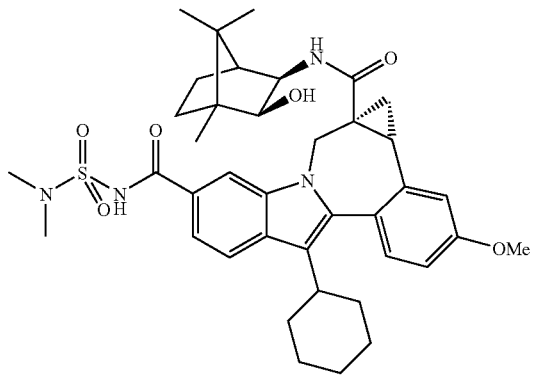

Cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aS)-[partial]-. TBTU (437 mg, 1.36 mmol) and DIPEA (0.95 mL, 5.436 mmol) were added to a solution of (+/−) cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-(500 mg, 0.906 mmol) in DMSO (20.0 mL). The reaction mixture was stirred at rt for 15 min. Then (2S, 3R)-3-amino-1,7,7-trimethylbicyclo[2.2.1]heptan-2-ol (280 mg, 1.36 mmol) was added, and the reaction mixture was stirred at rt overnight. The reaction mixture was quenched with water and then acidified with 1N HCl solution. A brown colored solid separated that was collected by filtration. This material was then fractionated by Prep. HPLC under the following conditions. Column: Waters Sunfire 19 mm×100 mm; Solvent A: 10% CH3CN-90% H2O-0.1% TFA; Solvent B: 90% CH3CN-10% H2O-0.1% TFA; Program: Start with 65% solvent B, initial hold time for 5 min, then gradually increase to 90% solvent B in 30 min with flow rate 25 mL/min. Load: 50-60 mg/run.

Cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aS)-[partial]- elutes after cycloprop[d]indolo[2,1-a][2]benzazepine-1a,5(2H)-dicarboxamide, 8-cyclohexyl-N$^5$-[(dimethylamino)sulfonyl]-1,12b-dihydro-N$^{1a}$-[(2R,3S)-3-hydroxy-4,7,7-trimethylbicyclo[2.2.1]hept-2-yl]-11-methoxy-, (1aR)-[partial]-under the HPLC conditions described above. Product obtained as a light yellow solid, 215 mg, 34% yield). MS m/703 (MH$^+$), Retention time: 4.038 min. 1H NMR (500 MHz, MeOD) δ ppm 0.20 (m, 0.38H) 0.75 (s, 1.86H) 0.76 (s, 1.86H) 0.84 (s, 1.86H) 0.85 (s, 1.14H) 0.89-2.18 (m, 18.9H) 2.52 (m, 0.38H) 2.70 (m, 0.62H) 2.85 (m, 0.38H) 2.97 (m, 0.62H) 3.03 (s, 2.28H) 3.04 (s, 3.72H) 3.33-3.39 (m, 0.62H) 3.43-3.51 (m, 1.24H) 3.73-3.77 (m, 0.38H) 3.78-3.84 (m, 0.38H) 3.90 (s, 1.86H) 3.90 (s, 1.14H) 4.14 (d, J=14.65 Hz, 0.38H) 5.11 (d, J=14.65 Hz, 0.38H) 5.44 (d, J=15.26 Hz, 0.62H) 6.68 (d, J=4.88 Hz, 0.62H) 6.96-7.03 (m, 1H) 7.07 (d, J=5.19 Hz, 0.38H) 7.12 (d, J=2.44 Hz, 0.38H) 7.23 (d, J=2.14 Hz, 0.62H) 7.27 (d, J=8.54 Hz, 0.62H) 7.33 (d, J=8.54 Hz, 0.38H) 7.55 (dd, J=8.39, 1.68 Hz, 0.62H) 7.62 (dd, J=8.55, 1.53 Hz, 0.38H) 7.87 (d, J=8.54 Hz, 0.62H) 7.91 (d, J=8.55 Hz, 0.38H) 8.08 (d, J=1.22 Hz, 0.38H) 8.10 (d, J=1.22 Hz, 0.62H).

Experimentals for Examples 67-79 use the general methods described below until further noted. LCMS data: Stop time: Gradient time+1 minute; Starting conc: 0% B unless otherwise noted; Ending conc: 100% B unless otherwise noted; Eluent A: 5% CH$_3$CN/95% H$_2$O with 10 mM NH$_4$OAc (for columns A, D and E); 10% MeOH/90% H$_2$O with 0.1% TFA (for columns B and C); Eluent B: 95% CH$_3$CN/5% H$_2$O with 10 mM NH$_4$OAc (for columns A, D and E); 90% MeOH/10% H$_2$O with 0.1% TFA (for columns B and C); Column A: Phenomenex 10μ 4.6×50 mm C18; Column B: Phenomenex C18 10μ 3.0×50 mm; Column C: Phenomenex 4.6×50 mm C18 10μ; Column D: Phenomenex Lina C18 5μ 3.0×50 mm; Column E: Phenomenex 5μ 4.6×50 mm C18. Preparative HPLC data: Conditions for H$_2$O/CH$_3$CN with 10 mM NH$_4$OAc buffer; Gradient: Linear over 20 min. unless otherwise noted; Starting conc: 15% B unless otherwise noted; Ending conc: 100% B; Eluent A: 5% CH$_3$CN/95% H$_2$O with 10 mM NH$_4$OAc; Eluent B: 95% CH$_3$CN/5% H$_2$O with 10 mM NH$_4$OAc; Column: Sunfire Prep C$_{18}$ OBD 5μ 30×100 mm; Conditions for H$_2$O/MeOH with 0.1% TFA buffer; Gradient: Linear over 20 min. unless otherwise noted; Starting conc: 30% B unless otherwise noted; Ending conc: 100% B; Eluent A: 10% MeOH/90% H$_2$O with 0.1% TFA; Eluent B: 90% MeOH/10% H$_2$O with 0.1% TFA; Column: phenomenex 21×100 mm C18H$_2$O.

EXAMPLE 67

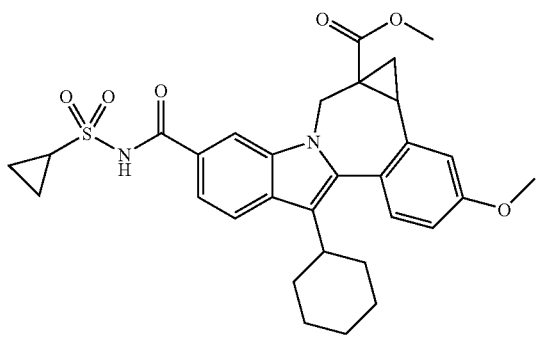

Methyl 8-cyclohexyl-5-((cyclopropylsulfonyl)carbamoyl)-11-methoxy-1,12b-dihydrocyclopropa[d]indolo[2,1-a][2]benzazepine-1a(2H)-carboxylate. To slurry of sodium hydride (60% dispersion in mineral oil, 370 mg, 9.2 mmol) in DMSO (8 mL) stirring under $N_2$ was added trimethylsulfoxonium iodide (2.03 g, 9.2 mmol). The reaction mixture was stirred for 45 min and then methyl 13-cyclohexyl-10-((cyclopropylsulfonyl)carbamoyl)-3-methoxy-7H-indolo[2,1-a][2]benzazepine-6-carboxylate (2.2 g, 4.0 mmol) in DMSO (5 mL) was added (flask rinsed with DMSO (2×3 mL)). The reaction mixture was stirred 1 h, poured into 0.25N HCl (100 mL), and extracted with EtOAc (150 mL). The organic layer was washed with brine (20 mL) and the combined aqueous layers were extracted with EtOAc (100 mL). The combine organic layers were washed with brine (~20 mL), dried ($MgSO_4$), filtered and concentrated to dryness. The residue was stirred with EtOAc/$Et_2O$ (1:3, 50 mL) and the solids were removed by filtration. The motherliquor was concentrated and dried under high vacuum to yield methyl 8-cyclohexyl-5-((cyclopropylsulfonyl)carbamoyl)-11-methoxy-1,12b-dihydrocyclopropa[d]indolo[2,1-a][2]benzazepine-1a(2H)-carboxylate (1.92 g, 3.4 mmol, 85%) as a yellow solid which was used without further purification. Presents as a ~2:1 mixture of rotamers or atrope isomers. $^1$HNMR (300 MHz, $CD_3OD$) δ 0.19-0.26 (m, 0.4H), 0.78-2.19 (m, 15.6H), 2.64-3.02 (m, 2H), 3.16-3.28 (m, 1H), 3.41 (d, J=15.0 Hz, 0.6H), 3.51 (s, 1.8H), 3.80 (s, 1.2H), 3.88 (s, 3H), 4.00 (d, J=15.0 Hz, 0.4H), 5.22 (d, J=15.0 Hz, 0.4H), 5.42 (d, J=15.0 Hz, 0.6H), 6.93-7.01 (m, 1H), 7.12 (d, J=2.6 Hz, 0.4H), 7.19 (d, J=2.6 Hz, 0.6H), 7.25 (d, J=8.8 Hz, 0.6H), 7.29 (d, J=8.8 Hz, 0.4H), 7.55 (dd, J=8.8, 1.5 Hz, 0.6H), 7.63 (dd, J=8.8, 1.5 Hz, 0.4H), 7.85 (d, J=8.8 Hz, 0.6H), 7.88 (d, J=8.8 Hz, 0.4H), 8.08 (d, J=1.5 Hz, 0.4H), 8.31 (d, J=1.5 Hz, 0.6H). LCMS: m/e 563 (M+H)$^+$, ret time 3.75 min, column B, 4 minute gradient.

EXAMPLE 68

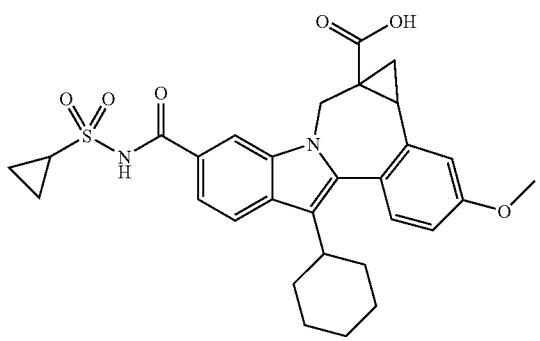

8-Cyclohexyl-5-((cyclopropylsulfonyl)carbamoyl)-11-methoxy-1,12b-dihydrocyclopropa[d]indolo[2,1-a][2]benzazepine-1a(2H)-carboxylic acid. Methyl 8-cyclohexyl-5-((cyclopropylsulfonyl)carbamoyl)-11-methoxy-1,12b-dihydrocyclopropa[d]indolo[2,1-a][2]benzazepine-1a(2H)-carboxylate (1.92 g, 3.41 mmol) was dissolved into MeOH//THF (1:1, 40 mL) and treated with 1M aqueous NaOH (8 mL). The reaction mixture was stirred and heated at 60° C. for 2 h and cooled to rt. The clear solution was neutralized with 1M aqueous HCl (8 mL) and concentrated to remove organic solvents. The resultant solids were collected by filtration, washed with $H_2O$ and dried under vacuum to yield 8-cyclohexyl-5-((cyclopropylsulfonyl)carbamoyl)-11-methoxy-1,12b-dihydrocyclopropa[d]indolo[2,1-a][2]benzazepine-1a(2H)-carboxylic acid (1.66 g, 3.03 mmol, 89%) as a yellow powder which was used without further purification. Presents as a 1:1 mixture of rotamers or atrope isomers. $^1$HNMR (300 MHz, $CDCl_3$) δ 0.32 (t, J=6.2 Hz, 0.5H), 0.71-2.12 (m, 15.5H), 2.61-2.94 (m, 2H), 3.16-3.27 (m, 1H), 3.41 (d, J=15.0 Hz, 0.5H), 3.82 (s, 1.5H), 3.86 (s, 1.5H), 3.99 (d, J=15.0 Hz, 0.5H), 5.28 (d, J=15.0 Hz, 0.5H), 5.49 (d, J=15.0 Hz, 0.5H), 6.85 (dd, J=8.4, 2.6 Hz, 0.5H), 6.91 (dd, J=8.4, 2.6 Hz, 0.5H), 6.96 (d, J=2.6 Hz, 0.5H), 7.08 (d, J=2.6 Hz, 0.5H), 7.19 (d, J=8.4 Hz, 0.5H), 7.24 (d, J=8.4 Hz, 0.5H), 7.61 (d, J=8.4 Hz, 0.5H), 7.67 (d, J=8.4 Hz, 0.5H), 7.83 (d, J=8.4 Hz, 0.5H), 7.85 (d, J=8.4 Hz, 0.5H), 8.06 (s, 0.5H), 8.35 (s, 0.5H), 9.31-10.35 (m, 1H). LCMS: m/e 547 (M–H)$^-$, ret time 2.06 min, column A, 4 minute gradient.

EXAMPLE 69

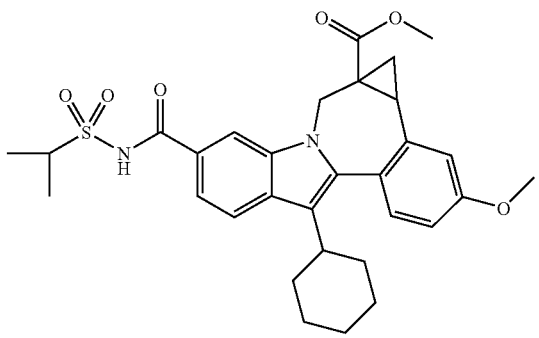

Methyl 8-cyclohexyl-5-((isopropylsulfonyl)carbamoyl)-11-methoxy-1,12b-dihydrocyclopropa[d]indolo[2,1-a][2]benzazepine-1a(2H)-carboxylate. To slurry of sodium hydride (60% dispersion in mineral oil, 97 mg, 2.4 mmol) in DMSO (2 mL) stirring under $N_2$ was added trimethylsulfoxonium iodide (530 g, 2.4 mmol). The reaction mixture was stirred for 45 min and then methyl 13-cyclohexyl-10-((isopropylsulfonyl)carbamoyl)-3-methoxy-7H-indolo[2,1-a][2]benzazepine-6-carboxylate (578 g, 1.05 mmol) in DMSO (1.5 mL) was added (flask rinsed with DMSO (2×0.75 mL)). The reaction mixture was stirred 1 h, poured into 0.25N HCl (25 mL), and extracted with EtOAc (40 mL). The organic layer was washed with brine (10 ml) and the combined aqueous layers were extracted with EtOAc (25 mL). The combine organic layers were washed with brine (~10 mL), dried ($MgSO_4$), filtered and concentrated to dryness. The residue was stirred with EtOAc/$Et_2O$ (1:4, 10 mL) and the solids were removed by filtration. The motherliquor was concentrated and dried under high vacuum to yield methyl 8-cyclohexyl-5-((isopropylsulfonyl)carbamoyl)-11-methoxy-1,12b-dihydrocyclopropa[d]indolo[2,1-a][2]benzazepine-1a(2H)-carboxylate (620 mg, 1.0 mmol, quant.) as a yellow solid which was used without further purification. Presents as a ~2:1 mixture of rotamers or atrope isomers. $^1$HNMR (300 MHz, $CDCl_3$) δ 0.32-0.39 (m, 0.4H), 0.77-2.09 (m, 17.6H), 2.60-2.96 (m, 2H), 3.41 (d, J=15.0 Hz, 0.6H), 3.53 (s, 1.8H), 3.79 (s, 1.2H), 3.87 (s, 3H), 4.02-4.14 (m, 1.4H), 5.14 (d, J=15.0 Hz, 0.4H), 5.39 (d, J=15.0 Hz, 0.6H), 6.89 (dd, J=8.4, 2.6 Hz, 0.4H), 6.91 (dd, J=8.4, 2.6 Hz, 0.6H), 7.00 (d, J=2.6 Hz, 0.4H), 7.11 (d, J=2.6 Hz, 0.6H), 7.23 (d, J=8.4 Hz, 0.6H), 7.25 (d, J=8.4 Hz, 0.4H), 7.38 (dd, J=8.4, 1.5 Hz, 0.6H), 7.43 (dd, J=8.4, 1.5 Hz, 0.4H), 7.83 (d, J=8.4 Hz, 0.6H), 7.86 (d, J=8.4 Hz, 0.4H), 7.96 (d, J=1.5 Hz, 0.4H), 8.20 (d, J=1.5 Hz, 0.6H), 8.39 (s, 0.4H), 8.43 (s, 0.6H). LCMS: m/e 563 (M−H)⁻, ret time 3.00 min, column A, 4 minute gradient.

EXAMPLE 70

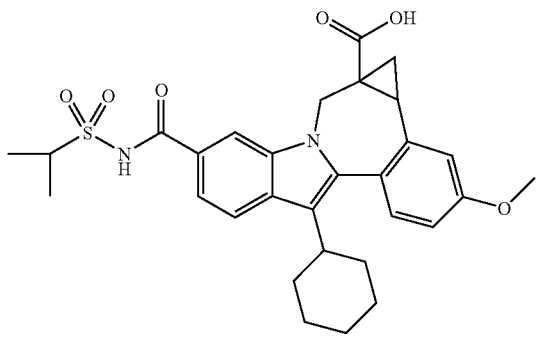

8-Cyclohexyl-5-((isopropylsulfonyl)carbamoyl)-11-methoxy-1,12b-dihydrocyclopropa[d]indolo[2,1-a][2]benzazepine-1a(2H)-carboxylic acid. Methyl 8-cyclohexyl-5-((isopropylsulfonyl)carbamoyl)-11-methoxy-1,12b-dihydrocyclopropa[d]indolo[2,1-a][2]benzazepine-1a(2H)-carboxylate (606 mg, 1.07 mmol) was dissolved into MeOH// THF (1:1, 14 mL) and treated with 1M aqueous NaOH (2.5 mL). The reaction mixture was stirred and heated at 60° C. for 2 h and cooled to rt. The clear solution was neutralized with 1M aqueous HCl (2.5 mL) and concentrated to remove organic solvents. The residue was stirred with H₂O (10 mL) overnight and the resultant solids were collected by filtration, washed with H₂O and dried under vacuum to yield 8-cyclohexyl-5-((isopropylsulfonyl)carbamoyl)-11-methoxy-1, 12b-dihydrocyclopropa[d]indolo[2,1-a][2]benzazepine-1a (2H)-carboxylic acid (530 mg, 0.96 mmol, 90%) as a bright yellow solid which was used without further purification. Presents as a ~2:1 mixture of rotamers or atrope isomers. ¹HNMR (300 MHz, CD₃OD) δ 0.23-0.30 (m, 0.4H), 0.80-2.24 (m, 17.6H), 2.70-3.11 (m, 2H), 3.46 (d, J=15.0 Hz, 0.6H), 3.95 (s, 3H), 3.93-4.10 (m, 1.4H), 5.29 (d, J=15.0 Hz, 0.4H), 5.48 (d, J=15.0 Hz, 0.6H), 6.98-7.05 (m, 1H), 7.16 (d, J=2.6 Hz, 0.4H), 7.23 (d, J=2.6 Hz, 0.6H), 7.29 (d, J=8.8 Hz, 0.6H), 7.33 (d, J=8.8 Hz, 0.4H), 7.56 (dd, J=8.8, 1.5 Hz, 0.6H), 7.64 (dd, J=8.4, 1.5 Hz, 0.4H), 7.87 (d, J=8.8 Hz, 0.6H), 7.92 (d, J=8.4 Hz, 0.4H), 8.13 (d, J=1.5 Hz, 0.4H), 8.31 (d, J=1.5 Hz, 0.6H). LCMS: m/e 551 (M+H)⁺, ret time 3.74 min, column B, 4 minute gradient.

EXAMPLE 71

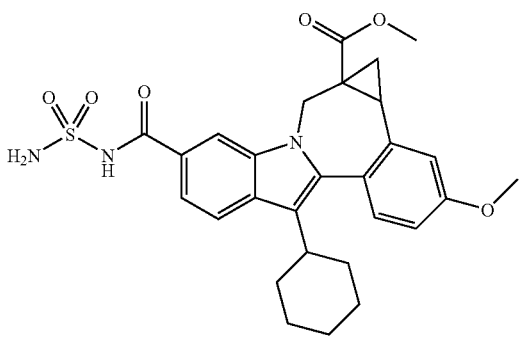

Methyl 5-((aminosulfonyl)carbamoyl)-8-cyclohexyl-11-methoxy-1,12b-dihydrocyclopropa[d]indolo[2,1-a][2]benzazepine-1a(2H)-carboxylate. To slurry of sodium hydride (60% dispersion in mineral oil, 350 mg, 8.8 mmol) in DMSO (8 mL) stirring under N₂ was added trimethylsulfoxonium iodide (1.93 g, 8.8 mmol) in three portions. The reaction mixture was stirred for 0.5 h and then methyl 10-((aminosulfonyl)carbamoyl)-13-cyclohexyl-3-methoxy-7H-indolo[2, 1-a][2]benzazepine-6-carboxylate (2.0 g, 3.8 mmol) in DMSO (8 mL) was added (flask rinsed with DMSO (2×2 mL)). The reaction mixture was stirred 1 h, poured into 0.25N HCl (100 mL), and diluted with CH₂Cl₂ (100 mL). The solution was filtered to collect solids, and the organic layer of the motherliquor was separated and concentrated to dryness. The residue was dissolved into EtOAc (~150 mL) was washed with H₂O (~50 mL) and brine (~50 mL) dried (MgSO₄), filtered and concentrated to dryness. The residue was stirred with EtOAc/Et₂O (4:1, 50 mL) and the solids were collected by filtration and washed with EtOAc. These solids were combined with the initially collected solids to yield methyl 5-((aminosulfonyl)carbamoyl)-8-cyclohexyl-11-methoxy-1, 12b-dihydrocyclopropa[d]indolo[2,1-a][2]benzazepine-1a (2H)-carboxylate (1.39 g, 2.6 mmol, 68%) as a tan solid which was used without further purification. Presents as a 1:1 mixture of rotamers or atrope isomers. ¹HNMR (300 MHz, DMSO-d₆) δ 0.13-0.21 (m, 0.5H), 1.06-2.12 (m, 11.5H), 2.64-2.94 (m, 2H), 3.46 (s, 1.5H), 3.49 (d, J=15.0 Hz, 0.5H), 3.75 (s, 1.5H), 3.85 (s, 3H), 4.02 (d, J=15.0 Hz, 0.5H), 5.21 (d, J=15.0 Hz, 0.5H), 5.42 (d, J=15.0 Hz, 0.5H), 6.99-7.09 (m, 1H), 7.17-7.31 (m, 1H), 7.41 (s, 0.5H), 7.43 (s, 0.5H), 7.66-7.56 (m, 1H), 7.82 (d, J=8.4 Hz, 0.5H), 7.87 (d, J=8.8 Hz, 0.5H), 8.25 (s, 0.5H), 8.47 (s, 0.5H), 11.62 (s, 0.5H), 11.69 (s, 0.5H). LCMS: m/e 538 (M+H)⁺, ret time 3.56 min, column B, 4 minute gradient.

EXAMPLE 72

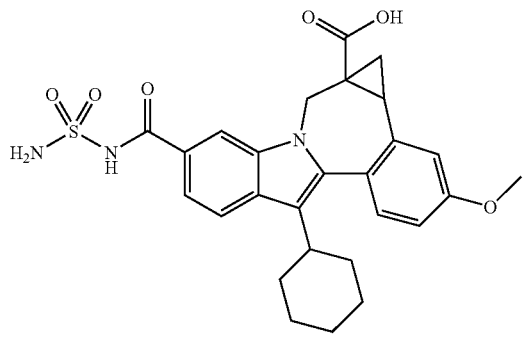

5-((Aminosulfonyl)carbamoyl)-8-cyclohexyl-11-methoxy-1,12b-dihydrocyclopropa[d]indolo[2,1-a][2]benzazepine-1a(2H)-carboxylic acid. Methyl 5-((aminosulfonyl) carbamoyl)-8-cyclohexyl-11-methoxy-1,12b-dihydrocyclopropa[d]indolo[2,1-a][2]benzazepine-1a(2H)-carboxylate (1.1 mg, 2.0 mmol) was dissolved into MeOH// THF (1:1, 24 mL) and treated with 1M aqueous NaOH (5 mL). The reaction mixture was stirred and heated at 60° C. for 2 h and cooled to rt. The clear solution was neutralized with 1M aqueous HCl (5 mL) and concentrated to remove organic solvents. The residue was stirred with H₂O (10 mL) for 1 h and the resultant solids were collected by filtration, washed with H₂O and dried under vacuum to yield 5-((aminosulfonyl)carbamoyl)-8-cyclohexyl-11-methoxy-1,12b-dihydrocyclopropa[d]indolo[2,1-a][2]benzazepine-1a(2H)-carboxylic acid (1.05 mg, 2.0 mmol, 98%) as a light yellow solid which was used without further purification. Presents as a 1:1 mixture of rotamers or atrope isomers. $^1$HNMR (300 MHz, DMSO-d$_6$) δ 0.08-0.17 (m, 0.5H), 0.79-2.13 (m, 11.5H), 2.65-2.94 (m, 2H), 3.44 (d, J=14.6 Hz, 0.5H), 3.85 (s, 3H), 3.96 (d, J=14.6 Hz, 0.5H), 5.20 (d, J=14.6 Hz, 0.5H), 5.40 (d, J=14.6 Hz, 0.5H), 6.98-7.08 (m, 1H), 7.17-7.46 (m, 4H), 7.58 (d, J=8.1 Hz, 0.5H), 7.62 (d, J=8.1 Hz, 0.5H), 7.81 (d, J=8.8 Hz, 0.5H), 7.87 (d, J=8.8 Hz, 0.5H), 8.25 (s, 0.5H), 8.44 (s, 0.5H), 11.48-13.19 (m, 2H). LCMS: m/e 524 (M+H)$^+$, ret time 3.51 min, column B, 4 minute gradient.

EXAMPLE 73

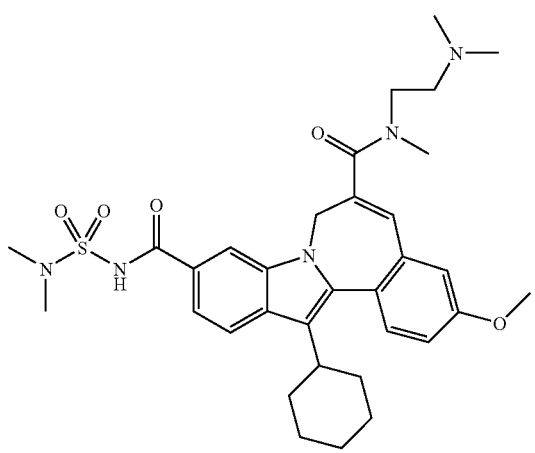

13-Cyclohexyl-N$^6$-(2-(dimethylamino)ethyl)-N$^{10}$-((dimethylamino)sulfonyl)-3-methoxy-N$^6$-methyl-7H-indolo[2,1-a][2]benzazepine-6,10-dicarboxamide. Methyl 13-cyclohexyl-10-(((dimethylamino)sulfonyl)carbamoyl)-3-methoxy-7H-indolo[2,1-a][2]benzazepine-6-carboxylate (700 mg, 1.27 mmol) was dissolved into MeOH//THF (1:1, 14 mL) and treated with 1M aqueous NaOH (3 mL). The reaction mixture was stirred and heated at 80° C. with microwave irradiation for 15 min and cooled to rt. The clear solution was neutralized with 1M aqueous HCl (3 mL) and concentrated to remove organic solvents. The residue was stirred with H$_2$O (10 mL) for 1 h and the resultant solids were collected by filtration, washed with H$_2$O and dried under vacuum. To a solution of these solids, N$^1$,N$^1$,N$^2$-trimethylethane-1,2-diamine (191 mg, 1.88 mmol) and triethylamine (0.700 mL) in DMF (5 mL) was added HATU (620 mg, 1.63 mmol). The reaction mixture was stirred at rt for 1 h, diluted with H$_2$O (25 mL) and 1M HCl (aq.) (5 mL) and stirred 20 The precipitates were collected by filtration, rinsed with H$_2$O and dried to yield impure 13-cyclohexyl-N$^6$-(2-(dimethylamino)ethyl)-N$^{10}$-((dimethylamino)sulfonyl)-3-methoxy-N$^6$-methyl-7H-indolo[2,1-a][2]benzazepine-6,10-dicarboxamide (960 mg) as a yellow powder. A crude sample of 13-cyclohexyl-N$^6$-(2-(dimethylamino)ethyl)-N$^{10}$-((dimethylamino)sulfonyl)-3-methoxy-N$^6$-methyl-7H-indolo[2,1-a][2]benzazepine-6,10-dicarboxamide (100 mg) was dissolved into MeOH/DMF (3:1, 4 mL), filtered and purified by preparative HPLC (H$_2$O/CH$_3$CN with 10 mM NH$_4$OAc buffer) to yield 13-cyclohexyl-N$^6$-(2-(dimethylamino)ethyl)-N$^{10}$-((dimethylamino)sulfonyl)-3-methoxy-N$^6$-methyl-7H-indolo[2,1-a][2]benzazepine-6,10-dicarboxamide (78 mg, 0.13 mmol, 95%) $^1$HNMR (300 MHz, CD$_3$OD) δ 1.11-3.07 (m, 24H), 2.99 (s, 6H), 3.50-3.76 (m, 2H), 3.93 (s, 3H), 4.27-4.44 (m, 1H), 5.05-5.25 (m, 1H), 7.05 (s, 1H) 7.08 (d, J=2.6 Hz, 1H), 7.16 (dd, J=8.8, 2.6 Hz, 1H), 7.56 (d, J=8.4 Hz, 1H), 7.64 (dd, J=8.8, 1.5 Hz, 1H), 7.88 (d, J=8.4 Hz, 1H), 8.16 (br s, 1H). LCMS: m/e 620 (M–H)$^-$, ret time 2.32 min, column A, 4 minute gradient.

EXAMPLE 74

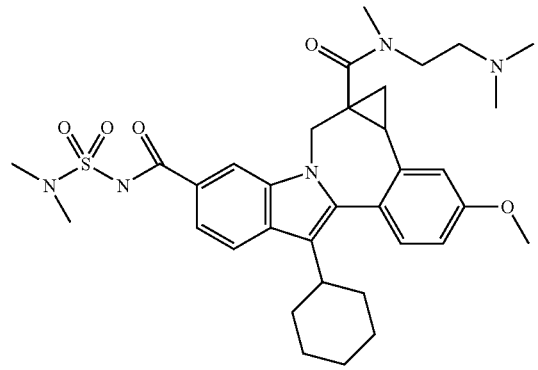

8-Cyclohexyl-N$^{1a}$-(2-(dimethylamino)ethyl)-N$^5$-((dimethylamino)sulfonyl)-11-methoxy-N$^{1a}$-methyl-1,12b-dihydrocyclopropa[d]indolo[2,1-a][2]benzazepine-1a,5(2H)-dicarboxamide. To a solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (120 mg, 0.22 mmol) and N$^1$,N$^1$,N$^2$-trimethylethane-1,2-diamine (29 mg, 0.28 mmol) in DMF (2 mL) and TEA (0.1 mL) was added HATU (108 mg, 0.28 mmol). The reaction was stirred at rt for 3 h, diluted with MeOH and purified by prep HPLC (H$_2$O/MeOH with 0.1% TFA buffer) to yield 8-cyclohexyl-N$^{1a}$-(2-(dimethylamino)ethyl)-N$^5$-((dimethylamino)sulfonyl)-11-methoxy-N$^{1a}$-methyl-1,12b-dihydrocyclopropa[d]indolo[2,1-a][2]benzazepine-1a,5(2H)-dicarboxamide (104 mg, 0.16 mmol, 74%) as a yellow solid. Presents as a 1:4 mixture of rotamers or atrope isomers. $^1$H NMR (300 MHz, MeOD) δ ppm 8.05-8.12 (m, 0.2H), 7.86-7.98 (m, 1.8H), 7.59 (dd, J=8.4, 1.5 Hz, 0.8H), 7.53-7.64 (m, 0.2H), 7.34 (d, J=8.4 Hz, 1H), 7.15-7.22 (m, 1H), 7.04 (dd, J=8.4, 2.6 Hz, 1H), 5.11 (d, J=15.4 Hz, 0.8H), 4.80-4.90 (m, 0.2H), 4.10-4.20 (m, 0.2H), 3.92 (s, 0.6H), 3.91 (s, 2.4H), 3.08-3.86 (m, 4.8H), 3.04 (s, 4.8H), 3.03 (s, 1.2H), 2.54-3.05 (m, 11H), 1.06-2.21 (m, 11.8H), 0.13-0.23 (m, 0.2H). LCMS: m/e 636 (M+H)$^+$, Column A, Gradient time: 2 min, ret time 1.20 min. LCMS: m/e 660 (M+H)$^+$, Column C, Gradient time: 2 min, ret time 1.91 min.

EXAMPLE 75

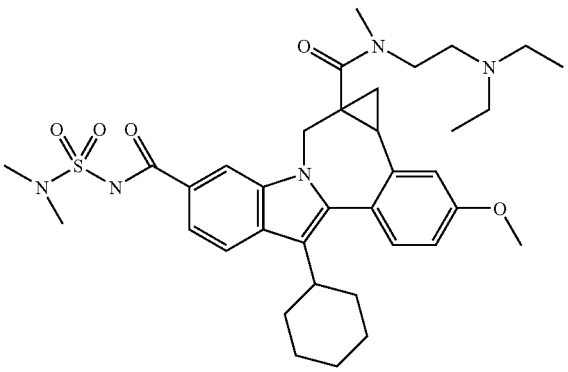

8-Cyclohexyl-N$^{1a}$-(2-(diethylamino)ethyl)-N$^5$-((dimethylamino)sulfonyl)-11-methoxy-N$^{1a}$-methyl-1,12b-dihydrocyclopropa[d]indolo[2,1-a][2]benzazepine-1a,5(2H)-dicarboxamide. To a solution of 8-cyclohexyl-5-

(((dimethylamino)sulfonyl)carbamoyl)-11-methoxy-1,12b-dihydrocyclopropa[d]indolo[2,1-a][2]benzazepine-1a(2H)-carboxylic acid (120 mg, 0.22 mmol) and $N^1,N^1$-diethyl-$N^2$-methylethane-1,2-diamine (31 mg, 0.24 mmol) in DMF (2 mL) and TEA (0.1 mL) was added HATU (90 mg, 0.24 mmol). The reaction was stirred at rt for 16 h, diluted with MeOH and purified by prep HPLC ($H_2O$/MeOH with 0.1% TFA buffer) to yield 8-cyclohexyl-$N^{1a}$-(2-(diethylamino)ethyl)-$N^5$-((dimethylamino)sulfonyl)-11-methoxy-$N^{1a}$-methyl-1,12b-dihydrocyclopropa[d]indolo[2,1-a][2]benzazepine-1a,5(2H)-dicarboxamide (87 mg, 0.13 mmol, 73%) as a yellow solid. Presents as a 1:7 mixture of rotamers or atrope isomers. $^1$H NMR (300 MHz, MeOD) δ ppm 8.08-8.12 (m, 0.12H), 7.98 (s, 0.88H), 7.93 (d, J=8.4 Hz, 1H), 7.60 (d, J=8.4 Hz, 0.88H), 7.58-7.64 (m, 0.12H), 7.35 (d, J=8.4 Hz, 1H), 7.20 (s, 1H), 7.04 (dd, J=8.4, 2.2 Hz, 1H), 5.14 (d, J=15.4 Hz, 0.88H), 4.77-4.91 (m, 0.12H), 4.13-4.23 (m, 0.12H), 3.92 (s, 0.36H), 3.91 (s, 2.64H), 3.04 (s, 6H), 2.52-3.87 (m, 13.88H), 0.99-2.20 (m, 17.88H), 0.16-0.25 (m, 0.12H). LCMS: m/e 664 (M+H)$^+$, Column A, Gradient time: 2 min, ret time 1.28 min.

EXAMPLE 76

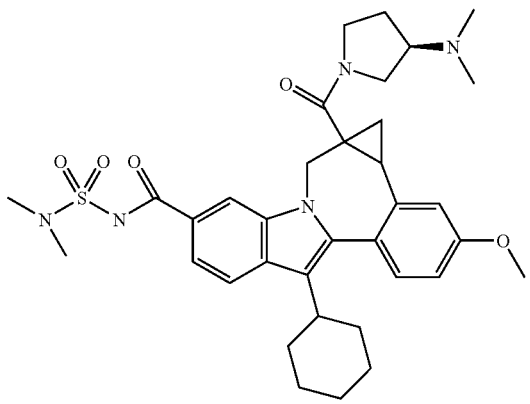

8-Cyclohexyl-1a-(((3R)-3-(dimethylamino)-1-pyrrolidinyl)carbonyl)-N-((dimethylamino)sulfonyl)-11-methoxy-1,1a,2,12b-tetrahydrocyclopropa[d]indolo[2,1-a][2]benzazepine-5-carboxamide. To a solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (60 mg, 0.11 mmol) and (R)—N,N-dimethylpyrrolidin-3-amine (16 mg, 0.14 mmol) in DMF (1 mL) and TEA (0.06 mL) was added HATU (54 mg, 0.14 mmol). The reaction was stirred at rt for 2 h, diluted with MeOH and purified by prep HPLC ($H_2O$/MeOH with 0.1% TFA buffer) to yield 8-cyclohexyl-1a-(((3R)-3-(dimethylamino)-1-pyrrolidinyl)carbonyl)-N-((dimethylamino)sulfonyl)-11-methoxy-1,1a,2,12b-tetrahydrocyclopropa[d]indolo[2,1-a][2]benzazepine-5-carboxamide (66 mg, 0.10 mmol, 93%) as a yellow solid. Presents as a 3:1 mixture of diatereomers. $^1$H NMR (300 MHz, MeOD) δ ppm 8.12 (br s, 0.25H), 7.86-8.01 (m, 1.75H), 7.57-7.65 (m, 0.25H), 7.59 (d, J=8.4 Hz, 0.75H), 7.34 (d, J=8.4 Hz, 0.75H), 7.27-7.35 (m, 0.25H), 7.16-7.23 (m, 1H), 7.04 (dd, J=8.4, 2.6 Hz, 0.75H), 6.96-7.04 (m, 0.25H), 5.13 (dd, J=15.4, 2.2 Hz, 0.75H), 4.15-4.24 (m, 0.25H), 3.92 (s, 0.75H), 3.90 (s, 2.25H), 3.62 (dd, J=15.4, 4.4 Hz, 0.75H), 3.40-4.11 (m, 3.25H), 3.14-3.29 (m, 1H), 3.03 (s, 1.5H), 3.04 (s, 4.5H), 2.83-2.98 (m, 6H), 2.47-3.09 (m, 3H), 1.03-2.40 (m, 13.75H), 0.09-0.22 (m, 0.25H). LCMS: m/e 648 (M+H)$^+$, Column A, Gradient time: 2 min, ret time 1.14 min.

EXAMPLE 77

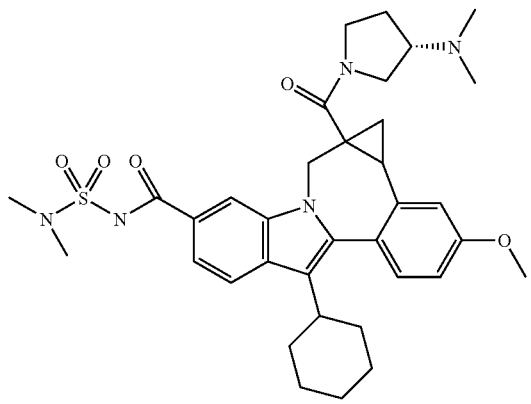

8-Cyclohexyl-1a-(((3S)-3-(dimethylamino)-1-pyrrolidinyl)carbonyl)-N-((dimethylamino)sulfonyl)-11-methoxy-1,1a,2,12b-tetrahydrocyclopropa[d]indolo[2,1-a][2]benzazepine-5-carboxamide. To a solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (60 mg, 0.11 mmol) and (S)—N,N-dimethylpyrrolidin-3-amine (16 mg, 0.14 mmol) in DMF (1 mL) and TEA (0.06 mL) was added HATU (54 mg, 0.14 mmol). The reaction was stirred at rt for 1 h, diluted with MeOH and purified by prep HPLC ($H_2O$/MeOH with 0.1% TFA buffer) to yield 8-cyclohexyl-1a-(((3S)-3-(dimethylamino)-1-pyrrolidinyl)carbonyl)-N-((dimethylamino)sulfonyl)-11-methoxy-1,1a,2,12b-tetrahydrocyclopropa[d]indolo[2,1-a][2]benzazepine-5-carboxamide (66 mg, 0.10 mmol, 93%) as a yellow solid. Presents as a 3:1 mixture of diastereomers. $^1$H NMR (300 MHz, MeOD) δ ppm 8.13 (br s, 0.25H), 7.86-8.01 (m, 1.75H), 7.57-7.65 (m, 0.25H), 7.59 (d, J=8.4 Hz, 0.75H), 7.35 (d, J=8.4 Hz, 0.75H), 7.27-7.35 (m, 0.25H), 7.16-7.23 (m, 1H), 7.04 (dd, J=8.4, 2.6 Hz, 0.75H), 6.96-7.04 (m, 0.25H), 5.14 (d, J=15.4, 0.75H), 4.15-4.24 (m, 0.25H), 3.92 (s, 0.75H), 3.91 (s, 2.25H), 3.62 (d, J=15.4, 4.4 Hz, 0.75H), 3.40-4.11 (m, 3.25H), 3.14-3.29 (m, 1H), 3.03 (s, 1.5H), 3.04 (s, 4.5H), 2.83-2.98 (m, 6H), 2.47-3.09 (m, 3H), 1.03-2.40 (m, 13.75H), 0.09-0.22 (m, 0.25H). LCMS: m/e 648 (M+H)$^+$, Column A, Gradient time: 4 min, ret time 2.13 min.

EXAMPLE 78

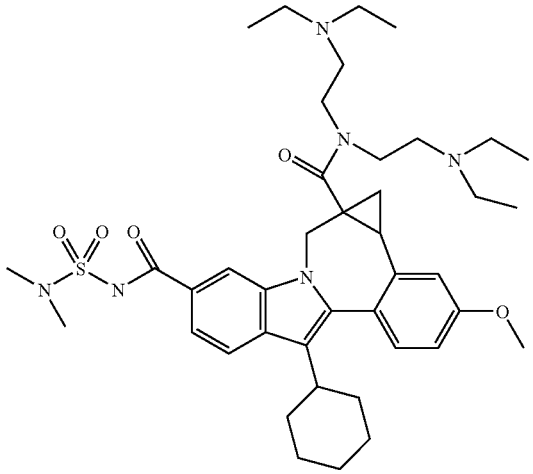

8-Cyclohexyl-$N^{1a},N^{1a}$-bis(2-(diethylamino)ethyl)-$N^5$-((dimethylamino)sulfonyl)-11-methoxy-1,12b-dihydrocyclopropa[d]indolo[2,1-a][2]benzazepine-1a,5(2H)-dicarboxamide. To a solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (60 mg, 0.11 mmol) and $N^1$-(2-(diethylamino)ethyl)-$N^2$,$N^2$-diethylethane-1,2-diamine (31 mg, 0.14 mmol) in DMF (1 mL) and TEA (0.06 mL) was added HATU (54 mg, 0.14 mmol). The reaction was stirred at rt for 1 h, diluted with MeOH and purified by prep HPLC ($H_2O$/MeOH with 0.1% TFA buffer) to yield 8-cyclohexyl-$N^{1a}$,$N^{1a}$-bis(2-(diethylamino)ethyl)-$N^5$-((dimethylamino)sulfonyl)-11-methoxy-1,12b-dihydrocyclopropa[d]indolo[2,1-a][2]benzazepine-1a,5(2H)-dicarboxamide (78 mg, 0.10 mmol, 93%) as a yellow solid. Presents as a 1:5 mixture of rotamers or atrope isomers. $^1$H NMR (300 MHz, MeOD) δ ppm 8.20 (d, J=1.5 Hz, 0.16H), 8.00 (d, J=1.5 Hz, 0.84H), 7.93 (d, J=8.4 Hz, 0.84H), 7.92-7.98 (m, 0.16H), 7.63 (dd, J=8.4, 1.5 Hz, 0.16H), 7.58 (dd, J=8.4, 1.5 Hz, 0.84H), 7.34-7.39 (m, 0.16H), 7.35 (d, J=8.4 Hz, 0.84H), 7.24 (d, J=2.6 Hz, 0.16H), 7.20 (d, J=2.6 Hz, 0.84H), 7.05 (dd, J=8.4, 2.6 Hz, 1H), 5.13 (d, J=15.4 Hz, 0.84H), 4.86-5.02 (m, 0.16H), 4.06-4.38 (m, 2H), 3.94 (s, 0.48H), 3.91 (s, 2.52H), 3.70 (d, J=15.4 Hz, 0.84H), 3.06-3.86 (m, 11.16H), 3.03 (s, 6H), 2.48-3.01 (m, 4H), 0.85-2.19 (m, 24.84H), 0.20-0.28 (m, 0.16H). LCMS: m/e 749 (M+H)$^+$, Column A, Gradient time: 4 min, ret time 2.77 min.

EXAMPLE 79

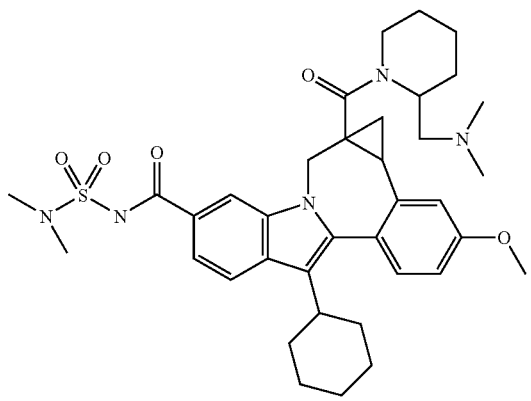

rac-(1aR,12bS)-8-Cyclohexyl-1a-(((2S)-2-((dimethylamino)methyl)-1-piperidinyl)carbonyl)-N-((dimethylamino)sulfonyl)-11-methoxy-1,1a,2,12b-tetrahydrocyclopropa[d]indolo[2,1-a][2]benzazepine-5-carboxamide and rac-(1aR,12bS)-8-cyclohexyl-1a-(((2R)-2-((dimethylamino)methyl)-1-piperidinyl)carbonyl)-N-((dimethylamino)sulfonyl)-11-methoxy-1,1a,2,12b-tetrahydrocyclopropa[d]indolo[2,1-a][2]benzazepine-5-carboxamide. To a solution of 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid (60 mg, 0.11 mmol) N,N-dimethyl-1-(piperidin-2-yl)methanamine (20 mg, 0.14 mmol) in DMF (1 mL) and TEA (0.06 mL) was added HATU (54 mg, 0.14 mmol). The reaction was stirred at rt for 1 h, diluted with MeOH and purified by prep HPLC ($H_2O$/MeOH with 0.1% TFA buffer) to yield two sets of diastereomeric products:

Isomer A: first eluting product: (26 mg, 0.039 mmol, 35%) as a yellow solid. Presents as a 1:6 ratio of rotamers or atrope isomers. $^1$H NMR (300 MHz, MeOD) δ ppm 8.03 (s, 1H), 7.92 (d, J=8.4 Hz, 1H), 7.57-7.64 (m, 0.15H), 7.58 (dd, J=8.4, 1.5 Hz, 0.85H), 7.33 (d, J=8.4 Hz, 0.85H), 7.29-7.36 (m, 0.15H), 7.20 (d, J=2.6 Hz, 0.85H), 7.18 (d, J=2.6 Hz, 0.15H), 7.04 (dd, J=8.4, 2.6 Hz, 0.85H), 6.99-7.05 (m, 0.15H), 5.06 (d, J=15.4 Hz, 1H), 4.73-4.80 (m, 0.15H), 4.47-4.58 (m, 0.85H), 3.92 (s, 0.45H), 3.91 (s, 2.55H), 3.70 (d, J=15.4 Hz, 1H), 3.03 (s, 6H), 2.80-4.18 (m, 11H), 2.54-2.66 (m, 1H), 1.13-2.20 (m, 17.85H), 0.17-0.26 (m, 0.15H). LCMS: m/e 676 (M+H)$^+$, Column C, Gradient time: 2 min, ret time 1.91 min.

Isomer B: second eluting product: (18 mg, 0.027 mmol, 25%) as a yellow solid. Presents as a 3:7 ratio of rotamers or atrope isomers. $^1$H NMR (300 MHz, MeOD) δ ppm 8.15 (d, J=1.5 Hz, 0.3H), 8.00 (d, J=1.5 Hz, 0.7H), 7.92 (d, J=8.4 Hz, 1H), 7.63 (dd, J=8.4, 1.5 Hz, 0.3H), 7.59 (dd, J=8.4, 1.5 Hz, 0.7H), 7.37 (d, J=8.4 Hz, 0.3H), 7.33 (d, J=8.4 Hz, 0.7H), 7.20 (d, J=2.6 Hz, 0.7H), 7.17 (d, J=2.6 Hz, 0.3H), 7.04 (dd, J=8.4, 2.6 Hz, 1H), 5.11 (d, J=15.4 Hz, 1H), 4.66-4.95 (m, 1H), 4.11 (d, J=15.4 Hz, 0.3H), 3.92 (s, 0.9H), 3.91 (s, 2.1H), 3.67 (d, J=15.4 Hz, 0.7H), 3.37-4.15 (m, 3H), 3.04 (s, 6H), 2.52-3.28 (m, 9H), 1.02-2.20 (m, 17.7H), 0.10-0.21 (m, 0.3H). LCMS: m/e 676 (M+H)$^+$, Column C, Gradient time: 2 min, ret time 1.95 min.

Examples 80-84 were analyzed by the following LC/MS method: Column: PHENOMENNEX-LUNA 3.0×50 mm S10; Mobile Phase: (A) 10:90 methanol-water; (B) 90:10 methanol-water; Buffer: 0.1% TFA; Gradient Range: 0-100% B; Gradient Time: 2 min; Flow Rate: 4 mL/min; Analysis Time: 3 min; Detection: Detector 1: UV at 220 nm; Detector 2: MS (ESI+).

EXAMPLE 80

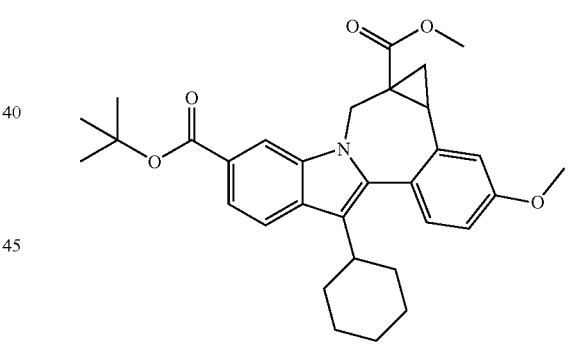

(+/−)-8-Cyclohexyl-1,1a,2,12b-tetrahydro-11-methoxy-1a-(methoxycarbonyl)-cycloprop[d]indolo[2,1-a][2]benzazepine-5-carboxylic acid, tert-butyl ester. Dry NaH (96 mg, 4 mmol) was added to a stirred suspension of trimethylsulfoxonium chloride (567 mg, 4.4 mmol) in an. DMSO (10 mL) under nitrogen. The resultant mixture was stirred at rt for 30-45 min and then neat olefin (1.0, 2 mmol) was added in small portions. The suspension was diluted with DMSO (5 mL) and heated at 50° C. for 3-4 h. Reaction mixture was allowed to cool to rt and water was added. Precipitated solid was filtered and washed with water and then air dried overnight to afford 1.15 g of crude product which was purified by flash column chromatography (silica gel, 3% MeOH in DCM), to provide pure desired cyclopropyl compound (0.96 g), as a off-white solid: LC/MS: Retention time 3.816 min; m/e 516 (MH$^+$). $^1$H NMR (400 MHz, CDCl$_3$): The product was observed to exist as inter-converting rotamers. LC/MS:

Retention time 3.816 min; m/e 516 (MH⁺). ¹H NMR (400 MHz, CDCl₃): The product was observed to exist as inter-converting rotamers.

EXAMPLE 81

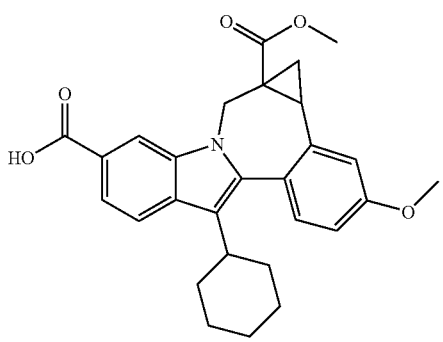

(+/−)-8-Cyclohexyl-1,1a,2,12b-tetrahydro-11-methoxy-1a-(methoxycarbonyl)-cycloprop[d]indolo[2,1-a][2]benzazepine-5-carboxylic acid. The tert-butyl ester (515 mg, 1 mmol) and TFA (5 mL) in an. DCM (10 mL) was stirred at rt until hydrolysis is complete (8-12 hr). Excess TFA and DCM were evaporated to dryness to afford desired acid (0.47 g, 100%) as a light beige solid. LC/MS: Retention time 2.245 min; m/e 460 (MH⁺). ¹H NMR (400 MHz, CDCl₃): The product was observed to exist as inter-converting rotamers. Retention time 2.245 min; m/e 460 (MH⁺). ¹H NMR (400 MHz, CDCl₃). The product was observed to exist as inter-converting rotamers.

EXAMPLE 82

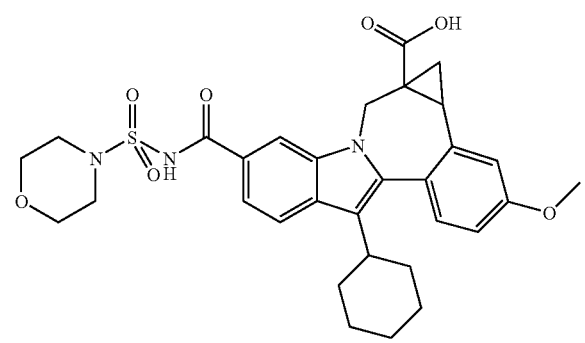

(+/−)-8-cyclohexyl-5-(morpholinosulfonylcarbamoyl)-1,1a,2,12b-tetrahydro-11-methoxy-cycloprop[d]indolo[2,1-a][2]benzazepine-1a-carboxylic acid. A mixture of acid (1 equiv) and carbonyldiimidazole (1.5 equiv) in an. THF was heated at 50° C. for 30 min and allowed to cool to rt. Then 1 equiv of either sulfamide or sulfonamide and DBU (2 equiv) were added consecutively. The resultant mixture was stirred at rt overnight. After acidic aqueous workup, isolated crude product was purified by prep. HPLC to afford the product. The ester moiety of was hydrolyzed using 1N NaOH in THF-MeOH to provide the corresponding acids. The acids were purified by prep HPLC and isolated. LC/MS: Retention time: 1.968 min; m/e 460 (MH⁺). ¹H NMR (400 MHz, CDCl₃): The product was observed to exist as inter-converting rotamers.

EXAMPLE 83

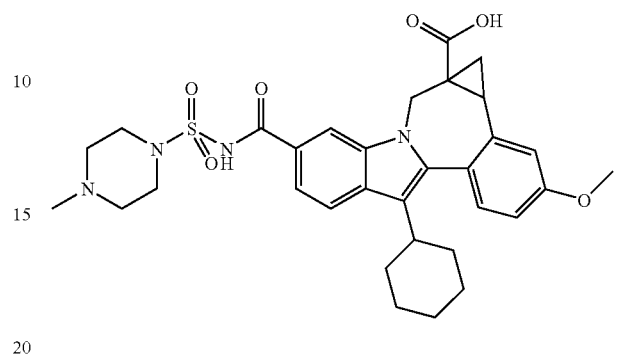

(+/−)-8-cyclohexyl-5-(4-methylpiperazin-1-ylsulfonyl-carbamoyl)-1,1a,2,12b-tetrahydro-11-methoxy-cycloprop[d]indolo[2,1-a][2]benzazepine-1a-carboxylic acid. The product was purified by prep HPLC and isolated in mono TFA salt form as a beige solid. LC/MS: Retention time: 1.687 min; m/e 607 (MH⁺). ¹H NMR (400 MHz, CDCl₃): The product was observed to exist as inter-converting rotamers.

EXAMPLE 84

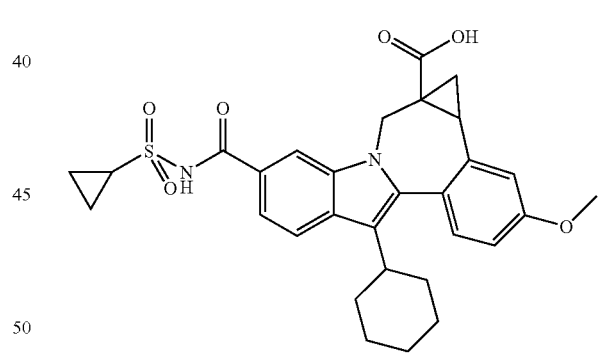

(+/−)-8-cyclohexyl-5-(cyclopropylsulfonylcarbamoyl)-1,1a,2,12b-tetrahydro-11-methoxy-cycloprop[d]indolo[2,1-a][2]benzazepine-1a-carboxylic acid. LC/MS: Retention time: 2.030 min; m/e 549 (MH⁺). ¹H NMR (400 MHz, CDCl₃): The product was observed to exist as inter-converting rotamers.

Example 85-97 were analyzed by the following LC/MS method: Start % B: 0; Final % B: 100; Gradient time: 3 min; Stop time: 4 min; Flow rate: 4 ml/min; Wavelength: 220; Solvent A: 10% MeOH/90% H₂O/0.1% Trifluoroacetic Acid; Solvent B: 10% H₂O/90% MeOH/0.1% Trifluoroacetic Acid; Column: XBridge 4.6×50 mm S5.

EXAMPLE 85

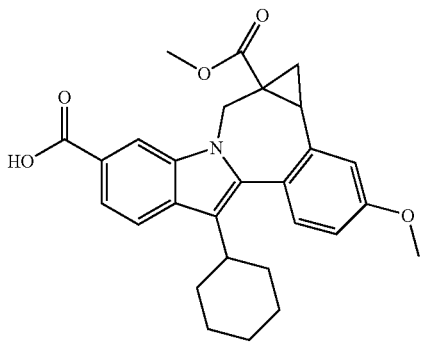

A mixture of acid (1.3 g, 2.83 mmol) and CDI (0.64 g, 3.97 mmol) in THF (20 mL) was heated at 50° C. for 0.5 h, cooled down and added methylsulfonamide (0.4 g, 4.2 mmol) and DBU (0.264 mL, 1.77 mmol). The mixture was stirred for 20 h and diluted with EtOAc, washed with cold 1N HCl (2×), brine, dried (MgSO$_4$), removed the solvent and purified by flash (Biotage 40 M) to afford the compound 1-2 (1.28 g, 85%) as a pale yellow solid. LC-MS retention time: 3.51; MS m/z 537 (M+H). The product was observed to exist as inter-converting rotamers. The major isomer: $^1$HNMR (400 MHz, CHLOROFORM-D) δ ppm 1.11-2.17 (m, 12H), 2.84-2.98 (m, 2H), 3.43 (d, J=14.86 Hz, 1H), 3.49 (s, 3H), 3.55 (s, 3H), 3.89 (s, 3H), 5.40 (d, J=15.11 Hz, 1H), 6.91-6.96 (m, 1H), 7.13 (d, J=2.52 Hz, 1H), 7.22-7.27 (m, 1H), 7.39 (dd, J=8.31, 1.51 Hz, 1H), 7.85 (d, J=8.81 Hz, 1H), 8.23 (d, J=1.26 Hz, 1H), 8.75 (s, 1H).

EXAMPLE 86

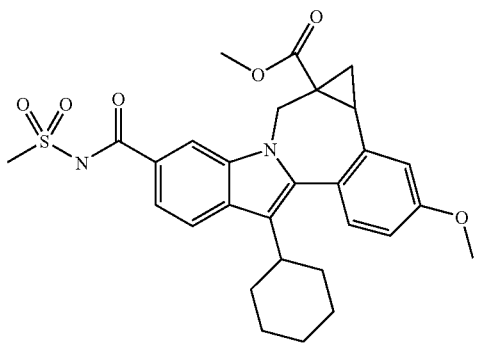

To a solution of the acid (1.28 g, 2.4 mmol) in THF (5 mL) and MeOH (5 mL) was added NaOH (1N, 12 mL, 12 mmol). After being stirred at room temperature for 3 h, the mixture was diluted with EtOAc, washed with cold 1N HCl, brine, dried (MgSO$_4$), and removed the solvent in vacuo to afford the compound 1-3 as a beige solid (1.20 g, 96%). LC-MS retention time: 3.46; MS m/z 523 (M+H). The product was observed to exist as inter-converting rotamers (~1/1) $^1$H NMR (400 MHz, CHLOROFORM-D).

EXAMPLE 87

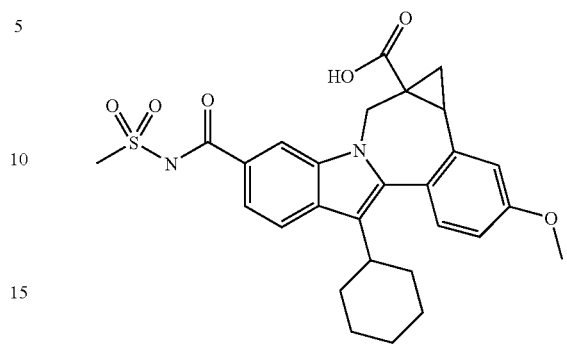

Typical general procedure for amine coupling: To a mixture of the acid (0.060 g, 0.11 mmol) and a secondary/tertiary amine containing diamine bishydrochloric acid salt (0.034 g, 0.17 mmol) in DMC (1.5 mL) was added Et$_3$N (0.096 mL, 0.69 mmol) and HBTU (0.065 g, 0.17 mmol). The mixture was stirred at room temperature for 0.5 h, diluted with MeOH, removed the solvent. The residue was dissolved in methanol, filtered, and purified by prep-HPLC to afford A TFA salt of an amide (0.0378 g, 82%).

EXAMPLE 88

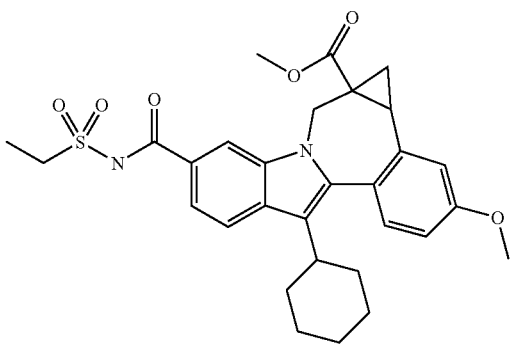

Prepared from the acid (0.47 g, 44%). LC-MS retention time: 3.54; MS m/z 551 (M+H).

EXAMPLE 89

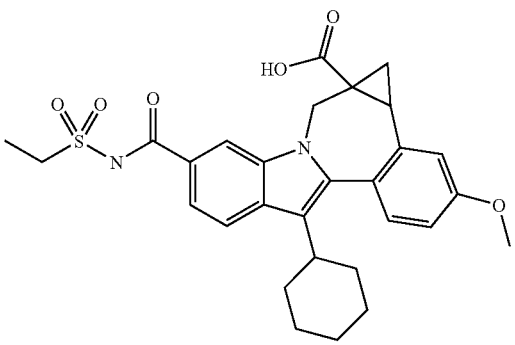

Prepared from ester (0.43 g, 94%). LC-MS retention time: 3.49; MS m/z 537 (M+H).

EXAMPLE 90

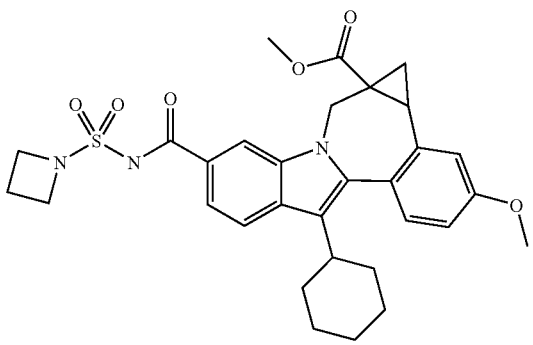

Prepared from the acid (0.96 g, 59%). LC-MS retention time: 3.58; MS m/z 578 (M+H). compound was observed to exist as inter-converting rotamers (3/4). The major isomer: ¹HNMR (400 MHz, CHLOROFORM-D) δ ppm 1.16-1.59 (m, 4H), 1.72 (dd, J=9.44, 4.15 Hz, 3H), 1.88-2.12 (m, 4H), 2.24-2.36 (m, 2H), 2.75-2.97 (m, 2H), 3.44 (d, J=14.86 Hz, 1H), 3.56 (s, 3H), 3.89 (s, 3H), 4.09 (d, 1H), 4.24-4.37 (m, 4H), 5.41 (d, J=14.86 Hz, 1H), 6.92-6.96 (m, 1H), 7.13 (d, J=2.01 Hz, 1H), 7.24-7.30 (m, 1H), 7.39 (dd, J=8.31, 1.51 Hz, 1H), 7.84-7.88 (m, 1H), 8.24 (d, J=1.51 Hz, 1H).

EXAMPLE 91

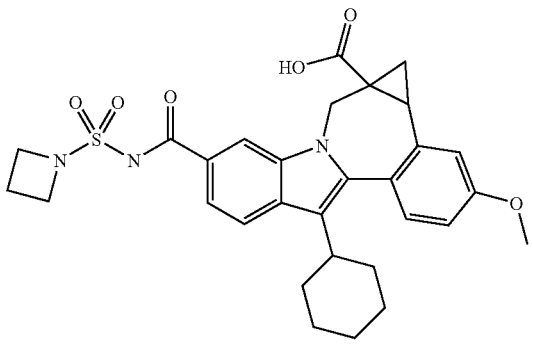

Prepared from the ester (0.93 g, 100%). LC-MS retention time: 3.51; MS m/z 564 (M+H). Compound was observed to exist as inter-converting rotamers (~3/4). The major isomer: ¹H NMR (400 MHz, ppm 0.34-0.42 (m, 1H), 1.15-2.10 (m, 11H), 2.22-2.38 (m, 2H), 2.65-2.78 (m, 1H), 2.84-2.94 (m, J=3.02 Hz, 1H), 3.84 (s, 3H), 4.03 (d, J=15.11 Hz, 1H), 4.21-4.43 (m, 4H), 5.34 (d, J=14.86 Hz, 1H), 6.87 (dd, J=8.56, 2.77 Hz, 1H), 6.98 (d, J=2.52 Hz, 1H), 7.21 (d, J=8.31 Hz, 1H), 7.69-7.75 (m, 1H), 7.86-7.90 (m, 1H), 8.13 (s, 1H).

EXAMPLE 92

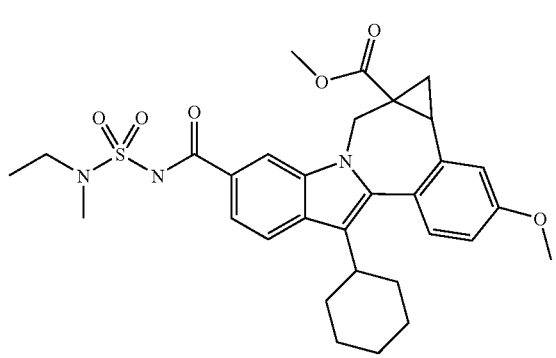

Prepared from the acid (0.109 g, 67%). LC-MS retention time: 3.60; MS m/z 580 (M+H). Compound was observed to exist as inter-converting rotamers (~5/4). The major isomer:

¹HNMR (400 MHz, ppm 1.16-2.09 (m, 14H), 2.73-2.93 (m, 2H), 3.07 (s, 3H), 3.31-3.52 (m, 3H), 3.76 (s, 3H), 3.88 (s, 3H), 4.05-4.10 (m, 1H), 5.40 (d, J=15.11 Hz, 1H), 6.88-6.93 (m, 1H), 7.13 (d, J=2.27 Hz, 1H), 7.22-7.29 (m, 1H), 7.33-7.42 (m, 1H), 7.82-7.86 (m, 1H), 8.19 (d, J=1.51 Hz, 1H)

EXAMPLE 93

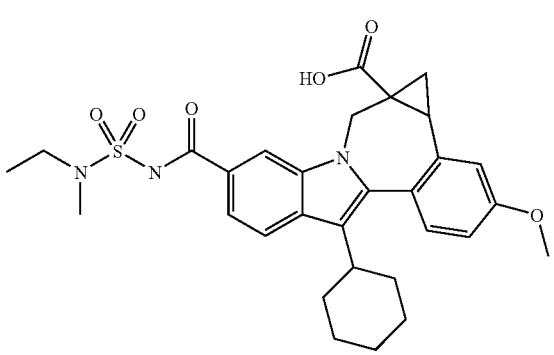

Prepared from ester (0.108 g, 100%). LC-MS retention time: 3.55; MS m/z 566 (M+H).

EXAMPLE 94

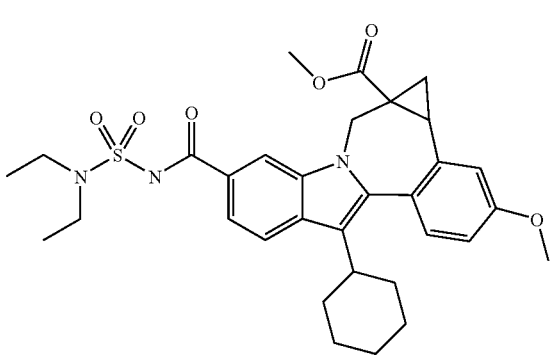

Prepared from the acid (0.127 g, 67%). LC-MS retention time: 3.64; MS m/z 594 (M+H). Compound was observed to exist as inter-converting rotamers: ¹H NMR (400 MHz, ppm 1.11-2.13 (m, 18H), 2.64 (dd, J=10.07, 6.80 Hz, 1H), 2.84-2.96 (m, 1H), 3.34-3.67 (m, 4H), 3.75 (s, 3H), 3.88 (s, 3H), 4.03-4.10 (m, 1H), 5.40 (d, J=15.36 Hz, 1H), 6.90-6.95 (m, 1H), 7.13 (d, J=2.01 Hz, 1H), 7.21-7.29 (m, 1H), 7.33-7.39 (m, 1H), 7.83 (d, J=8.06 Hz, 1H), 8.20 (d, J=1.26 Hz, 1H).

EXAMPLE 95

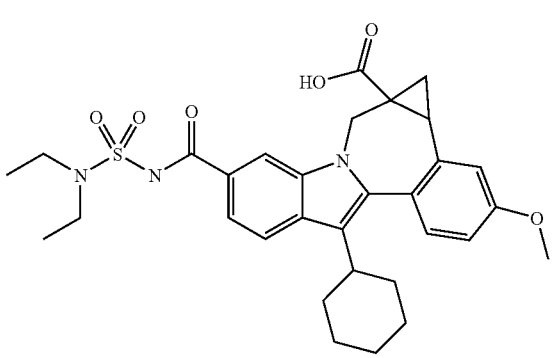

Prepared from ester (0.126 g, 100%). LC-MS retention time: 3.57; MS m/z 580 (M+H).

EXAMPLE 96

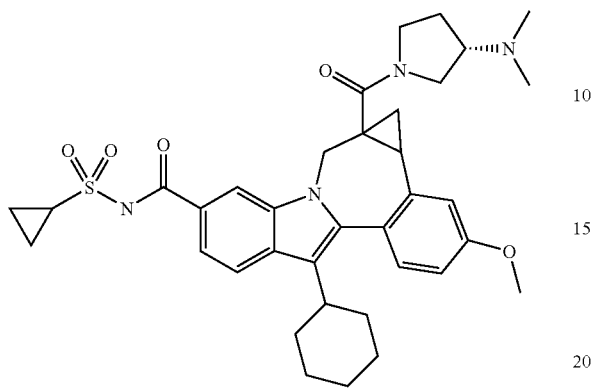

(+/−)-8-cyclohexyl-N-(cyclopropylsulfonyl)-1,1a,2,12b-tetrahydro-11-methoxy-1a-((S)-1-(3-(dimethylamino)pyrrolidin-1-yl))-8-carbonyl)-cycloprop[d]indolo[2,1-a][2]benzazepine-5-carboxamide. A TFA salt was prepared (0.0249 g, 36%). LC-MS retention time: 3.04; MS m/z 645 (M+H).

EXAMPLE 97

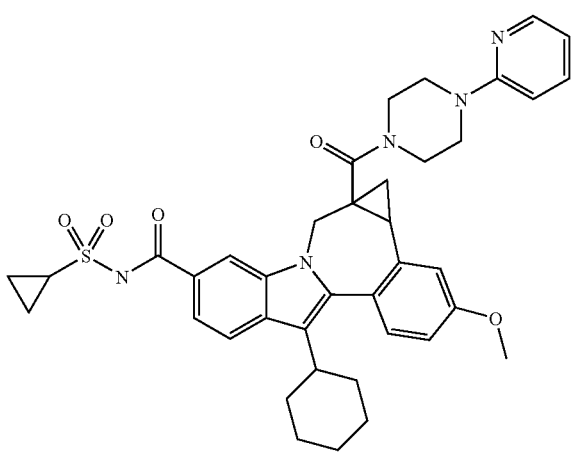

(+/−)-8-cyclohexyl-N-(cyclopropylsulfonyl)-1,1a,2,12b-tetrahydro-11-methoxy-1a-(1-(4-(pyridin-2-yl)piperazin-1-yl))-8-carbonyl)-cycloprop[d]indolo[2,1-a][2]benzazepine-5-carboxamide. A TFA salt was prepared (0.0447 g, 61%). LC-MS retention time: 3.06; MS m/z 694 (M+H). LC-MS retention time: 2.99; MS m/z 657 (M+H). Compound was observed to exist as inter-converting rotamers (~2/1). The major isomer: $^1$H NMR (400 MHz, ppm 0.92-2.09 (m, 16H), 2.66 (dd, J=8.94, 5.92 Hz, 1H), 2.87-2.98 (m, 1H), 3.01-3.10 (m, 1H), 3.10-4.09 (m, 8H), 3.60 (d, J=15.36 Hz, 1H), 3.90 (s, 3H), 5.01 (d, J=15.36 Hz, 1H), 6.86-6.98 (m, 2H), 7.11 (d, J=2.27 Hz, 1H), 7.26-7.29 (m, 1H), 7.48 (d, J=8.31 Hz, 1H), 7.81-7.94 (m, 2H), 7.98-8.07 (m, 2H).

EXAMPLE 98

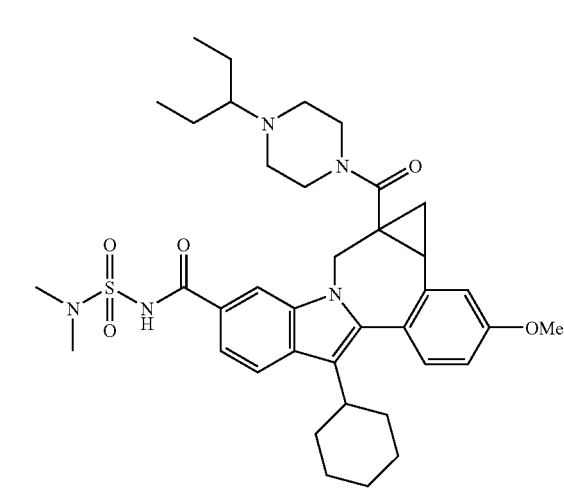

8-Cyclohexyl-N-((dimethylamino)sulfonyl)-1a-((4-(1-ethylpropyl)-1-piperazinyl)carbonyl)-11-methoxy-1,1a,2,12b-tetrahydrocyclopropa[d]indolo[2,1-a][2]benzazepine-5-carboxamide. To a mixture of the acid, 8-cyclohexyl-5-(((dimethylamino)sulfonyl)carbamoyl)-11-methoxy-1,12b-dihydrocyclopropa[d]indolo[2,1-a][2]benzazepine-1a(2H)-carboxylic acid, (50 mg, 90.6 μmol), N,N,N',N'-tetramethyluronium tetrafluoroborate (TBTU, 150 mg, 467 μmol) and 1-(3-pentyl)piperazine (24 mg, 153 μmol) in DMF (2 ml) at r.t. under $N_2$ was added N,N-diisopropylethylamine (0.11 ml, 631 μmol). The reaction mixture was stirred at r.t. for 4 hr. 5 min., and then concentrated. The residue was diluted with MeOH (4 ml), and purified by Shimadzu-VP preparative reverse phase HPLC with separation method: Solvent A=10% MeOH-90% $H_2O$-0.1% TFA, Solvent B=90% MeOH-10% $H_2O$-0.1% TFA, Start % B=0, Final % B=100, Gradient time=6 min, Flow Rate=30 mL/min, Column: Xterra Prep MS C18 5 u 30×50 mm, Fraction Collection: 6.23-6.82 min. (UV detection at 220 nm) to give the trifluoroacetic acid salt of the product (48.3 mg) as an off white solid; Analytical HPLC method: Solvent A=10% MeOH-90% $H_2O$-011% TFA, Solvent B=90% MeOH-10% $H_2O$-011% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=690.56, HPLC $R_t$=1.675 min. Analytical HPLC method: Solvent A=5% MeCN-95% $H_2O$-10 mM $NH_4OAc$, Solvent B=95% MeCN-5% $H_2O$-10 mM $NH_4OAc$, Start % B=0, Final % B=100, Gradient time=2 min, Flow Rate=5 ml/min, Column: Phenomenex Lina C18 5 um 3.0×50 mm; LC/MS: (ES+) m/z (M+H)$^+$=690.49, HPLC $R_t$=1.690 min.

Examples 99-102 were prepared in a similar manner to Example 98.

EXAMPLE 99

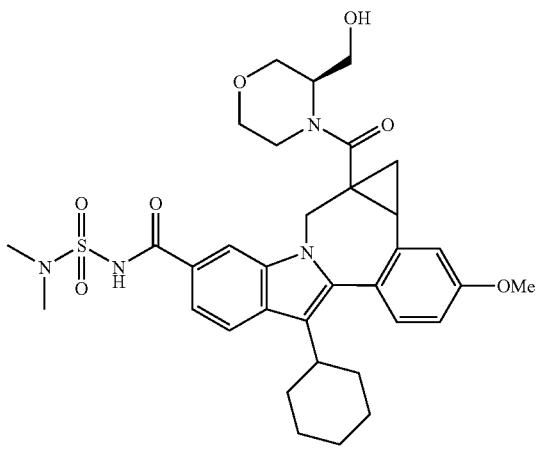

8-Cyclohexyl-N-((dimethylamino)sulfonyl)-1a-(((3R)-3-(hydroxymethyl)-4-morpholinyl)carbonyl)-11-methoxy-1,1a,2,12b-tetrahydrocyclopropa[d]indolo[2,1-a][2]benzazepine-5-carboxamide. Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=651.25, HPLC R$_t$=1.822 min. Analytical HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Flow Rate=5 ml/min, Column: Phenomenex Lina C18 5 um 3.0×50 mm; LC/MS: (ES+) m/z (M+H)$^+$=651.45, HPLC R$_t$=1.063 min.

EXAMPLE 100

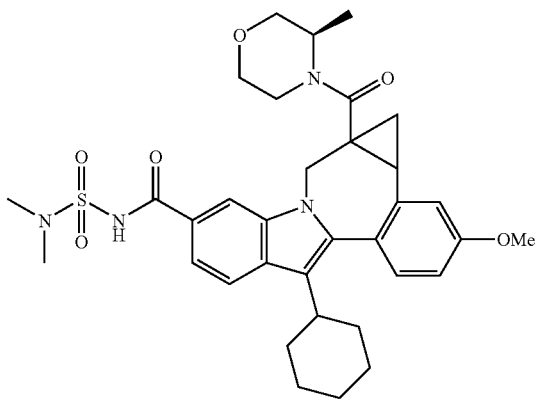

8-Cyclohexyl-N-((dimethylamino)sulfonyl)-11-methoxy-1a-(((3R)-3-methyl-4-morpholinyl)carbonyl)-1,1a,2,12b-tetrahydrocyclopropa[d]indolo[2,1-a][2]benzazepine-5-carboxamide. Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=635.26, HPLC R$_t$=1.867 min. Analytical HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Flow Rate=5 ml/min, Column: Phenomenex Lina C18 5 um 3.0×50 mm; LC/MS: (ES+) m/z (M+H)$^+$=635.63, HPLC R$_t$=1.113 min.

EXAMPLE 101

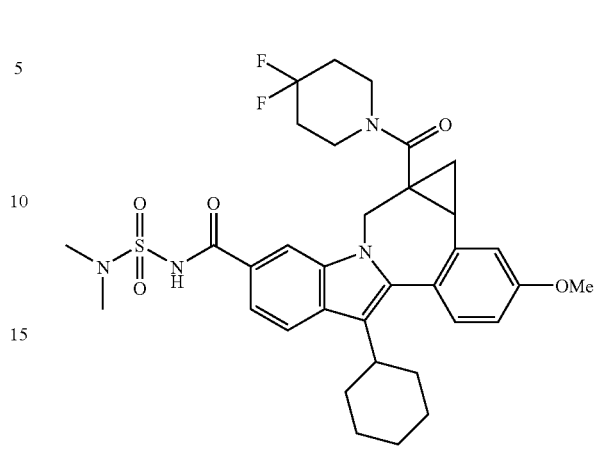

8-Cyclohexyl-1a-((4,4-difluoro-1-piperidinyl)carbonyl)-N-((dimethylamino)sulfonyl)-11-methoxy-1,1a,2,12b-tetrahydrocyclopropa[d]indolo[2,1-a][2]benzazepine-5-carboxamide. Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=655.26, HPLC R$_t$=1.922 min. Analytical HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Flow Rate=5 ml/min, Column: Phenomenex Lina C18 5 um 3.0×50 mm; LC/MS: (ES+) m/z (M+H)$^+$=655.32, HPLC R$_t$=1.212 min.

EXAMPLE 102

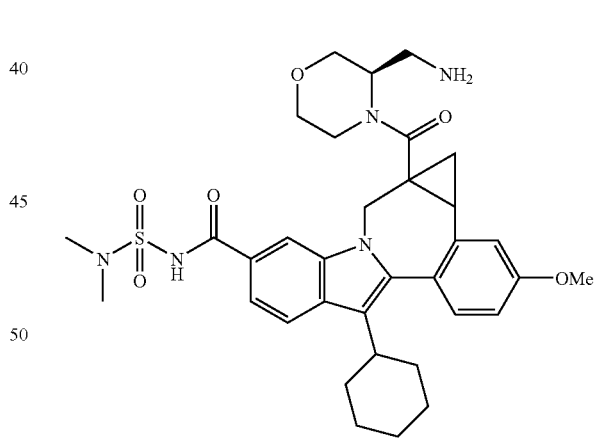

1a-(((3R)-3-(Aminomethyl)-4-morpholinyl)carbonyl)-8-cyclohexyl-N-((dimethylamino)sulfonyl)-11-methoxy-1,1a,2,12b-tetrahydrocyclopropa[d]indolo[2,1-a][2]benzazepine-5-carboxamide. The product was prepared as a trifluoroacetic acid salt from (8-cyclohexyl-N-((dimethylamino)sulfonyl)-1a-(((3R)-3-(hydroxymethyl)-4-morpholinyl)carbonyl)-11-methoxy-1,1a,2,12b-tetrahydrocyclopropa[d]indolo[2,1-a][2]benzazepine-5-carboxamide) via the reaction of the corresponding chloride with ammonia in MeOH under microwave irradiation at 100° C. for 5 min. Analytical HPLC method: Solvent A=10% MeOH-90% H$_2$O-0.1% TFA, Solvent B=90% MeOH-10% H$_2$O-011% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=650.20, HPLC $R_t$=1.603 min. Analytical HPLC method: Solvent A=5% MeCN-95% $H_2O$-10 mM $NH_4OAc$, Solvent B=95% MeCN-5% $H_2O$-10 mM $NH_4OAc$, Start % B=0, Final % B=100, Gradient time=2 min, Flow Rate=5 ml/min, Column: Phenomenex Lina C18 5 um 3.0×50 mm; LC/MS: (ES+) m/z $(M+H)^+$=650.02, HPLC $R_t$=1.167 min.

The general procedures below pertain to the experimental procedures that follow until noted. The acid (0.055 mmol, 1 eq.) was dissolved in dried DMF and followed by adding HATU (0.083 mmol, 1.5 eq.) and DIPEA (0.083. 1.5 eq.). The solution was stirred for 2 minutes and added into pre-weighted amine (0.083 mmol, 1.5 eq.) at room temperature. The mixture was stirred 14 h and purified by prep-HPLC. HPLC gradient methods: Method A: Column: Agilent SB CN4.6×100 mm 3.5 um; mobile phase: water, 10 mM $NH_4OH$, ACN; Method B: Column: Phenomenex Gemini 4.6×100 mm 5 um C18; mobile phase: water, 10 mM $NH_4OH$, ACN; Method C: Column: Waters x-Bridge C18 150×4.6 mm 5 micron; mobile phase: water, 10 mM $NH_4OH$, ACN; Method D: Column: Waters Xbridge 2.1×50 mm 5 um C18; mobile phase: water, 10 mM $NH_4OH$, ACN.

| Structure | HPLC retention time | HPLC purity | Mass | HPLC Method |
|---|---|---|---|---|
| 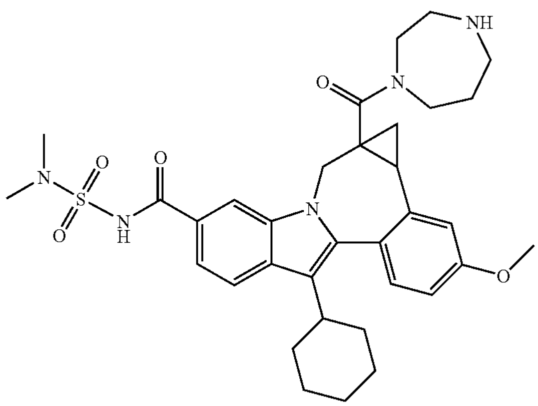 | 4.86 | 88.9 | 634.36 | Method A |
| 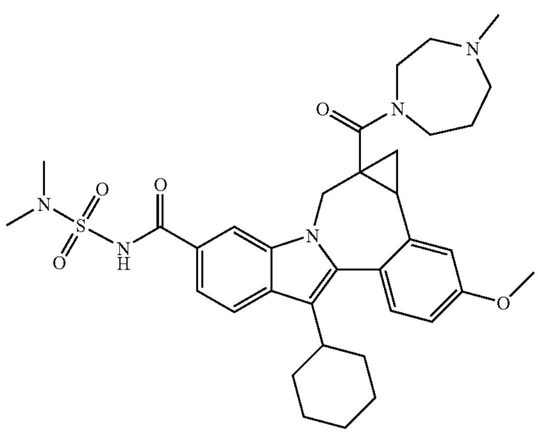 | 4.88 | 100 | 648.37 | Method A |

-continued
| Structure | HPLC retention time | HPLC purity | Mass | HPLC Method |
|---|---|---|---|---|
| 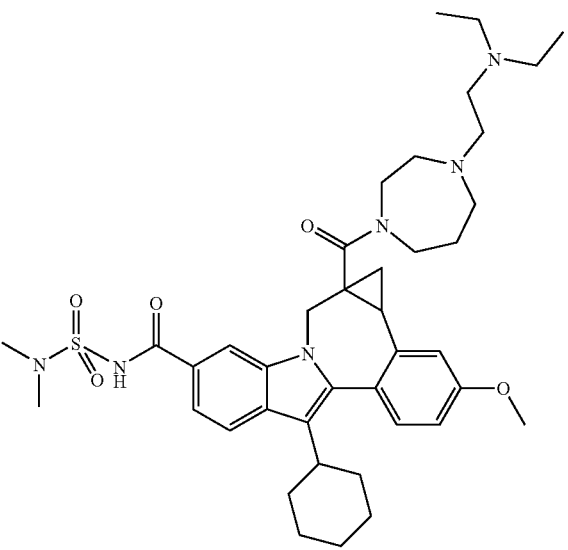 | 5.33 | 98.5 | 733.42 | Method B |
| 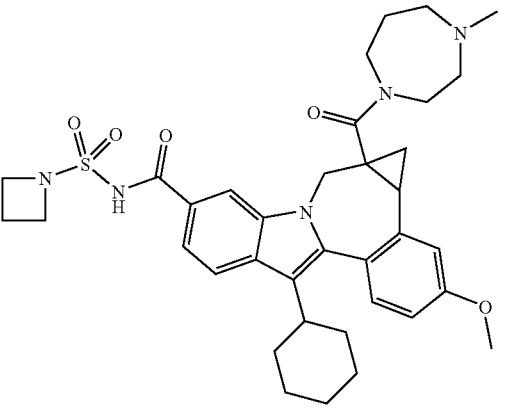 | 7.93 | 93.9 | 659.97 | Method C |
| 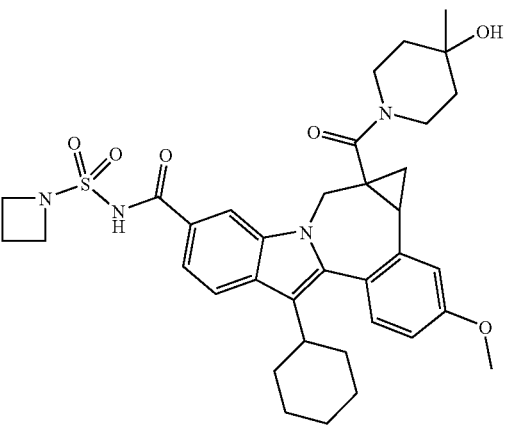 | 8.14 | 99.3 | 661.24 | Method C |

| Structure | HPLC retention time | HPLC purity | Mass | HPLC Method |
|---|---|---|---|---|
| 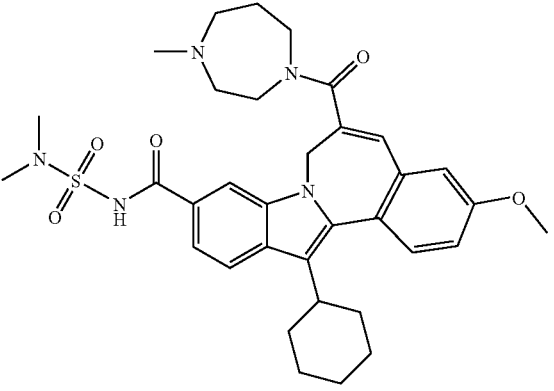 | 2.45 | 96.2 | 634.77 | Method D |
| 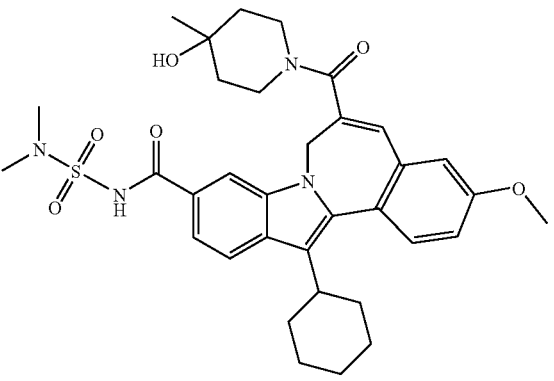 | 2.82 | 97.9 | 634.74 | Method D |
| 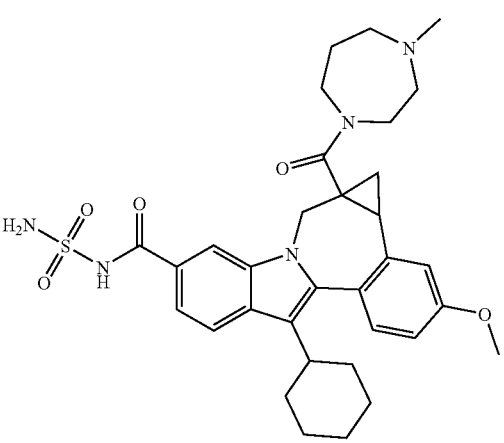 | 2.04 | 96.3 | 619.84 | Method D |

-continued

| Structure | HPLC retention time | HPLC purity | Mass | HPLC Method |
|---|---|---|---|---|
| 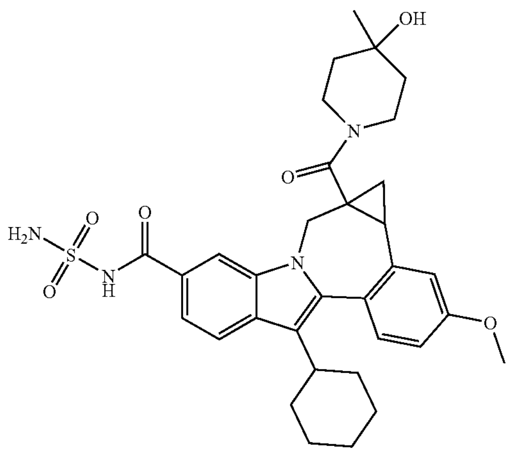 | 2.27 | 100 | 620.83 | Method D |
| 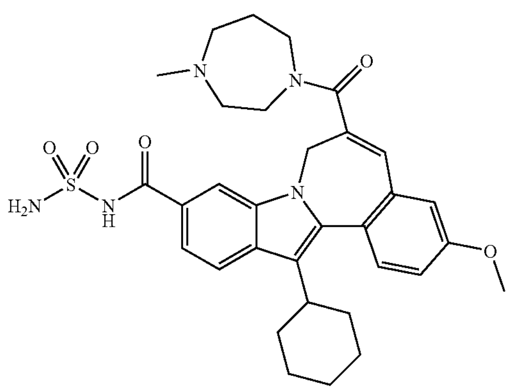 | 7.11 | 100 | 606.14 | Method D |
| 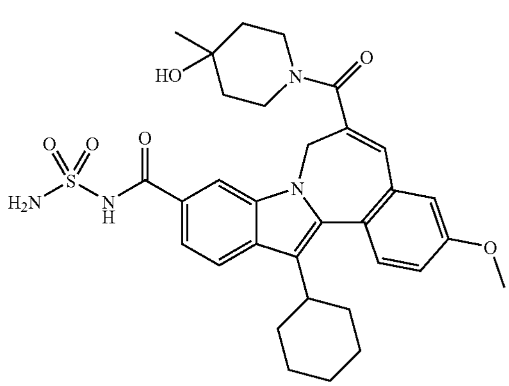 | 7.7 | 100 | 607.11 | Method D |

-continued

| Structure | HPLC retention time | HPLC purity | Mass | HPLC Method |
|---|---|---|---|---|
| 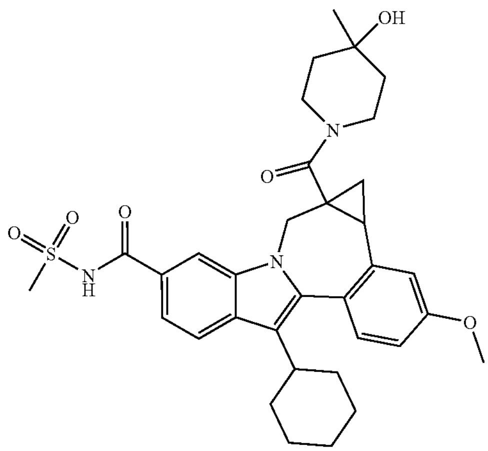 | 2.18 | 93.4 | 620.37 | Method D |
| 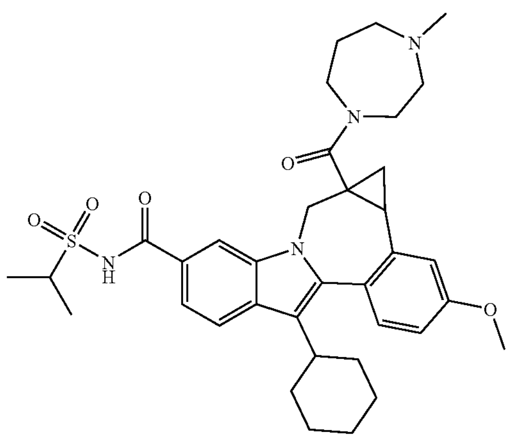 | 7.48 | 100 | 647.21 | Method D |
| 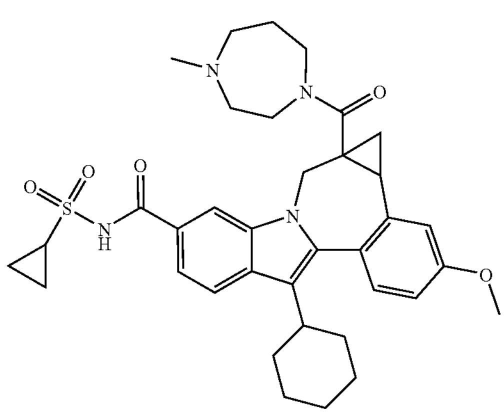 | 2.13 | 100 | 645.37 | Method D |

-continued
| Structure | HPLC retention time | HPLC purity | Mass | HPLC Method |
|---|---|---|---|---|
| 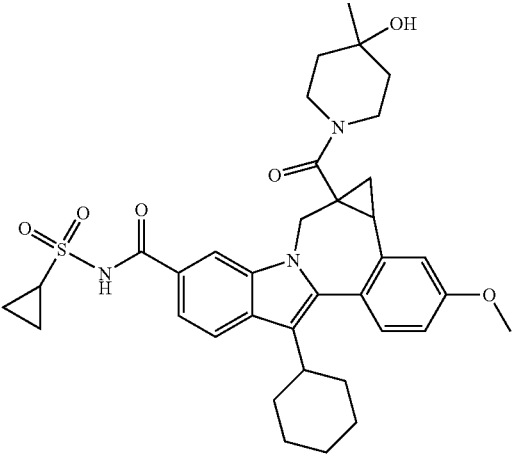 | 2.33 | 95.8 | 646.35 | Method D |
| 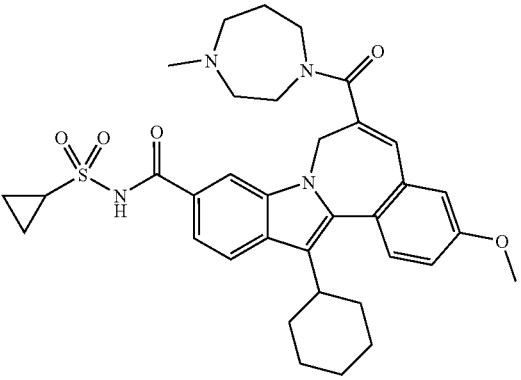 | 2.17 | 100 | 630.79 | Method D |
| 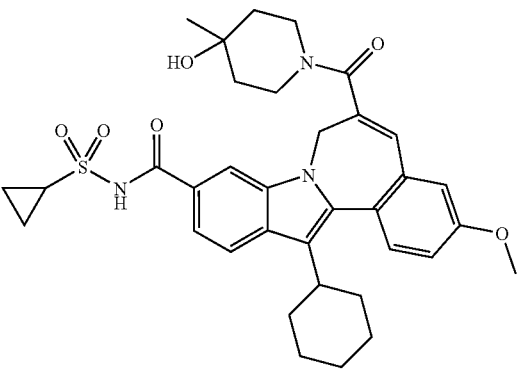 | 2.41 | 100 | 631.8 | Method D |

-continued
| Structure | HPLC retention time | HPLC purity | Mass | HPLC Method |
|---|---|---|---|---|
| 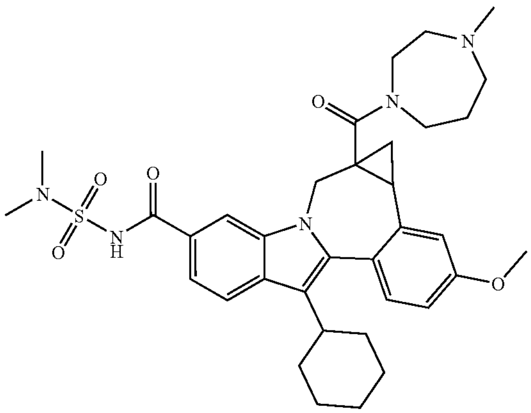 | 2.19 | 100.0 | 648.39 | Method D |
| 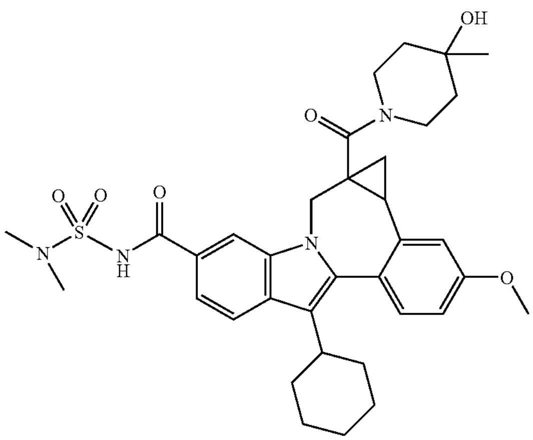 | 2.62 | 98.9 | 649.39 | Method D |
We claim:
1. A compound selected from the group consisting of
-continued
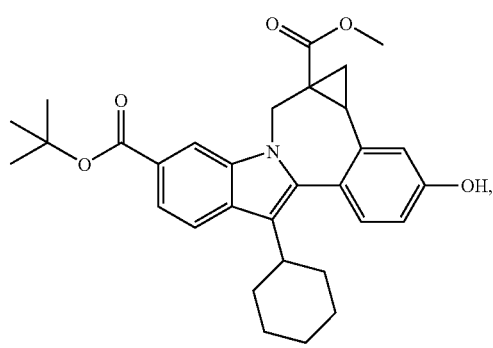
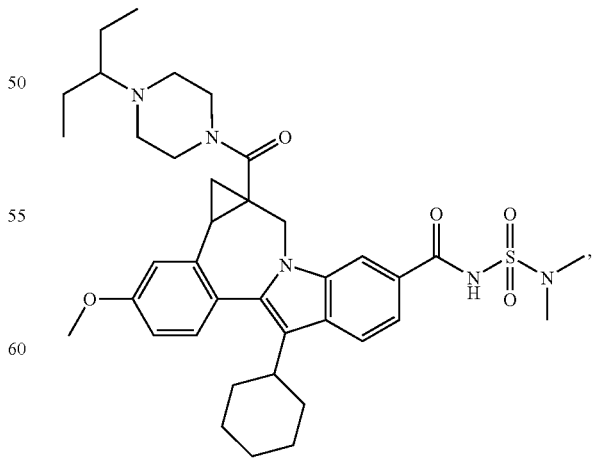

227
-continued
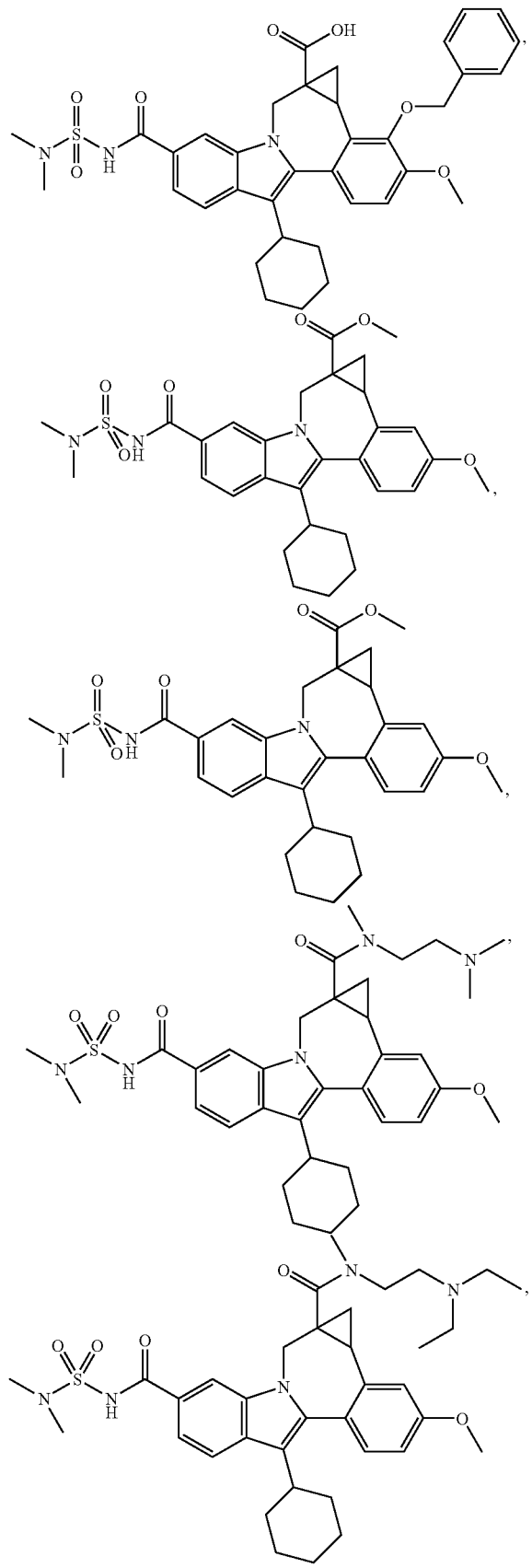
228
-continued
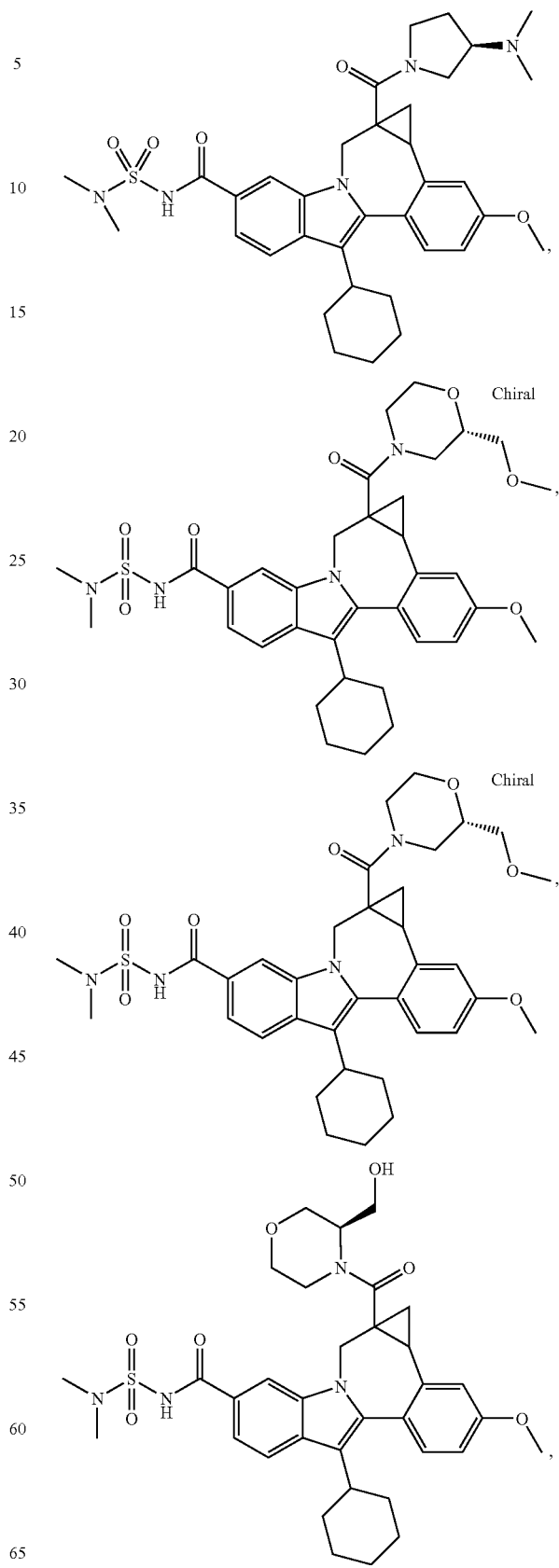

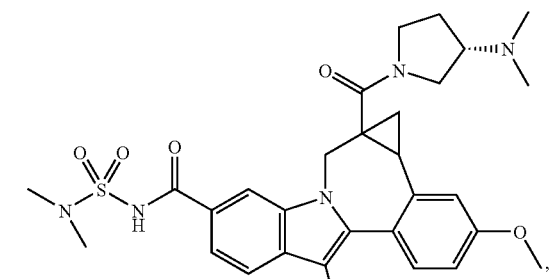
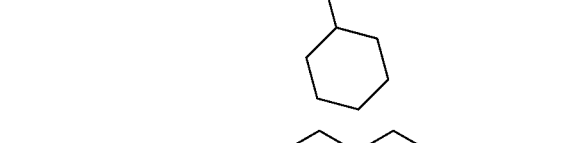
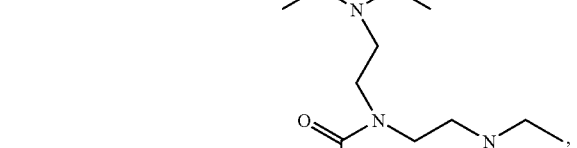
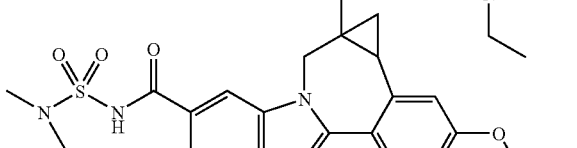
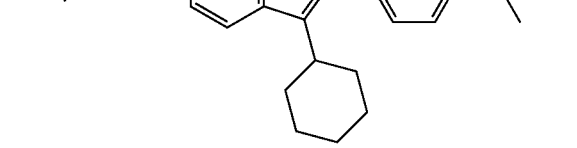
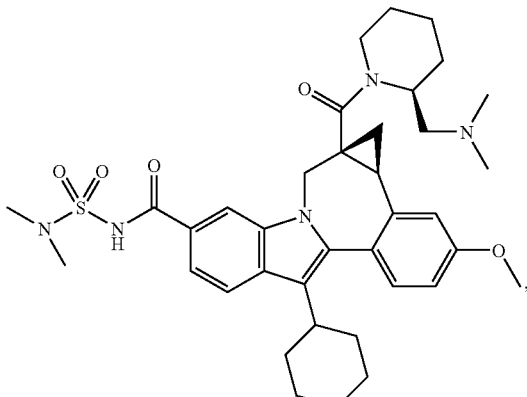
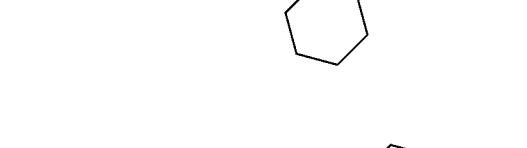
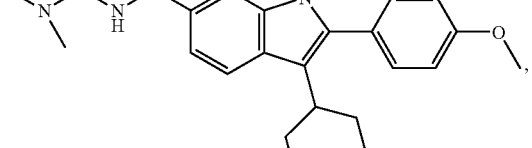
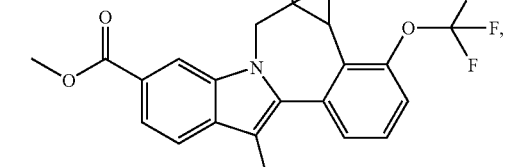

-continued
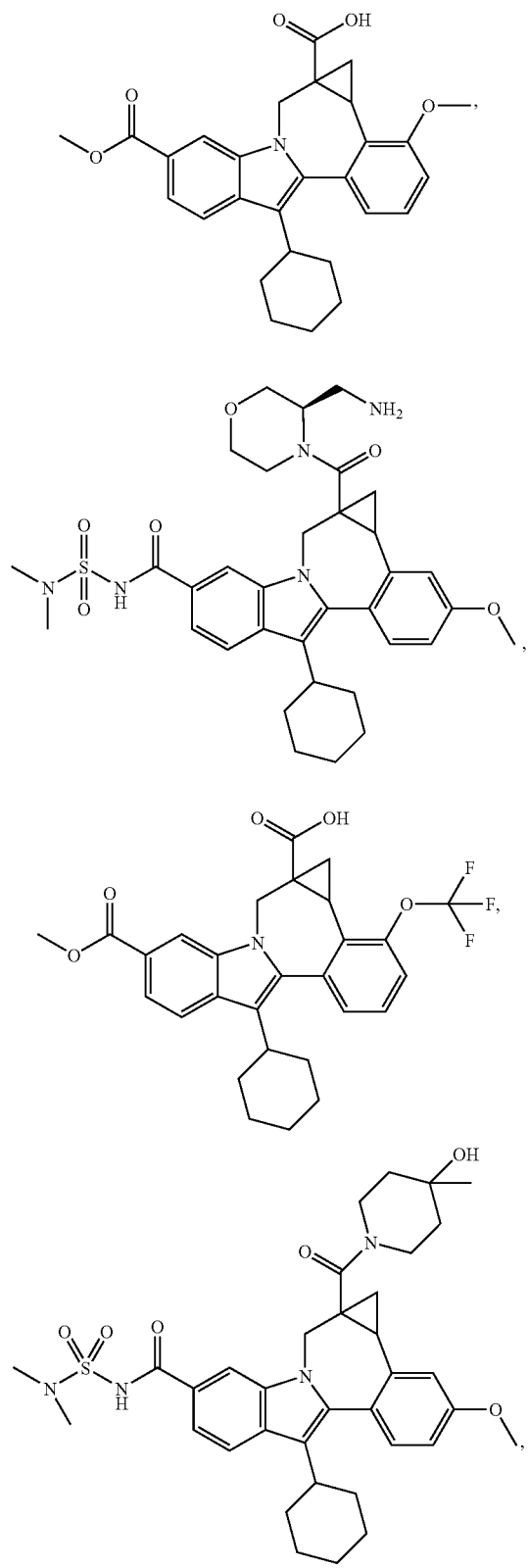
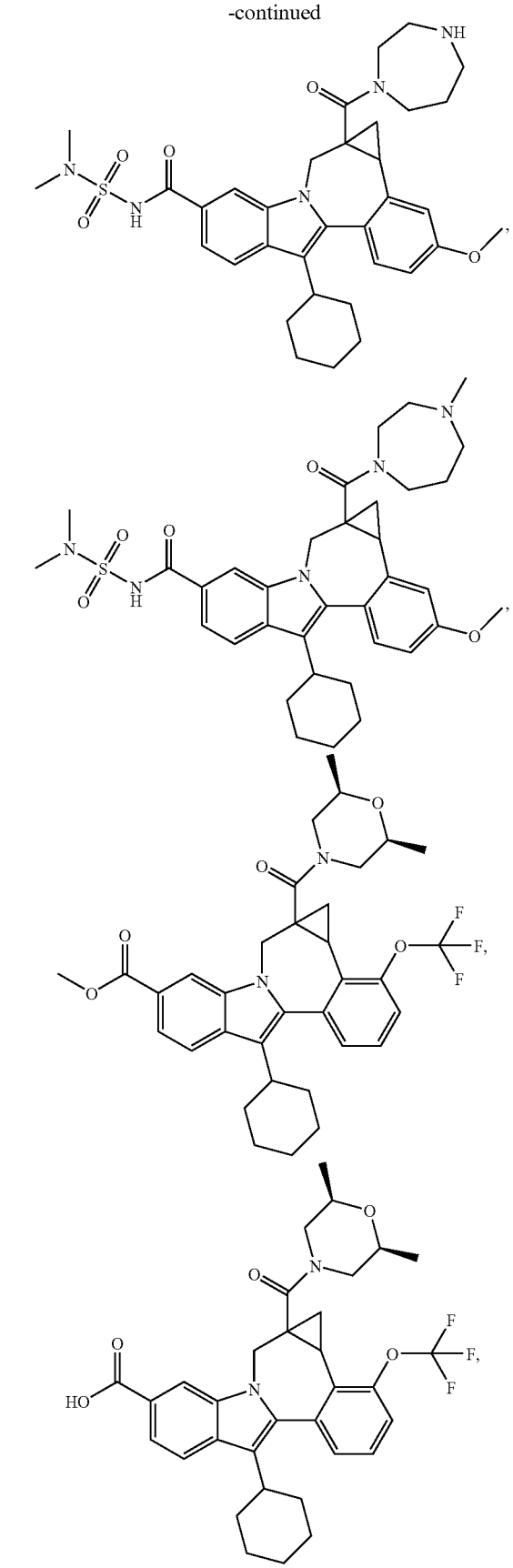

233
-continued
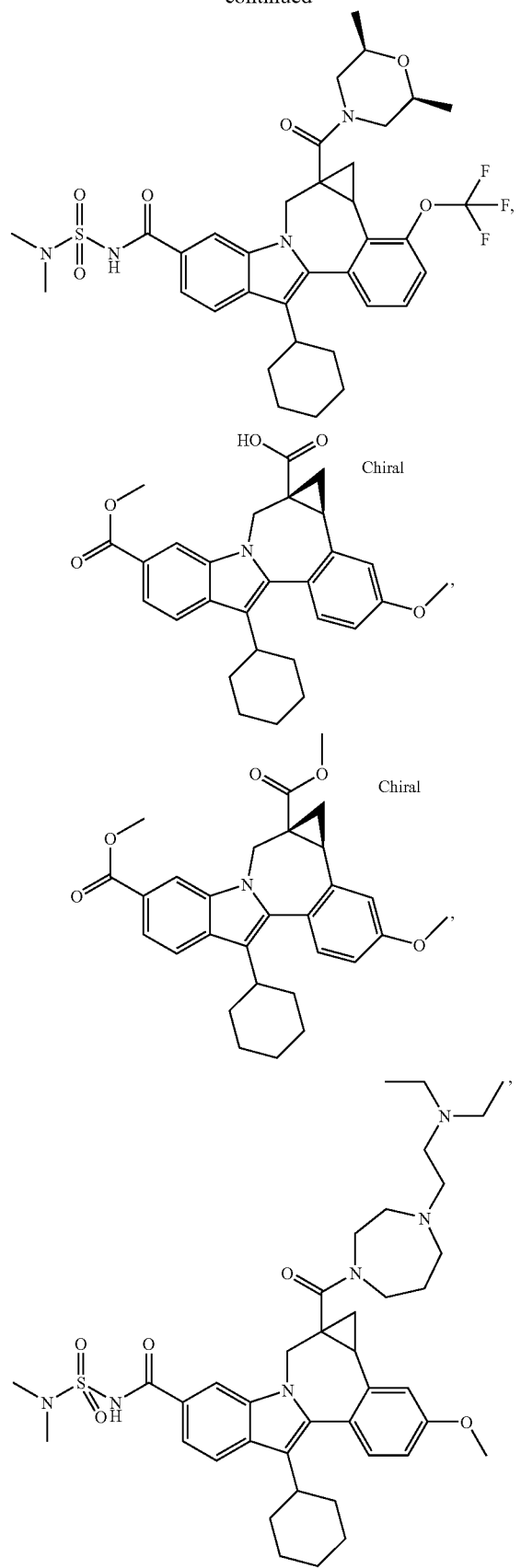
234
-continued
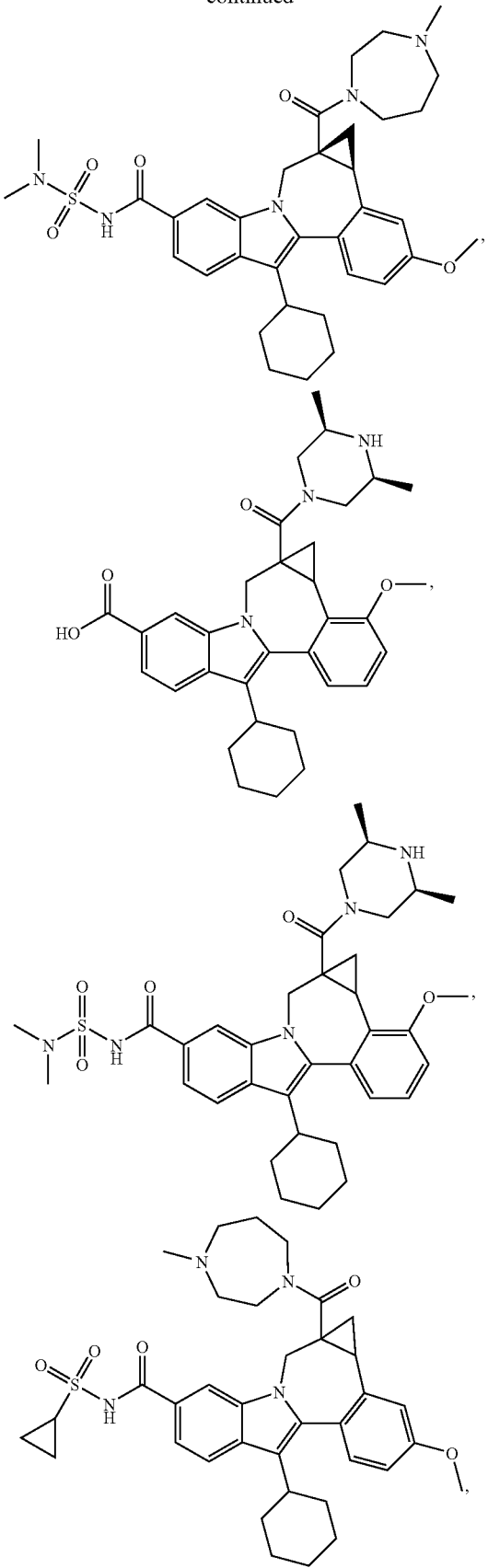

235
-continued
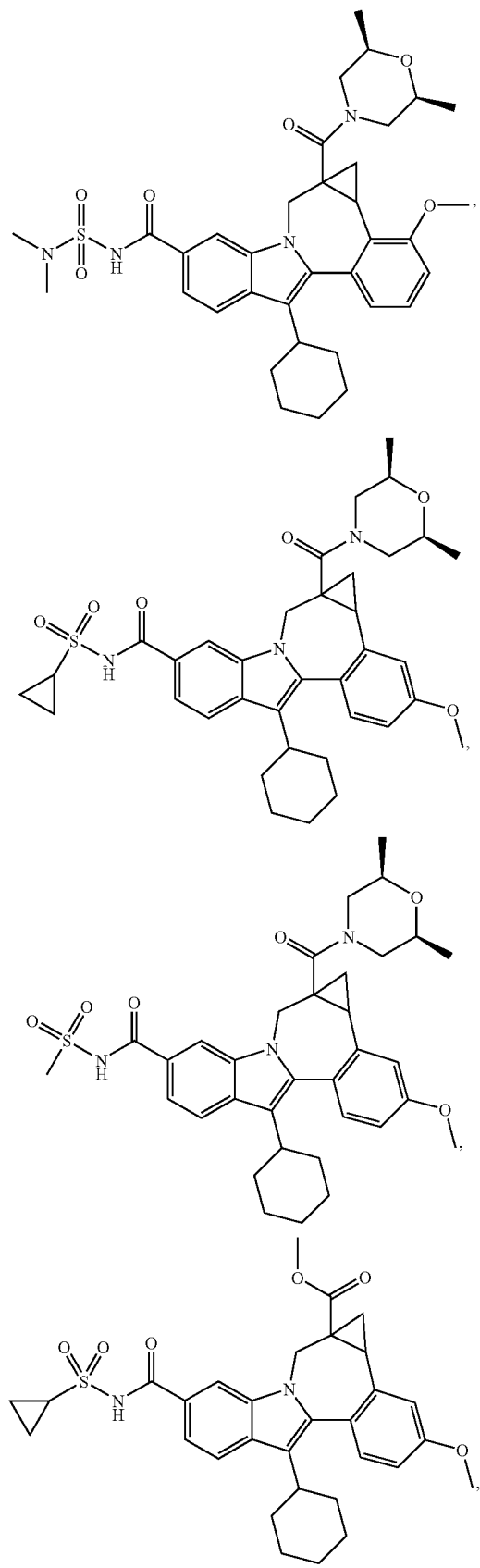
236
-continued
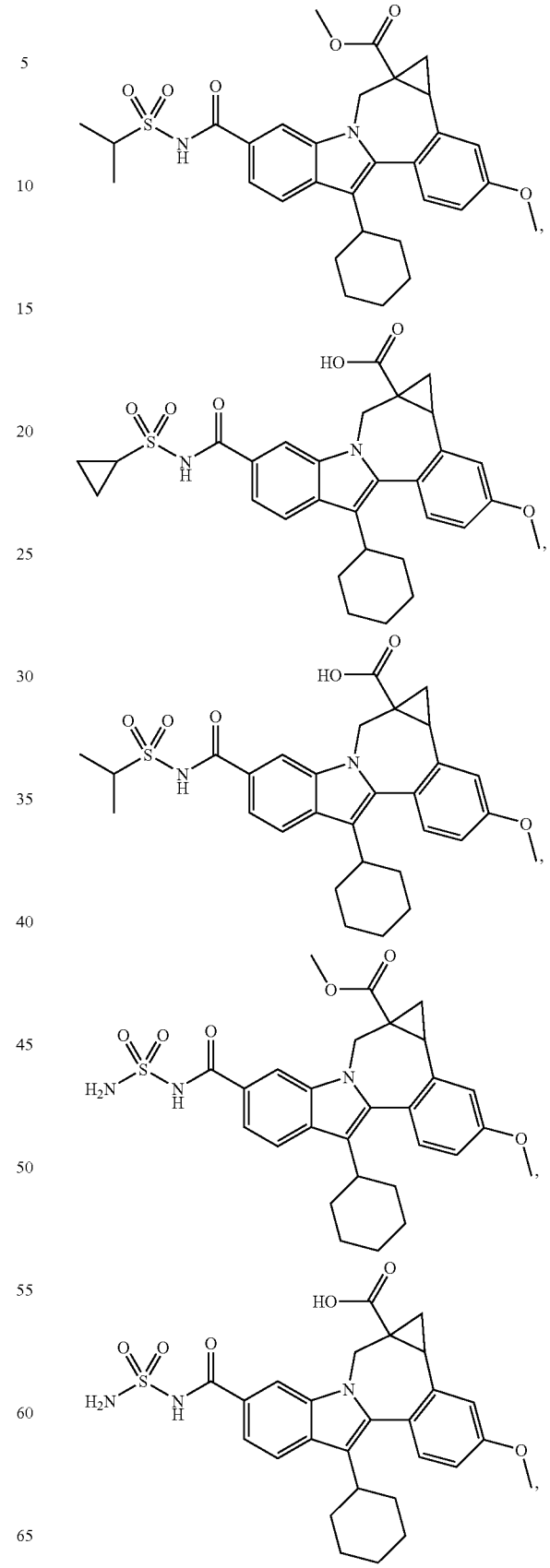

237
-continued
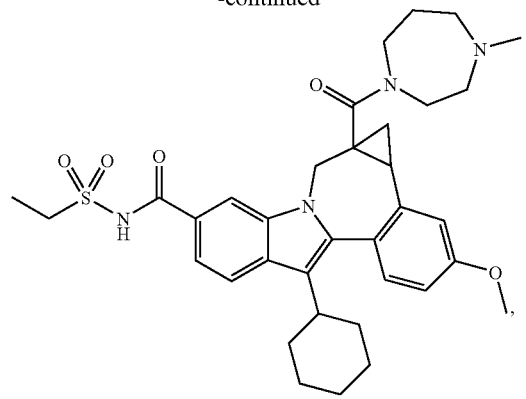
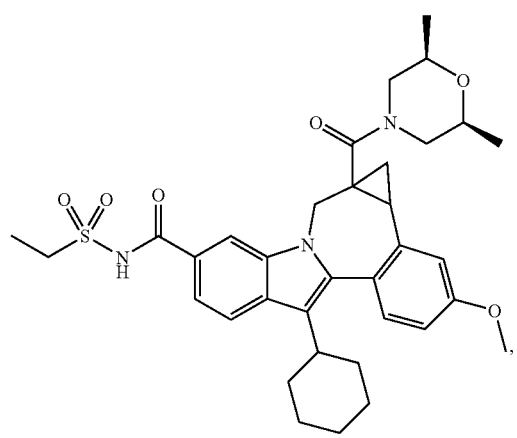
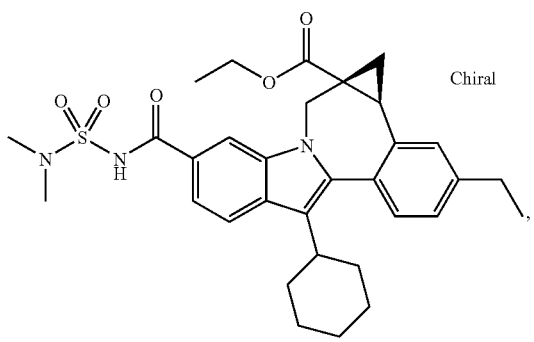
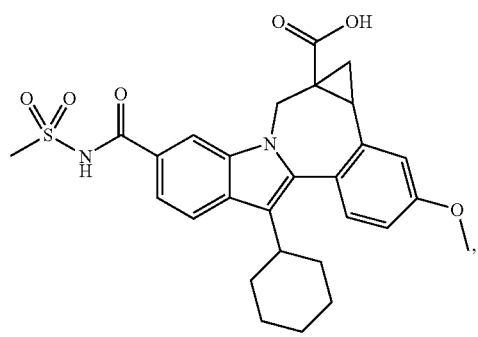
238
-continued
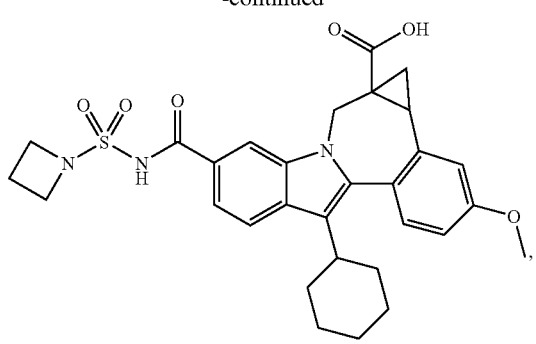
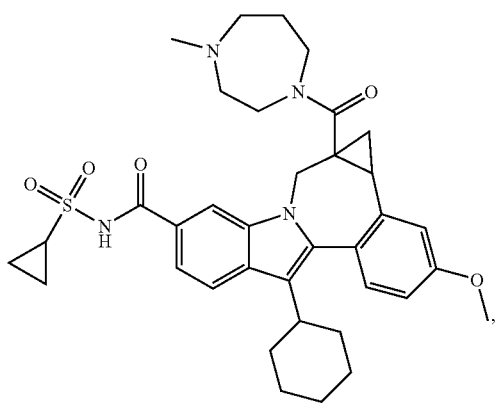
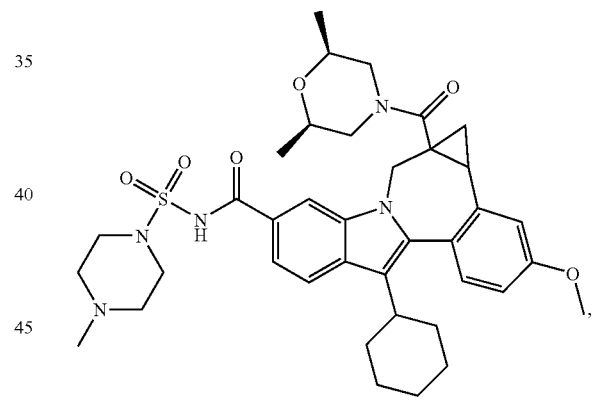
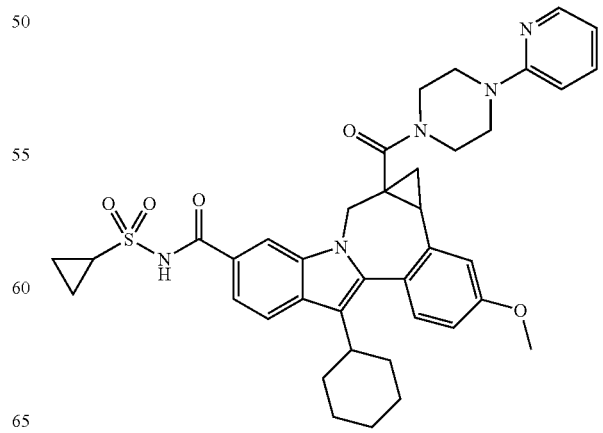

239
-continued
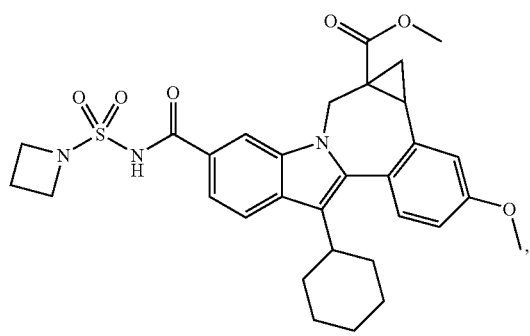
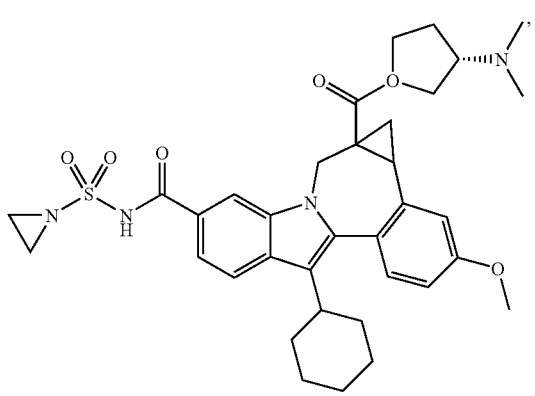
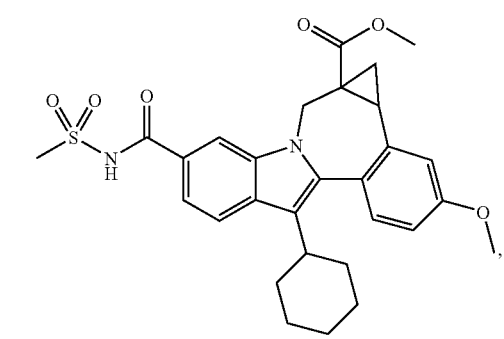
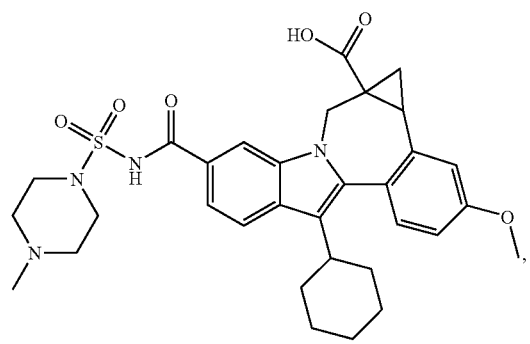
240
-continued
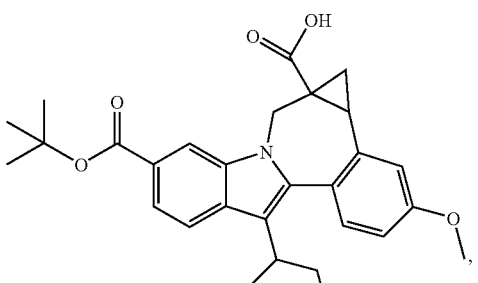
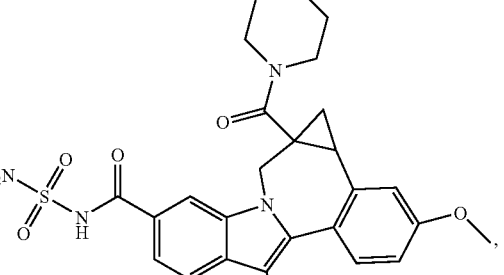
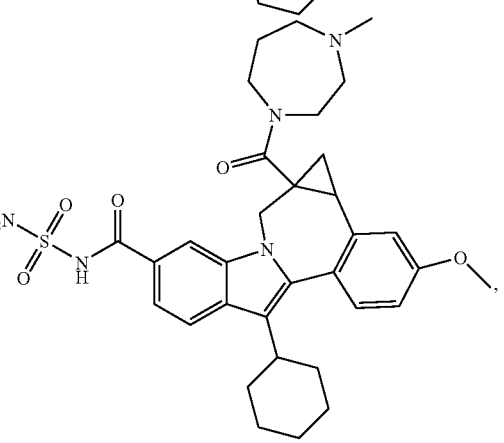
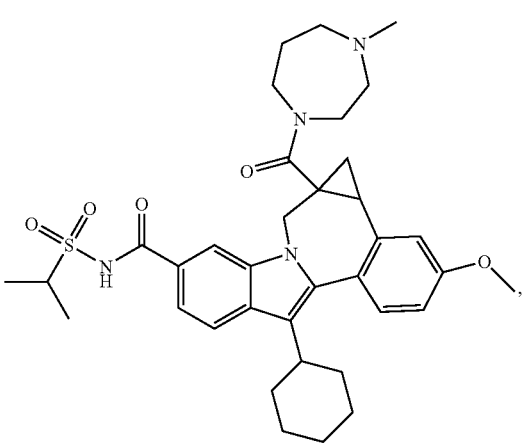

-continued
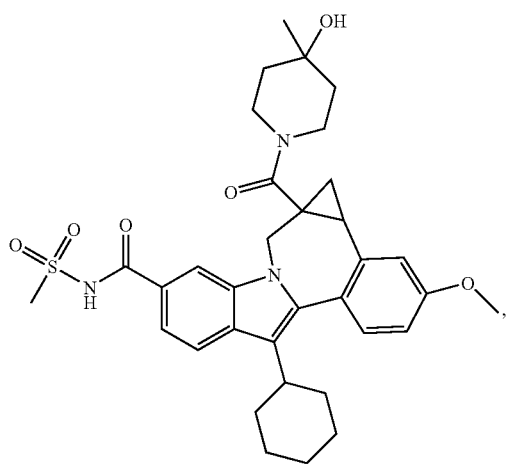
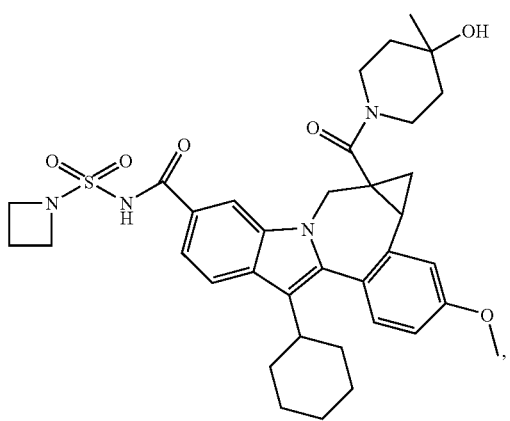
-continued
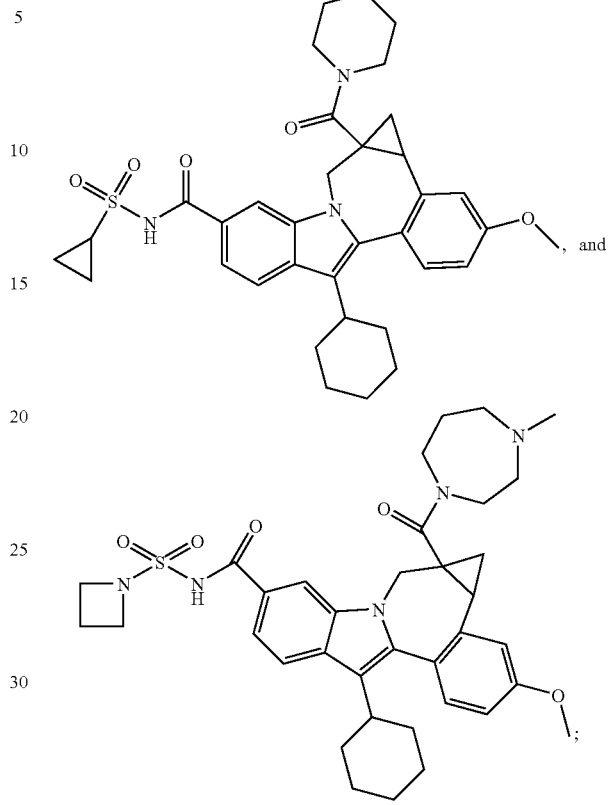
or a pharmaceutically acceptable salt thereof.
2. A composition comprising a compound of claim 1, or a pharmaceutically acceptable salt thereof, and a pharmaceutically acceptable carrier.
3. A method of treating hepatitis C infection comprising administering a therapeutically effective amount of a compound of claim 1 to a patient.
* * * * *